United States Patent
Furuyama et al.

(10) Patent No.: US 8,841,456 B2
(45) Date of Patent: Sep. 23, 2014

(54) 1,5-NAPHTHYRIDINE DERIVATIVE OR SALT THEREOF

(71) Applicant: FUJIFILM Corporation, Tokyo (JP)

(72) Inventors: Hidetomo Furuyama, Ashigarakami-gun (JP); Hideki Kurihara, Ashigarakami-gun (JP); Kentarou Furuya, Ashigarakami-gun (JP); Takahiro Terao, Ashigarakami-gun (JP); Shinichirou Sekine, Ashigarakami-gun (JP); Daisuke Nakagawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/166,105

(22) Filed: Jan. 28, 2014

(65) Prior Publication Data

US 2014/0142302 A1   May 22, 2014

Related U.S. Application Data

(63) Continuation of application No. PCT/JP2012/069246, filed on Jul. 27, 2012.

(30) Foreign Application Priority Data

Jul. 29, 2011 (JP) .................................. 2011-167489

(51) Int. Cl.
*C07D 471/04* (2006.01)
*C07F 7/10* (2006.01)
*C07D 519/00* (2006.01)

(52) U.S. Cl.
CPC ................ *C07D 471/04* (2013.01); *C07F 7/10* (2013.01); *C07D 519/00* (2013.01)
USPC .......................................... 546/122; 544/127

(58) Field of Classification Search
None
See application file for complete search history.

(56) References Cited

U.S. PATENT DOCUMENTS

| 6,822,097 B1 | 11/2004 | Norman et al. |
| 2007/0123494 A1 | 5/2007 | Seipelt et al. |
| 2011/0150831 A1 | 6/2011 | Schuster et al. |

FOREIGN PATENT DOCUMENTS

| JP | 2005-526029 A | 9/2005 |
| JP | 2009-515854 A | 4/2009 |
| WO | WO 2011/064250 A1 | 6/2011 |

OTHER PUBLICATIONS

Engelman et al "Effective use of PI3K and MEK inhibitors to treat mutant Kras G12D and PIK3CA H1047R murine lung cancers", Nature medicine, vol. 14, No. 12, pp. 1351-1356, Dec. 2008.
International Search Report issued in International Application No. PCT/JP2012/069246 on Oct. 2, 2012, with English translation.
Liu et al., "Targeting the phosphoinositide 3 kinase pathway in cancer", Nature Reviews Drug Discovery, 8(8), pp. 627-644, Aug. 2009.
Marone et al., "Targeting phosphoinositide 3 kinase—Moving towards therapy", Biochimica et Biophysica Acta, 1784, pp. 159-185, 2008.
Written Opinion of the ISA issued in International Application No. PCT/JP2012/069246 on Oct. 2, 2012, with partial English Translation.
Yap et al., "Small-Molecule Inhibitors of the ERK Signaling Pathway:Towards Novel Anticancer Therapeutics", ChemMedChem, 6(1), pp. 38-48, 2011.
Yu et al., "ResponSe and determinants of cancer cell susceptibility to PI3K inhibitors", Cancer Biology & Therapy, 7(2), pp. 307-315, 2008.

*Primary Examiner* — Janet L Andres
*Assistant Examiner* — Timothy R Rozof
(74) *Attorney, Agent, or Firm* — Birch, Stewart, Kolasch & Birch, LLP

(57) ABSTRACT

A 1,5-naphthyridine derivative represented by Formula [1] (in which $R^1$, $R^2$, $R^3$, $R^4$ and $R^5$ represent a hydrogen atom, -L-Z (in which Z represents a non-aromatic heterocyclic group or the like; and L represents a single bond or the like), or the like, $R^6$ represents -L-Z or the like, $R^7$ and $R^8$ represent a hydrogen atom or the like, and Q represents an oxygen atom or the like), or a salt thereof has an excellent inhibitory activity with respect to the PI3K-AKT pathway and the Ras-Raf-MEK-ERK pathway, and is useful for treatments such as prophylactic treatments and therapeutic treatments of diseases in which the PI3K-AKT pathway and the Ras-Raf-MEK-ERK pathway are involved.

12 Claims, No Drawings

1,5-NAPHTHYRIDINE DERIVATIVE OR SALT THEREOF

CROSS-REFERENCE TO RELATED APPLICATION

This application is a continuation application of International Application No. PCT/JP/2012/069246, filed Jul. 27, 2012, the disclosure of which is incorporated herein by reference in its entirety. Further, this application claims priority from Japanese Patent Application No. 2011-167489, filed Jul. 29, 2011.

TECHNICAL FIELD

The present invention relates to a 1,5-naphthyridine derivative or a salt thereof.

BACKGROUND ART

The PI3K-AKT pathway is an important signaling pathway which plays a central role in growth, proliferation, differentiation, invasion, migration, apoptosis, glucose metabolism, and the like of cells. It has been known that in plural malignant tumors, the PI3K-AKT pathway is constantly activated by activation of receptors upstream of the PI3K-AKT pathway and mutation, deficiency, and amplification of the molecules constituting the PI3K-AKT pathway (Nature Reviews Drug Discovery Vol. 8, No. 8, pp. 627-644, 2009).

It has been reported that the PI3K-AKT pathway contributes to not only malignant tumors but also other diseases such as, for example, cell proliferative diseases, allergy and autoimmune diseases, neurodegenerative diseases, cardiovascular diseases, inflammatory diseases, endocrine abnormalities, metabolic abnormalities, and infectious diseases (Biochimica et Biophysica Acta, Vol. 1784, No. 1, pp. 159-185, 2008).

Therefore, it is believed that control of the PI3K-AKT pathway would be beneficial in the treatment of various diseases.

The Ras-Raf-MEK-ERK pathway is a pathway which is located downstream of various receptors and plays an important role in cell physiological functions such as, for example, cell proliferation, apoptosis, and cell differentiation (ChemMedChem, Vol. 6, No. 1, pp. 38-48, 2011).

Examples of diseases in which the Ras-Raf-MEK-ERK pathway is involved include malignant tumors, allergy and autoimmune diseases, cardiovascular diseases, and neurodegenerative diseases.

Therefore, control of the Ras-Raf-MEK-ERK pathway is expected to be beneficial in the treatment of various diseases.

Here, the PI3K-AKT pathway and the Ras-Raf-MEK-ERK pathway function in cell proliferation in a complementary manner, and it has been reported that simultaneous control of both of the pathways is beneficial in the treatment of malignant tumors (Cancer Biology & Therapy, Vol. 7, No. 2, pp. 307-315, 2008, and Nature medicine, Vol. 14, No. 12, pp. 1351-1356, 2008).

Since the PI3K-AKT pathway and the Ras-Raf-MEK-ERK pathway are very important for the treatment of diseases, PI3K-AKT pathway inhibitors or Ras-Raf-MEK-ERK pathway inhibitors have been hitherto developed. However, compounds which have led to commercial launch are extremely rare (International publication WO 2011/064250). In addition, there have only been a few reports of compounds which inhibit directly and simultaneously both of the signaling pathways (Japanese National-Phase Publication (JP-A) No. 2009-515854).

On the other hand, a 1,5-naphthyridine derivative having a urea structure in a molecule thereof, which inhibits Aurora B, the Ras-Raf-MEK-ERK pathway, and Erk2 (International publication WO 2011/064250) has been known. However, a 1,5-naphthyridine derivative which has a urea structure in a molecule thereof and inhibits a PI3K-AKT pathway has not been known.

In International publication WO 2011/064250, it is described that a 1,5-naphthyridine derivative having a urea structure in a molecule thereof can be prepared from 7-bromo-2-chloro-1,5-naphthyridine.

As a method for preparing 7-bromo-2-chloro-1,5-naphthyridine, a method in which 3-bromo-1,5-naphthyridine is oxidized with m-chlorobenzoic acid and then halogenated with phosphorous oxychloride (International publication WO 2011/064250) has been described.

However, this preparation method has drawbacks such as (1) a low yield, (2) the need for column chromatography, and (3) the expensiveness of and difficulty of obtaining 3-bromo-1,5-naphthyridine which is a raw material.

PRIOR ART LITERATURE

Patent Literature

Patent Literature 1: International publication WO 2011/064250
Patent Literature 2: Japanese National-Phase Publication (JP-A) No. 2009-515854

Non-Patent Literature

Non-patent Literature 1: Nature Reviews Drug Discovery Vol. 8, No. 8, pp. 627-644, 2009
Non-patent Literature 2: Biochimica et Biophysica Acta, Vol. 1784, No. 1, pp. 159-185, 2008
Non-patent Literature 3: ChemMedChem, Vol. 6, No. 1, pp. 38-48, 2011
Non-patent Literature 4: Cancer Biology & Therapy, Vol. 7, No. 2, pp. 307-315, 2008
Non-patent Literature 5: Nature Medicine, Vol. 14, No. 12, pp. 1351-1356, 2008

SUMMARY OF INVENTION

Technical Problem

It is an object of the present invention to provide a compound having an excellent inhibitory activity with respect to at least one of the PI3K-AKT pathway or the Ras-Raf-MEK-ERK pathway.

It is another object of the present invention to provide an excellent PI3K inhibitor.

It is still another object of the present invention to provide a method for preparing an intermediate for the preparation of a compound having an excellent inhibitory activity with respect to the PI3K-AKT pathway.

Solution to Problem

Under these circumstances, the present inventors have conducted extensive studies and as a result, they have found that a 1,5-naphthyridine derivative represented by Formula [1] or a salt thereof has an excellent inhibitory activity with respect to at least one of the PI3K-AKT pathway or the Ras-Raf-MEK-ERK pathway, and is useful for treatments such as prophylactic and therapeutic treatments of diseases related to at least one of the PI3K-AKT pathway or the Ras-Raf-MEK-ERK pathway.

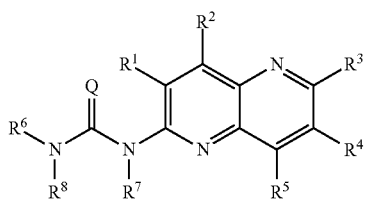

[1]

In formula [1], each of $R^1$, $R^2$, $R^3$, $R^4$ and $R^5$ independently represents a hydrogen atom, a halogen atom, a cyano group, an optionally substituted $C_{1-6}$ alkyl group, an optionally substituted $C_{2-6}$ alkenyl group, an optionally substituted $C_{2-6}$ alkynyl group, or a monovalent group represented by —$OR^9$, —$SR^9$, —$N(R^9)_2$, —$S(=O)_nR^9$, —$C(=O)R^9$, —$C(=NR^9)R^9$, —$C(=N—OR^9)R^9$, —$S(=O)_nN(R^9)_2$, —$C(=O)N(R^9)_2$, —$C(=O)OR^9$, —$S(=O)_nR^9$, —$C(=NR^9)N(R^9)_2$, —$C(=NR^9)OR^9$, —$NR^9S(=O)_nR^9$, —$NR^9C(=O)R^9$, —$NR^9C(=NR^9)R^9$, —$OC(=O)R^9$, —$OC(=NR^9)R^9$, —$OS(=O)_nR^9$, —$NR^9C(=O)N(R^9)_2$, —$NR^9C(=S)N(R^9)_2$, —$NR^9C(=O)OR^9$, —$OC(=O)N(R^9)_2$ or -L-Z, wherein each of $R^9$ independently represents a hydrogen atom, an optionally substituted $C_{1-6}$ alkyl group, an optionally substituted $C_{3-8}$ cycloalkyl group, an optionally substituted non-aromatic heterocyclic group, an optionally substituted aryl group, or an optionally substituted heteroaryl group; n represents 1 or 2; Z represents an optionally substituted $C_{3-8}$ cycloalkyl group, an optionally substituted non-aromatic heterocyclic group, an optionally substituted aryl group, or an optionally substituted heteroaryl group; and L represents a single bond or a divalent linking group containing a hydrogen atom and at least one selected from the group consisting of a carbon atom, a nitrogen atom, an oxygen atom, and a sulfur atom;

$R^6$ represents a hydrogen atom, an optionally substituted $C_{1-6}$ alkyl group, an optionally substituted $C_{2-6}$ alkenyl group, an optionally substituted $C_{2-6}$ alkynyl group, or a monovalent group represented by -L-Z, wherein L and Z represent the same as those described above; and each of $R^7$ and $R^8$ independently represents a hydrogen atom, an optionally substituted $C_{1-6}$ alkyl group, an optionally substituted $C_{3-8}$ cycloalkyl group, an optionally substituted $C_{2-6}$ alkenyl group, or an optionally substituted $C_{2-6}$ alkynyl group;

and Q represents an oxygen atom, a sulfur atom, or a nitrogen atom having a hydrogen atom, an optionally substituted $C_{1-6}$ alkyl group, an optionally substituted $C_{1-6}$ alkoxy group, an optionally substituted $C_{3-8}$ cycloalkyl group, an optionally substituted $C_{2-6}$ alkenyl group, or an optionally substituted $C_{2-6}$ alkynyl group:

provided that the 1,5-naphthyridine derivative represented by Formula [1] is not any of the following compounds A1 to A16.

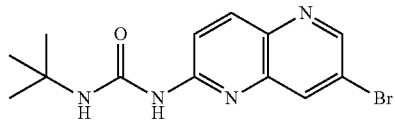
A1

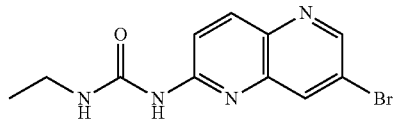
A2

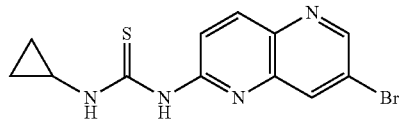
A3

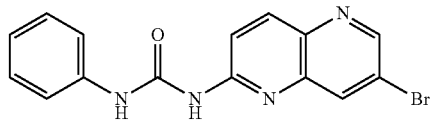
A4

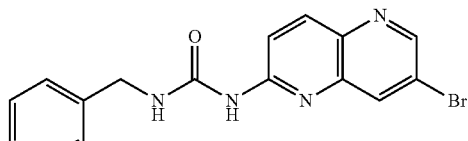
A5

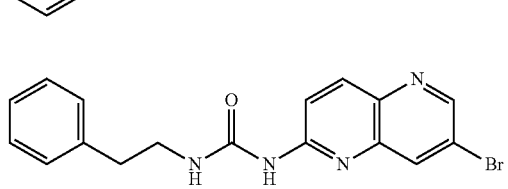
A6

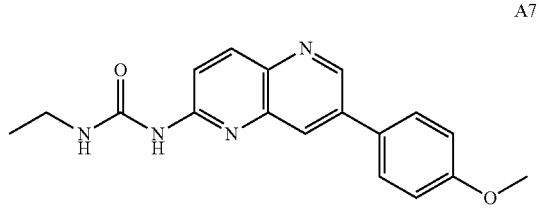
A7

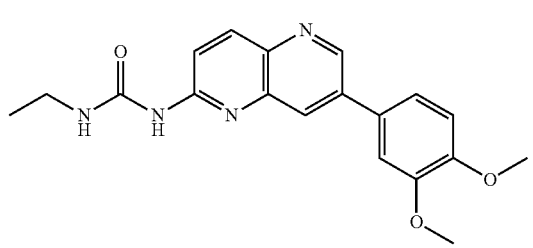
A8

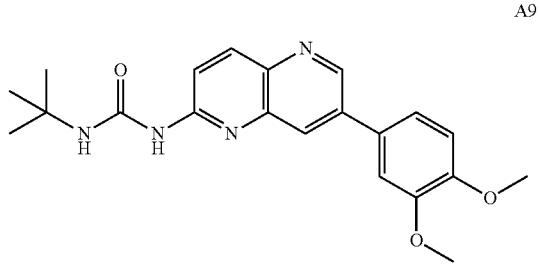
A9

-continued

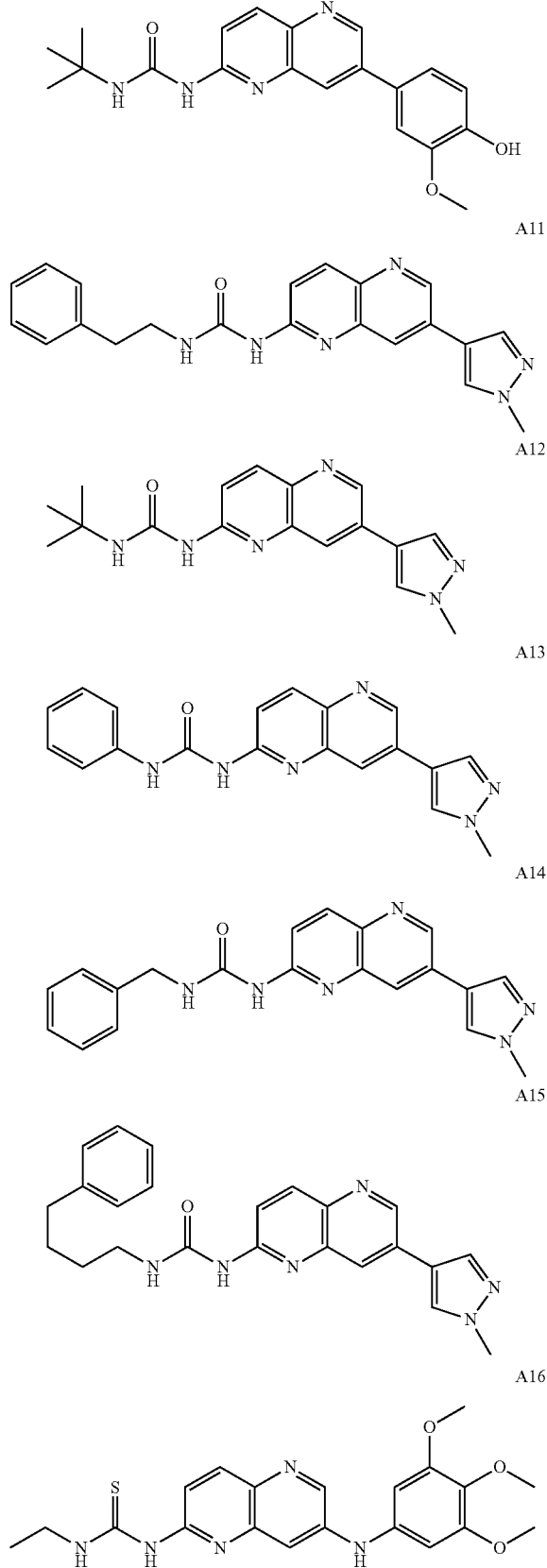

A10

A11

A12

A13

A14

A15

A16

The present inventors have also found that a 1,5-naphthyridine derivative represented by Formula [1] or a salt thereof has an excellent inhibitory activity with respect to the PI3K-AKT pathway and is useful as a PI3K inhibitor.

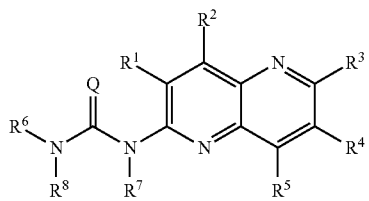

[1]

In Formula [1], each of $R^1$, $R^2$, $R^3$, $R^4$ and $R^5$ each independently represent a hydrogen atom, a halogen atom, a cyano group, an optionally substituted $C_{1-6}$ alkyl group, an optionally substituted $C_{2-6}$ alkenyl group, an optionally substituted $C_{2-6}$ alkynyl group, or a monovalent group represented by —$OR^9$, —$SR^9$, —$N(R^9)_2$, —$S(=O)_nR^9$, —$C(=O)R^9$, —$C(=NR^9)R^9$, —$C(=N-OR^9)R^9$, —$S(=O)_nN(R^9)_2$, —$C(=O)N(R^9)_2$, —$C(=O)OR^9$, —$S(=O)_nR^9$, —$C(=NR^9)N(R^9)_2$, —$C(=NR^9)OR^9$, —$NR^9S(=O)_nR^9$, —$NR^9C(=O)R^9$, —$NR^9C(=NR^9)R^9$, —$OC(=O)R^9$, —$OC(=NR^9)R^9$, —$OS(=O)_nR^9$, —$NR^9C(=O)N(R^9)_2$, —$NR^9C(=S)N(R^9)_2$, —$NR^9C(=O)OR^9$, —$OC(=O)N(R^9)_2$ or -L-Z, wherein each of $R^9$ independently represents a hydrogen atom, an optionally substituted $C_{1-6}$ alkyl group, an optionally substituted $C_{3-8}$ cycloalkyl group, an optionally substituted non-aromatic heterocyclic group, an optionally substituted aryl group, or an optionally substituted heteroaryl group; n represents 1 or 2; Z represents an optionally substituted $C_{3-8}$ cycloalkyl group, an optionally substituted non-aromatic heterocyclic group, an optionally substituted aryl group, or an optionally substituted heteroaryl group; and L represents a single bond or a divalent linking group containing a hydrogen atom and at least one selected from the group consisting of a carbon atom, a nitrogen atom, an oxygen atom, and a sulfur atom);

$R^6$ represents a hydrogen atom, an optionally substituted $C_{1-6}$ alkyl group, an optionally substituted $C_{2-6}$ alkenyl group, an optionally substituted $C_{2-6}$ alkynyl group or a monovalent group represented by -L-Z, wherein L and Z represents the same as described above;

each of $R^7$ and $R^8$ independently represents a hydrogen atom, an optionally substituted $C_{1-6}$ alkyl group, an optionally substituted $C_{3-8}$ cycloalkyl group, an optionally substituted $C_{2-6}$ alkenyl group, or an optionally substituted $C_{2-6}$ alkynyl group; and Q represents an oxygen atom, a sulfur atom, or a nitrogen atom having a hydrogen atom, an optionally substituted $C_{1-6}$ alkyl group, an optionally substituted $C_{1-6}$ alkoxy group, an optionally substituted $C_{3-8}$ cycloalkyl group, an optionally substituted $C_{2-6}$ alkenyl group, or an optionally substituted $C_{2-6}$ alkynyl group.

The inventors have still further found that a compound represented by Formula [6] can be obtained by reacting a compound represented by Formula [2] with a compound represented by Formula [3] to obtain a compound represented by Formula [4], thereafter reacting the compound represented by Formula [4] with a halogenating agent, sulfonic acid anhydride, or sulfonic acid halide to obtain a compound represented by Formula [5], and then reacting the compound represented by Formula [5] with a brominating agent to prepare a compound represented by Formula [6], thereby completing the present invention.

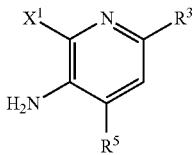
[2]

In Formula [2], each of $R^3$ and $R^5$ independently represents a hydrogen atom, a halogen atom, a cyano group, an optionally substituted $C_{1-6}$ alkyl group, an optionally substituted $C_{2-6}$ alkenyl group, an optionally substituted $C_{2-6}$ alkynyl group, or a monovalent group represented by —$OR^9$, —$SR^9$, —$N(R^9)_2$, —$S(=O)_nR^9$, —$C(=O)R^9$, —$C(=NR^9)R^9$, —$C(=N—OR^9)R^9$, —$S(=O)_nN(R^9)_2$, —$C(=O)N(R^9)_2$, —$C(=O)OR^9$, —$S(=O)_nOR^9$, —$C(=NR^9)N(R^9)_2$, —$C(=NR^9)OR^9$, —$NR^9S(=O)_nR^9$, —$NR^9C(=O)R^9$, —$NR^9C(=NR^9)R^9$, —$OC(=O)R^9$, —$OC(=NR^9)R^9$, —$OS(=O)_nR^9$, —$NR^9C(=O)N(R^9)_2$, —$NR^9C(=S)N(R^9)_2$, —$NR^9C(=O)OR^9$, —$OC(=O)N(R^9)_2$ or -L-Z, wherein each of $R^9$ independently represents a hydrogen atom, an optionally substituted $C_{1-6}$ alkyl group, an optionally substituted $C_{3-8}$ cycloalkyl group, an optionally substituted non-aromatic heterocyclic group, an optionally substituted aryl group, or an optionally substituted heteroaryl group; n represents 1 or 2; Z represents an optionally substituted $C_{3-8}$ cycloalkyl group, an optionally substituted non-aromatic heterocyclic group, an optionally substituted aryl group, or an optionally substituted heteroaryl group; and L represents a single bond or a divalent linking group containing a hydrogen atom and at least one selected from the group consisting of a carbon atom, a nitrogen atom, an oxygen atom, and a sulfur atom;

$X^1$ represents a halogen atom, an optionally substituted $C_{1-6}$ alkylsulfonyloxy group, or an optionally substituted arylsulfonyloxy group.

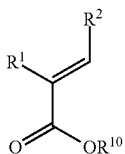
[3]

In Formula [3], $R^1$ and $R^2$ each independently represent a hydrogen atom, a halogen atom, a cyano group, an optionally substituted $C_{1-6}$ alkyl group, an optionally substituted $C_{2-6}$ alkenyl group, an optionally substituted $C_{2-6}$ alkynyl group, or a monovalent group represented by —$OR^9$, —$SR^9$, —$N(R^9)_2$, —$S(=O)_nR^9$, —$C(=O)R^9$, —$C(=NR^9)R^9$, —$C(=N—OR^9)R^9$, —$S(=O)_nN(R^9)_2$, —$C(=O)N(R^9)_2$, —$C(=O)OR^9$, —$S(=O)_nOR^9$, —$C(=NR^9)N(R^9)_2$, —$C(=NR^9)OR^9$, —$NR^9S(=O)_nR^9$, —$NR^9C(=O)R^9$, —$NR^9C(=NR^9)R^9$, —$OC(=O)R^9$, —$OC(=NR^9)R^9$, —$OS(=O)_nR^9$, —$NR^9C(=O)N(R^9)_2$, —$NR^9C(=S)N(R^9)_2$, —$NR^9C(=O)OR^9$, —$OC(=O)N(R^9)_2$ or -L-Z, wherein $R^9$, L, Z and n represent the same meanings as described above.

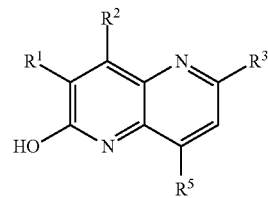
[4]

In Formula [4], $R^1$, $R^2$, $R^3$ and $R^5$ represent the same as described above.

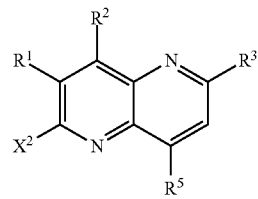
[5]

In Formula [5], $X^2$ represents a halogen atom, an optionally substituted $C_{1-6}$ alkylsulfonyloxy group, or an optionally substituted arylsulfonyloxy group; and $R^1$, $R^2$, $R^3$ and $R^5$ represent the same as described above.

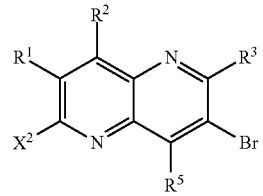
[6]

In Formula [6], $R^1$, $R^2$, $R^3$, $R^5$ and $X^2$ represent the same as described above.

Advantageous Effects of Invention

The 1,5-naphthyridine derivative or a salt thereof of the present invention has an excellent inhibitory activity with respect to at least one of the PI3K-AKT pathway or the Ras-Raf-MEK-ERK pathway, and is useful for treatments such as prophylactic treatments and therapeutic treatments of diseases such as cell proliferative diseases, allergy and autoimmune diseases, neurodegenerative diseases, cardiovascular diseases, inflammatory diseases, endocrine abnormalities, metabolic abnormalities, and infectious diseases, and in particular, diseases such as malignant tumors.

Furthermore, the PI3K inhibitor of the present invention has an excellent inhibitory activity against the PI3K-AKT pathway, and is useful for treatments such as prophylactic and therapeutic treatments of diseases such as cell proliferative diseases, allergy and autoimmune diseases, neurodegenerative diseases, cardiovascular diseases, inflammatory diseases, endocrine abnormalities, metabolic abnormalities, and infectious diseases.

In addition, according to the preparation method of the present invention, (1) a high yield is obtained, (2) the operation is simple, (3) the raw materials are inexpensive, and (4) the raw materials are readily available, and the preparation method of the present invention is useful as a method for preparing an intermediate for the preparation of a compound having an excellent inhibitory activity against the PI3K-AKT pathway.

DESCRIPTION OF EMBODIMENTS

The present invention is described in detail below.

In the present specification, the respective terms have the following definitions unless otherwise specified.

A halogen atom means a fluorine atom, a chlorine atom, a bromine atom, or an iodine atom.

A $C_{1-3}$ alkyl group means a methyl group, an ethyl group, a propyl group, or an isopropyl group.

A $C_{1-6}$ alkyl group means a linear or branched $C_{1-6}$ alkyl group such as a methyl group, an ethyl group, a propyl group, an isopropyl group, a butyl group, a sec-butyl group, an isobutyl group, a tert-butyl group, a pentyl group, an isopentyl group, or a hexyl group.

A $C_{2-6}$ alkenyl group means a linear or branched $C_{2-6}$ alkenyl group such as a vinyl group, an allyl group, a propenyl group, an isopropenyl group, a butenyl group, an isobutenyl group, a 1,3-butadienyl group, a pentenyl group, and a hexenyl group.

A $C_{2-6}$ alkynyl group means a linear or branched $C_{2-6}$ alkynyl group such as an ethynyl group, a propynyl group, a butynyl group, a pentynyl group, and a hexynyl group.

A $C_{4-8}$ crosslinked cyclic hydrocarbon ring group means a hydrocarbon ring group having two or more rings, such as a bicyclo[1,1,0]butyl group, a bicyclo[2,2,1]heptyl group, a bicyclo[3,2,1]octyl group, and a tricyclo[2,2,1,0]heptyl group.

A $C_{5-8}$ crosslinked cyclic hydrocarbon ring group means a hydrocarbon ring group having two or more rings, such as a bicyclo[2,2,1]heptyl group, a bicyclo[3,2,1]octyl group, and a tricyclo[2,2,1,0]heptyl group.

A $C_{3-8}$ cycloalkyl group means a monocyclic $C_{3-8}$ cycloalkyl group such as a cyclopropyl group, a cyclobutyl group, a cyclopentyl group, or a cyclohexyl group, or a $C_{4-8}$ crosslinked cyclic hydrocarbon ring group.

A $C_{5-8}$ cycloalkyl group means a monocyclic $C_{5-8}$ cycloalkyl group such as a cyclopentyl group or a cyclohexyl group, or a $C_{5-8}$ crosslinked cyclic hydrocarbon ring group.

A condensed polycyclic hydrocarbon ring group means a bi- to tetracyclic hydrocarbon ring group such as a naphthyl group, an anthryl group, a phenanthryl group or a pyrenyl group, a fluorenyl group, an indenyl group, an acenaphthylenyl group, or the like.

A partially saturated and condensed polycyclic hydrocarbon ring group is a condensed polycyclic hydrocarbon ring group which is partially hydrogenated, and means an indanyl group, an acenaphthenyl group, or the like.

An aryl group means a phenyl group, a condensed polycyclic hydrocarbon ring group, or a partially saturated and condensed polycyclic hydrocarbon ring group.

An ar-$C_{1-6}$ alkyl group means an ar-$C_{1-6}$ alkyl group such as a benzyl group, a diphenylmethyl group, a trityl group, a phenethyl group, or a naphthylmethyl group.

A $C_{1-6}$ alkoxy group means a linear or branched $C_{1-6}$ alkyloxy group such as a methoxy group, an ethoxy group, a propoxy group, an isopropoxy group, a butoxy group, an isobutoxy group, a sec-butoxy group, a tert-butoxy group, a pentyloxy group, or a hexyloxy group.

A $C_{1-6}$ alkoxy-$C_{1-6}$ alkyl group means a $C_{1-6}$ alkyloxy-$C_{1-6}$ alkyl group such as a methoxymethyl group or a 1-ethoxyethyl group.

A $C_{2-6}$ alkanoyl group means a linear or branched $C_{2-6}$ alkanoyl group such as an acetyl group, a propionyl group, a valeryl group, an isovaleryl group, or a pivaloyl group.

An aroyl group means a benzoyl group or a naphthoyl group.

The heterocyclic carbonyl group means a nicotinoyl, a thenoyl group, a pyrrolidinocarbonyl group or a furoyl group.

An (α-substituted)aminoacetyl group means an (α-substituted)aminoacetyl group of which N-terminal may be protected, and which is derived from an amino acid (examples thereof including an amino acid such as glycine, alanine, valine, leucine, isoleucine, serine, threonine, cysteine, methionine, asparatic acid, glutamic acid, asparagine, glutamine, arginine, lysine, histidine, hydroxylysine, phenylalanine, tyrosine, tryptophane, proline or hydroxyproline).

An acyl group means a formyl group, a succinyl group, a glutaryl group, a maleoyl group, a phthaloyl group, a $C_{2-6}$ alkanoyl group, an aroyl group, a heterocyclic carbonyl group, or an (α-substituted)aminoacetyl group.

A $C_{1-6}$ alkoxycarbonyl group means a linear or branched $C_{1-6}$ alkyloxycarbonyl group such as a methoxycarbonyl group, an ethoxycarbonyl group, an isopropoxycarbonyl group, a tert-butoxycarbonyl group, or a 1,1-dimethylpropoxycarbonyl group.

An aryloxycarbonyl group means a phenyloxycarbonyl group or a naphthyloxycarbonyl group.

An ar-$C_{1-6}$ alkoxycarbonyl group means an ar-$C_{1-6}$ alkyloxycarbonyl group such as a benzyloxycarbonyl group or a phenethyloxycarbonyl group.

A $C_{1-6}$ alkylsulfonyl group means a $C_{1-6}$ alkylsulfonyl group such as a methylsulfonyl group or an ethylsulfonyl group.

An arylsulfonyl group means a benzenesulfonyl group, a p-toluenesulfonyl group, or a naphthalenesulfonyl group.

A $C_{1-6}$ alkylsulfonyloxy group means a $C_{1-6}$ alkylsulfonyloxy group such as a methylsulfonyloxy group or an ethylsulfonyloxy group.

An arylsulfonyloxy group means a benzenesulfonyloxy group, a p-toluenesulfonyloxy group, or a naphthalenesulfonyl group.

A $C_{1-6}$ alkylamino group means a linear or branched $C_{1-6}$ alkylamino group such as a methylamino group, an ethylamino group, a propylamino group, an isopropylamino group, a butylamino group, a sec-butylamino group, a tert-butylamino group, a pentylamino group, or a hexylamino group.

A di($C_{1-6}$ alkyl)amino group means a linear or branched di($C_{1-6}$ alkyl) amino group such as a dimethylamino group, a diethylamino group, a dipropylamino group, a diisopropylamino group, a dibutylamino group, a di(tert-butyl)amino group, a dipentylamino group, a dihexylamino group, an (ethyl)(methyl)amino group, or a (methyl)(propyl)amino group.

A $C_{1-6}$ alkylamino $C_{1-6}$ alkyl group means a $C_{1-6}$ alkyl group substituted with a $C_{1-6}$ alkylamino group.

A di($C_{1-6}$ alkyl)amino $C_{1-6}$ alkyl group means a $C_{1-6}$ alkyl group substituted with a di($C_{1-6}$ alkyl)amino group.

A non-aromatic heterocyclic group means a heterocyclic group in which a ring containing at least one hetero atom (for example, an oxygen atom, a nitrogen atom, or a sulfur atom) is non-aromatic, and may be condensed with another aromatic ring or aliphatic ring. Specifically, it means a monocyclic nitrogen-containing non-aromatic heterocyclic group such as azetidinyl, pyrrolidinyl, pyrrolinyl, piperidyl, tetrahydropyridyl, homopiperidinyl, octahydroazocinyl, imidazolidinyl, imidazolinyl, pyrazolidinyl, pyrazolinyl, piperazinyl, homopiperazinyl or 2-piperadinonyl; a monocyclic oxygen-containing non-aromatic heterocyclic group such as tetrahydrofuranyl, tetrahydropyranyl, or pyranyl; a monocyclic nitrogen-and-oxygen-containing non-aromatic heterocyclic group containing only a nitrogen atom and an oxygen atom as a heteroatom as a component of a ring, such as a morpholinyl group; a monocyclic nitrogen-and-sulfur-containing non-aromatic heterocyclic group such as a thiomorpholinyl group; a bicyclic oxygen-containing non-aromatic heterocyclic group such as indolinyl, isoindolinyl, tetrahydroquinolinyl, tetrahydroisoquinolinyl, 2,3-dihydrobenzofuranyl, chromanyl, chromenyl, isochromanyl, 1,3-benzodioxolyl, 1,3-benzodioxanyl, or 1,4-benzodioxanyl; a bicyclic sulfur-containing non-aromatic heterocyclic group such as 2,3-dihydrobenzothienyl; a bicyclic nitrogen-and-oxygen-containing non-aromatic heterocyclic group such as benzomorpholinyl, dihydropyranopyridyl, dihydrodioxynopyridyl, or dihydropyridoxadinyl; or a heterocyclic spiro ring group such as 2-azaspiro[3,3]octyl, 2-oxaspiro[3,3]octyl, 6-aza-2-oxaspiro[3,3]octyl, 1-azaspiro[4,5]decyl, or 1-oxaspiro[4,5]decyl.

A heteroaryl group means a heterocyclic group in which a ring containing at least one hetero atom (for example, an oxygen atom, a nitrogen atom, or a sulfur atom) is aromatic, and may be condensed with another aromatic ring or aliphatic ring. Specifically, the heteroaryl group means a monocyclic nitrogen-containing heterocyclic group such as pyrrolyl, pyridyl, imidazolyl, pyrazolyl, pyradinyl, pyridazinyl, pyrimidinyl, triazolyl or tetrazolyl; a monocyclic oxygen-containing heteroaryl group such as a furanyl group; a monocyclic sulfur-containing heteroaryl group such as thienyl; a monocyclic nitrogen-and-oxygen-containing heteroaryl group such as oxazolyl, isoxazolyl, or oxadiazolyl; a monocyclic nitrogen-and-sulfur-containing heteroaryl group such as thiazolyl, isothiazolyl, or thiadiazolyl; a bicyclic nitrogen-containing heteroaryl group such as indolyl, isoindolyl, benzimidazolyl, indazolyl, benzotriazolyl, tetrahydroquinolyl, quinolyl, tetrahydroisoquinolyl, isoquinolyl, quinolidinyl, cinnolinyl, phthalazinyl, quinazolinyl, quinoxalinyl, naphthyridinyl, pyrrolopyridyl, imidazopyridyl, pyrazolopyridyl, pyridopyrazyl, purinyl, or pteridinyl; a bicyclic oxygen-containing heteroaryl group such as benzofuranyl or isobenzofuranyl; a bicyclic sulfur-containing heteroaryl group such as benzothienyl; a bicyclic nitrogen-containing•oxygen heteroaryl group such as benzoxazolyl, benzoisoxazolyl or benzoxadiazolyl; or a bicyclic nitrogen-and-sulfur-containing heteroaryl group such as a benzothiazolyl group, a benzoisothiazolyl group, a benzothiadiazolyl group, or a thiazolopyridyl group.

A non-aromatic heterocyclic $C_{1-6}$ alkyl group means a $C_{1-6}$ alkyl group substituted with a non-aromatic heterocyclic group.

A silyl group means a trimethylsilyl group, a triethylsilyl group, or a tributylsilyl group.

A $C_{1-6}$ alkylene group means a linear or branched $C_{1-6}$ alkylene group such as a methylene group, an ethylene group, a propylene group, a butylene group, or a hexylene group.

A $C_{2-6}$ alkenylene group means a linear or branched $C_{2-6}$ alkenylene group such as a vinylene group, a propenylene group, a butenylene group, or a pentenylene group.

A $C_{2-6}$ alkynylene group means a linear or branched $C_{2-6}$ alkynylene group such as an ethynylene group, a propynylene group, a butynylene group, or a pentenylene group.

A divalent linking group containing a hydrogen atom and at least one selected from the group consisting of a carbon atom, a nitrogen atom, an oxygen atom, and a sulfur atom means a divalent group containing one atom as an atom other than a hydrogen atom, such as —NH—, —O— or —S—; a divalent group containing two atoms as an atom other than a hydrogen atom, such as —C(O)— or —SO—; a divalent group containing three atoms as an atom other than a hydrogen atom, such as —NHCO—, —CONH—, or —SO$_2$—; or a divalent group containing four or more atoms as an atom other than a hydrogen atom, such as —NHSO$_2$—, —SO$_2$NH—, or —NHCONH—.

Examples of the amino protecting group include all the groups which can be used as a usual protecting group for an amino group, and examples of which include the groups described in "W. Greene et al., Protective Groups in Organic Synthesis, Fourth edition, pages 696 to 926, 2007, John Wiley & Sons, INC.", and specific examples of the amino protecting group include an ar-$C_{1-6}$ alkyl group, a $C_{1-6}$ alkoxy-$C_{1-6}$ alkyl group, an acyl group, a $C_{1-6}$ alkoxycarbonyl group, an ar-$C_{1-6}$ alkoxycarbonyl group, an aryloxycarbonyl group, a $C_{1-6}$ alkylsulfonyl group, an arylsulfonyl group, and a silyl group.

Examples of the hydroxyl protecting group include all the groups which can be used as a usual protecting group for an hydroxyl group, and examples of which include the groups described in "W. Greene et al., Protective Groups in Organic Synthesis, Fourth edition, pages 16 to 366, 2007, John Wiley & Sons, INC.", and specific examples of the hydroxyl protecting group include a $C_{1-6}$ alkyl group, a $C_{2-6}$ alkenyl group, an ar-$C_{1-6}$ alkyl group, a $C_{1-6}$ alkoxy-$C_{1-6}$ alkyl group, an acyl group, a $C_{1-6}$ alkoxycarbonyl group, an ar-$C_{1-6}$ alkoxycarbonyl group, a $C_{1-6}$ alkylsulfonyl group, an arylsulfonyl group, a silyl group, a tetrahydrofuranyl group, and a tetrahydropyranyl group.

Examples of the carboxyl protecting group include all the groups which can be used as a usual protecting group for an carboxyl group, and examples of which include the groups described in "W. Greene et al., Protective Groups in Organic Synthesis, Fourth edition, pages 533 to 646, 2007, John Wiley & Sons, INC.", and specific examples of the carboxyl protecting group include a $C_{1-6}$ alkyl group, a $C_{2-6}$ alkenyl group, an aryl group, an ar-$C_{1-6}$ alkyl group, a $C_{1-6}$ alkoxy-$C_{1-6}$ alkyl group, and a silyl group.

An aliphatic hydrocarbon means pentane, hexane, cyclohexane, or the like.

A halogenated hydrocarbon means methylene chloride, chloroform, dichloroethane, or the like.

An alcohol means methanol, ethanol, propanol, 2-propanol, butanol, 2-methyl-2-propanol, or the like.

A glycol means ethylene glycol, diethylene glycol, triethylene glycol, propylene glycol, or the like.

An ether means diethylether, diisopropylether, dioxane, tetrahydrofuran, anisole, ethylene glycol dimethylether, diethylene glycol dimethylether, diethylene glycol diethylether, or the lie.

A ketone means acetone, 2-butanone, 4-methyl-2-pentanone, or the like.

An ester means methyl acetate, ethyl acetate, propyl acetate, butyl acetate, cyclohexyl acetate, amyl acetate, or the like.

An amide means N,N-dimethylformamide, N,N-dimethylacetamide, 1-methyl-2-pyrrolidone, or the like.

A sulfoxide means dimethyl sulfoxide or the like.

A carboxylic acid means acetic acid or the like.

An aromatic hydrocarbon means benzene, toluene, xylene, or the like.

A palladium catalyst means metal palladium such as palladium-carbon or palladium black; an inorganic palladium salt such as palladium chloride; an organic palladium salt such as palladium acetate; an organic palladium complex such as tetrakis(triphenylphosphine)palladium (0), bis(tritert-butylphosphine)palladium (0), bis(triphenylphosphine) palladium (II) dichloride, 1,1'-bis(diphenylphosphino)ferrocene palladium (II) dichloride, (E)-di(μ-acetate)bis(o-(di-o-tollylphosphino)benzyl)dipalladium (II) or tris(dibenzylideneacetone)dipalladium (0); or a polymer-immobilized organic palladium complex such as polymer-supported bis(acetate)triphenylphosphine palladium (II) or polymer-supported di(acetate)dicyclohexylphenylphosphine palladium (II). These compounds may be used in combination of two or more thereof.

Examples of the ligand include trialkylphosphines such as trimethylphosphine and tri-tert-butylphosphine; tricycloalkylphosphines such as tricyclohexylphosphine; triarylphosphines such as triphenylphosphine and tritolylphosphine; trialkylphosphites such as trimethylphosphite, triethylphosphite and tributylphosphite; tricycloalkylphosphites such as tricyclohexylphosphite; triarylphosphites such as triphenylphosphite; imidazolium salts such as 1,3-bis(2,4,6-trimethylphenyl)imidazolium chloride; diketones such as acetylacetone and octafluoroacetylacetone; amines such as trimethylamine, triethylamine, tripropylamine and triisopropylamine; 1,1'-bis(diphenylphosphino)ferrocene, 2,2'-bis(diphenylphosphino)-1,1'-binaphthyl, 2-dicyclohexylphosphino 2',6'-dimethoxybiphenyl, 2-dicyclohexylphosphino 2',4',6'-triisopropylbiphenyl, 2-(di-tert-butylphosphino)-2',4',6'-triisopropylbiphenyl, 4,5'-bis(diphenylphosphino)9,9'-dimethylxantene, and 2-(di-tert-butylphosphino)biphenyl. These compounds may be used in combination of two or more thereof.

Examples of the salt of the compound of Formula [1] include a usually known salt of a basic group such as an amino group, or an acidic group such as a phenolic hydroxyl group or a carboxyl group.

Examples of the salt of the basic group include salts with a mineral acid such as hydrochloric acid, hydrogen bromide, or sulfuric acid; salts with an organic carboxylic acid such as tartaric acid, formic acid, acetic acid, citric acid, trichloroacetic acid, or trifluoroacetic acid; and salts with a sulfonic acid such as methanesulfonic acid, benzenesulfonic acid, p-toluenesulfonic acid, mesitylene sulfonic acid, and naphthalene sulfonic acid.

Examples of the salt of an acidic group include salts with an alkali metal such as sodium or potassium; salts with an alkaline earth metal such as calcium or magnesium; ammonium salts and salts with an nitrogen-containing organic base, such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine or N,N'-dibenzylethylenediamine.

Further, among the salts, examples of the preferable salt of the compound of Formula [1] include pharmacologically acceptable salts.

A $C_{1-6}$ alkyl group, a $C_{2-6}$ alkenyl group, or a $C_{2-6}$ alkynyl group of $R^1$, $R^2$, $R^3$, $R^4$ or $R^5$ may be substituted with at least one group selected from substituent group α.

A $C_{1-6}$ alkyl group, a $C_{2-6}$ alkenyl group, or a $C_{2-6}$ alkynyl group of $R^6$ may be substituted with at least one group selected from substituent group α.

A $C_{1-6}$ alkyl group, a $C_{3-8}$ cycloalkyl group, a $C_{2-6}$ alkenyl group, or a $C_{2-6}$ alkynyl group of $R^7$ or $R^8$ may be substituted with at least one group selected from substituent group α.

A $C_{1-6}$ alkyl group, a $C_{3-8}$ cycloalkyl group, a non-aromatic heterocyclic group, an aryl group, or a heteroaryl group of $R^9$ may be substituted with at least one group selected from substituent group α.

A non-aromatic heterocyclic group, an aryl group, or a heteroaryl group of $R^{9a}$ may be substituted with at least one group selected from substituent group α.

A $C_{1-6}$ alkyl group, a $C_{1-6}$ alkoxy group, a $C_{3-8}$ cycloalkyl group, a $C_{2-6}$ alkenyl group, or a $C_{2-6}$ alkynyl group which is bonded to a nitrogen atom of Q may be substituted with at least one group selected from substituent group α.

A $C_{1-6}$ alkylsulfonyloxy group or an arylsulfonyloxy group of $X^1$ may be substituted with at least one group selected from substituent group α.

A $C_{1-6}$ alkylsulfonyloxy group or an arylsulfonyloxy group of $X^2$ may be substituted with at least one group selected from substituent group α.

A $C_{3-8}$ cycloalkyl group, a non-aromatic heterocyclic group, an aryl group, or a heteroaryl group of Z may be substituted with at least one group selected from substituent group α.

A non-aromatic heterocyclic group, an aryl group, or a heteroaryl group of $Z^a$ may be substituted with at least one group selected from substituent group α.

Substituent group α: halogen atom, a cyano group, a $C_{1-6}$ alkyl group, a $C_{2-6}$ alkenyl group, a $C_{2-6}$ alkynyl group, a $C_{3-8}$ cycloalkyl group, an aryl group, a non-aromatic heterocyclic group, a heteroaryl group, a $C_{1-6}$ alkylamino $C_{1-6}$ alkyl group, a di($C_{1-6}$ alkyl)amino $C_{1-6}$ alkyl group, a non-aromatic heterocyclic $C_{1-6}$ alkyl group, an oxo group, and a monovalent substituent represented by —OR, —SR, —$NR_2$, —S(=O)$_n$R, —C(=O)R, —C(=NR)R, —C(=N—OR)R, —S(=O)$_n$$NR_2$, —C(=O)$NR_2$, —C(=O)OR, —S(=O)$_n$R, —C(=NR)$NR_2$, —C(=NR)OR, —NRS(=O)$_n$R, —NRC(=O)R, —NRC(=NR)R, —OC(=O)R, —OC(=NR)R, —OS(=O)$_n$R, —NRC(=O)$NR_2$, —NRC(=S)$NR_2$, —NRC(=O)OR and —OC(=O)$NR_2$, in which each of R independently represents a hydrogen atom, $C_{1-6}$ alkyl group, a $C_{3-8}$ cycloalkyl group, an aryl group, a non-aromatic heterocyclic group, or a heteroaryl group, and n represents 1 or 2.

Each group of substituent group a may have one or more substituents, if possible. Further, in the case where the group has a substituent, examples of the substituent include the groups selected from substituent group α.

Among the compounds of Formula [1] of the present invention, the following compounds are preferable.

A compound in which $R^1$ is a hydrogen atom, a halogen atom, a cyano group, an optionally substituted $C_{1-6}$ alkyl group, or a monovalent group represented by —$OR^9$ (in which $R^9$ has the same meanings as those described above) is preferable, and a compound in which $R^1$ is a hydrogen atom is more preferable.

A compound in which $R^2$ is a hydrogen atom, a halogen atom, a cyano group, an optionally substituted $C_{1-6}$ alkyl group, or a monovalent group represented by —$OR^9$ (in which $R^9$ has the same meanings as those described above) is preferable, and a compound in which $R^2$ is a hydrogen atom is more preferable.

A compound in which $R^3$ is a hydrogen atom, a halogen atom, a cyano group, an optionally substituted $C_{1-6}$ alkyl group, or a monovalent group represented by —$OR^9$ (in which $R^9$ has the same meanings as those described above) is preferable, and a compound in which $R^3$ is a hydrogen atom is more preferable.

A compound in which $R^1$, $R^2$ and $R^3$ are hydrogen atoms is preferable.

A compound in which $R^4$ is a hydrogen atom, a halogen atom, a cyano group, an optionally substituted $C_{1-6}$ alkyl group, an optionally substituted $C_{2-6}$ alkenyl group, an optionally substituted $C_{2-6}$ alkynyl group, or a monovalent group represented by —$OR^9$, —$N(R^9)_2$, —C(=O)$R^9$, —C(=O)N($R^9$)$_2$, —$NR^9$C(=O)$R^9$ or —Z (in which $R^9$ and Z have the same meanings as those described above) is preferable; a compound in which $R^4$ is a monovalent group represented by —NH($R^{9a}$) or —$Z^a$ (in which $R^{9a}$ represents an optionally substituted non-aromatic heterocyclic group, an optionally substituted aryl group, or an optionally substituted heteroaryl group; and $Z^a$ represents an optionally substituted non-aromatic heterocyclic group, an optionally substituted aryl group, or an optionally substituted heteroaryl group) is more preferable; a compound in which $R^4$ is an optionally substituted pyrazolyl group is still more preferable compound, and the compound in which $R^4$ is a pyrazolyl group substituted with a non-aromatic heterocyclic $C_{1-6}$ alkyl group is particularly preferable.

A compound in which $R^4$ is a pyrazolyl group substituted with a non-aromatic heterocyclic $C_{1-6}$ alkyl group has excellent PI3K inhibitory activity, excellent cell proliferation inhibitory activity, and excellent solubility.

The compound in which $R^5$ is a hydrogen atom, a halogen atom, a cyano group, an optionally substituted $C_{1-6}$ alkyl group or a monovalent group represented by —$OR^9$ (in which $R^9$ has the same meanings as those described above) is preferable; the compound in which $R^5$ is a hydrogen atom, a halogen atom, an optionally substituted $C_{1-3}$ alkyl group, or a monovalent group represented by —$OR^9$ (in which $R^9$ has the same meanings as those described above) is more preferable, and the compound in which $R^5$ is a hydrogen atom is still more preferable.

The compound in which $R^6$ is an optionally substituted $C_{1-6}$ alkyl group, an optionally substituted $C_{2-6}$ alkenyl group, an optionally substituted $C_{2-6}$ alkynyl group, or a monovalent group represented by -$L^a$-Z (in which $L^a$ represents a group represented by —$S(O)_2N(R^9)$— (in which $R^9$ has the same meanings as those described above) or —C(=O)—, or a single bond; and Z has the same meanings as those described above) is preferable; the compound in which $R^6$ is an optionally substituted $C_{1-6}$ alkyl group or a monovalent group represented by —Z (in which Z has the same meanings as those described above) is more preferable; the compound in which $R^6$ is an optionally substituted $C_{1-6}$ alkyl group or an optionally substituted $C_{3-8}$ cycloalkyl group is still more preferable; and the compound in which $R^6$ is a $C_{5-8}$ cycloalkyl group is particularly preferable.

The compound in which $R^6$ is a $C_{5-8}$ cycloalkyl group has excellent PI3K inhibitory activity and excellent ERK inhibitory activity.

It is preferable that in the compound, in a case where $R^6$ is an ethyl group, a cyclopropyl group, a tert-butyl group, a phenyl group, a benzyl group, a 2-phenylethyl group, or a 4-phenylbutyl group, $R^4$ is an optionally substituted non-aromatic heterocyclic group, a heteroaryl group substituted with an optionally substituted di($C_{1-6}$ alkyl)amino group, or a heteroaryl group substituted with an optionally substituted non-aromatic heterocyclic $C_{1-6}$ alkyl group is preferable.

The compound in which $R^7$ is a hydrogen atom, an optionally substituted $C_{1-6}$ alkyl group, or an optionally substituted $C_{3-8}$ cycloalkyl group is preferable; and the compound in which $R^7$ is a hydrogen atom is more preferable.

The compound in which $R^8$ is a hydrogen atom, an optionally substituted $C_{1-6}$ alkyl group, or an optionally substituted $C_{3-8}$ cycloalkyl group is preferable; and the compound in which $R^8$ is a hydrogen atom is more preferable.

The compound in which $R^7$ and $R^8$ are each a hydrogen atom is preferable.

The compound in which Q is an oxygen atom or a sulfur atom is preferable; and the compound in which Q is an oxygen atom is more preferable.

Among the PI3K inhibitors containing the compound of Formula [1] of the present invention or a salt thereof, the following PI3K inhibitors are preferable.

A PI3K inhibitor containing the compound in which $R^1$ is a hydrogen atom, a halogen atom, a cyano group, an optionally substituted $C_{1-6}$ alkyl group or a monovalent group represented by —$OR^9$ (in which $R^9$ has the same meanings as those described above) or a salt thereof is preferable; and a PI3K inhibitor containing the compound in which $R^1$ is a hydrogen atom or a salt thereof is more preferable.

A PI3K inhibitor containing the compound in which $R^2$ is a hydrogen atom, a halogen atom, a cyano group, an optionally substituted $C_{1-6}$ alkyl group, or a monovalent group represented by —$OR^9$ (in which $R^9$ has the same meanings as those described above) or a salt thereof is preferable; and a PI3K inhibitor containing the compound in which $R^2$ is a hydrogen atom or a salt thereof is more preferable.

A PI3K inhibitor containing the compound in which $R^3$ is a hydrogen atom, a halogen atom, a cyano group, an optionally substituted $C_{1-6}$ alkyl group, or a monovalent group represented by —$OR^9$ (in which $R^9$ has the same meanings as those described above) or a salt thereof is preferable; and a PI3K inhibitor containing the compound in which $R^3$ is a hydrogen atom or a salt thereof is more preferable.

A PI3K inhibitor containing the compound in which $R^4$ is a hydrogen atom, a halogen atom, a cyano group, an optionally substituted $C_{1-6}$ alkyl group, an optionally substituted $C_{2-6}$ alkenyl group, an optionally substituted $C_{2-6}$ alkynyl group, or a monovalent group represented by —$OR^9$, —$N(R^9)_2$, —C(=O)$R^9$, —C(=O)N($R^9$)$_2$, —$NR^9$C(=O)$R^9$ or —Z (in which $R^9$ and Z have the same meanings as those described above) or a salt thereof is preferable; a PI3K inhibitor containing the compound in which $R^4$ is a monovalent group represented by —NH($R^{9a}$) or —$Z^a$ (in which $R^{9a}$ represents an optionally substituted non-aromatic heterocyclic group, an optionally substituted aryl group, or an optionally substituted heteroaryl group; and $Z^a$ represents an optionally substituted non-aromatic heterocyclic group, an optionally substituted aryl group, or an optionally substituted heteroaryl group) or a salt thereof is more preferable; a PI3K inhibitor containing the compound in which $R^4$ is an optionally substituted pyrazolyl group or a salt thereof is still more preferable; and a PI3K inhibitor containing the compound in which $R^4$ is a pyrazolyl group substituted with a non-aromatic heterocyclic $C_{1-6}$ alkyl group or a salt thereof is particularly preferable.

The compound in which $R^4$ is a pyrazolyl group substituted with a non-aromatic heterocyclic $C_{1-6}$ alkyl group has excellent PI3K inhibitory activity, excellent cell proliferation inhibitory activity, and excellent solubility.

A PI3K inhibitor containing the compound in which $R^5$ is a hydrogen atom, a halogen atom, a cyano group, an optionally substituted $C_{1-6}$ alkyl group, or a monovalent group represented by —$OR^9$ (in which $R^9$ has the same meanings as those described above) or a salt thereof is preferable; a PI3K inhibitor containing the compound in which $R^5$ is a hydrogen atom, a halogen atom, or an optionally substituted $C_{1-3}$ alkyl group or a salt thereof is more preferable; and a PI3K inhibitor containing the compound in which $R^5$ is a hydrogen atom or a salt thereof is still more preferable.

A PI3K inhibitor containing the compound in which $R^6$ is an optionally substituted $C_{1-6}$ alkyl group, an optionally substituted $C_{2-6}$ alkenyl group, an optionally substituted $C_{2-6}$ alkynyl group, or a monovalent group represented by -$L^a$-Z (in which $L^a$ represents a group represented by —$S(O)_2N(R^9)$— (in which $R^9$ has the same meanings as those described above) or —C(=O)—, or a single bond; and Z has the same meanings as those described above) or a salt thereof is preferable; a PI3K inhibitor containing the compound in which $R^6$ is an optionally substituted $C_{1-6}$ alkyl group or a monovalent group represented by —Z (in which Z has the same meanings as those described above) or a salt thereof is more preferable; a PI3K inhibitor containing the compound in which $R^6$ is an optionally substituted $C_{1-6}$ alkyl group, or an optionally substituted $C_{3-8}$ cycloalkyl group or a salt thereof is still more preferable; and a PI3K inhibitor containing the compound in which $R^6$ is a $C_{5-8}$ cycloalkyl group or a salt thereof is particularly preferable.

The compound in which $R^6$ is a $C_{5-8}$ cycloalkyl group has excellent PI3K inhibitory activity and excellent ERK inhibitory activity.

A PI3K inhibitor containing the compound in which $R^7$ is a hydrogen atom, an optionally substituted $C_{1-6}$ alkyl group, or an optionally substituted $C_{3-8}$ cycloalkyl group or a salt thereof is preferable; and a PI3K inhibitor containing the compound in which $R^7$ is a hydrogen atom or a salt thereof is more preferable.

A PI3K inhibitor containing the compound in which $R^8$ is a hydrogen atom, an optionally substituted $C_{1-6}$ alkyl group, or an optionally substituted $C_{3-8}$ cycloalkyl group or a salt thereof is preferable; and a PI3K inhibitor containing the compound in which $R^8$ is a hydrogen atom or a salt thereof is more preferable.

A PI3K inhibitor containing the compound in which $R^7$ and $R^8$ are each a hydrogen atom or a salt thereof is preferable.

A PI3K inhibitor containing the compound in which Q is an oxygen atom or a sulfur atom or a salt thereof is preferable; and a PI3K inhibitor containing the compound in which Q is an oxygen atom or a salt thereof is more preferable.

With respect to the method for preparing the compound of Formula [6] of the present invention, the following preparation method is preferable.

The preparation method using the compound in which $R^1$ is a hydrogen atom, a halogen atom, a cyano group, an optionally substituted $C_{1-6}$ alkyl group, or a monovalent group represented by —$OR^9$ (in which $R^9$ has the same meanings as those described above) is preferable; and the preparation method using the compound in which $R^1$ is a hydrogen atom is more preferable.

The preparation method using the compound in which $R^2$ is a hydrogen atom, a halogen atom, a cyano group, an optionally substituted $C_{1-6}$ alkyl group, or a monovalent group represented by —$OR^9$ (in which $R^9$ has the same meanings as those described above) is preferable; and the preparation method using the compound in which $R^2$ is a hydrogen atom is more preferable.

The preparation method using the compound in which $R^3$ is a hydrogen atom, a halogen atom, a cyano group, an optionally substituted $C_{1-6}$ alkyl group, or a monovalent group represented by —$OR^9$ (in which $R^9$ has the same meanings as those described above) is preferable; and the preparation method using the compound in which $R^3$ is a hydrogen atom is more preferable.

The preparation method using the compound in which $R^5$ is a hydrogen atom, a halogen atom, a cyano group, an optionally substituted $C_{1-6}$ alkyl group, or a monovalent group represented by —$OR^9$ (in which $R^9$ has the same meanings as those described above) is preferable; the preparation method using the compound in which $R^5$ is a hydrogen atom, a halogen atom, or an optionally substituted $C_{1-3}$ alkyl group is more preferable; and the preparation method using the compound in which $R^5$ is a hydrogen atom is still more preferable.

The preparation method using the compound in which $R^{10}$ is a $C_{1-6}$ alkyl group is preferable; and the preparation method using the compound in which $R^{10}$ is a $C_{1-3}$ alkyl group is more preferable.

The preparation method using the compound in which $X^2$ is a halogen atom is preferable.

When isomers (for example, tautomers, optical isomers, and geometric isomers) are present in the compound of Formula [1], the present invention encompasses these isomers as well as solvates, hydrates, and crystals various shapes.

Next, a method for preparing the compound of the present invention will be described.

The compound of the present invention can be prepared by combining well-known methods. For example, the present compound can be prepared according to the preparation methods as described below.

[Preparation Method 1]

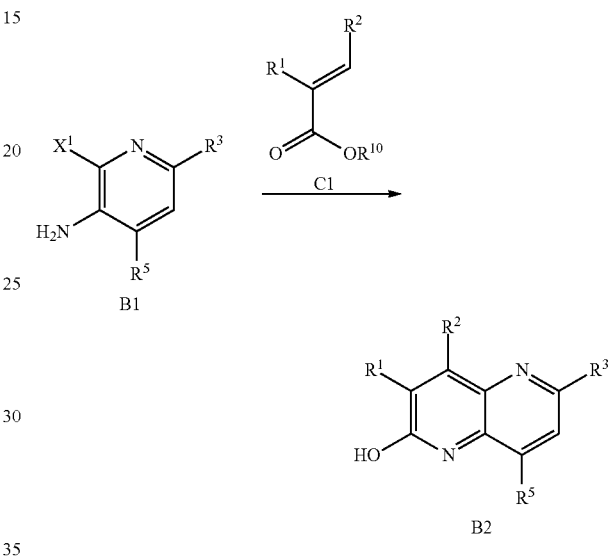

In the formulae B1, B2 and C1, $R^1$, $R^2$, $R^3$, $R^5$ and $X^1$ have the same meanings as those described above.

As compounds represented by Formula B1, for example, 2-chloro-3-aminopyridine and the like have been known.

As compounds represented by Formula C1, for example, methyl acrylate, ethyl acrylate, tert-butyl acrylate, and the like have been known.

A compound represented by Formula B2 can be prepared by reacting the compound represented by Formula B1 with the compound represented by Formula C1 in the presence or absence of a base, in the presence of a palladium catalyst, in the presence or absence of a ligand.

The solvent used in this reaction is not particularly limited as long as it does not affect the reaction adversely. Examples of such a solvent include aliphatic hydrocarbons, halogenated hydrocarbons, alcohols, glycols, ethers, ketones, esters, amides, sulfoxides, aromatic hydrocarbons, and water. These solvents may be used in mixture of two or more thereof.

Preferred examples of the solvent include esters, and cyclohexyl acetate is more preferable.

Examples of the base which may be optionally used for this reaction include inorganic bases such as sodium hydrogen carbonate, sodium carbonate, potassium carbonate, cesium carbonate, and tripotassium phosphate, and organic bases such as pyridine, 4-(dimethylamino)pyridine, triethylamine, diisopropylethylamine and sodium tert-butoxide.

Preferred examples of the base include organic bases, and triethylamine is more preferable.

The amount of the base to be used is 1- to 50-fold moles, preferably 1- to 10-fold moles, and more preferably 1- to 4-fold moles, with respect to the compound represented by Formula B1.

Preferred examples of the palladium catalyst used in the reaction include organic palladium complexes, and bis(tri-tert-butylphosphine)palladium (0) is more preferable.

The amount of the palladium catalyst to be used is 0.001- to 1-fold mole, preferably 0.002- to 0.5-fold moles, and more preferably 0.005- to 0.1-fold moles, with respect to the compound represented by Formula B1.

The amount of the ligand to be used is 0.00001- to 1-fold mole, preferably 0.0001- to 0.5-fold moles, and more preferably 0.001- to 0.5-fold moles, with respect to the compound represented by Formula B1.

The amount of the compound represented by Formula C1 to be used is 1- to 10-fold moles, preferably 1- to 5-fold moles, and more preferably 1- to 2-fold moles, with respect to the compound represented by Formula B1.

This reaction may be carried out at 120° C. to 180° C. for 1 minute to 96 hours under an inert gas (for example, nitrogen and argon) atmosphere.

[Preparation Method 2]

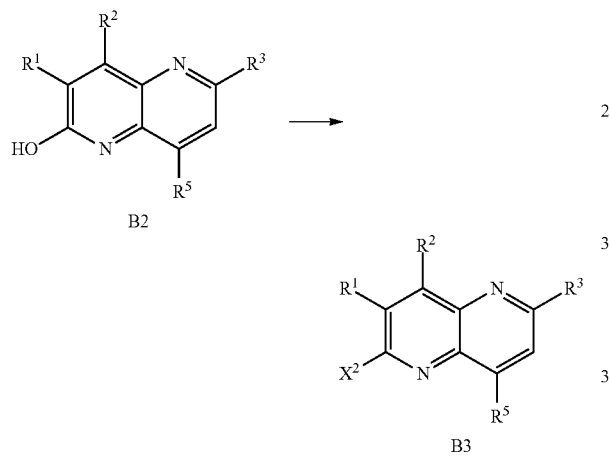

In the formulae B2 and B3, $R^1$, $R^2$, $R^3$, $R^5$ and $X^2$ have the same meanings as those described above.

The compound represented by Formula B3 can be prepared by reacting the compound represented by Formula B2 with a halogenating agent, sulfonic acid anhydride, or sulfonic acid halide.

The solvent used in this reaction is not particularly limited as long as it does not affect the reaction adversely. Examples thereof include aliphatic hydrocarbons, halogenated hydrocarbons, and aromatic hydrocarbons. These may be used in mixture of two or more thereof.

The halogenating agent or sulfonic acid anhydride may also be used as a solvent.

Examples of the halogenating agent used in this reaction include phosphorous oxychloride, thionyl chloride, and thionyl bromide.

Preferred examples of the halogenating agent include phosphorous oxychloride and thionyl chloride, and phosphorous oxychloride is more preferable.

The amount of the halogenating agent to be used is 1- to 10-fold moles, preferably 2- to 8-fold moles, and more preferably 4- to 6-fold moles, with respect to the compound represented by Formula B2.

Examples of the sulfonic acid anhydride used in this reaction include trifluoromethanesulfonic anhydride.

Examples of the sulfonic acid halide used in this reaction include methylsulfonyl chloride, ethylsulfonyl chloride, benzenesulfonyl chloride, and p-toluenesulfonyl chloride.

In the case of using sulfonic acid halide, it is preferable to carry out the reaction in the presence of a base.

Examples of the base used in this reaction include organic bases such as pyridine, 4-(dimethylamino)pyridine, triethylamine, and diisopropylethylamine.

The amount of the base to be used is 1- to 50-fold moles, preferably 1- to 10-fold moles, and more preferably 1- to 4-fold moles, with respect to the compound represented by Formula B2.

For this reaction, it is preferable to use a halogenating agent as a solvent, and it is more preferable to use phosphorous oxychloride as a solvent.

This reaction may be carried out at 80° C. to the boiling point of a solvent, and preferably the boiling point of a solvent, for 1 minute to 24 hours.

[Preparation Method 3]

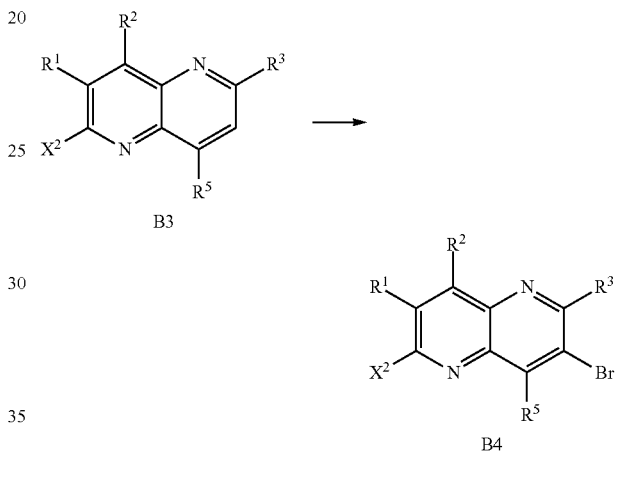

In Formulae B3 and B4, $R^1$, $R^2$, $R^3$, $R^5$ and $X^2$ have the same meanings as those described above.

The compound represented by Formula B4 can be prepared by reacting the compound represented by Formula B3 with a brominating agent in the presence or absence of a base.

The solvent used in this reaction is not particularly limited as long as it does not affect the reaction adversely. Examples thereof include aliphatic hydrocarbons, halogenated hydrocarbons, carboxylic acids, and water. These may be used in mixture or two or more thereof.

Preferred examples of the solvent include carboxylic acids, and acetic acid is more preferable.

Examples of the brominating agent used in this reaction include bromine and thionyl bromide, and bromine is more preferable.

The amount of the brominating agent used in this reaction is 1- to 2-fold moles, and preferably 1.0- to 1.2-fold moles, with respect to the compound represented by Formula B3.

Examples of the base which may optionally be used in this reaction include sodium acetate and potassium acetate, and sodium acetate is more preferable.

The amount of the base to be used is 1- to 5-fold moles, preferably 1- to 2-fold moles, and more preferably 1.0- to 1.2-fold moles, with respect to the compound represented by Formula B3.

This reaction may be carried out at 60° C. to 120° C., and preferably 80° C. to 100° C., for 1 minute to 24 hours.

[Preparation Method 4]

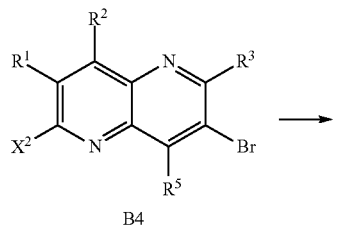

B4

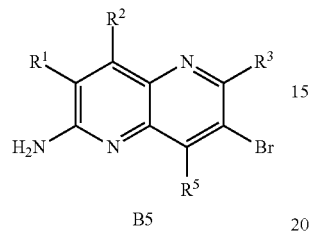

B5

[Preparation Method 5]

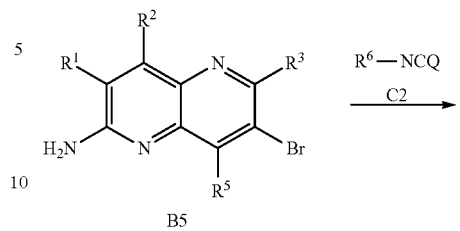

B5

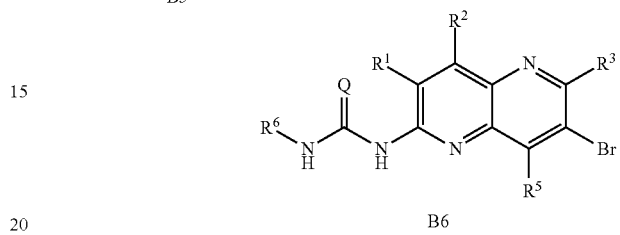

B6

In Formulae B4 and B5, $R^1$, $R^2$, $R^3$, $R^5$ and $X^2$ have the same meanings as those described above.

The compound represented by Formula B5 can be prepared by reacting the compound represented by Formula B4 with ammonia.

The solvent used in this reaction is not particularly limited as long as it does not affect the reaction adversely. Examples thereof include aliphatic hydrocarbons, halogenated hydrocarbons, alcohols, glycols, ethers, amides, sulfoxides, aromatic hydrocarbons, and water. These may be used in mixture of two or more thereof.

Preferred examples of the solvent include a mixed solvent with ethers and water, and a mixed solvent with 1,4-dioxane and water is more preferable.

The use amount of ammonia used in this reaction is 1- to 100-fold moles, and preferably 1- to 50-fold moles, with respect to the compound represented by Formula B4.

This reaction is preferably carried out in a closed environment such as an autoclave or a microwave reaction device.

This reaction may be carried out at 50° C. to 200° C., and preferably 100° C. to 150° C., for 10 minutes to 24 hours.

In Formulae B5, B6 and C2, $R^1$, $R^2$, $R^3$, $R^5$, $R^6$ and Q have the same meanings as those described above.

As the compounds represented by Formula C2, for example, cyclopentyl isocyanate, cyclohexyl isocyanate, and cyclopentyl isothiocyanate have been known.

A compound represented by Formula B6 can be prepared by reacting the compound represented by Formula B5 with the compound represented by Formula C2.

The solvent used in this reaction is not particularly limited as long as it does not affect the reaction adversely. Examples thereof include aliphatic hydrocarbons, halogenated hydrocarbons, ethers, ketones, esters, amides, sulfoxides, and aromatic hydrocarbons. These may be used in mixture of two or more thereof.

Preferred examples of the solvent include ethers, and 1,4-dioxane is more preferable.

The use amount of the compound represented by Formula C2 used in this reaction is 1- to 10-fold moles, and preferably 1- to 5-fold moles, with respect to the compound represented by Formula B5.

This reaction may be carried out at 10° C. to 200° C., and preferably 100° C. to 140° C., for 10 minutes to 12 hours.

[Preparation Method 6]

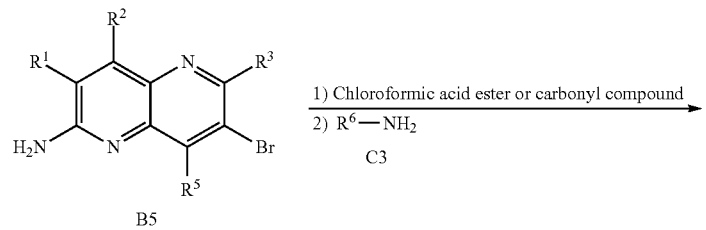

B5

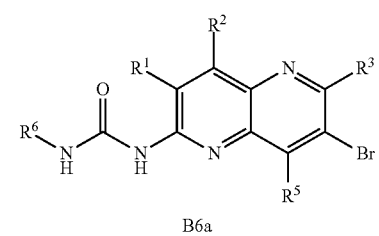

B6a

In Formulae B5, B6a and C3, $R^1$, $R^2$, $R^3$, $R^5$ and $R^6$ have the same meanings as those described above.

As the compound represented by Formula C3, for example, 2-aminoethanol, 3-methoxypropylamine, and N,N-diethylethylenediamine have been known.

The compound represented by Formula B6a can be prepared by reacting the compound represented by Formula B5 with a chloroformic acid ester or a carbonyl compound in the presence of a base, and then with the compound represented by Formula C3.

The solvent used in this reaction is not particularly limited as long as it does not affect the reaction adversely. Examples thereof include aliphatic hydrocarbons, halogenated hydrocarbons, ethers, ketones, esters, sulfoxides, and aromatic hydrocarbons. These may be used in mixture of two or more thereof.

Examples of the base used in this reaction include organic bases such as pyridine, 4-(dimethylamino)pyridine, triethylamine, and diisopropylethylamine.

Preferred examples of the base include pyridine, 4-(dimethylamino)pyridine, and triethylamine.

In the case of using pyridine, pyridine may be used as a solvent.

The amount of the base to be used is 1-fold mole or more with respect to the compound represented by Formula B5.

Examples of the chloroformic acid ester used in this reaction include ethyl chloroformate, phenyl chloroformate, and (p-nitro phenyl)ethyl chloroformate.

Preferred examples of the chloroformic acid ester include phenyl chloroformate.

The amount of the chloroformic acid ester to be used is 1- to 10-fold moles, preferably 1- to 5-fold moles, and more preferably 1- to 2-fold moles, with respect to the compound represented by Formula B5.

Examples of the carbonyl compound used in this reaction include diphosgen, diphenyl carbonate, and carbonyldiimidazole.

Preferred examples of the carbonyl compound include carbonyldiimidazole.

The amount of the carbonyl compound to be used is 1- to 10-fold moles, preferably 1-to 5-fold moles, and more preferably 1- to 2-fold moles, with respect to the compound represented by Formula B5.

The reaction for the compound represented by Formula B5 with the chloroformic acid ester or the carbonyl compound may be carried out at 0° C. to 50° C., and preferably 10° C. to 30° C., for 10 minutes to 24 hours.

A compound represented by Formula B6a can be prepared by reacting the compound represented by Formula B5 with the chloroformic acid ester or the carbonyl compound, and then with the compound represented by Formula C3.

The amount of the compound represented by Formula C3 to be used is 1- to 10-fold moles, preferably 1- to 5-fold moles, and more preferably 1- to 2-fold moles, with respect to the compound represented by Formula B5.

The reaction for the compound represented by Formula C3 may be carried out at 0° C. to 100° C. for 10 minutes to 24 hours.

[Preparation Method 7]

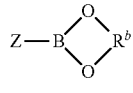

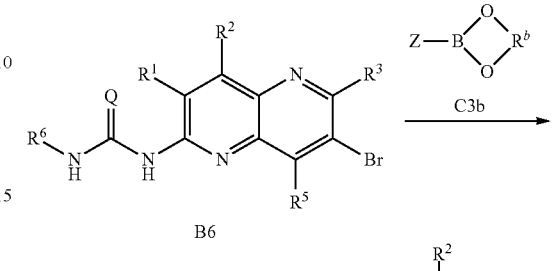

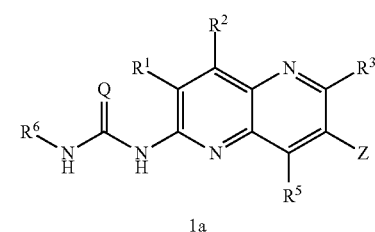

In Formulae B6, C3a, C3b and 1a, $R^a$ represents a hydrogen atom or an optionally substituted $C_{1-6}$ alkyl group; $R^b$ represents an optionally substituted $C_{1-6}$ alkylene group; and $R^1$, $R^2$, $R^3$, $R^5$, $R^6$, and Q and Z have the same meanings as those described above.

As the compounds represented by Formula C3a, for example, pyridine-3-boronic acid, 3-(methanesulfonamide) phenylboronic acid, thiophene-2-boronic acid, benzofuran-2-boronic acid and 3-methoxyphenylboronic acid, and the like have been known.

As the compounds represented by Formula C3b, for example, 3-(4,4,5,5-tetramethyl-1,3,2-dioxaborolan-2-yl)furan, and the like have been known.

The compound represented by Formula C3a and the compound represented by Formula C3b can be prepared, for example, from a halogeno form in accordance with the method described in Japanese Patent Application Laid-Open (JP-A) No. 2003-206290, The Journal of Organic Chemistry, 1995, Vol. 60, pp. 7508 to 7510, and the like.

The compound represented by Formula 1a can be prepared by reacting the compound represented by Formula B6 with the compound represented by Formula C3a or the compound represented by Formula C3b in the presence or absence of a ligand, in the presence of a palladium catalyst, and in the presence or absence of a base.

The solvent used in this reaction is not particularly limited as long as it does not affect the reaction adversely. Examples thereof include aliphatic hydrocarbons, halogenated hydrocarbons, ethers, ketones, esters, sulfoxides, aromatic hydrocarbons, acetonitrile, and water. These may be used as a mixture thereof.

Examples of the base used which may be optionally used for this reaction include inorganic bases such as sodium hydrogen carbonate, sodium carbonate, potassium carbonate, cesium carbonate, and tripotassium phosphate, and organic bases such as 1,8-diazabicyclo[5.4.0]-7-undecene, triethylamine, and N,N-diisopropylethylamine.

The amount of the base to be used is 1- to 50-fold moles, preferably 1- to 10-fold moles, and more preferably 2- to 5-fold moles, with respect to the compound represented by Formula B6.

The amount of the palladium catalyst used in this reaction is 0.00001- to 1-fold mole, and preferably 0.001- to 0.1-fold moles, with respect to the compound represented by Formula B6.

The amount of the ligand, which may be optionally used in this reaction, to be used is 0.00001- to 1-fold mole, and preferably 0.001- to 0.1-fold moles, with respect to the compound represented by Formula B6.

The amount of the compound represented by Formula C3a or compound represented by Formula C3b to be used is 1- to 50-fold moles, and preferably 1- to 2-fold moles, with respect to the compound represented by Formula B6.

This reaction may be preferably carried out under an inert gas (for example, nitrogen or argon) atmosphere at 40° C. to 180° C. for 10 minutes to 24 hours.

This reaction can be carried out using a tin reagent instead of the compound represented by Formula C3a or the compound represented by Formula C3b.

[Preparation Method 8]

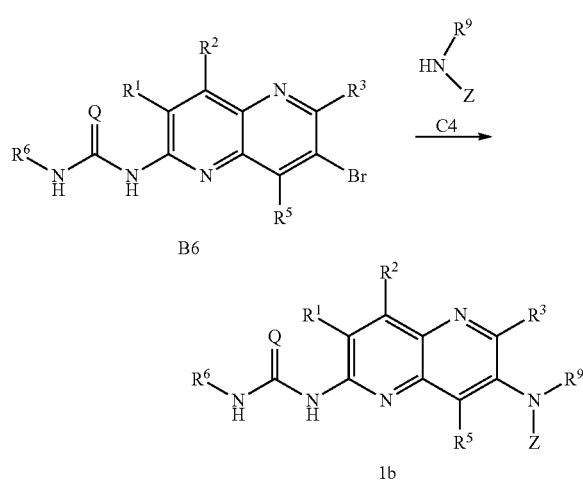

In Formulae B6, C4 and 1b, $R^1$, $R^2$, $R^3$, $R^5$, $R^6$, $R^9$, Q and Z have the same meanings as those described above).

As the compounds represented by Formula C4, for example, morpholine, 1-methylpiperazine, 3,5-dimethoxyaniline, and 4-methoxyaniline have been known.

The compound represented by Formula 1b can be prepared by reacting the compound represented by Formula B6 with the compound represented by Formula C4 in the presence or absence of a base and in the presence of a palladium catalyst.

The solvent used in this reaction is not particularly limited as long as it does not affect the reaction adversely. Examples thereof include aliphatic hydrocarbons, halogenated hydrocarbons, ethers, ketones, esters, sulfoxides, aromatic hydrocarbons, acetonitrile, and water. These may be used in mixture of two or more thereof.

Examples of the base which may optionally be used for this reaction include inorganic bases such as sodium hydrogen carbonate, sodium carbonate, potassium carbonate, cesium carbonate, and tripotassium phosphate, and organic bases such as 1,8-diazabicyclo[5.4.0]-7-undecene, triethylamine, and N,N-diisopropylethylamine.

The amount of the base to be used is 1- to 50-fold moles, preferably 1- to 10-fold moles, and more preferably 2- to 5-fold moles, with respect to the compound represented by Formula B6.

The amount of the palladium catalyst to be used in this reaction is 0.00001- to 1-fold mole, and preferably 0.001- to 0.1-fold moles, with respect to the compound represented by Formula B6.

The amount of the ligand, which may be optionally used in this reaction, is 0.00001-to 1-fold mole, and preferably 0.001- to 0.1-fold moles, with respect to the compound represented by Formula B6.

The amount of the compound represented by Formula C4 to be used is 1- to 50-fold moles, and preferably 1- to 2-fold moles, with respect to the compound represented by Formula B6.

This reaction may be carried out at 40° C. to 180° C. for 10 minutes to 24 hours under an inert gas (for example, nitrogen and argon) atmosphere.

[Preparation Method 9]

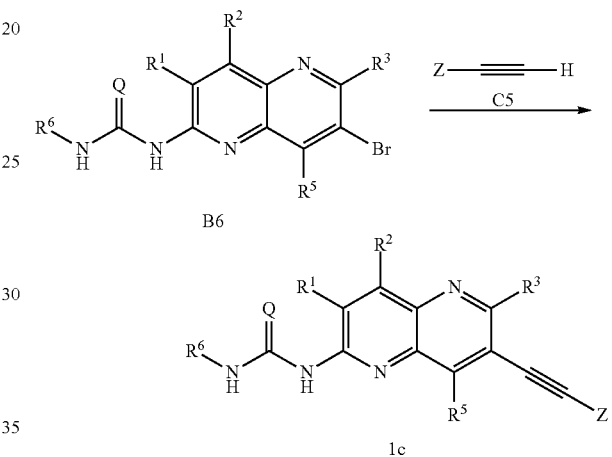

In formulae B6, C5 and 1c, $R^1$, $R^2$, $R^3$, $R^5$, $R^6$, Q and Z have the same meanings as those described above).

As the compounds represented by Formula C5, for example, trimethylsilylacetylene and methyl propionate have been known.

The compound represented by Formula 1c can be prepared by reacting the compound represented by Formula B6 with the compound represented by Formula C5 in the presence or absence of a base and in the presence of a palladium catalyst.

The solvent used in this reaction is not particularly limited as long as it does not affect the reaction adversely. Examples thereof include aliphatic hydrocarbons, halogenated hydrocarbons, ethers, ketones, esters, sulfoxides, aromatic hydrocarbons, acetonitrile, and water. These may be used in mixture of two or more thereof.

Examples of the base which may optionally be used in this reaction include inorganic bases such as sodium hydrogen carbonate, sodium carbonate, potassium carbonate, cesium carbonate, and tripotassium phosphate, and organic bases such as 1,8-diazabicyclo[5.4.0]-7-undecene, triethylamine, and N,N-diisopropylethylamine.

The amount of the base to be used is 1- to 50-fold moles, preferably 1- to 10-fold moles, and more preferably 2- to 5-fold moles, with respect to the compound represented by Formula B6.

The amount of the palladium catalyst used in this reaction is 0.00001- to 1-fold mole, and preferably 0.001 to 0.1-fold moles, with respect to the compound represented by Formula B6.

The amount of the ligand, which may optionally be used in this reaction, to be used is 0.00001- to 1-fold mole, and preferably 0.001 to 0.1-fold moles, with respect to the compound represented by Formula B6.

The amount of the compound represented by Formula C5 to be used is 1- to 50-fold moles, preferably 1- to 2-fold moles, with respect to the compound represented by Formula B6.

This reaction may be preferably carried out at 40° C. to 180° C. for 10 minutes to 24 hours under an inert gas (for example, nitrogen, argon) atmosphere.

In the compounds used in the preparation method of the present invention, if isomers (for example, optical isomers, geometrical isomers, and tautomers) are present, it is possible to use also these isomers. Further, if any of the solvates, hydrates, and crystals in various shapes are present, these solvates, hydrates, and various forms of crystals may also be used.

In the compounds used in the preparation method of the present invention, compounds having an amino group, a hydroxyl group, a carboxyl group, or the like can have the group protected with an ordinary protecting group in advance, and then have the protecting group removed by a per se known method.

The compound prepared by the preparation method of the present invention can be induced to another compound by subjecting them to a per se known reaction such as condensation, addition, oxidation, reduction, dislocation, substitution, halogenation, dehydration, and hydrolysis, or by any combination of these reactions, as appropriate.

If the compound or a salt thereof of the present invention is used as a medicament, formulation additives such as an excipient, a carrier, and a diluent usually used in the formulation may be suitably mixed. According to a common method, the compound or a salt thereof of the present invention may be administered orally or parenterally in the form of tablets, capsules, powders, syrups, granules, pills, suspensions, emulsions, liquids, powder preparations, suppositories, ophthalmic preparations, nasal preparations, ear preparations, patches, ointment, or injections. A method for administration, a dose of administration, and a frequency of administration can be appropriately chosen according to the age, body weight, and symptoms of a patient. Usually, for adults, 0.01 to 1000 mg/kg of the compound or a salt thereof of the present invention can be administered orally or parenterally (for example, administration by injection or drip infusion, or administration to a rectal site) once or in several divided doses per day.

The 1,5-naphthyridine derivative or a salt thereof of the present invention may be used for treatments such as prophylactic and therapeutic treatments of diseases related to PI3K and ERK.

Examples of the diseases related to PI3K and ERK include cell proliferative diseases, allergy and autoimmune diseases, neurodegenerative diseases, cardiovascular diseases, inflammatory diseases, endocrine abnormalities, metabolic abnormalities, and infectious diseases, and malignant tumors with increase in a PI3K-AKT pathway and a Ras-Raf-MEK-ERK pathway are preferred. Specifically, the 1,5-naphthyridine derivative or a salt thereof of the present invention can be used for treatments such as prophylactic and therapeutic treatments of malignant tumors that are resistant to a PI3K-AKT pathway inhibitor or a Ras-Raf-MEK-ERK pathway inhibitor.

The PI3K inhibitor of the present invention can be used for treatments such as prophylactic and therapeutic treatments of diseases related to PI3K.

Examples of the diseases related to PI3K include cell proliferative diseases, allergy and autoimmune diseases, neurodegenerative diseases, cardiovascular diseases, inflammatory diseases, endocrine abnormalities, metabolic abnormalities, and infectious diseases.

EXAMPLES

Hereinafter, the present invention is described with respect to Examples in detail, but the present invention is not limited to these Examples. Further, "%" is based on mass unless particularly specified.

For the synthesis of the following compounds, purification is carried out using an automatic purification apparatus ISOL-ERA (manufactured by Biotage) unless otherwise specified.

As the silica gel column, a SNAP KP-Sil Cartridge (manufactured by Biotage) and a SNAP KP-NH Cartridge (manufactured by Biotage, the "NH silica" in Examples indicates this silica gel column) were used.

For reverse phase preparative separation HPLC, one system of a Waters 2998 Photodiode Array (PDA) Detector (manufactured by Waters) and a Waters 600 Controller (manufactured by Waters), and a Waters 2767 Sample Manager (manufactured by Waters), and a YMC-Actus ProC 18, 30×50 mm column (manufactured by YMC) were used.

As a microwave synthesis apparatus, an INITIATOR SIXTY (manufactured by BIOTAGE) was used.

The MS spectrum was measured using an ACQUITY SQD LC/MS System (manufactured by Waters).

For the NMR spectrum, tetramethylsilane was used as an inner standard, and measured using a Bruker AV300 (manufactured by Bruker), and all the δ values were expressed in ppm.

The meanings of abbreviations in the NMR measurement are shown below.
s: singlet
d: doublet
dd: double doublet
ddd: double double doublet
t: triplet
dt: double triplet
q: quartet
m: multiplet
bs: broad singlet
bd: broad doublet
bt: broad triplet
DMSO-$d_6$: deuterated dimethylsulfoxide
MeOH-$d_4$: deuterated methanol Example 1

Preparation of Exemplary Compound 0001

(Synthesis of Compound 0001-1)

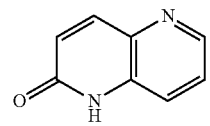

0001-1

Triethylamine (13 mL), butyl acrylate (10 mL), and bis(tritert-butylphosphine)palladium (0) (350 mg) were added to a solution of 2-chloro-3-aminopyridine (6.00 g) in cyclohexyl acetate (60 mL), and the mixture was stirred at 150° C. for 40 hours under a nitrogen atmosphere. The resulting mixture was left to be cooled at room temperature. When the mixture was cooled to 70° C., water (30 mL) was added thereto, and the resulting mixture was left to be cooled at room temperature under stirring. After subjecting the resulting mixture to sonication for 30 minutes, the mixture was filtered and the residue was washed with water (3 mL). The obtained residue was suspended in ethyl acetate (3 mL)/2-propanol (4 mL) and then subjected to sonication. Further, the suspension was filtered, and the residue was washed with ethyl acetate (3 mL) and hexane, and thereafter is dried to obtain a compound 0001-1 (2.51 g) as a pale yellow solid.

$^1$H-NMR (DMSO-d$_6$) δ: 11.90 (1H, s), 8.47 (1H, dd), 7.93 (1H, d), 7.68 (1H, ddd), 7.51 (1H, dd), 6.75 (1H, dd).

MS m/z (M+H): 147.

(Synthesis of Compound 0001-2)

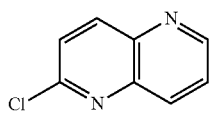

0001-2

To the compound 0001-1 (2.76 g), phosphorous oxychloride (8.3 mL) was added, and the mixture was stirred at 100° C. for 5 hours. The reaction solution which had been cooled to room temperature was added dropwise to a mixture of ethyl acetate (30 mL), water (30 mL), and sodium carbonate (9.57 g) in an ice-cooling bath over one hour. Further, water (10 mL) was added thereto, and sodium carbonate was added thereto until the pH reached 8.3. After stirring at room temperature for 10 minutes, the resulting mixture was subjected to liquid separation by the addition of ethyl acetate (270 mL) and water (200 mL). Further, the aqueous layer was extracted with ethyl acetate (200 mL) twice. The collected organic layer was dried over sodium sulfate and the solvent was evaporated under reduced pressure to obtain a compound 0001-2 (2.86 g) was obtained as a pale yellow solid.

$^1$H-NMR (DMSO-d$_6$) δ: 9.05 (1H, dd), 8.50 (1H, dd, J=8.9), 8.41 (1H, ddd), 7.87, (1H, d), 7.86 (1H, m).

(Synthesis of Compound 0001-3)

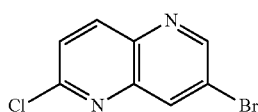

0001-3

A solution of the compound 0001-2 (2.88 g) and sodium acetate (2.89 g) in acetic acid (15 mL) was stirred at 85° C. for 5 minutes. A solution of bromine (0.99 mL) in acetic acid (2.5 mL) was dropwise added thereto. Further acetic acid (2 mL) was added dropwise thereto, and the mixture was stirred at 85° C. for 3 hours. To a 6 M aqueous sodium hydroxide solution (60 mL) under stirring with ice-cooling, the reaction solution which had been cooled to room temperature was added dropwise. The precipitated solid was separated by filtration, and the solid was then suspended in methanol (5 mL), and thereafter subjected to sonication. Thereafter, the suspension was filtered, and then the resulting solid was washed with methanol (3 mL). The obtained solid was suspended in a 75 v/v % aqueous methanol solution (8 mL), subjected to sonication, and then the suspension was filtered, and the residue was then washed with a 75 v/v % aqueous methanol solution twice to obtain a compound 0001-3 (3.33 g) as a pale yellow solid.

$^1$H-NMR (DMSO-d$_6$) δ: 9.13 (1H, d), 8.77 (1H, dd), 8.53 (1H, dd), 7.91 (1H, d).

MS m/z (M+H): 245.

(Synthesis of Compound 0001-4)

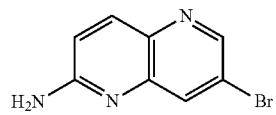

0001-4

A mixed solution of the compound 0001-3 (100 mg) in 1,4-dioxane (2 ml) and a 25% aqueous ammonia solution was stirred at 120° C. for 3 hours using a microwave reaction device. The reaction solution was cooled, and brine and ethyl acetate were added thereto. The organic layer was separated and then dried over sodium sulfate. The solvent was evaporated under reduced pressure to obtain a 0001-4 (90 mg) as a white solid.

$^1$H-NMR (DMSO-d$_6$) δ: 8.53 (1H, d), 8.02 (1H, d), 7.92 (1H, d), 7.01 (1H, d), 6.94 (1H, s).

MS m/z (M+H): 224,226.

(Synthesis of Compound 0001-5)

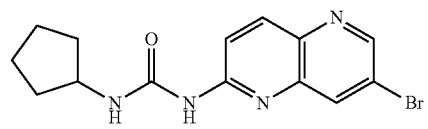

0001-5

A mixed solution of 0001-4 (90 mg) and cyclopentyl isocyanate (93 µl) in 1,4-dioxane (2 ml) was stirred at 140° C. for 1 hour using a microwave reaction device. The precipitated solid was filtered and washed with ethyl acetate to obtain a compound 0001-5 (90 mg) as a white solid.

$^1$H-NMR (DMSO-d$_6$) δ: 9.92 (1H, s), 8.97 (1H, d), 8.83 (1H, d), 8.46 (1H, d), 8.27 (1H, d), 7.62 (1H, d), 4.07 (1H, d), 2.05-1.85 (2H, m), 1.82-1.42 (6H, m).

MS m/z (M+H): 335,337.

(Synthesis of Compound 0001)

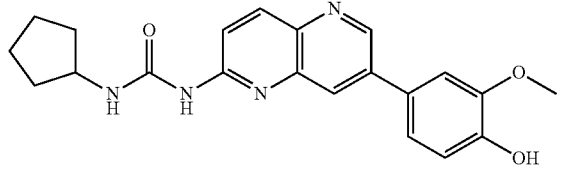

0001

To the compound 0001-5 (30 mg), 2-methoxy-4-(4,4,5,5-tetramethyl-1,3,2-dioxaborolan-2-yl)phenol (45.2 mg), bis(di-tert-butyl (4-dimethylaminophenyl)-phosphine)dichloropalladium (II) (6.3 mg), and sodium carbonate (19.0 mg) were added 1,4-dioxane (0.5 mL) and water (0.05 mL) under a nitrogen atmosphere, and the mixture was stirred at 120° C. for 1.5 hours. The reaction solution was cooled to room temperature and purified by silica gel column chromatography (chloroform-methanol, NH silica). The solvent was evaporated under reduced pressure and the obtained solid was washed with ethyl acetate to obtain a compound 0001 (19.5 mg) as a white solid.

¹H-NMR (DMSO-d₆) δ: 9.79 (1H, s), 9.37 (1H, s), 9.19 (1H, bd), 9.09 (1H, d), 8.25 (1H, d), 8.18 (1H, d), 7.55 (1H, d), 7.43 (1H, d), 7.32 (1H, dd), 6.95 (1H, d), 4.03-4.18 (1H, m), 3.91 (3H, s), 1.85-2.05 (2H, m), 1.51-1.84 (6H, m).

MS m/z (M+H): 379.

Example 2

Synthesis of Compound 0002

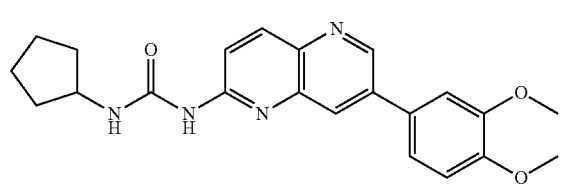

0002

The same method as in Example 1 except for using 3,4-dimethoxyphenylboronic acid instead of 2-methoxy-4-(4,4,5,5-tetramethyl-1,3,2-dioxaborolan-2-yl)phenol used for the synthesis of the compound 0001 in Example 1 was used to obtain a compound 0002 (22.1 mg) as a pale yellow solid.

¹H-NMR (DMSO-d₆) δ: 9.80 (1H, s), 9.18 (1H, d), 9.11 (1H, bd), 8.27 (1H, d), 8.22 (1H, d), 7.57 (1H, d), 7.47-7.40 (2H, m), 7.14 (1H, d), 4.18-3.99 (1H, m), 3.90 (3H, s), 3.83 (3H, s), 2.02-1.85 (2H, m), 1.85-1.48 (6H, m).

MS m/z (M+H): 393.

Example 3

Synthesis of Compound 0003

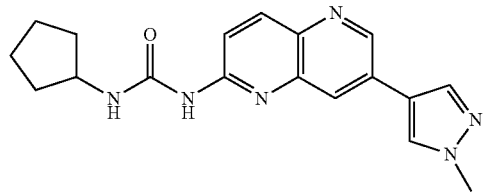

0003

The same method as in Example 1 except for using 1-methylpyrazole-4-boronic acid pinacol ester instead of 2-methoxy-4-(4,4,5,5-tetramethyl-1,3,2-dioxaborolan-2-yl)phenol used for the synthesis of the compound 0001 in Example 1 was used to obtain a compound 0003 (16.7 mg) as a white solid.

¹H-NMR (DMSO-d₆) δ: 9.77 (1H, s), 9.18 (1H, bd), 9.06 (1H, d), 8.48 (1H, s), 8.15-8.25 (2H, m), 8.13 (1H, d), 7.49 (1H, d), 3.99-4.17 (1H, m), 3.92 (3H, s), 1.88-2.05 (2H, m), 1.49-1.84 (6H, m).

MS m/z (M+H): 337.

Example 4

Synthesis of Compound 0004

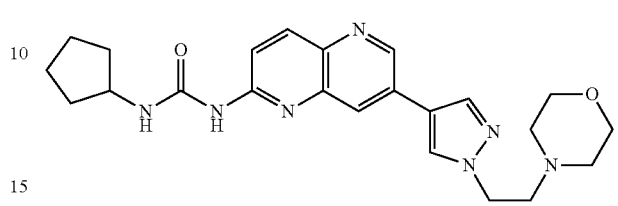

0004

The same method as in Example 1 except for using 1-(2-morpholinoethyl)-1H-pyrazole-4-boronic acid pinacol ester instead of 2-methoxy-4-(4,4,5,5-tetramethyl-1,3,2-dioxaborolan-2-yl)phenol used for the synthesis of the compound 0001 in Example 1 was used to obtain a compound 0004 (12.4 mg) as a white solid.

¹H-NMR (DMSO-d₆) δ: 9.78 (1H, s), 9.20 (1H, bd), 9.06 (1H, d), 8.52 (1H, s), 8.26-8.16 (2H, m), 8.13 (1H, d), 7.49 (1H, d), 4.30 (2H, t), 4.18-3.99 (1H, m), 3.56 (4H, t), 2.77 (2H, t), 2.44 (4H, t), 2.05-1.87 (2H, m), 1.85-1.48 (6H, m).

MS m/z (M+H): 436.

Example 5

Synthesis of Compound 0005

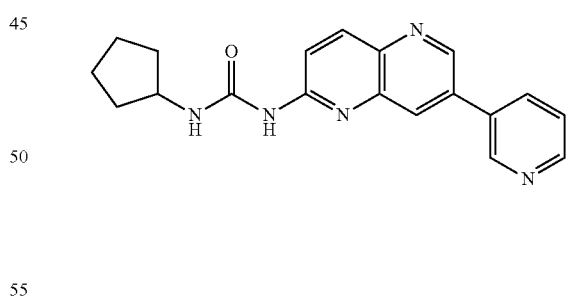

0005

The same method as in Example 1 except for using 3-pyridineboronic acid instead of 2-methoxy-4-(4,4,5,5-tetramethyl-1,3,2-dioxaborolan-2-yl)phenol used for the synthesis of the compound 0001 in Example 1 was used to obtain a compound 0005 (14.1 mg) as a white solid.

¹H-NMR (DMSO-d₆) δ: 9.87 (1H, s), 9.10-9.20 (3H, m), 8.69 (1H, dd), 8.41 (1H, d), 8.26-8.37 (2H, m), 7.51-7.67 (2H, m), 3.94-4.21 (1H, m), 1.87-2.04 (2H, m), 1.48-1.86 (6H, m).

MS m/z (M+H): 334.

Example 6

Synthesis of Compound 0006

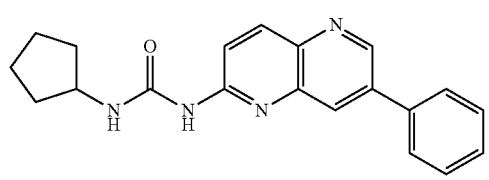

The same method as in Example 1 except for using phenylboronic acid instead of 2-methoxy-4-(4,4,5,5-tetramethyl-1,3,2-dioxaborolan-2-yl)phenol used for the synthesis of the compound 0001 in Example 1 was used to obtain a compound 0006 (20.7 mg) as a white solid.

$^1$H-NMR (DMSO-$d_6$) δ: 9.85 (1H, s), 9.20 (1H, bd), 9.10 (1H, s), 8.29 (1H, d), 8.28 (1H, s), 7.90 (2H, d), 7.37-7.68 (4H, m), 3.99-4.19 (1H, m), 1.85-2.03 (2H, m), 1.47-1.84 (6H, m).

MS m/z (M+H): 333.

Example 7

Synthesis of Compound 0007

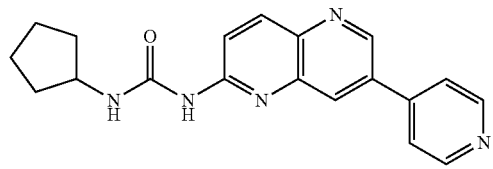

The same method as in Example 1 except for using 4-pyridineboronic acid instead of 2-methoxy-4-(4,4,5,5-tetramethyl-1,3,2-dioxaborolan-2-yl)phenol used for the synthesis of the compound 0001 in Example 1 was used to obtain a compound 0007 (21.0 mg) as a white solid.

$^1$H-NMR (DMSO-$d_6$) δ: 9.89 (1H, s), 9.19 (1H, d), 9.12 (1H, bd), 8.69-8.80 (2H, m), 8.45 (1H, d), 8.32 (1H, d), 7.90-8.02 (2H, m), 7.64 (1H, d), 3.98-4.18 (1H, m), 1.84-2.02 (2H, m), 1.45-1.83 (6H, m).

MS m/z (M+H): 334.

Example 8

Synthesis of Compound 0008

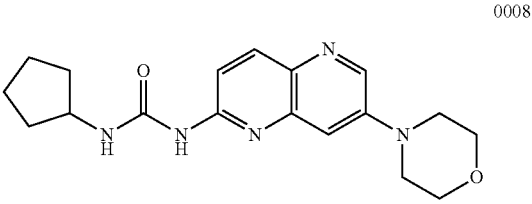 [SMILES: O=C(Nc1ccc2ncc(N3CCOCC3)cc2n1)NC1CCCC1]

1,4-dioxane (2.0 mL) was added to the compound 0001-5 (100 mg), morpholine (104 mg), tris(dibenzylideneacetone)dipalladium (0) (17.1 mg), 2-dicyclohexylphosphino-2',4',6'-triisopropylbiphenyl (28.4 mg) and sodium tert-butoxide (57.3 mg) under a nitrogen atmosphere, and the mixture was stirred at 100° C. for 1 hour. The reaction solution was returned to room temperature and purified by silica gel column chromatography (chloroform-methanol, NH silica). The solvent was evaporated under reduced pressure and the obtained solid was washed with ethyl acetate to obtain a compound 0008 (60.8 mg) as a yellow solid.

$^1$H-NMR (DMSO-$d_6$) δ: 9.64 (1H, s), 9.27 (1H, bd), 8.72 (1H, d), 8.08 (1H, d), 7.27 (1H, d), 7.20 (1H, d), 3.97-4.15 (1H, m), 3.80 (4H, t), 1.84-2.03 (2H, m), 1.41-1.82 (6H, m).

MS m/z (M+H): 342.

Example 9

Synthesis of Compound 0009

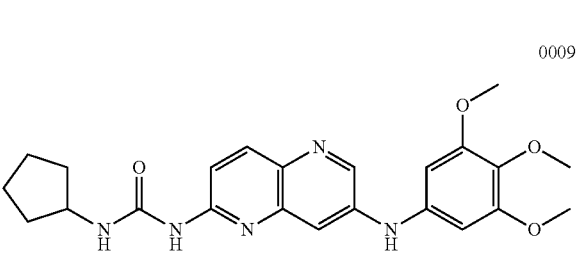 [SMILES: COc1cc(Nc2cnc3ccc(NC(=O)NC4CCCC4)nc3c2)cc(OC)c1OC]

The same method as in Example 8 except for using 3,4,5-trimethoxyaniline instead of morpholine used for the synthesis of the compound 0008 in Example 8, using (2-biphenyl)dicyclohexylphosphine instead of 2-dicyclohexylphosphino-2',4',6'-triisopropylbiphenyl used for the synthesis of the compound 0008 in Example 8, and using toluene instead of 1,4-dioxane used for the synthesis of the compound 0008 in Example 8 was used to obtain a compound 0009 (3.0 mg) as a yellow solid.

$^1$H-NMR (DMSO-$d_6$) δ: 9.69 (1H, s), 9.57 (1H, bd), 8.86 (1H, s), 8.51 (1H, d), 8.05 (1H, d), 7.48 (1H, d), 7.16 (1H, d), 6.57 (2H, s), 4.19-3.99 (1H, m), 3.78 (6H, s), 3.64 (3H, s), 1.99-1.78 (2H, m), 1.77-1.40 (6H, m).

MS m/z (M+H): 438.

Example 10

Synthesis of Compound 0010

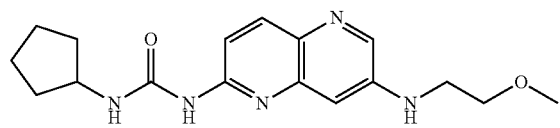

0010

The same method as in Example 8 except for using 2-methoxyethylamine instead of morpholine in Example 8 was used to obtain a compound 0010 (8.8 mg) as a white solid.

$^1$H-NMR (DMSO-d$_6$) δ: 9.53 (1H, s), 9.48 (1H, bd), 8.34 (1H, d), 7.96 (1H, d), 7.07 (1H, d), 6.80 (1H, d), 6.64 (1H, t), 3.95-4.20 (1H, m), 3.57 (2H, t), 3.31 (3H, s), 1.82-2.01 (2H, m), 1.46-1.81 (6H, m).
MS m/z (M+H): 331.

Example 11

Synthesis of Compound 0011

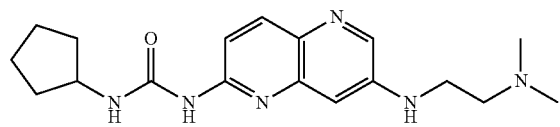

0011

The same method as in Example 8 except for using 2-dimethylaminoethylamine instead of morpholine in Example 8 was used to obtain a compound 0011 (16.0 mg) as a white solid.

$^1$H-NMR (DMSO-d$_6$) δ: 9.41-9.60 (2H, m), 8.34 (1H, d), 7.95 (1H, d), 7.05 (1H, d), 6.77 (1H, d), 6.48 (1H, t), 3.90-4.21 (1H, m), 3.23 (2H, dt), 2.22 (6H, s), 2.12-2.32 (2H, m), 1.81-1.98 (2H, m), 1.45-1.79 (6H, m).
MS m/z (M+H): 343.

Example 12

Synthesis of Compound 0012

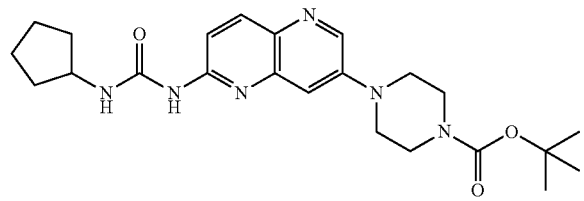

0012

The same method as in Example 8 except for using 1-tert-butoxycarbonylpiperazine instead of morpholine in Example 8 was used to obtain a compound 0012 (5.3 mg) as a pale yellow solid.

$^1$H-NMR (DMSO-d$_6$) δ: 9.64 (1H, s), 9.26 (1H, bd), 8.71 (1H, d), 8.07 (1H, d), 7.27 (1H, d), 7.21 (1H, d), 3.95-4.19 (1H, m), 3.44-3.62 (4H, m), 3.23-3.42 (4H, m), 1.84-2.04 (2H, m), 1.43 (9H, s), 1.34-1.83 (6H, m).
MS m/z (M+H): 442.

Example 13

Synthesis of Compound 0013

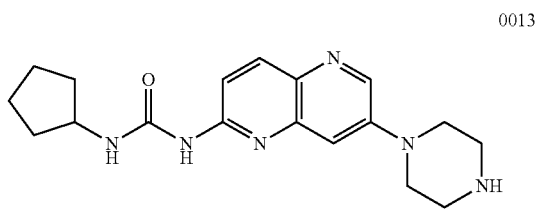 [SMILES: O=C(Nc1ccc2ncc(N3CCNCC3)cc2n1)NC1CCCC1]

0013

To the compound 0012 (3.0 mg) obtained in Example 12, a 4 M hydrogen chloride/1,4-dioxane solution was added, and the mixture was stirred at 50° C. for 30 minutes. The reaction solution was returned to room temperature, the solvent was removed under reduced pressure, and the residue was purified by silica gel column chromatography (chloroform-methanol, NH silica). The solvent was evaporated under reduced pressure and the obtained solid was washed with ethyl acetate to obtain a compound 0013 (1.5 mg) as a yellow solid.

$^1$H-NMR (MeOH-d$_4$) δ: 8.98-8.82 (1H, m), 8.49 (1H, bd), 7.85-7.70 (1H, m), 7.29 (1H, d), 4.27-4.10 (1H, m), 3.90-3.78 (4H, m), 3.53-3.38 (4H, m), 2.13-1.95 (2H, m), 1.90-1.53 (6H, m).
MS m/z (M+H): 341.

Example 14

Synthesis of Compound 0014

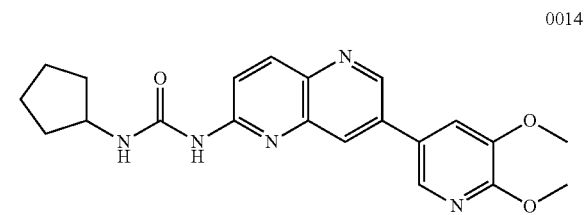 [SMILES: COc1cc(-c2cnc3ccc(NC(=O)NC4CCCC4)nc3c2)cnc1OC]

0014

The same method as in Example 1 except for using 2,3-dimethoxy-5-pyridineboronic acid pinacol ester instead of 2-methoxy-4-(4,4,5,5-tetramethyl-1,3,2-dioxaborolan-2-yl)phenol used for the synthesis of the compound 0001 in Example 1 was used to obtain a compound 0014 (24.5 mg) as a white solid.

$^1$H-NMR (DMSO-d$_6$) δ: 9.82 (1H, s), 9.04-9.17 (2H, m), 8.32 (1H, d), 8.29 (1H, d), 8.25 (1H, d), 7.79 (1H, d), 7.60 (1H, d), 4.00-4.17 (1H, m), 3.94 (3H, s), 3.93 (3H, s), 1.84-2.04 (2H, m), 1.49-1.83 (6H, m).
MS m/z (M+H): 394.

Example 15

Synthesis of Compound 0015

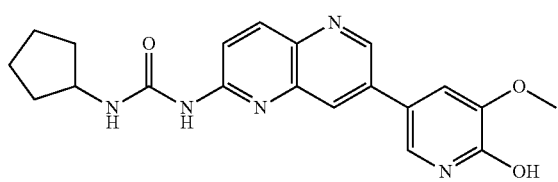

To the compound 0014 (10.0 mg) obtained in Example 14, concentrated hydrochloric acid (0.2 mL) was added, and the mixture was stirred at 80° C. for 30 minutes. Concentrated hydrochloric acid was removed under reduced pressure and the residue was purified by silica gel column chromatography (chloroform-methanol, NH silica) to obtain a compound 0015 (5.2 mg) as a white solid.

$^1$H-NMR (DMSO-d$_6$) δ: 12.18-11.87 (1H, m), 9.87 (1H, s), 9.16-8.95 (2H, m), 8.33-8.18 (2H, m), 7.70-7.51 (2H, m), 7.36 (1H, d), 4.15-3.98 (1H, m), 3.85 (3H, s), 2.05-1.84 (2H, m), 1.84-1.50 (6H, m).

MS m/z (M+H): 380.

Example 16

Synthesis of Compound 0016

(Synthesis of Compound 0016-1)

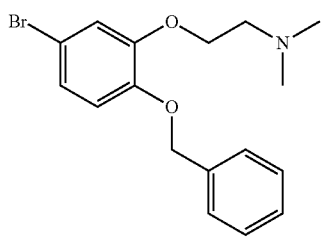

A 40% diethyl azodicarboxylate in toluene solution (0.179 mL) was added at 0° C. to a solution of 2-dimethylaminoethanol (38.4 mg) and triphenylphosphine (95.5 mg) in dichloromethane (0.5 mL), and the mixture was stirred for 5 minutes. A solution of 2-benzyloxy-5-bromophenol (100 mg, synthesized according to Angew. Chem., Int. Ed. 2008, 47, 3552.) in dichloromethane (0.5 mL) was added thereto, and the mixture was stirred at room temperature for 3 hours. To the reaction solution was added water, the mixture was extracted with ethyl acetate, and the organic layer was washed with brine, and then dried over sodium sulfate. The solvent was evaporated under reduced pressure and the obtained residue was purified by silica gel column chromatography (chloroform-methanol) to obtain a compound 0016-1 (159 mg), which was a mixture of compound 0016-1 and impurities, but was used in the next reaction without further purification.

$^1$H-NMR (CDCl$_3$) δ: 7.88-6.32 (8H, m), 5.09 (2H, s), 4.10 (2H, t), 2.77 (2H, t), 2.34 (6H, s).

MS m/z (M+H): 350,352.

(Synthesis of Compound 0016-2)

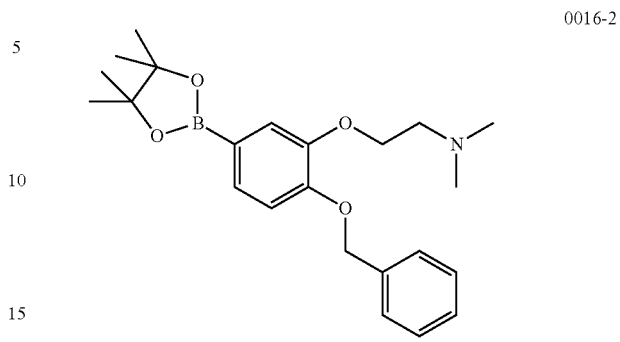

Triethylamine (0.198 mL) and 4,4,5,5-tetramethyl-1,3,2-dioxaborolane (0.154 mL) were added to a solution of the compound 0016-1 obtained above (159 mg), palladium acetate (8.0 mg) and dicyclohexylbiphenylphosphine (50.1 mg) in 1,4-dioxane (1.8 mL), and the mixture was stirred at 100° C. for 2 hours under a nitrogen atmosphere. The reaction solution was returned to room temperature and saturated sodium bicarbonate was added thereto. The mixture was extracted with ethyl acetate, and the organic layer was washed with brine, and then dried over sodium sulfate. The solvent was evaporated under reduced pressure and the obtained residue was purified by silica gel column chromatography (chloroform-methanol) to obtain a compound 0016-2 (109 mg) as a brown oily substance, which was a mixture of the compound 0016-2 and impurities, but was used in the next reaction without further purification.

$^1$H-NMR (CDCl$_3$) δ: 7.48-7.41 (2H, m), 7.41-7.28 (4H, m), 6.97-6.85 (2H, m), 5.21-5.06 (2H, m), 4.24-4.08 (2H, m), 2.87-2.64 (2H, m), 2.35 (6H, s), 1.25 (12H, s).

MS m/z (M+H): 398.

(Synthesis of Compound 0016-3)

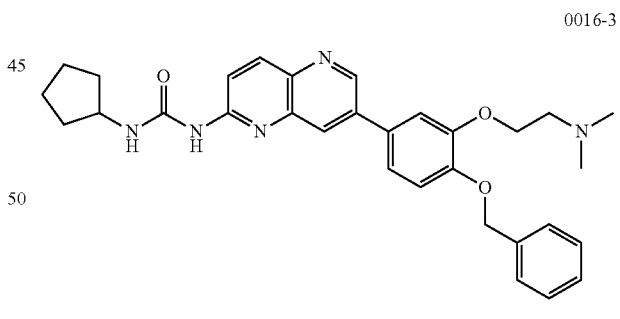

The same method as in Example 1 except for using the compound 0016-2 instead of 2-methoxy-4-(4,4,5,5-tetramethyl-1,3,2-dioxaborolan-2-yl)phenol used for the synthesis of the compound 0001 of Example 1 was used to obtain a compound 0016-3 (20.2 mg) as a yellow solid.

$^1$H-NMR (DMSO-d$_6$) δ: 9.80 (1H, s), 9.20 (1H, bd), 9.10 (1H, d), 8.26 (1H, d), 8.22 (1H, d), 7.56 (1H, d), 7.54-7.27 (7H, m), 7.20 (1H, d), 5.21 (2H, s), 4.24 (2H, t), 4.16-4.00 (1H, m), 2.69 (2H, t), 2.25 (6H, s), 1.98-1.83 (2H, m), 1.81-1.48 (6H, m).

MS m/z (M+H): 526.2.

(Synthesis of Compound 0016)

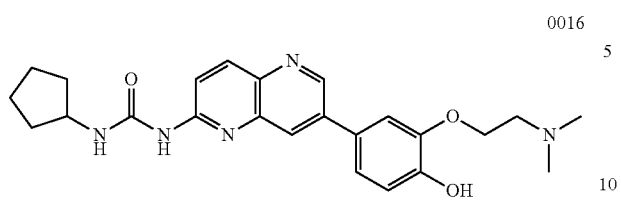

The same method as in Example 15 except for using a compound 0016-3 instead of the compound 0014 used for the synthesis of the compound 0015 in Example 15 was used to obtain a compound 0016 (2.0 mg) as a white solid.

$^1$H-NMR (DMSO-$d_6$) δ: 10.25-10.00 (1H, m), 9.92-9.78 (1H, m), 9.19-9.03 (2H, m), 8.32-8.22 (2H, m), 7.60 (1H, d), 7.55 (1H, d), 7.43 (1H, dd), 7.01 (1H, d), 4.47 (2H, t), 4.19-3.96 (1H, m), 2.91 (3H, s), 2.89 (3H, s), 2.04-1.86 (2H, m), 1.84-1.49 (6H, m).

MS m/z (M+H): 436.

Example 17

Synthesis of Compound 0017

(Synthesis of Compound 0017-1)

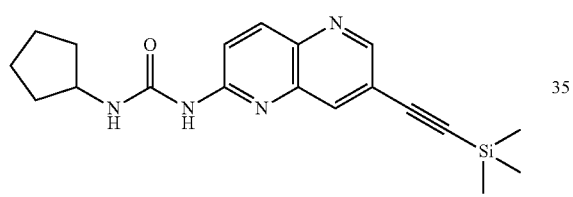

Trimethylsilylacetylene (0.0412 mL), triethylamine (0.104 mL), copper iodide (I) (6.8 mg), and tetrakis(triphenylphosphine)palladium (0) (17.2 mg) were added to a solution of the compound 0001-5 (50 mg) in 1,4-dioxane (1.0 mL) under a nitrogen atmosphere, and the mixture was stirred at room temperature for 30 minutes and at 100° C. for 1 hour. The reaction solution was returned to room temperature, water and 25% aqueous ammonia were added thereto, and the formed solid was separated by filtration. The obtained solid was washed with aqueous ammonia and dried under reduced pressure to obtain a compound 0017-1 (50.3 mg) as a grey solid.

MS m/z (M+H): 353.

(Synthesis of Compound 0017)

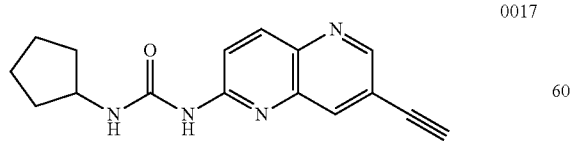

To a solution of the compound 0017-1 (50.3 mg) in methanol (1.5 mL), potassium carbonate (41.2 mg) was added, and the mixture was stirred at room temperature for 30 minutes. The formed solid was separated by filtration, and the obtained solid was washed with methanol and water, and dried under reduced pressure to obtain a compound 0017 (30.2 mg) as a grey solid.

$^1$H-NMR (DMSO-$d_6$) δ: 9.91 (1H, s), 9.16-8.99 (1H, m), 8.78 (1H, d), 8.33-8.20 (2H, m), 7.59 (1H, d), 4.65 (1H, s), 4.19-3.99 (1H, m), 2.02-1.81 (2H, m), 1.81-1.44 (6H, m).

MS m/z (M+H): 281.

Examples 18 and 19

Synthesis of Compound 0018 and Compound 0019

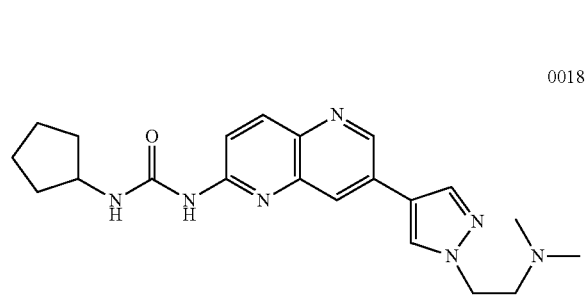

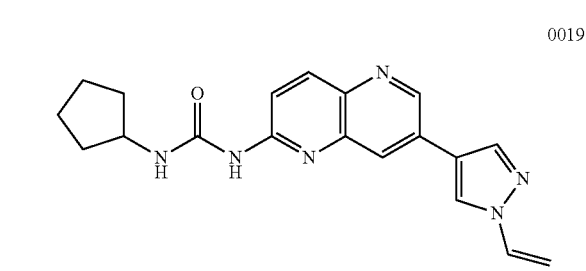

The same method as in Example 1 except for using a 1-(2-dimethylaminoethyl)-1H-pyrazole-4-boronic acid pinacol ester (which was synthesized according to US2006/293358A1) instead of 2-methoxy-4-(4,4,5,5-tetramethyl-1,3,2-dioxaborolan-2-yl)phenol used in Example 1 was used to obtain a compound 0018 (3.3 mg) as a white solid and a compound 0019 (5.3 mg) as a white solid.

(Compound 0018)

$^1$H-NMR (DMSO-$d_6$) δ: 9.76 (1H, s), 9.16 (1H, bd), 9.06 (1H, d), 8.51 (1H, s), 8.26-8.06 (3H, m), 7.49 (1H, d), 4.26 (2H, t), 4.21-3.96 (1H, m), 2.71 (2H, t), 2.69 (6H, s), 2.05-1 84 (2H, m), 1.84-1.48 (6H, m).

MS m/z (M+H): 394.

(Compound 0019)

$^1$H-NMR (DMSO-$d_6$) δ: 9.78 (1H, s), 9.15-9.06 (2H, m), 8.88 (1H, s), 8.42 (1H, s), 8.24 (1H, s), 8.22 (1H, d), 7.54 (1H, d), 7.30 (1H, dd), 5.69 (1H, d), 4.97 (1H, d), 4.18-3.99 (1H, m), 2.06-1.88 (2H, m), 1.84-1.49 (6H, m).

MS m/z (M+H): 349.

Example 20

Synthesis of Compound 0020

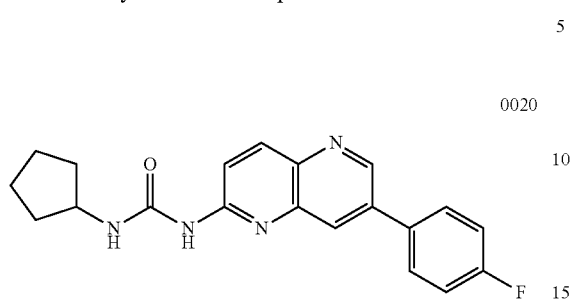

The same method as in Example 1 except for using 4-fluorophenylboronic acid instead of 2-methoxy-4-(4,4,5,5-tetramethyl-1,3,2-dioxaborolan-2-yl)phenol used for the synthesis of the compound 0001 in Example 1 was used to obtain a compound 0020 (17.4 mg) as a white solid.

$^1$H-NMR (DMSO-$d_6$) δ: 9.85 (1H, s), 9.18 (1H, bd), 9.09 (1H, d), 8.34-8.23 (2H, m), 8.02-7.92 (2H, m), 7.58 (1H, d), 7.47-7.34 (2H, m), 4.19-4.00 (1H, m), 2.03-1.83 (2H, m), 1.83-1.47 (6H, m).

MS m/z (M+H): 351.

Example 21

Synthesis of Compound 0021

(Synthesis of Compound 0021-1)

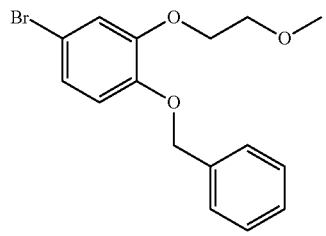

To a suspension of 2-benzyloxy-5-bromophenol (100 mg) and potassium carbonate (99 mg) in N,N-dimethylformamide (0.4 mL), 2-bromoethylmethylether (0.0673 mL) was added, and the mixture was stirred at 80° C. for 15 hours. The reaction mixture was returned to room temperature, water was added thereto, and the mixture was extracted with ethyl acetate. The organic layer was washed with brine and then dried over sodium sulfate. The solvent was evaporated under reduced pressure and the obtained residue was purified by silica gel column chromatography (hexane-ethyl acetate) to obtain a compound 0021-1 (116 mg) as a colorless oily substance.

$^1$H-NMR (DMSO-$d_6$) δ: 7.47-7.26 (5H, m), 7.16 (1H, d), 7.04 (1H, dd), 6.98 (1H, d), 5.10 (2H, s), 4.18-4.07 (2H, m), 3.70-3.61 (2H, m), 3.30 (3H, s).

MS m/z (M+H): 337, 339.

(Synthesis of Compound 0021-2)

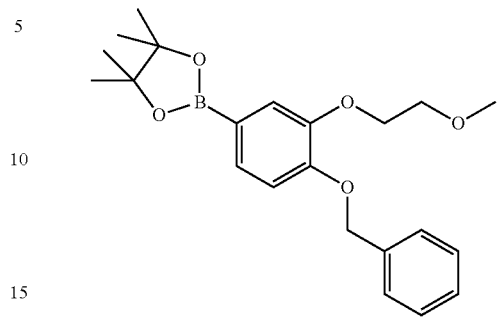

1,4-dioxane (1.0 mL) was added to the compound 0021-1 (116 mg), bis(pinacolato)diboron (131 mg), [1,1-bis(diphenylphosphino)ferrocene]palladium (II) dichloride (28.1 mg) and potassium acetate (67.5 mg) under a nitrogen atmosphere, and the mixture was stirred at 80° C. for 2 hours. The reaction solution was returned to room temperature, ethyl acetate and saturated aqueous sodium bicarbonate were added thereto, and the resulting mixture was extracted with ethyl acetate and dried over sodium sulfate. The solvent was evaporated under reduced pressure and the residue was purified by silica gel column chromatography (hexane-ethyl acetate) to obtain a compound 0021-2 (68.8 mg) as a colorless oily substance.

$^1$H-NMR (CDCl$_3$) δ: 7.55-7.21 (7H, m), 6.92 (1H, d), 5.15 (2H, d), 4.23 (2H, t), 3.79 (2H, t), 3.45 (3H, s), 1.33 (12H, s).

(Synthesis of Compound 0021-3)

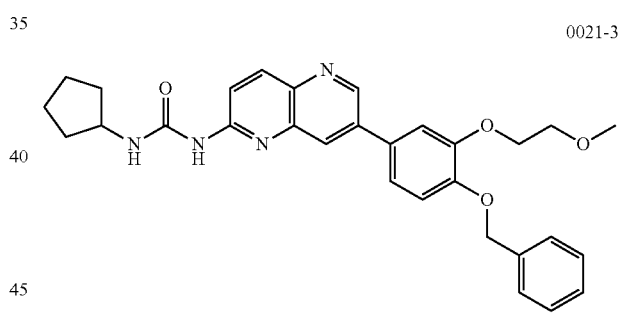

The same method as in Example 1 except for using the compound 0021-2 instead of 2-methoxy-4-(4,4,5,5-tetramethyl-1,3,2-dioxaborolan-2-yl)phenol used for the synthesis of the compound 0001 in Example 1 was used to obtain a compound 0021-3 (20.0 mg) as a yellow solid, which was a mixture of the compound 0021-3 and impurities, but used to carry out the next reaction without further purification.

MS m/z (M+H): 513.

(Synthesis of Compound 0021)

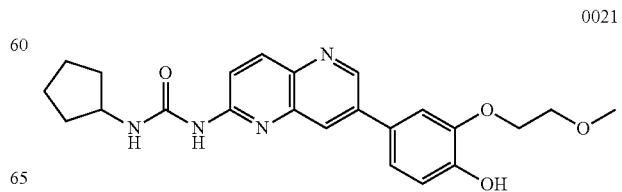

To the compound 0021-3 (20 mg), concentrated hydrochloric acid (0.2 mL) was added, and the mixture was heated at 50° C. for 10 minutes, and at 80° C. for 30 minutes. The reaction solution was returned to room temperature and neutralized with a 5 M aqueous sodium hydroxide solution. Water was removed therefrom under reduced pressure and the residue was purified by silica gel column chromatography (chloroform-methanol) to obtain a compound 0021 (1.1 mg) as a white solid.

$^1$H-NMR (DMSO-d$_6$) δ: 9.79 (1H, s), 9.36 (1H, s), 9.19 (1H, bd), 9.07 (1H, d), 8.25 (1H, d), 8.17 (1H, d), 7.54 (1H, d), 7.44 (1H, d), 7.33 (1H, dd), 6.97 (1H, d), 4.25 (2H, t), 4.18-3.97 (1H, m), 3.72 (2H, t), 2.02-1.84 (2H, m), 1.84-1.49 (6H, m).

MS m/z (M+H): 423.

Example 22

Synthesis of Compound 0022

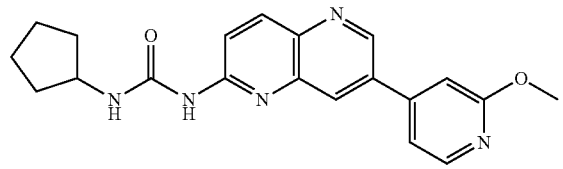

0022

The same method as in Example 1 except for using 2-methoxypyridine-4-boronic acid pinacol ester instead of 2-methoxy-4-(4,4,5,5-tetramethyl-1,3,2-dioxaborolan-2-yl)phenol used for the synthesis of the compound 0001 in Example 1 was used to obtain a compound 0022 (2.2 mg) as a white solid.

$^1$H-NMR (DMSO-d$_6$) δ: 9.88 (1H, s), 9.16 (1H, d), 9.12 (1H, bd), 8.42 (1H, d), 8.37-8.22 (2H, m), 7.63 (1H, d), 7.55 (1H, dd), 7.40 (1H, s), 4.18-4.00 (1H, m), 3.94 (3H, s), 2.02-1.86 (2H, m), 1.82-1.51 (6H, m).

MS m/z (M+H): 364.

Example 23

Synthesis of Compound 0023

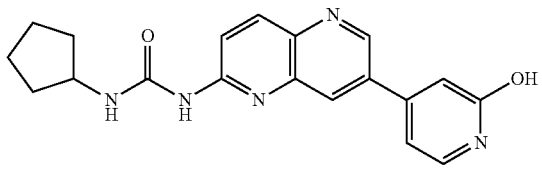

0023

The same method as in Example 21 except for using the compound 0022 instead of the compound 0021-3 used for the synthesis of the compound 0021 in Example 21 was used to obtain a compound 0023 (2.2 mg) as a white solid.

$^1$H-NMR (DMSO-d$_6$): 11.96-11.49 (1H, m), 9.88 (1H, s), 9.14 (1H, d), 9.07 (1H, d), 8.37-8.20 (2H, m), 7.62 (1H, d), 7.55 (1H, d), 6.88 (1H, d), 6.72 (1H, dd), 4.19-3.97 (1H, m), 2.04-1.86 (2H, m), 1.86-1.44 (6H, m).

MS m/z (M+H): 350.

Example 24

Synthesis of Compound 0024

(Synthesis of Compound 0024-1)

[Chem. 52]

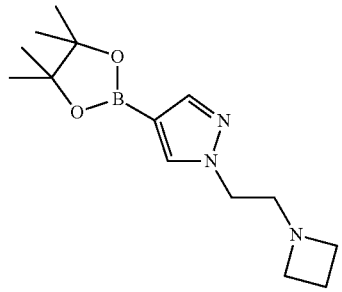

0024-1

Azetidine (37.9 mg) was added to a suspension of 1-(2-bromoethyl)-1H-pyrazole-4-boronic acid pinacol ester (which was synthesized according to WO2009/97233A1) (99.8 mg) and potassium carbonate (91.8 mg) in acetonitrile (0.3 mL), and the mixture was stirred at room temperature for 15 hours and at 60° C. for 3 hours. The reaction mixture was returned to room temperature, ethyl acetate and saturated aqueous sodium bicarbonate were added thereto, and the resulting mixture was extracted with ethyl acetate. The organic layer was washed with water and brine, and then dried over sodium sulfate. The solvent was evaporated under reduced pressure and the obtained residue was purified by silica gel column chromatography (hexane-ethyl acetate) to obtain a compound 0024-1 (49.6 mg) as a colorless oily substance.

$^1$H-NMR (CDCl$_3$) δ: 7.78 (1H, s), 7.72 (1H, s), 4.09 (2H, t), 3.15 (4H, t), 2.86 (2H, t), 2.13-1.92 (2H, m), 1.31 (12H, s).

MS m/z (M+H): 278.

(Synthesis of Compound 0024)

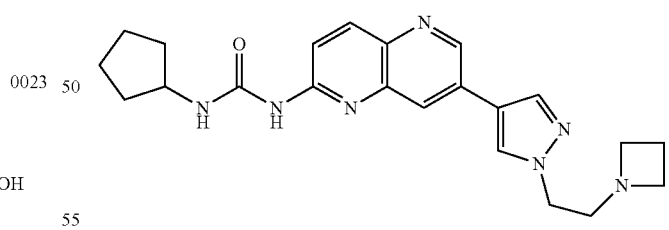

0024

The same method as in Example 1 except for using the compound 0024-1 instead of 2-methoxy-4-(4,4,5,5-tetramethyl-1,3,2-dioxaborolan-2-yl)phenol used for the synthesis of the compound 0001 in Example 1 was used to obtain a compound 0024 (22.6 mg) as a yellow solid.

$^1$H-NMR (DMSO-d$_6$): 9.77 (1H, s), 9.16 (1H, bd), 9.07 (1H, d), 8.51 (1H, s), 8.28-8.10 (3H, m), 7.51 (1H, d), 4.27-4.15 (2H, m), 4.15-4.02 (1H, m), 2.15-1.87 (4H, m), 1.82-1.48 (6H, m).

MS m/z (M+H): 406.

Example 25

Synthesis of Compound 0025

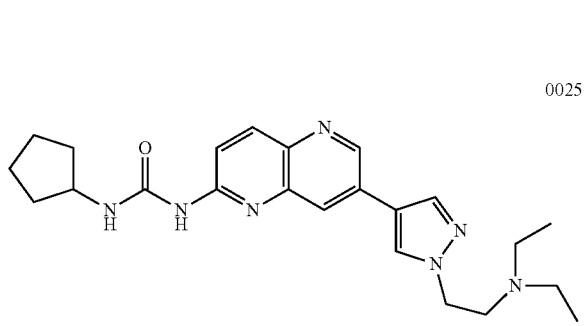 [SMILES: CCN(CC)CCn1cc(-c2cnc3ccc(NC(=O)NC4CCCC4)nc3c2)cn1]

0025

The same method as in Example 1 except for using 1-(2-diethylaminoethyl)-1H-pyrazole-4-boronic acid pinacol ester instead of 2-methoxy-4-(4,4,5,5-tetramethyl-1,3,2-dioxaborolan-2-yl)phenol used for the synthesis of the compound 0001 in Example 1 was used to obtain a compound 0025 (12.0 mg) as a yellow solid.

$^1$H-NMR (DMSO-d$_6$) δ: 9.77 (1H, s), 9.23-9.11 (1H, m), 9.06 (1H, d), 8.59-8.44 (1H, m), 8.28-8.07 (3H, m), 7.49 (1H, d), 4.30-4.16 (2H, m), 4.16-3.96 (1H, m), 2.93-2.72 (2H, m), 2.05-1.86 (2H, m), 1.84-1.49 (6H, m), 1.02-0.81 (6H, m).

MS m/z (M+H): 422.

Example 26

Synthesis of Compound 0026

[Chem. 55]

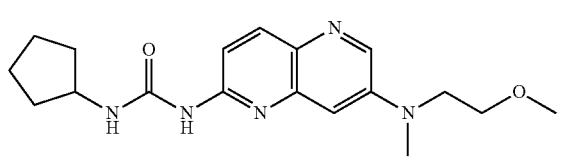

0026

The same method as in Example 8 except for using N-(2-methoxyethyl) methylamine instead of morpholine in Example 8 was used to obtain a compound 0026 (2.2 mg) as a pale yellow solid.

$^1$H-NMR (DMSO-d$_6$) δ: 9.57 (1H, s), 9.53-9.38 (1H, m), 8.55 (1H, d), 8.00 (1H, d), 7.13 (1H, d), 6.93 (1H, d), 4.22-3.97 (1H, m), 3.70 (2H, t), 3.56 (2H, t), 3.26 (3H, s), 3.07 (3H, s), 2.02-1.83 (2H, m), 1.83-1.47 (6H, m).

MS m/z (M+H): 344.

Example 27

Synthesis of Compound 0027

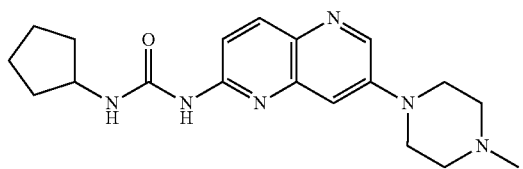

0027

The same method as in Example 8 except for using 1-methylpiperazine instead of morpholine in Example 8 was used to obtain a compound 0027 (3.2 mg) as a pale yellow solid.

$^1$H-NMR (DMSO-d$_6$) δ: 9.62 (1H, s), 9.27 (1H, bd), 8.71 (1H, d), 8.06 (1H, d), 7.25 (1H, d), 7.18 (1H, d), 4.15-3.96 (1H, m), 2.25 (3H, s), 2.02-1.83 (2H, m), 1.80-1.42 (6H, m).

MS m/z (M+H): 355.

Example 28

Synthesis of Compound 0028

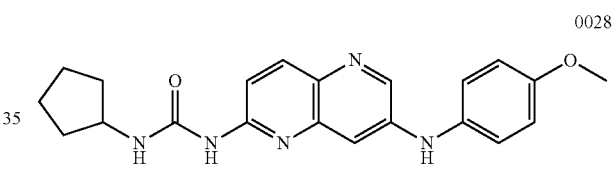

0028

The same method as in Example 8 except for using 4-methoxyaniline instead of morpholine in Example 8 was used to obtain a compound 0028 (13.9 mg) as a yellow solid.

$^1$H-NMR (DMSO-d$_6$) δ: 9.60 (1H, s), 9.48 (1H, bd), 8.67 (1H, s), 8.46 (1H, d), 8.02 (1H, d), 7.31-7.10 (4H, m), 7.03-6.82 (2H, m), 4.19-4.00 (1H, m), 3.76 (3H, s), 1.93-1.77 (2H, m), 1.77-1.34 (6H, m).

MS m/z (M+H): 378.

Example 29

Synthesis of Compound 0029

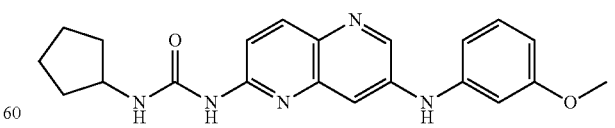

0029

The same method as in Example 8 except for using 3-methoxyaniline instead of morpholine in Example 8 was used to obtain a compound 0029 (19.6 mg) as a yellow solid.

$^1$H-NMR (DMSO-d$_6$) δ: 9.67 (1H, s), 9.59-9.44 (1H, m), 8.94 (1H, s), 8.54 (1H, d), 8.06 (1H, d), 7.51 (1H, d), 7.27 (1H, d), 7.21 (1H, d), 6.87-6.78 (2H, m), 6.59 (1H, dd), 4.16-4.00 (1H, m), 3.76 (3H, s), 2.01-1.77 (2H, m), 1.77-1.33 (6H, m).

MS m/z (M+H): 378.

Example 30

Synthesis of Compound 0030

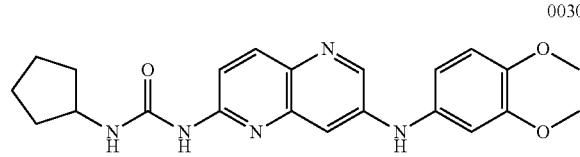 [SMILES: COc1ccc(Nc2cnc3ccc(NC(=O)NC4CCCC4)nc3c2)cc1OC]

0030

The same method as in Example 8 except for using 3,4-dimethoxyaniline instead of morpholine in Example 8 was used to obtain a compound 0030 (3.8 mg) as a yellow solid.

$^1$H-NMR (DMSO-d$_6$) δ: 9.69 (1H, s), 9.55 (1H, d), 8.94 (1H, s), 8.53 (1H, d), 8.06 (1H, d), 7.54 (1H, d), 7.20 (1H, d), 6.44-6.38 (2H, m), 6.17 (1H, t), 4.23-3.96 (1H, m), 3.74 (6H, s), 1.95-1.78 (2H, m), 1.78-1.43 (6H, m).

MS m/z (M+H): 408.

Example 31

Synthesis of Compound 0031

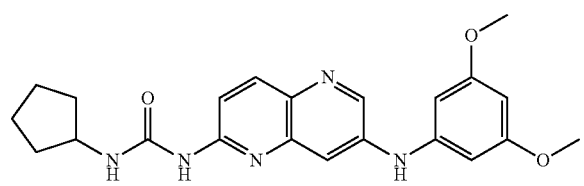

0031

The same method as in Example 8 except for using 3,5-dimethoxyaniline instead of morpholine in Example 8 was used to obtain a compound 0031 (9.4 mg) as a yellow solid.

$^1$H-NMR (DMSO-d$_6$) δ: 9.63 (1H, s), 9.58-9.44 (1H, m), 8.72 (1H, s), 8.48 (1H, d), 8.02 (1H, d), 7.32 (1H, d), 7.15 (1H, d), 6.96 (1H, d), 6.91 (1H, d), 6.78 (1H, dd), 4.16-3.99 (1H, m), 3.76 (6H, d), 1.95-1.77 (2H, m), 1.77-1.33 (6H, m).

MS m/z (M+H): 408.

Example 32

Synthesis of Compound 0032

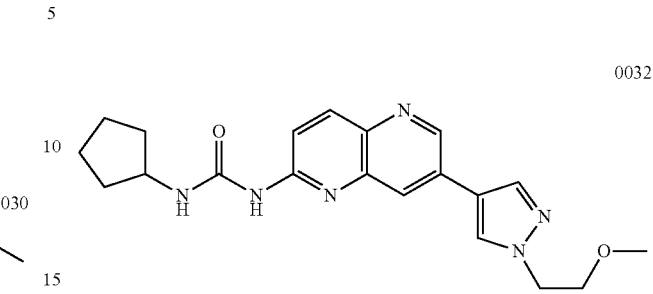

0032

The same method as in Example 1 except for using 1-(2-methoxyethyl)-1H-pyrazole-4-boronic acid pinacol ester instead of 2-methoxy-4-(4,4,5,5-tetramethyl-1,3,2-dioxaborolan-2-yl)phenol used for the synthesis of the compound 0001 in Example 1 was used to obtain a compound 0032 (26.9 mg) as a white solid.

$^1$H-NMR (DMSO-d$_6$) δ: 9.77 (1H, s), 9.17 (1H, bd), 9.07 (1H, d), 8.50 (1H, s), 8.28-8.09 (3H, m), 7.49 (1H, d), 4.34 (2H, t), 4.23-3.95 (1H, m), 3.75 (2H, t), 3.26 (3H, s), 2.03-1.84 (2H, m), 1.84-1.43 (6H, m).

MS m/z (M+H): 381.

Example 33

Synthesis of Compound 0033

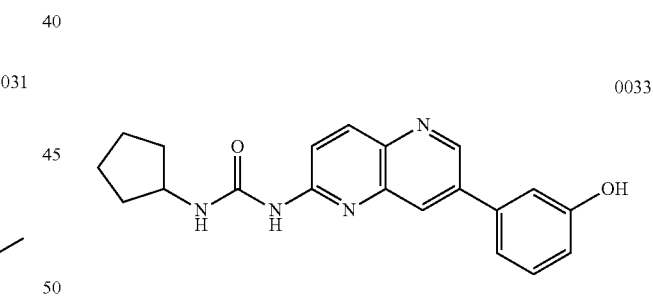

0033

The same method as in Example 1 except for using 3-hydroxyphenylboronic acid instead of 2-methoxy-4-(4,4,5,5-tetramethyl-1,3,2-dioxaborolan-2-yl)phenol used for the synthesis of the compound 0001 in Example 1 was used to obtain a compound 0033 (13.5 mg) as a white solid.

$^1$H-NMR (DMSO-d$_6$) δ: 9.85 (1H, s), 9.72 (1H, s), 9.22 (1H, bd), 9.02 (1H, d), 8.28 (1H, d), 8.20 (1H, d), 7.56 (1H, d), 7.40-7.32 (1H, m), 7.32-7.26 (1H, m), 7.23-7.19 (1H, m), 6.92-6.86 (1H, m), 4.25-3.94 (1H, m), 2.01-1.83 (2H, m), 1.83-1.51 (6H, m).

MS m/z (M+H): 349.

Example 34

Synthesis of Compound 0034

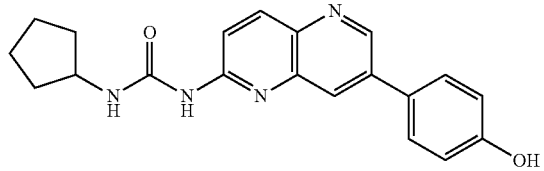

0034

The same method as in Example 1 except for using 4-hydroxyphenylboronic acid instead of 2-methoxy-4-(4,4,5,5-tetramethyl-1,3,2-dioxaborolan-2-yl)phenol used for the synthesis of the compound 0001 in Example 1 was used to obtain a compound 0034 (12.9 mg) as a white solid.

$^1$H-NMR (DMSO-$d_6$) δ: 9.81 (2H, s), 9.23 (1H, bd), 9.05 (1H, d), 8.24 (1H, d), 8.16 (1H, d), 7.74 (2H, d), 7.52 (1H, d), 6.94 (2H, d), 4.16-3.95 (1H, m), 2.01-1.84 (2H, m), 1.84-1.49 (6H, m).

MS m/z (M+H): 349.

Example 35

Synthesis of Compound 0035

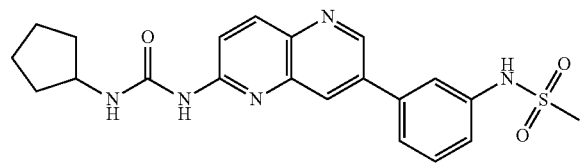

0035

The same method as in Example 1 except for using 3-(methylsulfonylamino)phenylboronic acid instead of 2-methoxy-4-(4,4,5,5-tetramethyl-1,3,2-dioxaborolan-2-yl)phenol used for the synthesis of the compound 0001 in Example 1 was used to obtain a compound 0035 (31.3 mg) as a white solid.

$^1$H-NMR (DMSO-$d_6$) δ: 9.97 (1H, s), 9.86 (1H, s), 9.20 (1H, bd), 9.04 (1H, d), 8.30 (1H, d), 8.21 (1H, d), 7.67-7.48 (4H, m), 7.36-7.29 (1H, m), 4.22-3.97 (1H, m), 3.09 (3H, s), 2.02-1.83 (2H, m), 1.83-1.48 (6H, m).

MS m/z (M+H): 426.

Example 36

Synthesis of Compound 0036

(Synthesis of Compound 0036-1)

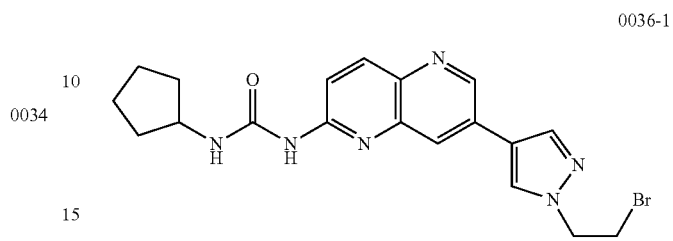

0036-1

The same method as in Example 1 except for using 1-(2-bromoethyl)-1H-pyrazole-4-boronic acid pinacol ester instead of 2-methoxy-4-(4,4,5,5-tetramethyl-1,3,2-dioxaborolan-2-yl)phenol used for the synthesis of the compound 0001 in Example 1 was used to obtain a compound 0036-1 (360 mg) as a white solid.

$^1$H-NMR (DMSO-$d_6$) δ: 9.78 (1H, s), 9.16 (1H, bd), 9.07 (1H, d), 8.59 (1H, s), 8.28 (1H, s), 8.21 (1H, d), 8.16 (1H, d), 7.50 (1H, d), 4.60 (2H, t), 4.17-4.01 (1H, m), 3.94 (2H, t), 2.04-1.88 (2H, m), 1.84-1.49 (6H, m).

MS m/z (M+H): 429, 431.

(Synthesis of Compound 0036)

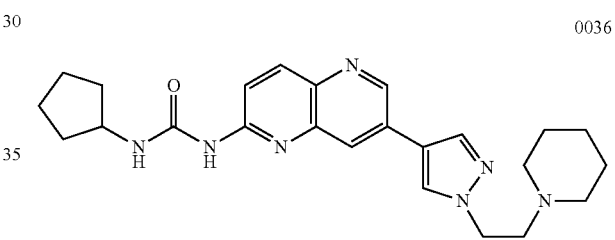

0036

To a suspension of the compound 0036-1 (20.0 mg) and potassium carbonate (12.9 mg) in 1,4-dioxane (0.2 mL), piperidine (0.0092 mL) was added, and the mixture was stirred at room temperature for 15 hours and at 80° C. for 3 hours. The reaction mixture was returned to room temperature and purified by silica gel column chromatography (chloroform-methanol, NH silica) to obtain a compound 0036 (10.2 mg) as a white solid.

$^1$H-NMR (DMSO-$d_6$) δ: 9.78 (1H, s), 9.21 (1H, bd), 9.06 (1H, d), 8.50 (1H, s), 8.20 (1H, d), 8.18 (1H, s), 8.12 (1H, d), 7.48 (1H, d), 4.27 (2H, t), 4.19-4.00 (1H, m), 2.72 (2H, t), 2.45-2.34 (4H, m), 2.03-1.88 (2H, m), 1.86-1.29 (12H, m).

MS m/z (M+H): 434.

Example 37

Synthesis of Compound 0037

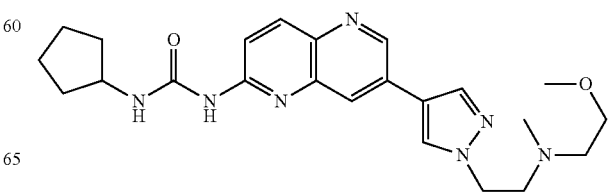

0037

The same method as in Example 36 except for using N-(2-methoxyethyl)methylamine instead of piperidine used for the synthesis of the compound 0036 in Example 36 was used to obtain a compound 0037 (9.2 mg) as a white solid.

$^1$H-NMR (DMSO-$d_6$) δ: 9.77 (1H, s), 9.17 (1H, bd), 9.05 (1H, d), 8.52 (1H, s), 8.24-8.15 (2H, m), 8.13 (1H, d), 7.49 (1H, d), 4.25 (2H, t), 4.16-3.99 (1H, m), 3.37 (2H, t), 3.21 (3H, s), 2.84 (2H, t), 2.56 (2H, t), 2.26 (3H, s), 2.02-1.88 (2H, m), 1.83-1.50 (6H, m).

MS m/z (M+H): 438.

Example 38

Synthesis of Compound 0038

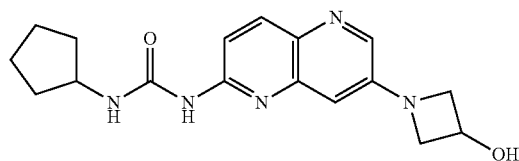

0038

The same method as in Example 8 except for using 3-hydroxyazetidine instead of morpholine in Example 8 was used to obtain a compound 0038 (17.8 mg) as a white solid.

$^1$H-NMR (DMSO-$d_6$) δ: 9.59 (1H, s), 9.31 (1H, bd), 8.17 (1H, d), 8.03 (1H, d), 7.18 (1H, d), 6.72 (1H, d), 5.75 (1H, d), 4.71-4.59 (1H, m), 4.35-4.22 (2H, m), 4.13-3.98 (1H, m), 3.79-3.69 (2H, m), 2.01-1.84 (2H, m), 1.80-1.45 (6H, m).

MS m/z (M+H): 328.

Example 39

Synthesis of Compound 0039

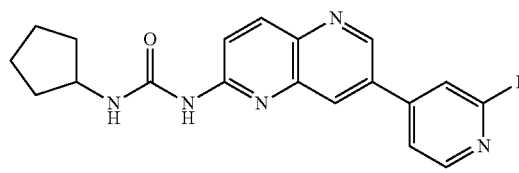

0039

The same method as in Example 1 except for using a 2-fluoro-4-pyridineboronic acid pinacol ester instead of 2-methoxy-4-(4,4,5,5-tetramethyl-1,3,2-dioxaborolan-2-yl) phenol used for the synthesis of the compound 0001 in Example 1 was used to obtain a compound 0039 (42.3 mg) as a white solid.

$^1$H-NMR (DMSO-$d_6$) δ: 9.90 (1H, s), 9.22 (1H, d), 9.07 (1H, bd), 8.52 (1H, d), 8.42 (1H, d), 8.33 (1H, d), 8.03-7.90 (1H, m), 7.85 (1H, s), 7.67 (1H, d), 4.18-3.96 (1H, m), 2.02-1.88 (2H, m), 1.82-1.49 (6H, m).

MS m/z (M+H): 352.

Example 40

Synthesis of Compound 0040

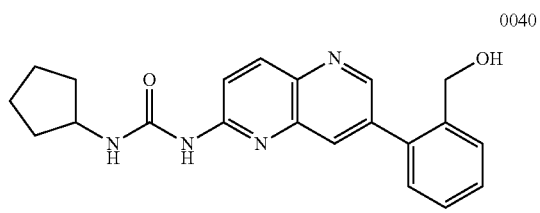 [SMILES: O=C(Nc1ccc2ncc(-c3ccccc3CO)cc2n1)NC1CCCC1]

0040

The same method as in Example 1 except for using 2-hydroxymethylphenylboronic acid instead of 2-methoxy-4-(4,4,5,5-tetramethyl-1,3,2-dioxaborolan-2-yl)phenol used for the synthesis of the compound 0001 in Example 1 was used to obtain a compound 0040 (22.8 mg) as a white solid.

$^1$H-NMR (DMSO-$d_6$) δ: 9.88 (1H, s), 9.27 (1H, bd), 8.79 (1H, d), 8.30 (1H, d), 8.16 (1H, d), 7.70-7.36 (5H, m), 5.36-5.13 (1H, m), 4.44 (2H, s), 4.18-3.97 (1H, m), 1.99-1.80 (2H, m), 1.80-1.43 (6H, m).

MS m/z (M+H): 364.

Example 41

Synthesis of Compound 0041

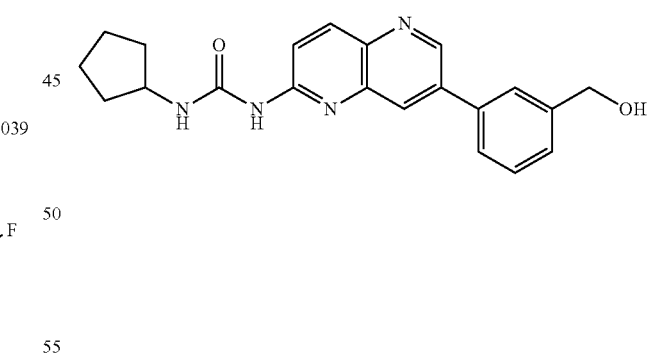

0041

The same method as in Example 1 except for using 3-hydroxymethylphenylboronic acid instead of 2-methoxy-4-(4,4,5,5-tetramethyl-1,3,2-dioxaborolan-2-yl)phenol used for the synthesis of the compound 0001 in Example 1 was used to obtain a compound 0041 (17.0 mg) as a white solid.

$^1$H-NMR (DMSO-$d_6$) δ: 9.84 (1H, s), 9.16 (1H, bd), 9.08 (1H, d), 8.33-8.22 (2H, m), 7.81 (1H, s), 7.76 (1H, d), 7.59 (1H, d), 7.53 (1H, t), 7.44 (1H, d), 5.32 (1H, t), 4.63 (2H, d), 4.16-4.00 (1H, m), 2.02-1.84 (2H, m), 1.81-1.51 (6H, m).

MS m/z (M+H): 363.

Example 42

Synthesis of Compound 0042

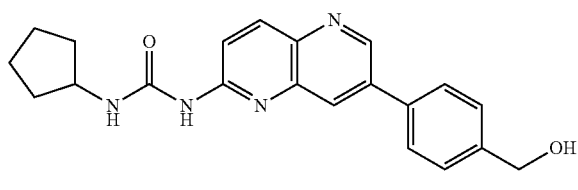

0042

The same method as in Example 1 except for using 4-hydroxymethylphenylboronic acid instead of 2-methoxy-4-(4,4,5,5-tetramethyl-1,3,2-dioxaborolan-2-yl)phenol used for the synthesis of the compound 0001 in Example 1 was used to obtain a compound 0042 (24.3 mg) as a white solid.

$^1$H-NMR (DMSO-d$_6$) δ: 9.84 (1H, s), 9.19 (1H, bd), 9.10 (1H, d), 8.32-8.20 (2H, m), 7.87 (2H, d), 7.57 (1H, d), 7.51 (2H, d), 5.30 (1H, t), 4.59 (2H, d), 4.18-4.02 (1H, m), 2.05-1.86 (2H, m), 1.83-1.47 (6H, m).

MS m/z (M+H): 363.

Example 43

Synthesis of Compound 0043

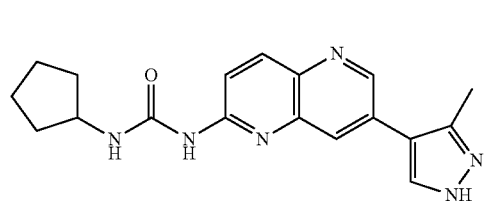

0043

The same method as in Example 1 except for using 3-methylpyrazole-4-boronic acid pinacol ester instead of 2-methoxy-4-(4,4,5,5-tetramethyl-1,3,2-dioxaborolan-2-yl)phenol used for the synthesis of the compound 0001 in Example 1, using sodium tert-butoxide instead of sodium carbonate used for the synthesis of the compound 0001 in Example 1, and using ethanol and toluene instead of 1,4-dioxane used for the synthesis of the compound 0001 in Example 1 was used to obtain a compound 0043 (24.3 mg) as a white solid.

$^1$H-NMR (DMSO-d$_6$) δ: 9.80 (1H, s), 9.40-9.19 (1H, m), 8.95 (1H, d), 8.23 (1H, d), 8.08-7.88 (2H, m), 7.50 (1H, d), 4.19-4.00 (1H, m), 2.01-1.84 (2H, m), 1.84-1.52 (6H, m).

MS m/z (M+H): 337.

Example 44

Synthesis of Compound 0044

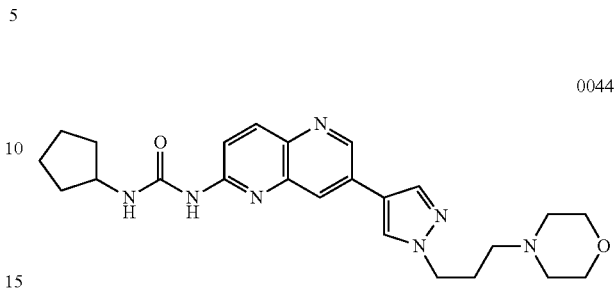

0044

The same method as in Example 1 except for using a 1-(3-morpholinopropyl)-1H-pyrazole-4-boronic acid pinacol ester (which was synthesized according to WO2008/148867A2) instead of 2-methoxy-4-(4,4,5,5-tetramethyl-1,3,2-dioxaborolan-2-yl)phenol used for the synthesis of the compound 0001 in Example 1 was used to obtain a compound 0044 (13.0 mg) as a white solid.

$^1$H-NMR (DMSO-d$_6$) δ: 9.77 (1H, s), 9.17 (1H, bd), 9.06 (1H, d), 8.52 (1H, s), 8.24-8.10 (3H, m), 7.49 (1H, d), 4.21 (2H, t), 4.15-3.99 (1H, m), 3.58 (4H, t), 2.40-2.23 (6H, m), 2.08-1.88 (4H, m), 1.86-1.48 (6H, m).

MS m/z (M+H): 450.

Example 45

Synthesis of Compound 0045

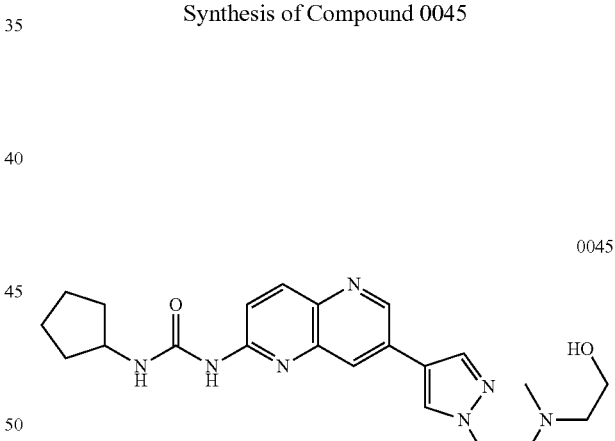

0045

The same method in Example 36 except for using N-(2-hydroxyethyl)methylamine instead of piperidine used for the synthesis of the compound 0036 in Example 36 was used to obtain a compound 0045 (13.8 mg) as a white solid.

$^1$H-NMR (DMSO-d$_6$) δ: 9.76 (1H, s), 9.16 (1H, d), 9.06 (1H, d), 8.55 (1H, s), 8.24-8.08 (3H, m), 7.50 (1H, d), 4.37 (1H, t), 4.25 (2H, t), 4.16-4.00 (1H, m), 2.84 (2H, t), 2.25 (3H, s), 2.04-1.87 (2H, m), 1.84-1.46 (6H, m).

MS m/z (M+H): 424.

Example 46

Synthesis of Compound 0046

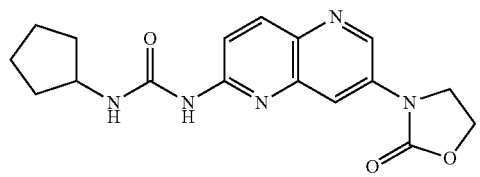

0046

A suspension of the compound 0001-5 (60 mg), 2-oxazolidone (18.7 mg), (1S, 2S)-(+)-N,N'-dimethylcyclohexane-1,2-diamine (56 μL), tripotassium phosphate (76 mg) and copper iodide (I) (34 mg) in 1,4-dioxane (1.8 mL) was stirred at 100° C. for 3 hours using a microwave reaction device. The reaction mixture was returned to room temperature and purified by silica gel column chromatography (chloroform-methanol, NH silica) to obtain a compound 0046 (6 mg) as a white solid.

$^{1}$H-NMR (DMSO-$d_6$) δ: 9.80 (1H, s), 9.19 (1H, d), 9.11 (1H, d), 8.22 (1H, d), 8.08 (1H, m), 7.49 (1H, m), 4.54 (2H, m), 4.26 (2H, m), 4.09 (1H, m), 2.00-1.85 (2H, m), 1.80-1.45 (6H, m).

MS m/z (M+H): 342.

Example 47

Synthesis of Compound 0047

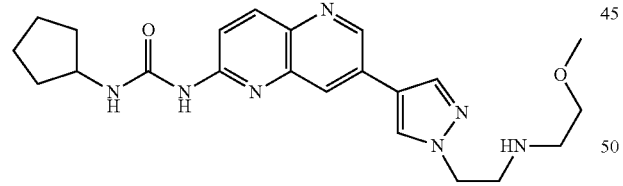

0047

The same method as in Example 36 except for using 2-methoxyethylamine instead of piperidine used for the synthesis of the compound 0036 in Example 36 was used to obtain a compound 0047 (2.8 mg) as a white solid.

$^{1}$H-NMR (DMSO-$d_6$) δ: 9.77 (1H, s), 9.17 (1H, d), 9.06 (1H, d), 8.50 (1H, s), 8.26-8.16 (2H, m), 8.14 (1H, d), 7.49 (1H, d), 4.23 (2H, t), 4.16-4.00 (1H, m), 3.22 (3H, s), 2.98 (2H, t), 2.68 (2H, t), 2.10-1.85 (2H, m), 1.85-1.45 (6H, m).

MS m/z (M+H): 424.

Example 48

Synthesis of Compound 0048

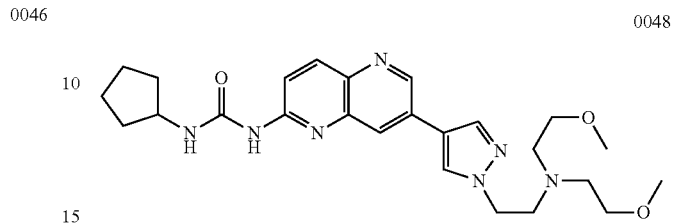

0048

The same method as in Example 36 except for using bis(2-methoxyethyl)amine instead of piperidine used for the synthesis of the compound 0036 in Example 36 was used to obtain a compound 0048 (1.4 mg) as a white solid.

$^{1}$H-NMR (DMSO-$d_6$) δ: 9.77 (1H, s), 9.19 (1H, bd), 9.05 (1H, d), 8.51 (1H, s), 8.24-8.14 (2H, m), 8.11 (1H, d), 7.48 (1H, d), 4.19 (2H, t), 4.16-4.01 (1H, m), 3.20 (6H, s), 2.95 (2H, t), 2.67 (4H, t), 2.04-1.84 (2H, m), 1.84-1.43 (6H, m).

MS m/z (M+H): 482.

Example 49

Synthesis of Compound 0049

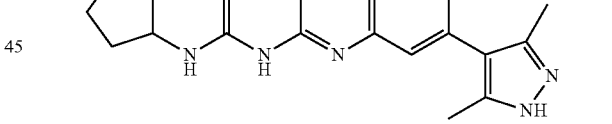

0049

The same method as in Example 1 except for using a 1-tert-butoxycarbonyl 3,5-dimethylpyrazole-4-boronic acid pinacol ester instead of 2-methoxy-4-(4,4,5,5-tetramethyl-1,3,2-dioxaborolan-2-yl)phenol used for the synthesis of the compound 0001 in Example 1 was used to obtain a compound 0049 (35.5 mg) as a white solid.

$^{1}$H-NMR (DMSO-$d_6$) δ: 9.81 (1H, s), 9.29 (1H, bd), 8.75 (1H, d), 8.25 (1H, d), 7.90 (1H, d), 7.53 (1H, d), 3.99-4.21 (1H, m), 2.33 (3H, s), 2.26 (3H, s), 1.82-1.99 (2H, m), 1.43-1.81 (6H, m).

MS m/z (M+H): 351.

Example 50

Synthesis of Compound 0050

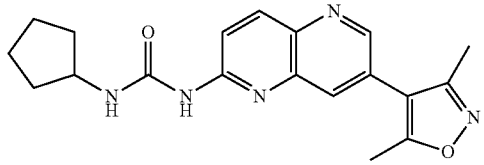

0050

The same method as in Example 1 except for using 3,5-dimethylisoxazole 4-boronic acid instead of 2-methoxy-4-(4,4,5,5-tetramethyl-1,3,2-dioxaborolan-2-yl)phenol used for the synthesis of the compound 0001 in Example 1 was used to obtain a compound 0050 (37.7 mg) as a white solid.

$^1$H-NMR (DMSO-d$_6$) δ: 9.86 (1H, s), 9.14 (1H, bd), 8.80 (1H, d), 8.30 (1H, d), 8.11 (1H, d), 7.62 (1H, d), 4.19-3.94 (1H, m), 2.55-2.47 (3H, m), 2.31 (3H, s), 2.00-1.82 (2H, m), 1.80-1.47 (6H, m).

MS m/z (M+H): 352.

Example 51

Synthesis of Compound 0051

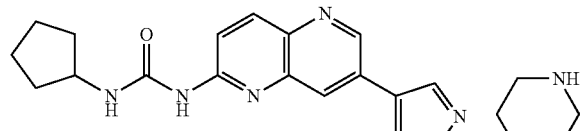

0051

The same method as in Example 36 except for using piperazine instead of piperidine used for the synthesis of the compound 0036 in Example 36 was used to obtain a compound 0051 (6.9 mg) as a white solid.

$^1$H-NMR (DMSO-d$_6$) δ: 9.77 (1H, s), 9.18 (1H, bd), 9.05 (1H, d), 8.50 (1H, s), 8.26-8.07 (3H, m), 7.49 (1H, d), 4.28 (2H, t), 4.17-3.99 (1H, m), 2.72 (4H, t), 2.66 (4H, t), 2.42-2.30 (3H, m), 2.06-1.87 (2H, m), 1.84-1.48 (6H, m).

MS m/z (M+H): 435.

Example 52

Synthesis of Compound 0052

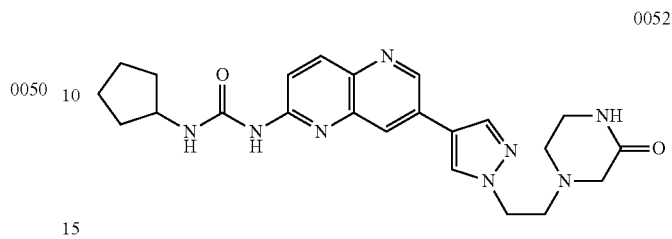

0052

The same method as in Example 36 except for using 2-piperazinone instead of piperidine used for the synthesis of the compound 0036 in Example 36 was used to obtain a compound 0052 (13.8 mg) as a white solid.

$^1$H-NMR (DMSO-d$_6$) δ: 9.77 (1H, s), 9.16 (1H, bd), 9.06 (1H, d), 8.52 (1H, s), 8.26-8.17 (2H, m), 8.13 (1H, d), 7.74 (1H, bs), 7.49 (1H, d), 4.32 (2H, t), 4.16-4.01 (1H, m), 3.18-3.07 (2H, m), 3.01 (2H, s), 2.86 (2H, t), 2.62 (2H, t), 2.06-1.88 (2H, m), 1.84-1.49 (6H, m).

MS m/z (M+H): 449.

Example 53

Synthesis of Compound 0053

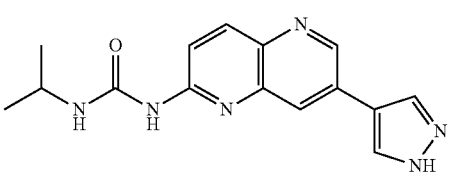

0053

A solution of the compound 0001-4 (25 mg) and isopropyl isocyanate (28 μL) in 1,4-dioxane (2 mL) was heated and stirred at 140° C. for 1 hour using a microwave reaction device. The reaction solution was cooled to room temperature, water (6 mL) was added thereto, and the mixture was subjected to sonication. The precipitated solid was filtered and washed with water (2 mL) to obtain a solid. A solution of the obtained solid, 1-tert-butoxycarbonyl-4-(4,4,5,5-tetramethyl-1,3,2-dioxaborolan-2-yl)pyrazole (71 mg), sodium carbonate (15 mg) and bis(di-tert-butyl (4-dimethylaminophenyl)phosphine)dichloropalladium (II) (7 mg) in water (0.1 mL) and 1,4-dioxane (1.9 mL) was stirred in a sealed tube at 100° C. for 9 hours under a nitrogen atmosphere. The reaction solution was cooled to room temperature, ethanol (6 mL) was added thereto, and, thereafter, the solvent was evaporated under reduced pressure. The residue was purified by silica gel chromatography (chloroform-methanol, NH silica). The solvent was evaporated under reduced pressure, ethyl acetate (3 mL) was added thereto, and the mixture was subjected to sonication. The precipitated solid was filtered and washed with ethyl acetate (1 mL) to obtain a compound 0053 (7.5 mg) as a white solid.

$^1$H-NMR (DMSO-d$_6$) δ: 13.21 (1H, s), 9.75 (1H, s), 9.14-9.08 (1H, m), 9.11 (1H, d), 8.56 (1H, s), 8.25 (1H, s), 8.25 (1H, s), 8.20 (1H, d), 7.48 (1H, d), 3.93 (1H, dq), 1.26 (6H, d)

MS m/z (M+H): 297. .

Example 54

Synthesis of Compound 0054

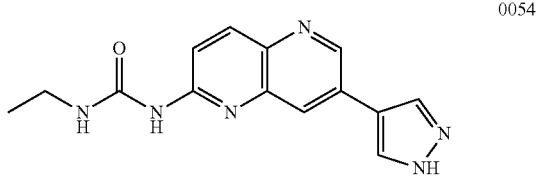 [SMILES: CCNC(=O)Nc1ccc2ncc(-c3cn[nH]c3)cc2n1]

0054

The same method as in Example 53 except for using ethyl isocyanate instead of isopropyl isocyanate in Example 53 was used to obtain a compound 0054 (2.3 mg) as a pale yellow solid.

$^1$H-NMR (DMSO-$d_6$) δ: 13.20 (1H, s), 9.82 (1H, s), 9.27 (1H, t), 9.11 (1H, d), 8.53 (1H, s), 8.36 (1H, d), 8.22 (1H, s), 8.20 (1H, d), 7.44 (1H, d), 3.34-3.27 (2H, m), 1.21 (3H, t).
MS m/z (M+H): 283.

Example 55

Synthesis of Compound 0055

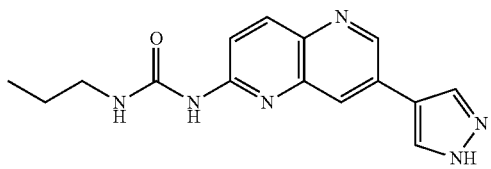

0055

The same method as in Example 53 except for using propyl isocyanate instead of isopropyl isocyanate in Example 53 was used to obtain a compound 0055 (3.2 mg) as a pale yellow solid.

$^1$H-NMR (DMSO-$d_6$) δ: 13.21 (1H, s), 9.82 (1H, s), 9.29 (1H, t), 9.11 (1H, d), 8.53 (1H, s), 8.31 (1H, d), 8.22 (1H, s), 8.20 (1H, d), 7.45 (1H, d), 3.30-3.20 (2H, m), 1.60 (2H, td), 0.96 (3H, t).
MS m/z (M+H): 297.

Example 56

Synthesis of Compound 0056

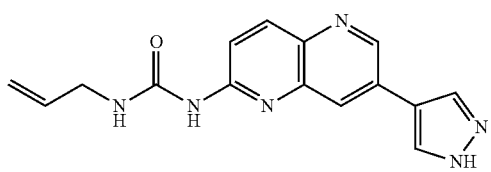

0056

The same method as in Example 53 except for using allyl isocyanate instead of isopropyl isocyanate in Example 53 was used to obtain a compound 0056 (4.0 mg) as a pale yellow solid.

$^1$H-NMR (DMSO-$d_6$) δ: 13.21 (1H, s), 11.06 (1H, s), 10.05 (1H, bs), 9.15 (1H, d), 8.58 (1H, s), 8.41 (1H, d), 8.33-8.12 (3H, m), 7.48 (1H, d), 6.77-6.64 (1H, m), 5.55-5.36 (1H, m), 3.38-3.26 (2H, m).
MS m/z (M+H): 295.

Example 57

Synthesis of Compound 0057

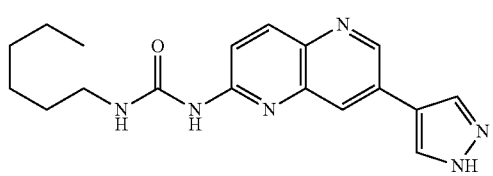

0057

The same method as in Example 53 except for using hexyl isocyanate instead of isopropyl isocyanate in Example 53 was used to obtain a compound 0057 (5.8 mg) as a pale yellow solid.

$^1$H-NMR (DMSO-$d_6$) δ: 13.21 (1H, s), 9.82 (1H, s), 9.31 (1H, s), 9.11 (1H, d), 8.52 (1H, s), 8.29 (1H, d), 8.21 (1H, d), 8.19 (1H, s), 7.44 (1H, d), 3.32-3.25 (2H, m), 1.63-1.54 (2H, m), 1.38-1.25 (6H, m), 0.87 (3H, t, J=6.9 Hz).
MS m/z (M+H): 340.

Example 58

Synthesis of Compound 0058

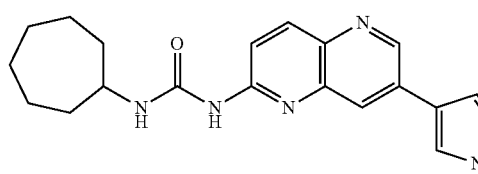

0058

The same method as in Example 53 except for using cycloheptyl isocyanate instead of isopropyl isocyanate in Example 53 was used to obtain a compound 0058 (15 mg) as a pale yellow solid.

$^1$H-NMR (DMSO-$d_6$) δ: 13.21 (1H, s), 9.77 (1H, s), 9.23 (1H, d), 9.11 (1H, d), 8.54 (1H, s), 8.22 (1H, s), 8.18 (1H, d), 8.16 (1H, d), 7.48 (1H, d), 3.92-3.78 (1H, m), 1.98-1.86 (2H, m), 1.74-1.46 (10H, m).
MS m/z (M+H): 351.

Example 59

Synthesis of Compound 0059

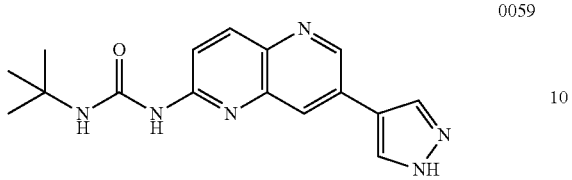

0059

The same method as in Example 53 except for using tert-butyl isocyanate instead of isopropyl isocyanate in Example 53 was used to obtain a compound 0059 (8.7 mg) as a pale yellow solid.

$^1$H-NMR (DMSO-$d_6$) δ: 13.21 (1H, s), 9.63 (1H, s), 9.27 (1H, bs), 9.10 (1H, d), 8.55 (1H, s), 8.23 (1H, s), 8.19 (1H, d), 8.13 (1H, d), 7.46 (1H, d), 1.43 (9H, s).

MS m/z (M+H): 311.

Example 60

Synthesis of Compound 0060

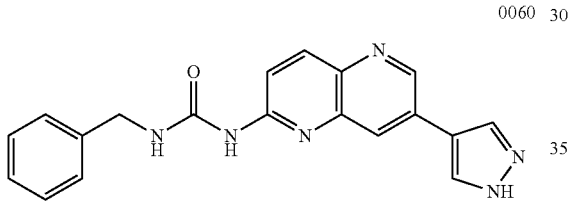

0060

The same method as in Example 53 except for using benzyl isocyanate instead of isopropyl isocyanate in Example 53 was used to obtain a compound 0060 (9.3 mg) as a pale yellow solid.

$^1$H-NMR (DMSO-$d_6$) δ: 13.20 (1H, s), 9.96 (1H, s), 9.73 (1H, t), 9.11 (1H, d), 8.51 (1H, s), 8.33 (1H, d), 8.23 (1H, d), 8.18 (1H, s), 7.49 (1H, d), 7.40-7.34 (4H, m), 7.30-7.22 (1H, m), 4.53 (2H, d).

MS m/z (M+H): 345.

Example 61

Synthesis of Compound 0061

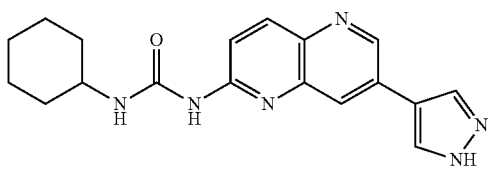

0061

The same method as in Example 53 except for using cyclohexyl isocyanate instead of isopropyl isocyanate in Example 53 was used to obtain a compound 0061 (6.7 mg) as a pale yellow solid.

$^1$H-NMR (DMSO-$d_6$) δ: 13.21 (1H, s), 9.78 (1H, s), 9.21 (1H, d), 9.11 (1H, d), 8.56 (1H, s), 8.26-8.17 (3H, m), 7.47 (1H, d), 3.72-3.57 (1H, d), 1.98-1.86 (2H, m), 1.79-1.66 (2H, m), 1.50-1.26 (6H, m).

MS m/z (M+H): 337.

Example 62

Synthesis of Compound 0062

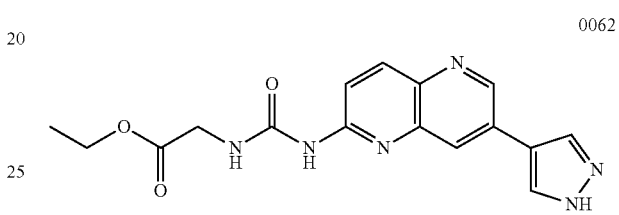

0062

A solution of the compound 0001-42, ethyl isocyanatoacetate (33 µL) in 1,4-dioxane (2 mL) was heated and stirred at 140° C. for 1 hour using a microwave reaction device. The reaction solution was cooled to room temperature, water (6 mL) was added thereto, and the mixture was subjected to sonication. The precipitated solid was filtered and washed with water (2 mL). A solution of the obtained solid, 1-tert-butoxycarbonyl-4-(4,4,5,5-tetramethyl-1,3,2-dioxaborolan-2-yl)pyrazole (72 mg), sodium carbonate (14 mg) and bis(di-tert-butyl (4-dimethylaminophenyl)phosphine) dichloropalladium (II) (6 mg) in water (0.1 mL) and 1,4-dioxane (1.9 mL) was stirred in a sealed tube at 100° C. for 9 hours under a nitrogen atmosphere. The reaction solution was cooled to room temperature, ethanol (6 mL) was added thereto, and, thereafter, the solvent was evaporated under reduced pressure. The residue was purified by silica gel column chromatography (chloroform-methanol, NH silica). The solvent was evaporated under reduced pressure, dichloromethane (0.9 mL) and trifluoroacetic acid (0.1 mL) were added thereto, and the mixture was stirred at room temperature for 16 hours. The solvent was evaporated under reduced pressure and the residue was purified by silica gel column chromatography (chloroform-methanol, NH silica). The solvent was evaporated under reduced pressure, ethyl acetate (3 mL) was added thereto, and the mixture was subjected to sonication. The precipitated solid was filtered and washed with ethyl acetate (1 mL) to obtain a compound 0062 (10 mg) as a pale yellow solid.

$^1$H-NMR (DMSO-$d_6$) δ: 10.06 (1H, s), 9.62 (1H, s), 9.13 (1H, d), 8.39 (1H, d), 8.33 (2H, s), 8.24 (1H, d), 7.46 (1H, d), 4.16 (2H, q), 4.08 (2H, d), 1.23 (3H, t).

MS m/z (M+H): 341.

Example 63

Synthesis of Compound 0063

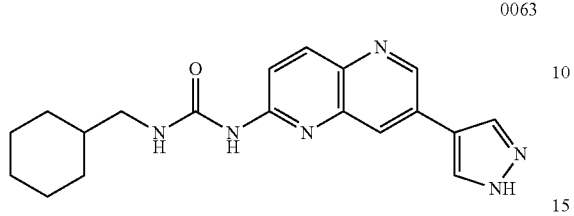

0063

The same method as in Example 53 except for using cyclohexylmethyl isocyanate instead of isopropyl isocyanate in Example 53 was used to obtain a compound 0063 (23 mg) as a pale yellow solid.

$^1$H-NMR (DMSO-$d_6$) δ: 9.83 (1H, s), 9.30 (1H, bs), 9.11 (1H, d), 8.35 (2H, bs), 8.24 (1H, d), 8.21 (1H, d), 7.47 (1H, d), 3.15 (3H, t), 1.83-1.49 (6H, m), 1.32-0.96 (5H, m).

MS m/z (M+H): 352.

Example 64

Synthesis of Compound 0064

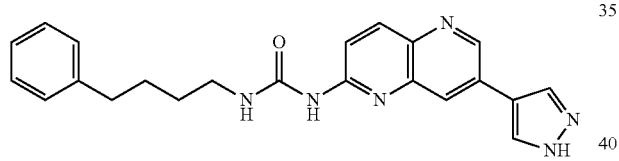

0064

A solution of the compound 0001-4 (32 mg) and phenyl chloroformate (28 μL) in pyridine (0.9 mL) was stirred at room temperature for 23 hours. 4-Phenylbutylamine (65 μL) was added thereto, and the mixture was then stirred at 50° C. for 6 hours. The reaction solution was cooled to room temperature and the solvent was concentrated. Water (1 mL) and a 6 M aqueous sodium hydroxide solution (30 μL) were added thereto and the mixture was subjected to sonication. The precipitated solid was filtered and washed with water (1 mL) and an aqueous methanol solution. A solution of the obtained solid, 1-tert-butoxycarbonyl 4-(4,4,5,5-tetramethyl-1,3,2-dioxaborolan-2-yl)pyrazole (84 mg), sodium carbonate (14 mg) and bis(di-tert-butyl (4-dimethylaminophenyl)phosphine)dichloropalladium (II) (7 mg) in water (100 μL) and 1,4-dioxane (1.9 mL) was stirred in a sealed tube at 100° C. for 8 hours under a nitrogen atmosphere. The reaction solution was cooled to room temperature, ethanol (4 mL) was added thereto, and then the solvent was evaporated. The residue was purified by silica gel chromatography (chloroform-methanol, NH silica). A fraction including a desired compound was concentrated, ethyl acetate (2 mL) was added thereto, and the mixture was subjected to sonication. The precipitated solid was separated by filtration and washed with ethyl acetate (1 mL) to obtain a pale yellow compound 0064 (30 mg) as a pale yellow solid.

$^1$H-NMR (DMSO-$d_6$) δ: 13.21 (1H, s), 9.83 (1H, s), 9.30 (1H, bt), 9.10 (1H, d), 8.48 (1H, s), 8.29 (1H, d), 8.20 (2H, d), 8.18 (1H, s), 7.44 (1H, d), 7.26-7.10 (5H, m), 2.66 (2H, t), 1.73-1.59 (4H, m).

MS m/z (M+H): 388.

Example 65

Synthesis of Compound 0065

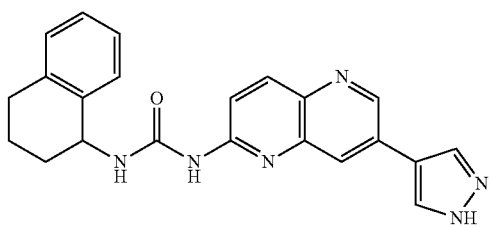

0065

The same method as in Example 64 except for using 1,2,3,4-tetrahydro-1-naphthylamine instead of 4-phenylbutylamine in Example 64 was used to obtain a compound 0065 (24 mg) as a pale yellow solid.

$^1$H-NMR (DMSO-$d_6$) δ: 13.19 (1H, s), 9.83 (1H, s), 9.36 (1H, d), 9.10 (1H, d), 8.48 (1H, s), 8.23 (1H, d), 8.13 (1H, s), 8.00 (1H, d), 7.62 (1H, d), 7.41-7.34 (1H, m), 7.23-7.12 (3H, m), 5.08-4.97 (1H, m), 2.98-2.71 (2H, m), 2.11-1.91 (4H, m).

MS m/z (M+H): 386.

Example 66

Synthesis of Compound 0066

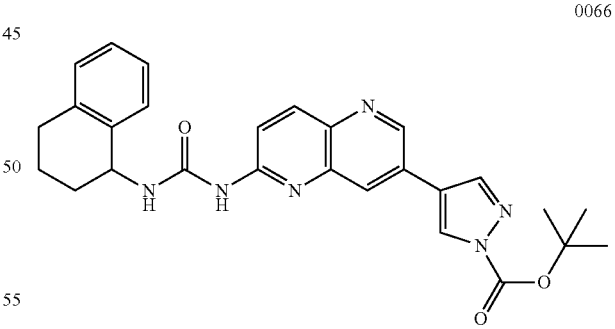

0066

The same method as in Example 64 except for using 1,2,3,4-tetrahydro-1-naphthylamine instead of 4-phenylbutylamine in Example 64 was used to obtain a compound 0066 (2.2 mg) as a pale yellow solid.

$^1$H-NMR (DMSO-$d_6$) δ: 9.84 (1H, s), 9.23 (1H, bs), 9.21 (1H, d), 9.04 (1H, s), 8.50 (1H, s), 8.27 (1H, d), 8.22 (1H, d), 7.72 (1H, d), 7.40-7.35 (1H, m), 7.21-7.13 (3H, m), 5.08-4.97 (1H, m), 2.97-2.70 (2H, m), 2.08-1.90 (4H, m), 1.62 (9H, s).

MS m/z (M+H): 486.

Example 67

Synthesis of Compound 0067

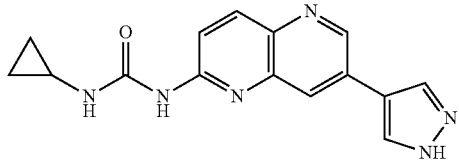

0067

The same method as in Example 64 except for using cyclopropylamine instead of 4-phenylbutylamine in Example 64 was used to obtain a compound 0067 (17 mg) as a pale yellow solid.

$^1$H-NMR (DMSO-$d_6$) δ: 13.20 (1H, bs), 9.83 (1H, s), 9.24 (1H, bs), 9.11 (1H, d), 8.56 (1H, s), 8.29 (1H, d), 8.26 (1H, s), 8.20 (1H, d), 7.46 (1H, d), 2.76-2.69 (1H, m), 0.78-0.61 (4H, m).

MS m/z (M+H): 295.

Example 68

Synthesis of Compound 0068

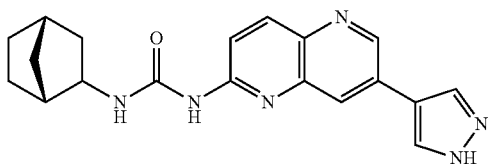

0068

The same method as in Example 64 except for using (1R, 2R, 4S)-bicyclo[2.2.1]heptan-2-amine instead of 4-phenylbutylamine in Example 64 was used to obtain a compound 0068 (10 mg) as a pale yellow solid.

$^1$H-NMR (DMSO-$d_6$) δ: 13.21 (1H, bs), 9.73 (1H, s), 9.11 (1H, d), 8.99 (1H, d), 8.55 (1H, s), 8.29 (1H, d), 8.25 (1H, s), 8.21 (1H, d), 7.52 (1H, d), 3.66-3.57 (1H, m), 2.31 (2H, bd), 1.78 (1H, ddd), 1.58-1.36 (4H, m), 1.24-1.15 (3H, m).

MS m/z (M+H): 349.

Example 69

Synthesis of Compound 0069

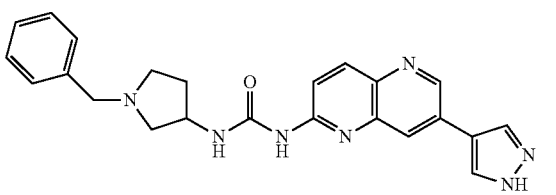

0069

The same method as in Example 64 except for using 1-benzyl-3-aminopyrrolidine instead of 4-phenylbutylamine in Example 64 was used to obtain a compound 0069 (14 mg) as a pale yellow solid.

$^1$H-NMR (DMSO-$d_6$) δ: 13.21 (1H, bs), 9.80 (1H, s), 9.31 (1H, bd), 9.12 (1H, d), 8.50 (1H, bs), 8.24-8.16 (3H, m), 7.51 (1H, d), 7.38-7.17 (5H, m), 4.26 (1H, bs), 3.66 (2H, s), 2.83-2.56 (3H, m), 2.45-2.20 (2H, m), 1.84-1.71 (1H, m).

MS m/z (M+H): 415.

Example 70

Synthesis of Compound 0070

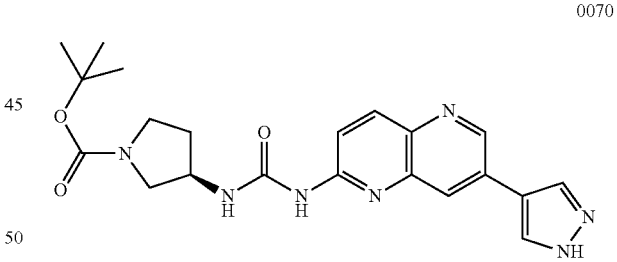

0070

The same method as in Example 64 except for using (3R)-1-(tert-butoxycarbonyl)-3-aminopyrrolidine instead of 4-phenylbutylamine in Example 64 was used to obtain a compound 0070 (7.7 mg) as a pale yellow solid.

$^1$H-NMR (DMSO-$d_6$) δ: 13.22 (1H, s), 9.91 (1H, d), 9.71 (0.5H, bd), 9.52 (0.5H, bs), 9.12 (1H, s), 8.54 (1H, d), 8.31-8.16 (3H, m), 7.46 (1H, t), 4.41-4.21 (1H, m), 3.55-3.16 (5H, m), 2.16-1.91 (2H, m), 1.37 (9H, s).

MS m/z (M+H): 424.

Example 71

Synthesis of Compound 0071

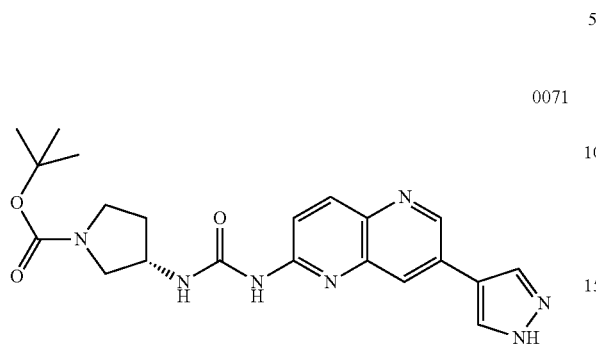

0071

The same method as in Example 64 except for using (3S)-1-(tert-butoxycarbonyl)-3-aminopyrrolidine instead of 4-phenylbutylamine in Example 64 was used to obtain a compound 0071 (8.2 mg) as a pale yellow solid.

$^1$H-NMR (DMSO-$d_6$) δ: 13.22 (1H, s), 9.91 (1H, d), 9.71 (0.5H, bd), 9.52 (0.5H, bs), 9.12 (1H, s), 8.54 (1H, d), 8.31-8.16 (3H, m), 7.46 (1H, t), 4.41-4.21 (1H, m), 3.55-3.16 (5H, m), 2.16-1.91 (2H, m), 1.37 (9H, s).

MS m/z (M+H): 424.

Example 72

Synthesis of Compound 0072

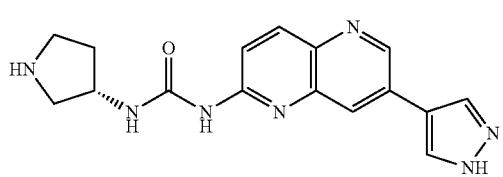

0072

The same method as in Example 64 except for using 1,2-dimethylpropylamine instead of 4-phenylbutylamine in Example 64 was used to obtain a compound 0072 (9.7 mg) as a pale yellow solid.

$^1$H-NMR (DMSO-$d_6$) δ: 13.22 (1H, s), 9.78 (1H, s), 9.19 (1H, d), 9.11 (1H, d), 8.54 (1H, s), 8.21 (1H, s), 8.21 (1H, d), 8.14 (1H, d), 7.49 (1H, d), 3.81-3.68 (1H, m), 1.91-1.79 (1H, m), 1.18 (3H, d), 0.99 (3H, d), 0.95 (3H, d).

MS m/z (M+H): 326.

Example 73

Synthesis of Compound 0073

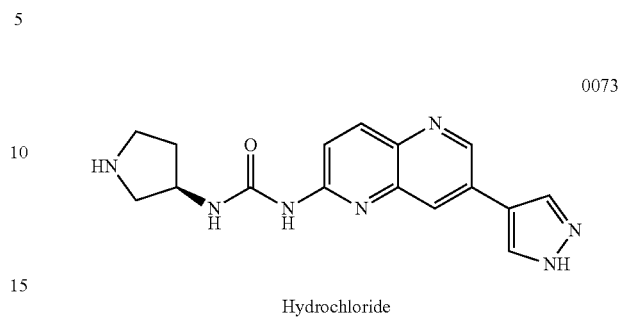

0073

Hydrochloride

To a solution of the compound 0070 in ethanol (0.75 mL), a 4 M hydrogen chloride/1,4-dioxane solution (0.25 mL) was added, and the mixture was stirred at room temperature for 18 hours. The solvent was evaporated, tetrahydrofuran was added thereto, and the mixture was subjected to sonication. The precipitated solid was separated by filtration and washed with tetrahydrofuran (1 mL) to obtain a compound 0073 hydrochloride (24 mg) as a yellow solid.

$^1$H-NMR (DMSO-$d_6$) δ: 10.09 (1H, s), 9.64 (1H, d), 9.53 (1H, bs), 9.18 (1H, d), 9.08 (1H, bs), 8.59 (1H, d), 8.47 (2H, s), 8.28 (1H, d), 7.49 (1H, d), 4.56-4.44 (1H, m), 3.52-3.26 (4H, m), 2.29 (1H, dt), 2.11 (1H, dt).

MS m/z (M+H): 324.

Example 74

Synthesis of Compound 0074

0074

Hydrochloride

The same method as in Example 73 except for using the compound 0071 instead of the compound 0070 in Example 73 was used to obtain a compound 0074 hydrochloride (21 mg) as a yellow solid.

$^1$H-NMR (DMSO-$d_6$) δ: 10.09 (1H, s), 9.65 (1H, d), 9.56 (1H, s), 9.18 (1H, d), 9.09 (1H, s), 8.61 (1H, d), 8.47 (2H, s), 8.28 (1H, d), 7.50 (1H, d, J=9.2 Hz), 4.56-4.44 (1H, m), 3.52-3.24 (4H, m), 2.29 (1H, dt), 2.10 (1H, td).

MS m/z (M+H): 324.

Example 75

Synthesis of Compound 0075

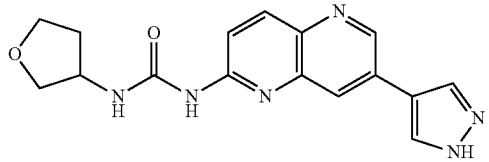

0075

The same method as in Example 64 except for using tetrahydrofuran-3-amine instead of 4-phenylbutylamine in Example 64 was used to obtain a compound 0075 (9.7 mg) as a pale yellow solid.

$^1$H-NMR (DMSO-$d_6$) δ: 13.21 (1H, s), 9.86 (1H, s), 9.34 (1H, d), 9.12 (1H, d), 8.55 (1H, s), 8.24 (1H, s), 8.23 (1H, d), 8.22 (1H, d), 7.51 (1H, d), 4.41-4.29 (1H, m), 3.98-3.75 (3H, m), 3.67 (1H, dd), 2.31-2.19 (1H, m), 2.03-1.90 (1H, m).

MS m/z (M+H): 325.

Example 76

Synthesis of Compound 0076

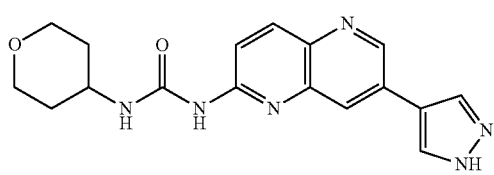

0076

The same method as in Example 64 except for using tetrahydro-2H-pyran-4-amine instead of 4-phenylbutylamine in Example 64 was used to obtain a compound 0076 (58 mg) as a pale yellow solid.

$^1$H-NMR (DMSO-$d_6$) δ: 13.21 (1H, s), 9.84 (1H, s), 9.35 (1H, d), 9.12 (1H, d), 8.57 (1H, s), 8.27 (1H, d), 8.26 (1H, s), 8.21 (1H, d), 7.45 (1H, d), 3.95-3.80 (3H, m), 3.49-3.40 (2H, m), 1.95-1.85 (2H, m), 1.74-1.58 (2H, m).

MS m/z (M+H): 339.

Example 77

Synthesis of Compound 0077

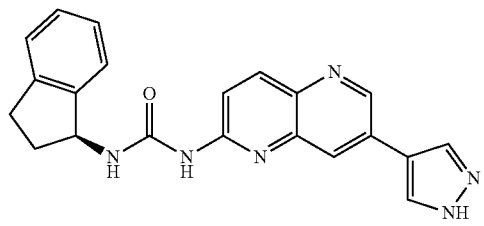

0077

The same method as in Example 64 except for using (2S)-2,3-dihydro-1H-inden-1-amine instead of 4-phenylbutylamine in Example 64 was used to obtain a compound 0077 (27 mg) as a pale yellow solid.

$^1$H-NMR (DMSO-$d_6$) δ: 12.34 (1H, s), 9.04 (1H, s), 8.55 (1H, d), 8.25 (1H, d), 7.64 (1H, bs), 7.39 (1H, d), 7.32 (1H, bs), 7.24 (1H, d), 6.75 (1H, d), 6.55-6.37 (4H, m), 4.48 (1H, q), 2.22-1.99 (2H, m), 1.78-1.64 (1H, m), 1.26-1.13 (1H, m).

MS m/z (M+H): 371.

Example 78

Synthesis of Compound 0078

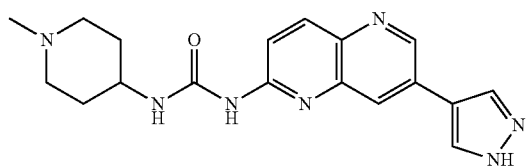

0078

The same method as in Example 64 except for using 1-methylpiperidin-4-amine instead of 4-phenylbutylamine in Example 64 was used to obtain a compound 0078 (26 mg) as a pale yellow solid.

$^1$H-NMR (DMSO-$d_6$) δ: 9.82 (1H, s), 9.33 (1H, bd), 9.11 (1H, d), 8.40 (1H, bs), 8.24 (1H, d), 8.21 (1H, d), 7.72 (1H, bs), 7.44 (1H, d), 3.65 (1H, s), 2.75-2.65 (2H, m), 2.20 (3H, s), 2.17-2.05 (2H, m), 1.94-1.83 (2H, m), 1.71-1.57 (2H, m).

MS m/z (M+H): 352.

Example 79

Synthesis of Compound 0079

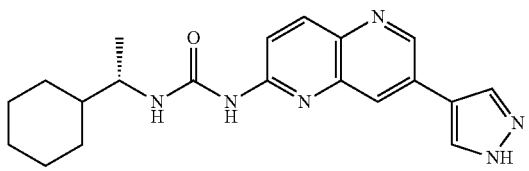

0079

The same method as in Example 64 except for using (1R)-1-cyclohexylethanamine instead of 4-phenylbutylamine in Example 64 was used to obtain a compound 0079 (22 mg) as a pale yellow solid.

$^1$H-NMR (DMSO-$d_6$) δ: 13.22 (1H, s), 9.77 (1H, s), 9.26 (1H, d), 9.11 (1H, d), 8.52 (1H, s), 8.21 (1H, d), 8.18 (1H, s), 8.13 (1H, d), 7.47 (1H, d), 3.75-3.66 (1H, m), 1.91-1.61 (5H, m), 1.56-1.43 (1H, m), 1.33-1.03 (8H, m).

MS m/z (M+H): 365.

Example 80

Synthesis of Compound 0080

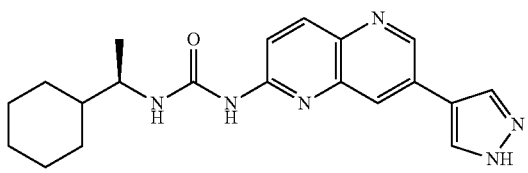

0080

The same method as in Example 64 except for using (1S)-1-cyclohexylethanamine instead of 4-phenylbutylamine in Example 64 was used to obtain a compound 0080 (25 mg) as a pale yellow solid.

$^1$H-NMR (DMSO-$d_6$) δ: 13.22 (1H, s), 9.77 (1H, s), 9.26 (1H, d), 9.11 (1H, d), 8.52 (1H, s), 8.21 (1H, d), 8.18 (1H, s), 8.13 (1H, d), 7.47 (1H, d), 3.75-3.66 (1H, m), 1.91-1.61 (5H, m), 1.56-1.43 (1H, m), 1.33-1.03 (8H, m).

MS m/z (M+H): 365.

Example 81

Synthesis of Compound 0081

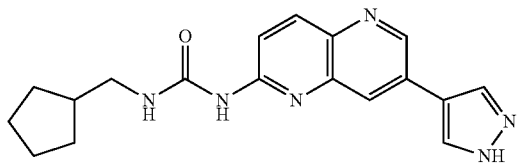

0081

The same method as in Example 64 except for using cyclopentylmethylamine instead of 4-phenylbutylamine in Example 64 was used to obtain a compound 0081 (17 mg) as a pale yellow solid.

$^1$H-NMR (DMSO-$d_6$) δ: 13.21 (1H, s), 9.82 (1H, s), 9.31 (1H, s), 9.11 (1H, d), 8.52 (1H, s), 8.24 (1H, d), 8.21 (1H, d), 8.20 (1H, s), 7.47 (1H, d), 3.23 (2H, dd), 2.23-2.13 (1H, m), 1.83-1.70 (2H, m), 1.67-1.50 (4H, m), 1.34-1.25 (2H, m).

MS m/z (M+H): 337.

Example 82

Synthesis of Compound 0082

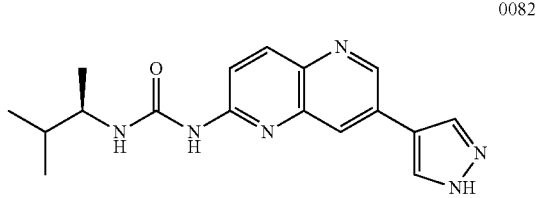 [SMILES: CC(C)[C@@H](C)NC(=O)Nc1ccc2ncc(-c3cn[nH]c3)cc2n1]

0082

The same method as in Example 64 except for using (2R)-3-methylbutan-2-amine instead of 4-phenylbutylamine in Example 64 was used to obtain a compound 0082 (21 mg) as a pale yellow solid.

$^1$H-NMR (DMSO-$d_6$) δ: 13.21 (1H, s), 9.78 (1H, s), 9.19 (1H, d), 9.11 (1H, d), 8.54 (1H, s), 8.21 (1H, d), 8.20 (1H, s), 8.14 (1H, d), 7.49 (1H, d), 3.74 (1H, dq), 1.91-1.79 (1H, m), 1.20-1.15 (3H, d), 0.99 (3H, d), 0.95 (3H, d).

MS m/z (M+H): 325.

Example 83

Synthesis of Compound 0083

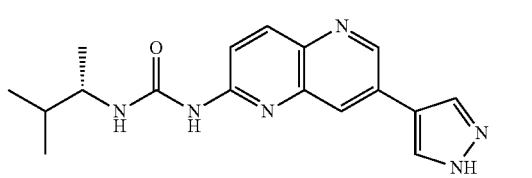

0083

The same method as in Example 64 except for using (2S)-3-methylbutan-2-amine instead of 4-phenylbutylamine in Example 64 was used to obtain a compound 0083 (19 mg) as a pale yellow solid.

$^1$H-NMR (DMSO-$d_6$) δ: 13.21 (1H, s), 9.78 (1H, s), 9.19 (1H, d), 9.11 (1H, d), 8.54 (1H, s), 8.21 (1H, d), 8.20 (1H, s), 8.14 (1H, d), 7.49 (1H, d), 3.74 (1H, dq), 1.91-1.79 (1H, m), 1.20-1.15 (3H, d), 0.99 (3H, d), 0.95 (3H, d).

MS m/z (M+H): 325.

Example 84

Synthesis of Compound 0084

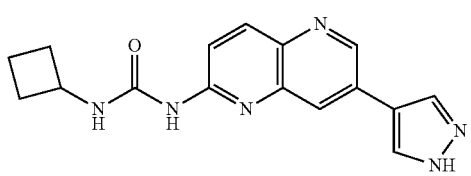

0084

The same method as in Example 64 except for using cyclobutylamine instead of 4-phenylbutylamine in Example 64 was used to obtain a compound 0084 (22 mg) as a pale yellow solid.

$^1$H-NMR (DMSO-$d_6$) δ: 9.81 (1H, s), 9.35 (1H, d), 9.13 (1H, d), 8.43 (2H, s), 8.35 (1H, d), 8.22 (1H, d), 7.49 (1H, d), 4.28 (1H, dt), 2.35-2.25 (2H, m), 2.19-2.03 (2H, m), 1.80-1.62 (2H, m).

MS m/z (M+H): 310.

Example 85

Synthesis of Compound 0085

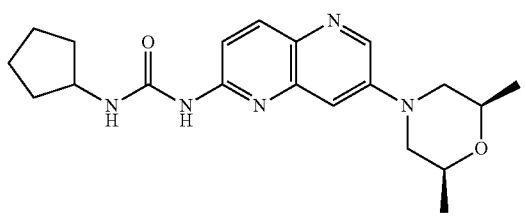

0085

A solution of the compound 0001-5 (34 mg), cis-2,6-dimethylmorpholine (21 μL), cesium carbonate (52 mg), 4,5-bis(diphenylphosphino)-9,9-dimethylxanthene (13 mg) and tris(dibenzylideneacetone)dipalladium (0) (12 mg) in 1,4-dioxane (2 mL) was stirred in a sealed tube at 100° C. for 4 hours under a nitrogen atmosphere. The reaction solution was cooled to room temperature, and the solvent of the reaction solution was then evaporated. The residue was purified by silica gel chromatography (chloroform-ethyl acetate and chloroform-methanol, NH silica). The solvent was evaporated under reduced pressure, diisopropyl ether (4 mL) was then added thereto, and the mixture was subjected to sonication. The precipitated solid was separated by filtration and washed with diisopropyl ether to obtain a compound 0085 (14 mg) as a pale yellow solid.

$^1$H-NMR (DMSO-$d_6$) δ: 9.58 (1H, s), 9.16 (1H, d), 8.72 (1H, d), 8.07 (1H, d), 7.30 (1H, d), 7.19 (1H, d), 4.09-4.02 (1H, m), 3.86 (2H, d), 3.78-3.72 (2H, m), 1.99-1.86 (2H, m), 1.75-1.52 (6H, m), 1.19 (6H, d).

MS m/z (M+H): 371.

Example 86

Synthesis of Compound 0086

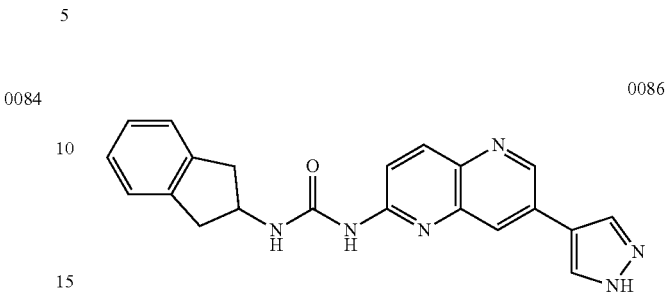

0086

The same method as in Example 64 except for using 2-aminoindane instead of 4-phenylbutylamine in Example 64 was used to obtain a compound 0086 (12 mg) as a pale yellow solid.

$^1$H-NMR (DMSO-$d_6$) δ: 13.21 (1H, s), 9.85 (1H, s), 9.69 (1H, d), 9.08 (1H, d), 8.49 (1H, s), 8.19 (1H, d), 8.17 (1H, s), 7.94 (1H, d), 7.44 (1H, d), 7.34 (2H, dd), 7.20 (2H, dd), 4.60 (1H, dd), 2.36-3.24 (2H, m), 2.99 (2H, dd).

MS m/z (M+H): 371.

Example 87

Synthesis of Compound 0087

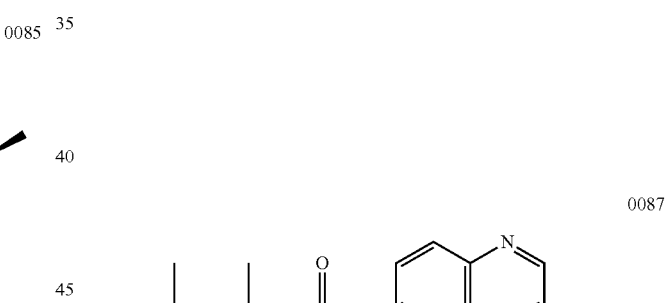

0087

The same method as in Example 64 except for using 4-methylpentan-2-amine instead of 4-phenylbutylamine in Example 64 was used to obtain a compound 0087 (22 mg) as a pale yellow solid.

$^1$H-NMR (DMSO-$d_6$) δ: 13.21 (1H, s), 9.73 (1H, s), 9.11 (1H, d), 9.10 (1H, bd), 8.55 (1H, s), 8.24-8.18 (3H, m), 7.48 (1H, d), 3.96-3.86 (1H, m), 1.72 (1H, td), 1.64-1.54 (1H, m), 1.40-1.31 (1H, m), 1.22 (3H, d), 0.94 (3H, d), 0.92 (3H, d).

MS m/z (M+H): 339.

Example 88

Synthesis of Compound 0088

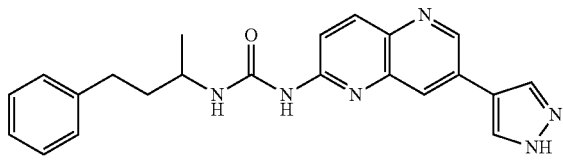

0088

The same method as in Example 64 except for using 4-phenylbutan-2-amine instead of 4-phenylbutylamine in Example 64 was used to obtain a compound 0088 (31 mg) as a pale yellow solid.

$^1$H-NMR (DMSO-d$_6$) δ: 13.21 (1H, s), 9.79 (1H, s), 9.27 (1H, d), 9.11 (1H, d), 8.52 (1H, s), 8.24 (1H, d), 8.21 (1H, d), 8.21 (1H, s), 7.48 (1H, d), 7.27-7.11 (5H, m), 3.89-3.80 (1H, m), 2.80-2.63 (2H, m), 2.02-1.80 (2H, m), 1.28 (3H, d).

MS m/z (M+H): 388.

Example 89

Synthesis of Compound 0089

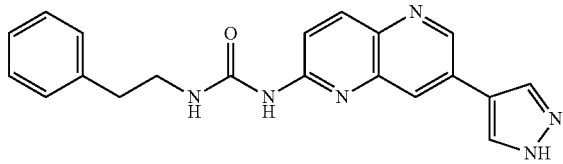

0089

The same method as in Example 64 except for using 2-phenylethanamine instead of 4-phenylbutylamine in Example 64 was used to obtain a compound 0089 (21 mg) as a pale yellow solid.

$^1$H-NMR (DMSO-d$_6$) δ: 13.23 (1H, s), 9.88 (1H, s), 9.36 (1H, s), 9.09 (1H, d), 8.50 (1H, s), 8.19 (1H, d), 8.17 (1H, s), 8.03 (1H, d), 7.40 (1H, d), 7.36-7.17 (5H, m), 3.59 (2H, dt), 2.91 (2H, t).

MS m/z (M+H): 360.

Example 90

Synthesis of Compound 0090

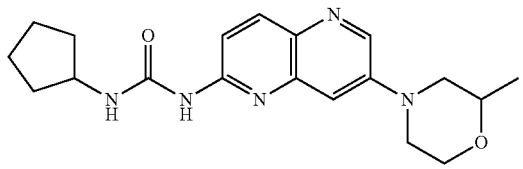

0090

The same method as in Example 85 except for using 2-methylmorpholine instead of cis-2,6-dimethylmorpholine in Example 85 was used to obtain a compound 0090 (11 mg) as a pale yellow solid.

$^1$H-NMR (DMSO-d$_6$) δ: 9.61 (1H, s), 9.22 (1H, d), 8.72 (1H, d), 8.07 (1H, d), 7.28 (1H, d), 7.19 (1H, d), 4.12-3.86 (3H, m), 3.79-3.62 (3H, m), 2.90-2.79 (1H, m), 1.99-1.88 (2H, m), 1.73-1.51 (6H, m), 1.19 (3H, d).

MS m/z (M+H): 357.

Example 91

Synthesis of Compound 0091

(Synthesis of Compound 0091-1)

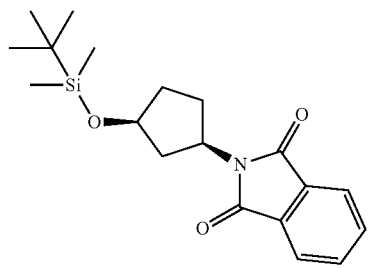

0091-1

A solution of trans-3-(tert-butyldimethylsilyloxy)cyclopentanol (302 mg, synthesized according to US2004/0204427A1), triphenylphosphine (734 mg) and phthalimide (414 mg) in tetrahydrofuran (9 mL) was cooled in an ice bath, a 40% diethyl azodicarboxylic acid solution in toluene (1.25 mL) was added thereto, and the mixture was warmed to room temperature and then stirred for 10 hours. The solvent was evaporated under reduced pressure and then subjected to liquid separation with ethyl acetate (30 mL) and water (10 mL). The organic layer was washed with brine and dried over sodium sulfate. The solvent was evaporated under reduced pressure and the residue was then purified by silica gel chromatography (hexane-ethyl acetate) to obtain a compound 0091-1 (276 mg) as a colorless oily substance.

$^1$H-NMR (CDCl$_3$) δ: 7.82 (2H, dd), 7.69 (2H, dd), 4.60-4.46 (1H, m), 4.28-4.16 (1H, m), 2.42-2.08 (3H, m), 2.05-1.80 (3H, m), 0.90 (9H, s), 0.07 (3H, s), 0.06 (3H, s).

(Synthesis of Compound 0091-2)

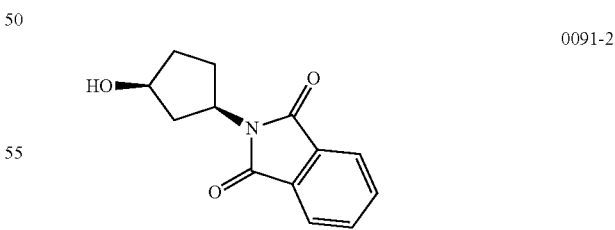

0091-2

To a solution of the compound 0091-1 (277 mg) and acetic acid (48 μL) in tetrahydrofuran (5 mL), a 1 M tetrabutylammonium fluoride solution in tetrahydrofuran (0.84 mL) was added under ice-cooling, and the reaction solution was warmed to 40° C. and stirred for 10 hours. After cooling to room temperature, the solvent was evaporated and the residue was subjected to liquid separation with ethyl acetate (20 mL) and water (5 mL). The solvent was evaporated under reduced pressure, the residue was then dried over sodium sulfate, and the solvent was evaporated. The obtained residue was purified by silica gel chromatography (hexane-ethyl acetate) to obtain a compound 0091-2 (102 mg) as a white solid.

$^1$H-NMR (CDCl$_3$) δ: 7.85 (2H, dd), 7.73 (2H, dd), 4.86-4.72 (1H, m), 4.38-4.29 (1H, m), 2.49-2.36 (1H, m), 2.32-2.18 (1H, m), 2.11-1.94 (3H, m), 1.74-1.61 (1H, m).

(Synthesis of Compound 0091-3)

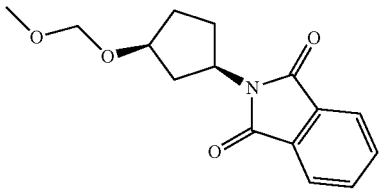

0091-3

To a solution of the compound 0091-2 (202 mg) and N,N-diisopropylethylamine (0.27 mL) in acetonitrile (3 mL), chloromethylmethyl ether (0.1 mL) was added, and the mixture was stirred at 50° C. for 10 hours. After cooling to room temperature, N,N-diisopropylethylamine (0.09 mL) and chloromethylmethyl ether (34 μL) were further added thereto, and the mixture was stirred at 50° C. for 10 hours. After cooling to room temperature, the mixture was subjected to liquid separation by addition of toluene (6 mL), ethyl acetate (3 mL), and water (3 mL), and further, the aqueous layer was washed with ethyl acetate (3 mL) twice. The organic layer was washed with brine and dried over sodium sulfate, the solvent was evaporated under reduced pressure, and the residue was then purified by silica gel chromatography (hexane-ethyl acetate) to obtain a compound 0091-3 (227 mg) as a colorless oily substance.

$^1$H-NMR (CDCl$_3$) δ: 7.83 (2H, dd), 7.70 (2H, dd), 4.69 (2H, dd), 4.64-4.51 (1H, m), 4.20-4.08 (1H, m), 3.39 (3H, s), 2.43-2.22 (3H, m), 2.16-1.78 (3H, m).

(Synthesis of Compound 0091-4)

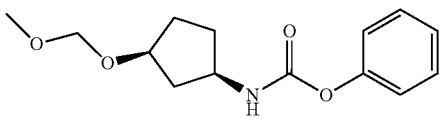

0091-4

A solution of the compound 0091-3 (227 mg) and hydrazine monohydrate (80 μL) in tetrahydrofuran (4 mL) was stirred at 45° C. for 5.5 hours. The reaction solution was cooled to room temperature and filtered over celite, and the residue was washed with ethyl acetate. The collected filtrate was washed with brine and dried over sodium sulfate, and then the solvent was evaporated under reduced pressure. To a solution of the obtained oily substance and triethylamine (0.34 mL) in tetrahydrofuran was added phenyl chloroformate (0.21 mL) under ice-cooling, and the mixture was stirred at room temperature for 2.5 hours. After completion of the reaction, isopropanol (1 mL) was added thereto, and the solvent was evaporated and the residue was subjected to liquid separation with ethyl acetate (4 mL) and water (1 mL). The aqueous layer was extracted with ethyl acetate (2 mL) twice. The collected organic layer was washed with brine, dried over sodium sulfate, and purified by silica gel chromatography (hexane-ethyl acetate) to obtain a compound 0091-4 (139 mg) as a colorless oily substance.

MS m/z (M+H): 266.

(Synthesis of Compound 0091-5)

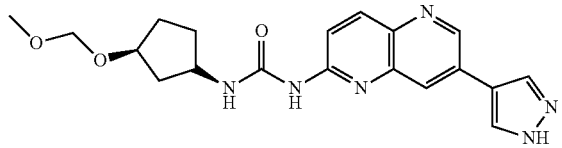

To a solution of the compound 0001-4 (30 mg) in N,N-dimethylformamide (0.7 mL), a 60% sodium hydride was added under ice-cooling, and the mixture was stirred at the same temperature for 15 minutes. To the reaction solution, a solution of the compound 0091-4 (45 mg) in N,N-dimethylformamide (0.2 mL) was added, and the mixture was warmed to room temperature and then stirred for 18 hours. To the reaction solution, water (3 mL) was added, and the mixture was subjected to sonication. The precipitated solid was separated by filtration and the solid was washed with water and an aqueous methanol solution. A solution of the obtained solid, 1-tert-butoxycarbonyl-4-(4,4,5,5-tetramethyl-1,3,2-dioxaborolan-2-yl)pyrazole (83 mg), sodium carbonate (16 mg), and bis(di-tert-butyl (4-dimethylaminophenyl)phosphine) dichloropalladium (II)) (7 mg) in water (0.10 mL) and 1,4-dioxane (1.9 mL) was stirred in a sealed tube at 100° C. for 7.5 hours under a nitrogen atmosphere. The reaction solution was cooled to room temperature, and then ethanol (4 mL) was added to the reaction solution, the solvent was evaporated under reduced pressure, and the residue was purified by silica gel chromatography (chloroform-methanol, NH silica). A fraction containing a desired compound was concentrated, acetonitrile (1 mL) was added thereto, and the mixture was subjected to sonication. The precipitated solid was separated by filtration and the solid was washed with acetonitrile (1 mL) to obtain a pale yellow compound 0091-5 (23 mg).

$^1$H-NMR (DMSO-d$_6$) δ: 9.80 (1H, s), 9.36 (1H, d), 9.10 (1H, d), 8.34 (1H, s), 8.23-8.18 (3H, m), 7.47 (1H, d), 4.63 (2H, dd), 4.27-4.16 (2H, m), 3.22 (3H, s), 2.26-1.60 (6H, m).

MS m/z (M+H): 383.

(Synthesis of Compound 0091)

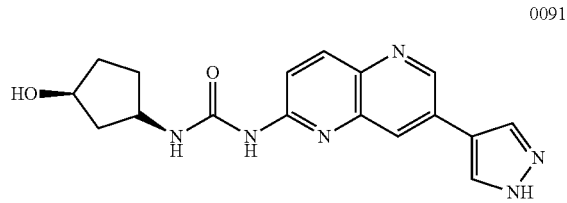

0091

The same method as in Example 73 except for using the compound 0091-5 instead of the compound 0070 used for the synthesis of the compound 0073 in Example 73 was used to obtain a compound 0091 (9.4 mg) as a yellow solid.

$^1$H-NMR (DMSO-d$_6$) δ: 9.85 (1H, s), 9.74 (1H, d), 9.13 (1H, d), 8.36 (2H, s), 8.29 (1H, d), 8.21 (1H, d), 7.42 (1H, d), 4.34-4.20 (2H, d), 2.09-1.51 (6H, m).

MS m/z (M+H): 339.

Example 92

Synthesis of Compound 0092

(Synthesis of Compound 0092-1)

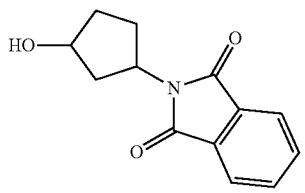

The same method as in Example 91 except for using 3-(tert-butyldimethylsiloxy)cyclopentanol (synthesized according to US2004/0204427A1) instead of trans-3-(tert-butyldimethylsiloxy)cyclopentanol in Example 91 was used to obtain a compound 0092-1 (1.17 g) as a white solid.

(Synthesis of Compound 0092-2)

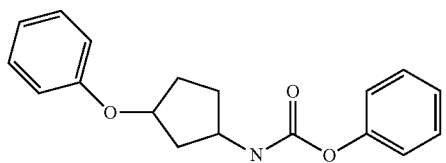

A 40% diethyl azodicarboxylic acid solution in toluene (1.25 mL) was added to a solution of the compound 0092-1 (204 mg), triphenylphosphine (340 mg), and phenol (132 mg) in tetrahydrofuran (4 mL) at room temperature, and the mixture was warmed to 50° C. and stirred for 6 hours. The reaction solution was cooled to room temperature, and then the solvent was evaporated under reduced pressure. The residue was subjected to liquid separation with ethyl acetate (6 mL) and water (2 mL). Then, the aqueous layer was extracted with ethyl acetate (3 mL). The collected organic layer was washed with brine and dried over sodium sulfate. The solvent was evaporated and the residue was then purified by silica gel column chromatography (hexane-ethyl acetate, NH silica). A solution of the obtained solid and hydrazine monohydrate (84 μL) in tetrahydrofuran (5 mL) was stirred at 50° C. for 6 hours. After cooling to room temperature, the solution was subjected to filtering over celite, and the residue was washed with ethyl acetate (2 mL) twice. Toluene (2 mL), brine (1 mL), and a 1 M aqueous sodium hydroxide solution (1 mL) were added to the filtrate to perform liquid separation. Then, the aqueous layer was extracted with ethyl acetate (3 mL) twice. The collected organic layer was dried over sodium sulfate and the solvent was evaporated. To a solution of the obtained oily substance and triethylamine (0.36 mL) in tetrahydrofuran (5 mL), phenyl chloroformate (0.22 mL) was added under ice-cooling, and the mixture was stirred at room temperature for 15 hours. The solvent of the reaction solution was evaporated, and the residue was subjected to liquid separation with ethyl acetate (6 mL) and water (2 mL). The aqueous layer was extracted with 3 mL of ethyl acetate twice. The collected organic layer was washed with brine and then dried over sodium sulfate, and the solvent was evaporated under reduced pressure. The residue was purified by silica gel column chromatography (hexane-ethyl acetate) to obtain a compound 0092-2 (120 mg) as a white solid.

MS m/z (M+H): 298.

(Synthesis of Compound 0092)

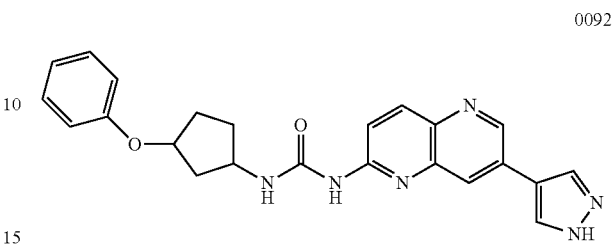

The same method as in Example 91 except for using the compound 0092-2 instead of the compound 0091-4 in Example 91 was used to obtain a compound 0092 (21 mg) as a yellow solid.

$^1$H-NMR (DMSO-$d_6$) δ: 13.21 (1H, s), 9.83 (1H, s), 9.35 (1H, d), 9.12 (1H, d), 8.55 (1H, s), 8.27 (1H, d), 8.25 (1H, s), 8.21 (1H, d), 7.47 (1H, d), 7.33-7.25 (1H, m), 6.97-6.86 (4H, m), 5.02-4.93 (1H, m), 4.40-4.22 (1H, m), 2.35-1.65 (6H, m).

MS m/z (M+H): 416.

Example 93

Synthesis of Compound 0093

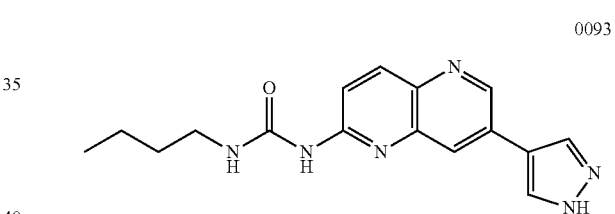

The same method as in Example 53 except for using butyl isocyanate instead of isopropyl isocyanate in Example 53 was used to obtain a compound 0093 (4 mg) as a white solid.

$^1$H-NMR (DMSO-$d_6$) δ: 13.22 (1H, bs), 9.83 (1H, s), 9.27 (1H, t), 9.11 (1H, d), 8.51-8.16 (4H, m), 7.45 (1H, d), 3.28 (2H, t), 1.63-1.53 (2H, m), 1.42-1.38 (2H, m), 0.95 (3H, t).

MS m/z (M+H): 311.

Example 94

Synthesis of Compound 0094

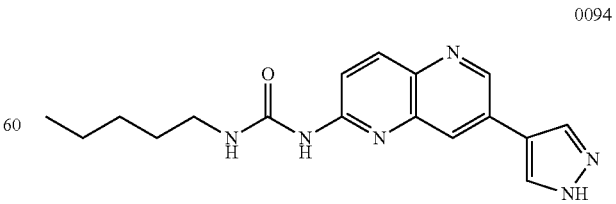

The same method as in Example 53 except for using pentyl isocyanate instead of isopropyl isocyanate in Example 53 was used to obtain a compound 0094 (7 mg) as a white solid.

¹H-NMR (DMSO-d₆) δ: 13.21 (1H, s), 9.82 (1H, s), 9.29 (1H, t), 9.11 (1H, d), 8.52 (1H, s), 8.29 (1H, d), 8.21 (2H, d), 7.44 (1H, d), 3.29 (2H, dd), 1.59 (2H, t), 1.41-1.33 (4H, m), 0.91 (3H, t).

MS m/z (M+H): 325.

Example 95

Synthesis of Compound 0095

(Synthesis of Compound 0095-1)

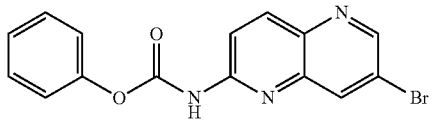

0095-1

Pyridine (9 mL) was added to the compound 0001-4 (300 mg) and phenyl chloroformate (280 μL), and the mixture was stirred at room temperature for 2 hours. Further, phenyl chloroformate (140 μL) was added thereto, and the mixture was stirred at room temperature for 1 hour. The solvent of the reaction solution was evaporated under reduced pressure and the residue was purified by silica gel column chromatography (chloroform-methanol). The obtained solid was washed with an ethyl acetate-hexane mixed solution (1:2) and dried under reduced pressure to obtain a compound 0095-1 (310 mg) as a white solid.

¹H-NMR (DMSO-d₆) δ: 11.41 (1H, s), 8.95 (1H, d), 8.47-8.46 (2H, m), 8.33 (1H, d), 7.47-7.45 (2H, m), 7.30-7.27 (3H, m).

MS m/z (M+H): 344, 346.

(Synthesis of Compound 0095)

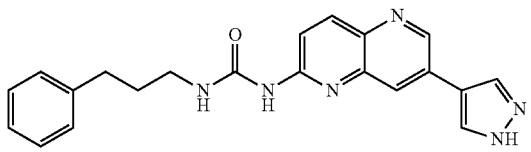

0095

To the compound 0095-1 (20 mg) and 3-phenylpropylamine (15 μL) was added 1,4-dioxane (1 mL), and the mixture was stirred at 130° C. for 0.5 hours using a microwave reaction device. To this reaction solution, 1-tert-butoxycarbonyl-4-(4,4,5,5-tetramethyl-1,3,2-dioxaborolan-2-yl)pyrazole (30 mg), a 2 M aqueous sodium carbonate solution (100 μL), and bis(di-tert-butyl (4-dimethylaminophenyl)phosphine)dichloropalladium (II) (5 mg) were added, and the mixture was stirred at 130° C. for 0.5 hours using a microwave reaction device. The reaction solution was purified by silica gel column chromatography (chloroform-methanol) to obtain a compound 0095 (0.7 mg) as a white solid.

¹H-NMR (DMSO-d₆) δ: 13.21 (1H, bs), 9.85 (1H, s), 9.34 (1H, bs), 9.11 (1H, d), 8.51 (1H, s), 8.32 (1H, d), 8.21 (2H, d), 7.45 (1H, d), 7.31-7.26 (4H, m), 7.18 (1H, td), 3.33-3.28 (2H, m), 2.70 (2H, t), 1.96-1.86 (2H, m).

MS m/z (M+H): 373.

Example 96

Synthesis of Compound 0096

(Synthesis of Compound 0096-1)

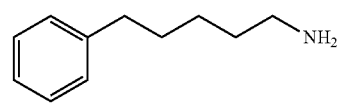

0096-1

Hydrochloride

N,N-dimethylformamide (2 mL) was added to (5-bromopentyl)benzene (227 mg) and phthalimidepotassium (195 mg), and the mixture was stirred at 60° C. for 1 hour. The reaction solution was cooled to room temperature and subjected to liquid separation with ethyl acetate (4 mL) and water (4 mL). The organic layer was washed with brine and dried over sodium sulfate, and then the solvent was evaporated under reduced pressure. A solution of the obtained oily substance and hydrazine monohydrate (100 μL) in ethanol (5 mL) was stirred at 70° C. for 5 hours. The reaction solution was cooled to room temperature and the solvent was evaporated under reduced pressure. The residue was subjected to liquid separation by the addition of ethyl acetate (4 mL) and water (2 mL), and the aqueous layer was extracted with ethyl acetate (2 mL) twice. The organic layer was washed with brine and dried over sodium sulfate, and then the solvent was evaporated under reduced pressure. The residue was purified by silica gel column chromatography (chloroform-methanol, NH silica) and to the obtained oily substance was added a 4 M hydrogen chloride/1,4-dioxane solution (1 mL), and the solvent was evaporated under reduced pressure. To the residue, methanol (1 mL) and ethyl acetate (1 mL) were added, and the resulting solid was separated by filtration and washed with ethyl acetate. The solid was dried under reduced pressure to obtain a compound 0096-1 hydrochloride (90 mg) as a white solid.

¹H-NMR (DMSO-d₆) δ: 7.83 (3H, bs), 7.30-7.26 (2H, m), 7.21-7.15 (3H, m), 2.75 (2H, dt), 2.57 (2H, t), 1.61-1.54 (4H, m), 1.37-1.27 (2H, m).

MS m/z (M+H): 164.

(Synthesis of Compound 0096)

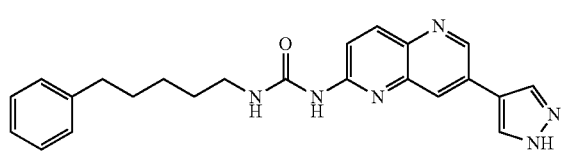

0096

The same method as in Example 95 except for using the compound 0096-1 (5-phenylpentan-1-amine hydrochloride) instead of 3-phenylpropylamine used for the synthesis of the compound 0095 in Example 95 and adding one equivalent amount of N,N-diisopropyl ethylamine with respect to 5-phenylpentan-1-amine hydrochloride was used to obtain a compound 0096 (9 mg) as a white solid.

¹H-NMR (DMSO-d₆) δ: 13.23 (1H, bs), 9.84 (1H, s), 9.31 (1H, bs), 9.11 (1H, d), 8.46-8.28 (3H, m), 8.21 (1H, d), 7.45 (1H, d), 7.24-7.09 (5H, m), 3.31-3.26 (2H, m), 2.61-2.58 (2H, m), 1.66-1.62 (4H, m), 1.43-1.38 (2H, m).

MS m/z (M+H): 401.

Example 97

Synthesis of Compound 0097

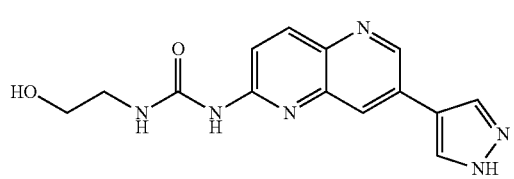
0097

The same method as in Example 95 except for using 2-aminoethanol instead of 3-phenylpropylamine used for the synthesis of the compound 0095 in Example 95 was used to obtain a compound 0097 (2 mg) as a white solid.

$^1$H-NMR (DMSO-$d_6$) δ: 13.21 (1H, bs), 9.85 (1H, s), 9.40 (1H, bs), 9.11 (1H, d), 8.51 (1H, bs), 8.27-8.20 (3H, m), 7.47 (1H, d), 4.90 (1H, t), 3.60-3.58 (2H, m), 3.39-3.36 (2H, m).
MS m/z (M+H): 299.

Example 98

Synthesis of Compound 0098

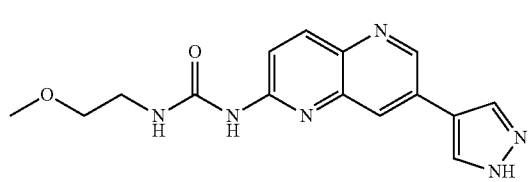
0098

The same method as in Example 95 except for using 2-methoxyethylamine instead of 3-phenylpropylamine used for the synthesis of the compound 0095 in Example 95 was used to obtain a compound 0098 (4 mg) as a white solid.

$^1$H-NMR (DMSO-$d_6$) δ: 13.21 (1H, bs), 9.87 (1H, s), 9.39 (1H, bs), 9.11 (1H, d), 8.51 (1H, bs), 8.24-8.18 (3H, m), 7.47 (1H, d), 3.55-3.51 (2H, m), 3.45-3.41 (2H, m), 3.36 (3H, s).
MS m/z (M+H): 313.

Example 99

Synthesis of Compound 0099

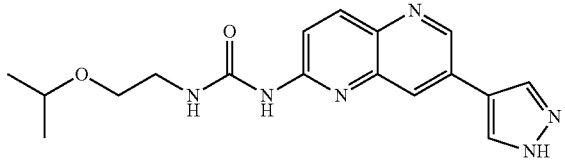
0099

The same method as in Example 95 except for using 2-aminoethylisopropyl ether instead of 3-phenylpropylamine used for the synthesis of the compound 0095 in Example 95 was used to obtain a compound 0099 (5.7 mg) as a white solid.

$^1$H-NMR (DMSO-$d_6$) δ: 13.23 (1H, bs), 9.91 (1H, s), 9.44 (1H, bs), 9.11 (1H, d), 8.32 (1H, bs), 8.22-8.21 (2H, m), 7.44 (1H, d), 3.70-3.61 (1H, m), 3.58-3.54 (2H, m), 3.44-3.42 (3H, m), 1.16 (3H, s), 1.14 (3H, s).
MS m/z (M+H): 341.

Example 100

Synthesis of Compound 0100

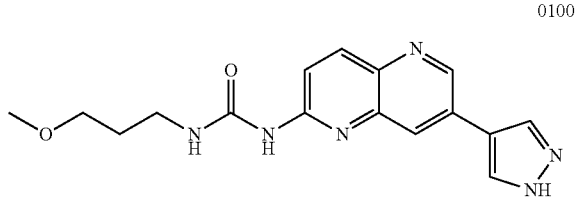 [SMILES: COCCCNC(=O)Nc1ccc2ncc(-c3cn[nH]c3)cc2n1]
0100

The same method as in Example 95 except for using 3-methoxypropylamine instead of 3-phenylpropylamine used for the synthesis of the compound 0095 in Example 95 was used to obtain a compound 0100 (3 mg) as a white solid.

$^1$H-NMR (DMSO-$d_6$) δ: 13.21 (1H, bs), 9.84 (1H, s), 9.31 (1H, bs), 9.11 (1H, d), 8.52 (1H, bs), 8.31 (1H, d), 8.22-8.19 (2H, m), 7.44 (1H, d), 3.45 (2H, t), 3.39-3.34 (2H, m), 3.27 (3H, s), 1.86-1.78 (2H, m).
MS m/z (M+H): 327.

Example 101

Synthesis of Compound 0101

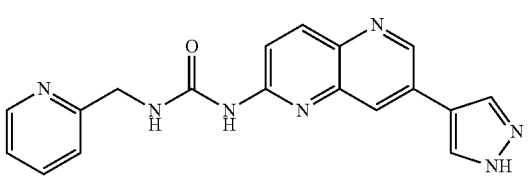
0101

The same method as in Example 95 except for using 2-picolylamine instead of 3-phenylpropylamine used for the synthesis of the compound 0095 in Example 95 was used to obtain a compound 0101 (2.3 mg) as a white solid.

$^1$H-NMR (DMSO-$d_6$) δ: 13.21 (1H, bs), 10.03 (2H, s), 9.12 (1H, d), 8.68-8.08 (5H, m), 7.79 (1H, dt), 7.48 (1H, d), 7.41 (1H, d), 7.31 (1H, dd), 4.63 (2H, d).
MS m/z (M+H): 346.

Example 102

Synthesis of Compound 0102

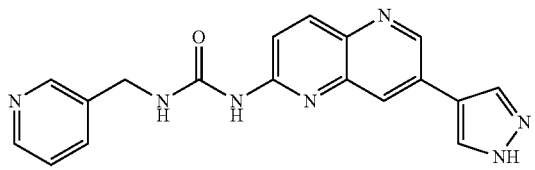

0102

The same method as in Example 95 except for using 3-(aminomethyl)pyridine instead of 3-phenylpropylamine used for the synthesis of the compound 0095 in Example 95 was used to obtain a compound 0102 (0.6 mg) as a white solid.

$^1$H-NMR (DMSO-$d_6$) δ: 13.18 (1H, bs), 10.01 (1H, s), 9.81 (1H, t), 9.12 (1H, d), 8.61 (1H, d), 8.55-8.19 (5H, m), 7.79 (1H, dt), 7.48 (1H, d), 7.41-7.37 (1H, m), 4.56 (2H, d).

MS m/z (M+H): 346.

Example 103

Synthesis of Compound 0103

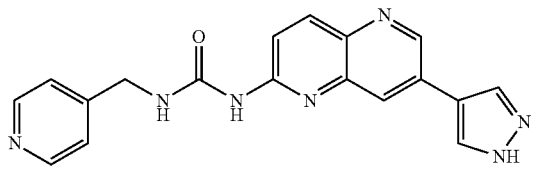

0103

The same method as in Example 95 except for using 4-(aminomethyl)pyridine instead of 3-phenylpropylamine used for the synthesis of the compound 0095 in Example 95 was used to obtain a compound 0103 (7 mg) as a white solid.

$^1$H-NMR (DMSO-$d_6$) δ: 13.24 (1H, bs), 10.10 (1H, s), 9.88 (1H, t), 9.12 (1H, d), 8.53 (2H, dd), 8.47-8.15 (4H, m), 7.49 (1H, d), 7.36 (2H, d), 4.56 (2H, d).

MS m/z (M+H): 346.

Example 104

Synthesis of Compound 0104

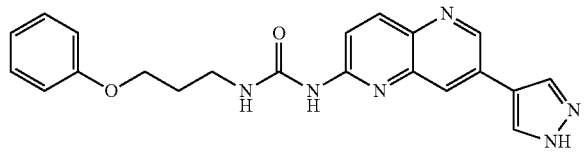

0104

The same method as in Example 95 except for using 3-phenoxypropylamine instead of 3-phenylpropylamine used for the synthesis of the compound 0095 in Example 95 was used to obtain a compound 0104 (4 mg) as a white solid.

$^1$H-NMR (DMSO-$d_6$) δ: 13.20 (1H, bs), 9.88 (1H, s), 9.41 (1H, bs), 9.10 (1H, d), 8.44 (1H, s), 8.27 (1H, d), 8.21 (1H, d), 8.15 (1H, bs), 7.44 (1H, d), 7.27-7.21 (2H, m), 6.97 (2H, dd), 6.91-6.86 (1H, m), 4.10 (2H, t), 3.47 (2H, ttt), 2.04 (2H, td).

MS m/z (M+H): 389.

Example 105

Synthesis of Compound 0105

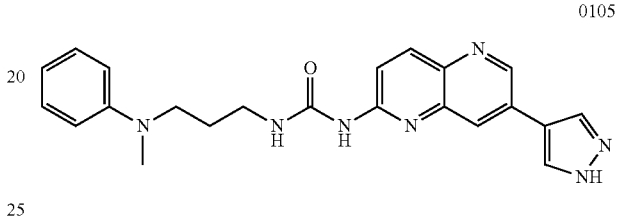

0105

The same method as in Example 95 except for using N-(3-aminopropyl)-N-methylaniline instead of 3-phenylpropylamine used for the synthesis of the compound 0095 in Example 95 was used to obtain a compound 0105 (3 mg) as a white solid.

$^1$H-NMR (DMSO-$d_6$) δ: 9.87 (1H, s), 9.32 (1H, bs), 9.11 (1H, d), 8.34-8.30 (3H, m), 8.22 (1H, d), 7.46 (1H, d), 7.09 (2H, dd), 6.70 (2H, d), 6.54 (1H, t), 3.44-3.39 (4H, m), 2.90 (3H, s), 1.89-1.80 (2H, m).

MS m/z (M+H): 402.

Example 106

Synthesis of Compound 0106

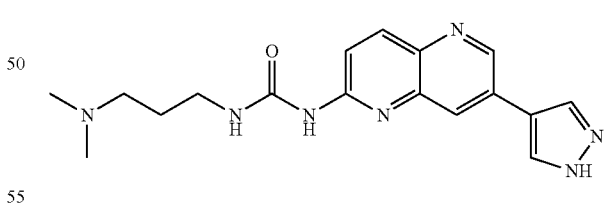

0106

The same method as in Example 95 except for using N,N-dimethyl-1,3-propanediamine instead of 3-phenylpropylamine used for the synthesis of the compound 0095 in Example 95 was used to obtain a compound 0106 (4 mg) as a white solid.

$^1$H-NMR (DMSO-$d_6$) δ: 9.84 (1H, bs), 9.29 (1H, bs), 9.11 (1H, d), 8.35 (2H, s), 8.29 (1H, d), 8.20 (1H, d), 7.45 (1H, d), 3.31-3.27 (2H, m), 2.37-2.27 (2H, m), 2.15 (6H, s), 1.75-1.66 (2H, m).

MS m/z (M+H): 340.

Example 107

Synthesis of Compound 0107

(Synthesis of Compound 0107-1)

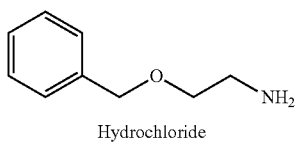
0107-1
Hydrochloride

The same method as in Example 96 except for using 1-(benzyloxy)-2-chloroethane (340 mg) instead of (5-bromopentyl)benzene used for the synthesis of the compound 0096-1 in Example 96 was used to obtain a compound 0107-1 hydrochloride (90 mg) as a white solid.

$^1$H-NMR (DMSO-$d_6$) δ: 7.96 (3H, bs), 7.49-7.28 (5H, m), 4.54 (2H, s), 3.62 (2H, t), 3.06-2.97 (2H, m).
MS m/z (M+H): 152.

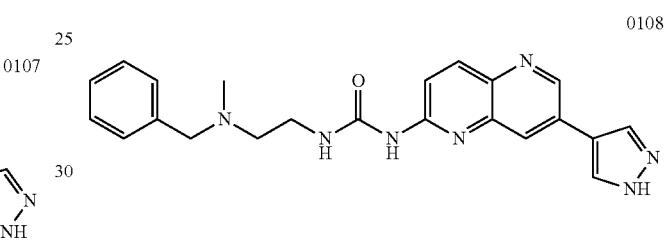
0107

The same method as in Example 95 except for using the compound 0107-1 (2-(benzyloxy)ethanamine hydrochloride) instead of 3-phenylpropylamine used for the synthesis of the compound 0095 in Example 95 and adding one equivalent of N,N-diisopropyl ethylamine with respect to 2-(benzyloxy)ethanamine hydrochloride was used to obtain a compound 0107 (3.4 mg) as a white solid.

$^1$H-NMR (DMSO-$d_6$) δ: 13.15 (1H, bs), 9.92 (1H, bs), 9.47 (1H, bs), 9.10 (1H, d), 8.26-8.18 (4H, m), 7.46 (1H, d), 7.37 (2H, dd), 7.28-7.17 (3H, m), 4.60 (2H, s), 3.64 (2H, t), 3.54-3.47 (2H, m).
MS m/z (M+H): 389.

Example 108

Synthesis of Compound 0108

(Synthesis of Compound 0108-1)

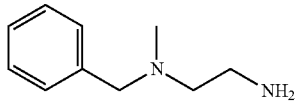
0108-1

N,N-dimethylformamide (4 mL) was added to N-methylbenzylamine (240 mg), N-(2-bromoethyl)phthalimide (500 mg), and potassium carbonate (400 mg), and the mixture was stirred at 70° C. for 1 hour. The reaction solution was cooled to room temperature and subjected to liquid separation with ethyl acetate (4 mL) and water (4 mL), and the organic layer was washed with brine and dried over sodium sulfate. Then, the solvent was evaporated under reduced pressure. To the obtained oily substance, a solution of hydrazine monohydrate (100 μL) in ethanol (5 mL) was added, and the mixture was stirred at 70° C. for 5 hours. The reaction solution was cooled to room temperature and the solvent was evaporated under reduced pressure. The residue was subjected to liquid separation by the addition of dichloromethane (4 mL) and 2 M hydrochloric acid (4 mL). The aqueous layer was neutralized with a 2 M aqueous sodium hydroxide solution and subjected to liquid separation by the addition of dichloromethane (4 mL). The aqueous layer was extracted with dichloromethane (2 mL) twice. The combined organic layer was washed with brine and dried over sodium sulfate, and then the solvent was evaporated under reduced pressure. The residue was purified by silica gel column chromatography (hexane-ethyl acetate, NH silica) to obtain a compound 0108-1 (95 mg) as a colorless oily substance.

$^1$H-NMR (DMSO-$d_6$) δ: 7.34-7.21 (5H, m), 3.45 (2H, s), 2.63 (2H, t), 2.33 (2H, t), 2.10 (3H, s), 1.35 (2H, bs).
MS m/z (M+H): 165.

(Synthesis of Compound 0108)

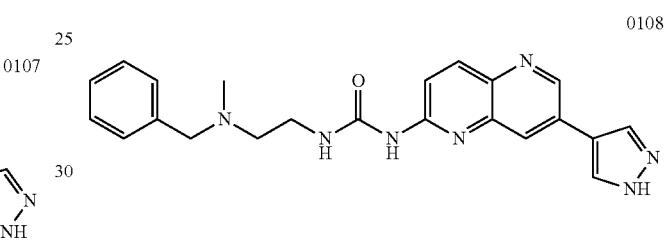
0108

The same method as in Example 95 except for using the compound 0108-1 ($N^1$-benzyl-$N^1$-methylethane-1,2-diamine) instead of 3-phenylpropylamine used for the synthesis of the compound 0095 in Example 95 was used to obtain a compound 0108 (3.7 mg) as a white solid.

$^1$H-NMR (DMSO-$d_6$) δ: 13.14 (1H, bs), 9.92 (1H, s), 9.66 (1H, bs), 9.09 (1H, d), 8.22 (1H, d), 8.12-8.06 (3H, m), 7.43 (1H, d), 7.35 (2H, dd), 7.16-7.07 (3H, m), 3.58 (2H, s), 3.50-3.42 (2H, m), 2.61 (2H, t), 2.26 (3H, s).
MS m/z (M+H): 402.

Example 109

Synthesis of Compound 0109

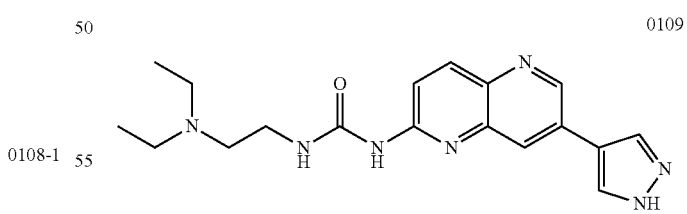
0109

The same method as in Example 95 except for using N,N-diethylethylenediamine instead of 3-phenylpropylamine used for the synthesis of the compound 0095 in Example 95 was used to obtain a compound 0109 (0.5 mg) as a white solid.

$^1$H-NMR (DMSO-$d_6$) δ: 9.88 (1H, s), 9.55 (1H, bs), 9.10 (1H, d), 8.28-8.27 (2H, m), 8.20 (2H, dd), 7.40 (1H, d), 2.61-2.55 (8H, m), 1.07-0.98 (6H, m).
MS m/z (M+H): 354.

Example 110

Synthesis of Compound 0110

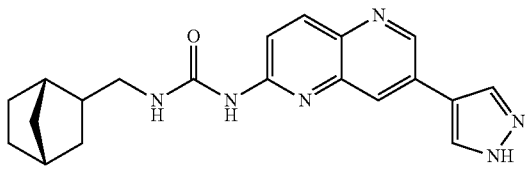

The same method as in Example 95 except for using bicyclo[2.2.1]hept-2-ylmethylamine instead of 3-phenylpropylamine used for the synthesis of the compound 0095 in Example 95 was used to obtain a compound 0110 (14 mg) as a white solid.

$^1$H-NMR (DMSO-$d_6$) δ: 13.23 (1H, bs), 9.82 (1H, s), 9.31-9.24 (1H, m), 9.11 (1H, d), 8.52 (1H, s), 8.28-8.15 (3H, m), 7.49 (1H, d), 3.25-3.01 (2H, m), 2.25-2.13 (2H, m), 1.99-1.07 (9H, m).

MS m/z (M+H): 363.

Example 111

Synthesis of Compound 0111

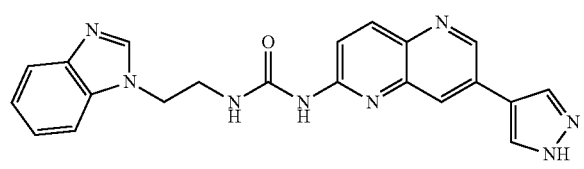

The same method as in Example 95 except for using 2-(1H-benzimidazol-1-yl)ethanamine instead of 3-phenylpropylamine used for the synthesis of the compound 0095 in Example 95 was used to obtain a compound 0111 (10 mg) as a white solid.

$^1$H-NMR (DMSO-$d_6$) δ: 13.26 (1H, bs), 9.93 (1H, s), 9.42 (1H, bs), 9.10 (1H, d), 8.62 (1H, s), 8.38 (1H, s), 8.32 (1H, s), 8.18 (1H, d), 8.04 (1H, t), 7.72 (1H, dd), 7.63 (1H, dd), 7.34 (1H, d), 7.23-7.13 (2H, m), 4.54-4.52 (2H, m), 3.84-3.77 (2H, m).

MS m/z (M+H): 399.

Example 112

Synthesis of Compound 0112

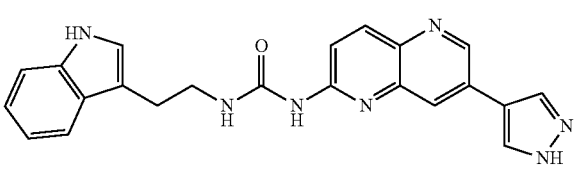

The same method as in Example 95 except for using tryptamine instead of 3-phenylpropylamine used for the synthesis of the compound 0095 in Example 95 was used to obtain a compound 0112 (8 mg) as a white solid.

$^1$H-NMR (DMSO-$d_6$) δ: 13.22 (1H, bs), 10.87 (1H, bs), 9.85 (1H, s), 9.40 (1H, bs), 9.08 (1H, d), 8.45 (1H, s), 8.18 (2H, t), 7.99 (1H, d), 7.64 (1H, d), 7.42 (1H, d), 7.33 (1H, d), 7.26 (1H, d), 7.06 (1H, td), 6.96 (1H, td), 3.68-3.59 (2H, m), 3.05-2.99 (2H, m).

MS m/z (M+H): 398.

Example 113

Synthesis of Compound 0113

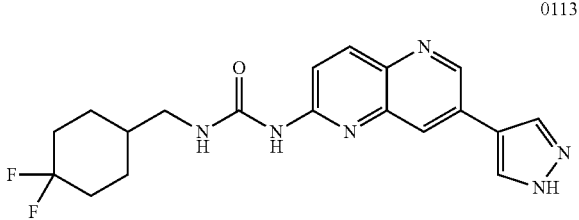 [SMILES: O=C(NCC1CCC(F)(F)CC1)Nc1ccc2ncc(-c3cn[nH]c3)cc2n1]

The same method as in Example 95 except for using (4,4-difluorocyclohexyl)methylamine hydrochloride instead of 3-phenylpropylamine used for the synthesis of the compound 0095 in Example 95 was used to obtain a compound 0113 (0.7 mg) as a white solid.

$^1$H-NMR (DMSO-$d_6$) δ: 9.88 (1H, s), 9.39 (1H, bs), 9.11 (1H, d), 8.35 (2H, bs), 8.26 (1H, d), 8.21 (1H, d), 7.45 (1H, d), 3.25-3.22 (2H, m), 2.03-1.86 (7H, m), 1.36-1.32 (2H, m).

MS m/z (M+H): 387.

Example 114

Synthesis of Compound 0114

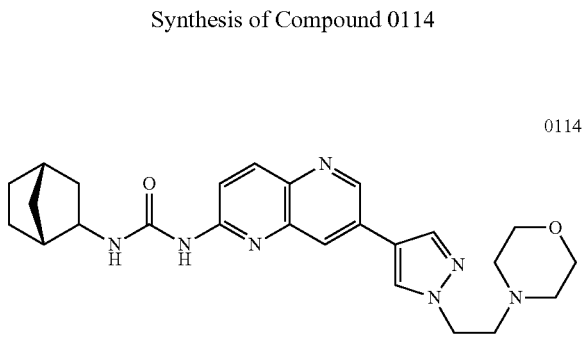

The same method as in Example 95 except for using (1R, 2R,4S)-bicyclo[2.2.1]heptan-2-amine instead of 3-phenylpropylamine used for the synthesis of the compound 0095 and using 1-(2-morpholinoethyl)-1H-pyrazole-4-boronic acid pinacol ester instead of 1-tert-butoxycarbonyl-4-(4,4,5,5-tetramethyl-1,3,2-dioxaborolan-2-yl)pyrazole used for the synthesis of the compound 0095 in Example 95 was used to obtain a compound 0114 (9.5 mg) as a white solid.

$^1$H-NMR (DMSO-d$_6$): 9.75 (1H, s), 9.10-8.98 (2H, m), 8.51 (1H, s), 8.25-8.15 (2H, m), 8.08 (1H, d), 7.51 (1H, d), 4.30 (2H, t), 3.68-3.50 (5H, m), 2.76 (2H, t), 2.48-2.39 (4H, m), 2.38-2.31 (1H, m), 2.30-2.22 (1H, m), 1.86-1.71 (1H, m), 1.58-1.34 (4H, m), 1.28-1.07 (3H, m).

MS m/z (M+H): 462.

Example 115

Synthesis of Compound 0115

(Synthesis of Compound 0115-1)

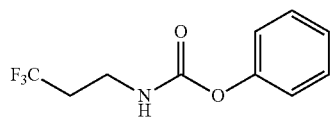

To 3,3,3-trifluoropropan-1-amine (113 mg) and phenyl chloroformate (150 μL) were added tetrahydrofuran (2 mL) and triethylamine (200 μL), and the mixture was stirred at room temperature for 0.5 hours. The solvent was evaporated under reduced pressure and the residue was purified by silica gel column chromatography (hexane-ethyl acetate) to obtain a compound 0115-1 (120 mg) as a colorless oily substance.

$^1$H-NMR (CDCl$_3$) δ: 7.37 (2H, t), 7.24-7.11 (3H, m), 5.27 (1H, s), 3.55 (2H, dd), 2.51-2.36 (2H, m).

MS m/z (M+H): 234.

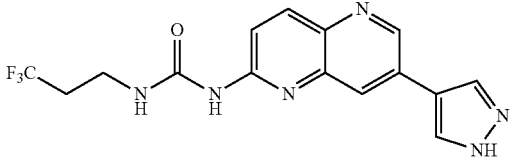

The same method as in Example 91 except for using the compound 0115-1 instead of the compound 0091-4 used for the synthesis of the compound 0091-5 in Example 91 was used to obtain a compound 0115 (3 mg) as a white solid.

$^1$H-NMR (DMSO-d$_6$) δ: 13.22 (1H, bs), 9.99 (1H, s), 9.55 (1H, t), 9.12 (1H, d), 8.50 (1H, s), 8.36 (1H, d), 8.22 (1H, d), 8.18 (1H, s), 7.43 (1H, d), 3.61-3.54 (2H, m), 2.72-2.59 (2H, m).

MS m/z (M+H): 351.

Example 116

Synthesis of Compound 0116

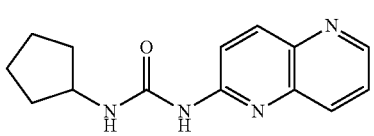

Triethylamine (17 μL), ammonium formate (8 mg), and tetrakis(triphenylphosphine)palladium (0) (7 mg) were added to a solution of the compound 0001-5 (20 mg) in 1,4-dioxane (0.6 mL), and the mixture was stirred at 120° C. for 30 minutes using a microwave reaction device. Then, tetrakis(triphenylphosphine)palladium (0) (7 mg) was further added thereto and the mixture was stirred at 120° C. for 30 minutes using a microwave reaction device. After completion of the reaction, the mixture was subjected to liquid separation by the addition of a saturated aqueous ammonium chloride solution, chloroform, and methanol. The organic layer was dried over sodium sulfate and then the solvent was evaporated under reduced pressure. The obtained crude product was purified by preparative thin layer chromatography to obtain a compound 0116 (4.6 mg) as a pale yellow solid.

$^1$H-NMR (DMSO-d$_6$) δ: 9.83 (1H, s), 9.25 (1H, bd), 8.77 (1H, dd), 8.26 (1H, d), 8.09 (1H, d), 7.68 (1H, dd), 7.56 (1H, d), 4.15-4.05 (1H, m), 1.98-1.87 (2H, m), 1.76-1.52 (6H, m).

MS m/z (M+H): 257.

Example 117

Synthesis of Compound 0117

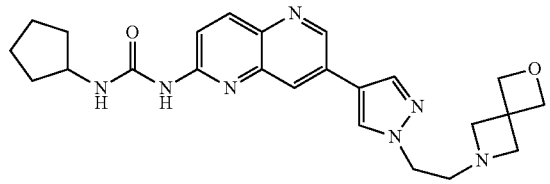

0117

The same method as in Example 36 except for using 2-oxa-6-azaspiro[3.3]heptane oxalate instead of piperidine used for the synthesis of the compound 0036 in Example 36 was used to obtain a compound 0117 (10 mg) as a white solid.

$^1$H-NMR (DMSO-$d_6$) δ: 9.77 (1H, s), 9.17 (1H, bd), 9.06 (1H, d), 8.49 (1H, s), 8.22-8.13 (3H, m), 7.50 (1H, d), 4.56 (4H, s), 4.14-4.04 (3H, m), 3.26 (4H, s), 2.81-2.76 (2H, m), 2.01-1.89 (2H, m), 1.82-1.52 (6H, m).

MS m/z (M+H): 448.

Example 118

Synthesis of Compound 0118

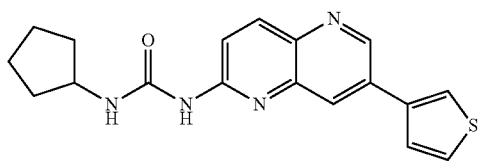

0118

The same method as in Example 1 except for using 3-thiophene boronic acid instead of 2-methoxy-4-(4,4,5,5-tetramethyl-1,3,2-dioxaborolan-2-yl)phenol used for the synthesis of the compound 0001 in Example 1 was used to obtain a compound 0118 (20 mg) as a white solid.

$^1$H-NMR (DMSO-$d_6$) δ: 9.81 (1H, s), 9.21-9.16 (2H, m), 8.31-8.30 (2H, m), 8.25 (1H, d), 7.85-7.84 (1H, m), 7.79-7.76 (1H, m), 7.55 (1H, d), 4.15-4.04 (1H, m), 2.01-1.89 (2H, m), 1.82-1.53 (6H, m).

MS m/z (M+H): 339.

Example 119

Synthesis of Compound 0119

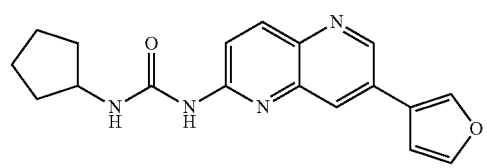

0119

The same method as in Example 1 except for using 3-furyl boronic acid instead of 2-methoxy-4-(4,4,5,5-tetramethyl-1,3,2-dioxaborolan-2-yl)phenol used for the synthesis of the compound 0001 in Example 1 was used to obtain a compound 0119 (12 mg) as a pale yellow solid.

$^1$H-NMR (DMSO-$d_6$) δ: 9.78 (1H, s), 9.12-9.10 (2H, m), 8.55 (1H, s), 8.25-8.20 (2H, m), 7.87-7.86 (1H, m), 7.55 (1H, d), 7.26 (1H, d), 4.14-4.03 (1H, m), 2.01-1.90 (2H, m), 1.81-1.52 (6H, m).

MS m/z (M+H): 323.

Example 120

Synthesis of Compound 0120

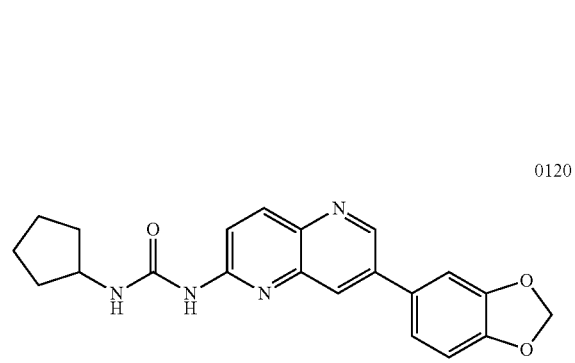 [SMILES: O=C(Nc1ccc2ncc(-c3ccc4c(c3)OCO4)cc2n1)NC1CCCC1]

0120

The same method as in Example 1 except for using 3,4-(methylenedioxy)phenylboronic acid instead of 2-methoxy-4-(4,4,5,5-tetramethyl-1,3,2-dioxaborolan-2-yl)phenol used for the synthesis of the compound 0001 in Example 1 was used to obtain a compound 0120 (8 mg) as a white solid.

$^1$H-NMR (DMSO-$d_6$): 9.82 (1H, s), 9.20 (1H, bd), 9.05 (1H, d), 8.26 (1H, d), 8.20 (1H, d), 7.56-7.53 (2H, m), 7.40 (1H, dd), 7.10 (1H, d), 6.12 (2H, s), 4.12-4.02 (1H, m), 1.98-1.88 (2H, m), 1.79-1.53 (6H, m).

MS m/z (M+H): 377.

Example 121

Synthesis of Compound 0121

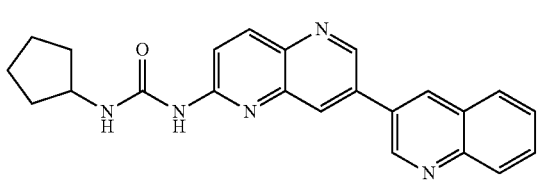

0121

The same method as in Example 1 except for using 3-(4,4,5,5-tetramethyl 1,3,2-dioxaborolan-2-yl) quinoline instead of 2-methoxy-4-(4,4,5,5-tetramethyl-1,3,2-dioxaborolan-2-yl)phenol used for the synthesis of the compound 0001 in Example 1 was used to obtain a compound 0121 (20 mg) as a white solid.

$^1$H-NMR (DMSO-$d_6$) δ: 9.88 (1H, s), 9.47 (1H, d), 9.30 (1H, d), 9.15 (1H, bd), 8.95 (1H, d), 8.57 (1H, d), 8.34 (1H, d), 8.15-8.10 (2H, m), 7.87-7.82 (1H, m), 7.74-7.69 (1H, m), 7.64 (1H, d), 4.16-4.04 (1H, m), 2.00-1.89 (2H, m), 1.81-1.52 (6H, m).

MS m/z (M+H): 384.

Example 122

Synthesis of Compound 0122

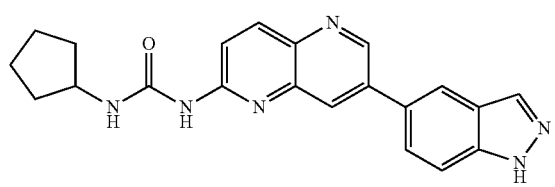

0122

The same method as in Example 1 except for using 5-(4,4,5,5-tetramethyl-1,3,2-dioxaborolan-2-yl)-1H-indazole instead of 2-methoxy-4-(4,4,5,5-tetramethyl-1,3,2-dioxaborolan-2-yl)phenol used for the synthesis of the compound 0001 in Example 1 was used to obtain a compound 0122 (15 mg) as a pale yellow solid.

$^1$H-NMR (DMSO-$d_6$) δ: 13.24 (1H, bs), 9.84 (1H, s), 9.22 (1H, bd), 9.16 (1H, d), 8.31-8.21 (4H, m), 7.89 (1H, dd), 7.73 (1H, d), 7.56 (1H, d), 4.15-4.04 (1H, m), 2.01-1.88 (2H, m), 1.82-1.53 (6H, m).

MS m/z (M+H): 373.

Example 123

Synthesis of Compound 0123

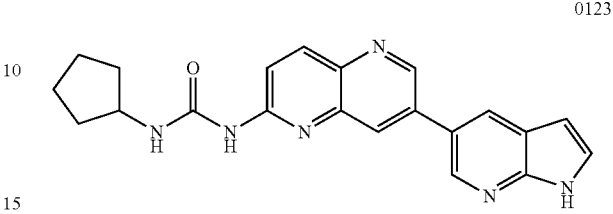

0123

The same method as in Example 1 except for using 5-(4,4,5,5-tetramethyl-1,3,2-dioxaborolan-2-yl)-1-pyrrolo[2,3-b]pyridine instead of 2-methoxy-4-(4,4,5,5-tetramethyl-1,3,2-dioxaborolan-2-yl)phenol used for the synthesis of the compound 0001 in Example 1 was used to obtain a compound 0123 (4 mg) as a white solid.

$^1$H-NMR (DMSO-$d_6$) δ: 11.87 (1H, bs), 9.84 (1H, s), 9.22 (1H, d), 9.16 (1H, d), 8.74 (1H, d), 8.48 (1H, d), 8.35 (1H, d), 8.29 (1H, d), 7.59-7.55 (2H, m), 6.58 (1H, dd), 4.15-4.04 (1H, m), 2.00-1.87 (2H, m), 1.82-1.53 (6H, m).

MS m/z (M+H): 373.

Example 124

Synthesis of Compound 0124

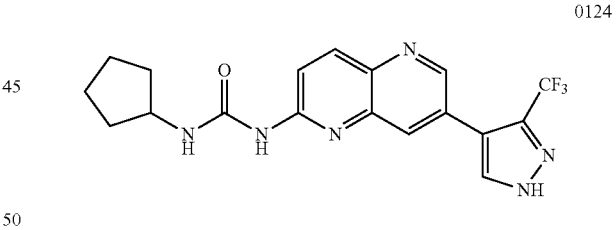

0124

The same method as in Example 1 except for using 4-(4,4,5,5-tetramethyl-1,3,2-dioxaborolan-2-yl)-3-(trifluoromethyl)-1H-pyrrole instead of 2-methoxy-4-(4,4,5,5-tetramethyl-1,3,2-dioxaborolan-2-yl)phenol used for the synthesis of the compound 0001 in Example 1 was used to obtain a compound 0124 (20 mg) as a yellow solid.

$^1$H-NMR (DMSO-$d_6$) δ: 14.03 (1H, bs), 9.90 (1H, s), 9.30 (1H, bd), 8.88 (1H, d), 8.56 (1H, s), 8.28 (1H, d), 8.07 (1H, d), 7.56 (1H, d), 4.17-4.07 (1H, m), 1.96-1.85 (2H, m), 1.79-1.49 (6H, m).

MS m/z (M+H): 391.

Example 125

Synthesis of Compound 0125

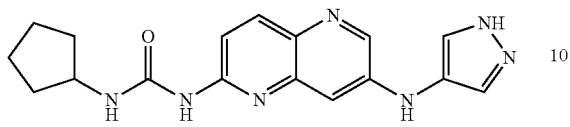

Tert-butyl 4-amino-1H-pyrazole-1-carboxylate (24 mg, which was synthesized according to WO2008/139161), 4,5-bis(diphenylphosphino)-9,9-dimethylxanthene (21 mg), cesium carbonate (97 mg), and tris(dibenzylideneacetone)dipalladium (0) (16 mg) were added to a solution of the compound 0001-5 (40 mg) in 1,4-dioxane solution (1.2 mL), and the mixture was heated and refluxed for 2 hours under a nitrogen atmosphere. The reaction solution was returned to room temperature, water was added thereto, and the mixture was extracted with a chloroform-methanol mixed solvent. The organic layer was dried over sodium sulfate and the solvent was then evaporated under reduced pressure. To the obtained residue, dichloromethane (1.2 mL) and trifluoroacetic acid (0.18 mL) were added, and the mixture was stirred at room temperature for 6 hours. Then, a saturated aqueous sodium hydrogen carbonate solution was added to the reaction solution, and the mixture was extracted with a chloroform-methanol mixed solvent. The organic layer was dried over sodium sulfate, the solvent was evaporated under reduced pressure, and the residue was purified by silica gel column chromatography (chloroform-methanol) to obtain a compound 0125 (18 mg) as a yellow solid.

$^1$H-NMR (DMSO-$d_6$) δ: 12.80 (1H, bs), 9.58 (1H, s), 9.51 (1H, bd), 8.42-8.41 (2H, m), 8.00 (1H, d), 7.85 (1H, bs), 7.53 (1H, bs), 7.12 (1H, d), 7.03 (1H, d), 4.14-4.03 (1H, m), 1.93-1.46 (8H, m).

MS m/z (M+H): 338.

Example 126

Synthesis of Compound 0126

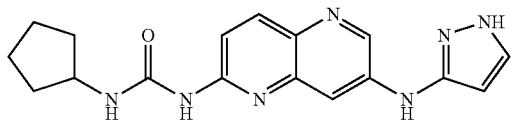

The same method as in Example 125 except for using tert-butyl 3-amino-1H-pyrazole-1-carboxylate (which was synthesized according to WO2005/121110, WO2006/125972 A1, and WO2008/139161) instead of tert-butyl 4-amino-1H-pyrazole-1-carboxylate in Example 125 was used to obtain a compound 0126 (18 mg) as a yellow solid.

$^1$H-NMR (DMSO-$d_6$) δ: 12.25 (1H, bs), 9.61-9.58 (2H, m), 9.26 (1H, s), 8.64 (1H, d), 8.17 (1H, d), 8.03 (1H, d), 7.66 (1H, t), 7.17 (1H, d), 5.94 (1H, t), 4.16-4.07 (1H, m), 1.96-1.47 (8H, m).

MS m/z (M+H): 338.

Example 127

Synthesis of Compound 0127

(Synthesis of Compound 0127-1)

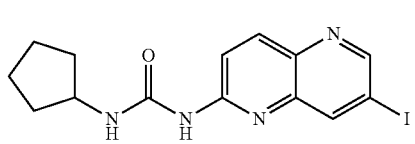

1,4-dioxane (2 mL) was added to the compound 0001-5 (50 mg), sodium iodide (45 mg), and copper iodide (I) (29 mg) under a nitrogen atmosphere. Trans-N,N'-dimethylcyclohexane-1,2-diamine (24 μL) was added thereto. After closing the vessel, the mixture was stirred at 100° C. for 7 hours. During the reaction, copper iodide (29 mg) and trans-N,N'-dimethylcyclohexane-1,2-diamine (24 μL) were added thereto. The reaction solution was cooled to room temperature, and aqueous ammonia and water were added thereto. The resulting solid was separated by filtration and the solid was washed with aqueous ammonia, water, and a hexane-ethyl acetate (1:1) mixed solvent. The solid was dried under reduced pressure to obtain a compound 0127-1 as a mixture (37 mg) of the compound 0127-1 and the compound 0001-5.

$^1$H-NMR (CDCl$_3$) δ: 9.82 (1H, bs), 9.11 (1H, bs), 8.92 (1H, d), 8.37 (1H, d), 8.21-8.15 (1H, m), 7.19 (1H, d), 4.38-4.28 (1H, m), 2.16-2.04 (2H, m), 1.84-1.58 (6H, m).

(Synthesis of Compound 0127)

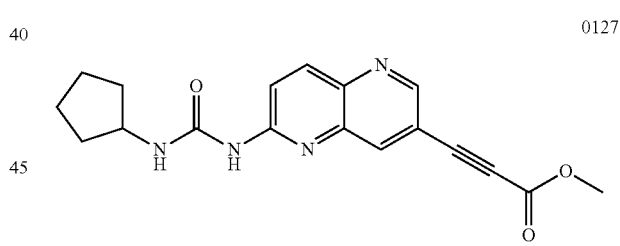

Tetrahydrofuran (2 mL) was added to a mixture (37 mg) of the compound 0127-1 and the compound 0001-5, methyl propionate (20 μL), copper iodide (I) (2.1 mg), bis(triphenylphosphine)palladium (II) dichloride (7.7 mg), and potassium carbonate (33 mg) under a nitrogen atmosphere, and the mixture was stirred at 50° C. for 5 hours. The reaction solution was returned to room temperature and the solvent was removed under reduced pressure. To the residue, aqueous ammonia and water were added. The resulting solid was separated by filtration, washed with water, and then purified by silica gel column chromatography (chloroform-methanol) to obtain a compound 0127 (15 mg) as a brown solid.

$^1$H-NMR (CDCl$_3$) δ: 9.89-9.83 (1H, m), 9.60 (1H, s), 8.87 (1H, d), 8.25-8.15 (2H, m), 7.29 (1H, d), 4.41-4.29 (1H, m), 3.90 (3H, s), 2.18-2.08 (2H, m), 1.90-1.63 (6H, m).

MS m/z (M+H): 339.

Example 128

Synthesis of Compound 0128

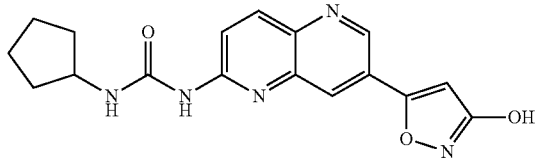

To the compound 0127 (24 mg), methanol (2 mL) was added, and tetrahydrofuran was added thereto until the raw materials were dissolved. To the obtained solution, hydroxyamine hydrochloride (39 mg) and a 1 M aqueous sodium hydroxide solution (426 µL) were added at room temperature, and the mixture was stirred at room temperature for 2 hours. To the reaction solution, 1 M hydrochloric acid (426 µL) was added. The solvent was evaporated under reduced pressure and the residue was subjected to reverse phase preparative separation HPLC (0.1% HCO$_2$H aqueous solution-0.1% HCO$_2$H acetonitrile solution) to obtain a compound 0128 (8.3 mg) as a pale brown solid.

$^1$H-NMR (DMSO-d$_6$) δ: 9.92 (1H, s), 9.15 (1H, d), 9.06 (1H, d), 8.42-8.39 (1H, m), 8.35 (1H, d), 8.29 (1H, d), 7.65 (1H, d), 6.84 (1H, s), 4.13-4.02 (1H, m), 2.00-1.88 (2H, m), 1.82-1.50 (6H, m).

MS m/z (M+H): 340.

Example 129

Synthesis of Compound 0129

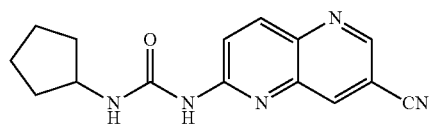

Anhydrous N,N-dimethylformamide (2 mL) was added to the compound 0001-5 (60 mg), zinc cyanide (41 mg), bis(diphenylphosphino)ferrocene (39 mg), and tris(dibenzylideneacetone)dipalladium (0) (33 mg) under a nitrogen atmosphere, and the mixture was stirred at 100° C. overnight. The reaction solution was cooled to room temperature, aqueous ammonia was added thereto, and the resulting solid was separated by filtration. The obtained crude product was purified by silica gel column chromatography (chloroform-methanol) to obtain a compound 0129 (32 mg) as a white solid.

$^1$H-NMR (DMSO-d$_6$) δ: 10.03 (1H, s), 9.05 (1H, d), 8.94 (1H, d), 8.84 (1H, d), 8.35 (1H, d), 7.74 (1H, d), 4.15-4.08 (1H, m), 1.99-1.54 (8H, m).

MS m/z (M+H): 282.

Example 130

Synthesis of Compound 0130

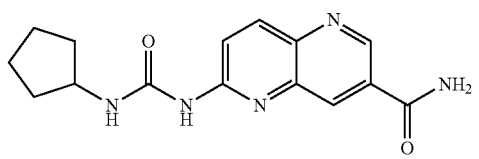

The compound 0129 (10 mg) was dissolved in dimethylsulfoxide (2 mL), and a 1 M aqueous sodium hydroxide solution (78 µL) and 30% aqueous hydrogen peroxide (20 µL) were added thereto at room temperature. The mixture was stirred at room temperature for 2 hours. Water was added to the reaction solution, and the resulting solid was separated by filtration. The obtained solid was washed with water and ethyl acetate, and dried under reduced pressure to obtain a compound 0130 (8.7 mg) as a white solid.

$^1$H-NMR (DMSO-d$_6$) δ: 9.91 (1H, s), 9.17-9.13 (2H, m), 8.48 (1H, s), 8.43 (1H, s), 8.30 (1H, d), 7.79 (1H, s), 7.65 (1H, d), 4.15-4.03 (1H, m), 2.02-1.89 (2H, m), 1.82-1.48 (6H, m).

MS m/z (M+H): 300.

Example 131

Synthesis of Compound 0131

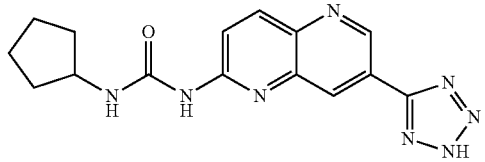

N,N-dimethylformamide (2 mL) was added to the compound 0129 (20 mg), sodium azide (14 mg), and ammonium chloride (11 mg), and the mixture was stirred at 100° C. overnight. The reaction solution was cooled to room temperature, water and 1 M hydrochloric acid (71 µL) were then added thereto, and the solvent was evaporated under reduced pressure. The obtained residue was subjected to reverse phase preparative separation HPLC (0.1% HCO$_2$H aqueous solution-0.1% HCO$_2$H acetonitrile solution) to obtain a compound 0131 (3.0 mg) as a pale brown solid.

$^1$H-NMR (MeOH-d$_4$) δ: 9.44 (1H, d), 8.75 (1H, s), 8.24 (1H, d), 7.38 (1H, d), 4.28-4.18 (1H, m), 2.16-2.01 (2H, m), 1.97-1.66 (6H, m).

MS m/z (M+H): 325.

Example 132

Synthesis of Compound 0132

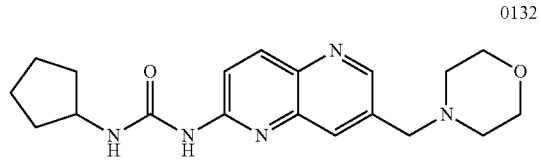 [SMILES: O=C(Nc1ccc2ncc(CN3CCOCC3)cc2n1)NC1CCCC1]

0132

A tetrahydrofuran-water mixed solvent (1.5 mL, 10:1) was added to the compound 0001-5 (20 mg), potassium N-(methyl trifluoroborate)morpholine (25 mg), cesium carbonate (59 mg), palladium acetate (2.6 mg), and 2-dicyclohexylphosphino-2',4',6'-triisopropylbiphenyl (11 mg) under a nitrogen atmosphere. After closing the reaction vessel, the reaction was carried out at 130° C. for 20 minutes using a microwave reaction device. The reaction solution was cooled and the solvent was then evaporated under reduced pressure. The residue was purified by silica gel chromatography (hexane-ethyl acetate and chloroform-methanol, NH silica) to obtain a compound 0132 (8.0 mg) as a white solid.

$^1$H-NMR (CDCl$_3$) δ: 9.98 (1H, s), 8.90-8.77 (2H, m), 8.22 (1H, d), 7.89 (1H, s), 7.13 (1H, d), 4.42-4.29 (1H, m), 3.82-3.68 (6H, m), 2.59-2.48 (4H, m), 2.18-2.05 (2H, m), 1.93-1.60 (6H, m).

MS m/z (M+H): 356.

Example 133

Synthesis of Compound 0133

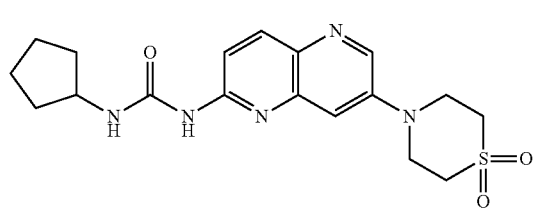

0133

The same method as in Example 8 except for using thiomorpholine-1,1-dioxide instead of morpholine used for the synthesis of the compound 0008 in Example 8 was used to obtain a compound 0133 (22 mg) as a white solid.

$^1$H-NMR (DMSO-d$_6$) δ: 9.62 (1H, s), 9.19 (1H, d), 8.75 (1H, d), 8.09 (1H, d), 7.36-7.28 (2H, m), 4.06 (1H, m), 3.98 (4H, m), 3.24 (4H, m), 2.02-1.86 (2H, m), 1.80-1.48 (6H, m).

MS m/z (M+H): 390.

Example 134

Synthesis of Compound 0134

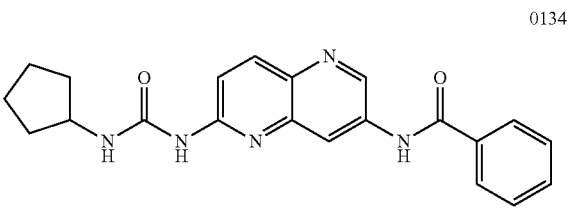 [SMILES: O=C(Nc1ccc2ncc(NC(=O)c3ccccc3)cc2n1)NC1CCCC1]

0134

1,4-dioxane (2 mL) was added to the compound 0001-5 (30 mg), benzamide (16 mg), cesium carbonate (87 mg), 4,5-bis(diphenylphosphino)-9,9-dimethylxanthene (10 mg), and tris(dibenzylideneacetone)dipalladium (0) (8.2 mg) under a nitrogen atmosphere, and the reaction vessel was closed. The reaction solution was stirred at 100° C. overnight and then cooled to room temperature, and the reaction solution was purified by silica gel column chromatography (chloroform-methanol) to obtain a compound 0134 (10 mg) as a pale yellow solid.

$^1$H-NMR (CDCl$_3$) δ: 9.95 (1H, s), 8.83 (1H, d), 8.64 (1H, d), 8.46 (1H, s), 8.18-8.15 (2H, m), 7.96-7.89 (2H, m), 7.63-7.46 (3H, m), 7.05 (1H, d), 4.38-4.26 (1H, m), 2.18-2.05 (2H, m), 1.93-1.60, (6H, m).

MS m/z (M+H): 376.

Example 135

Synthesis of Compound 0135

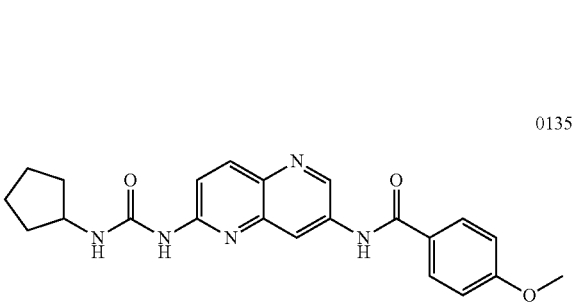 [SMILES: COc1ccc(C(=O)Nc2cnc3ccc(NC(=O)NC4CCCC4)nc3c2)cc1]

0135

The same method as in Example 134 except for using 4-methoxybenzamide instead of benzamide used for the synthesis of the compound 0134 in Example 134 was used to obtain a compound 0135 (10 mg) as a pale yellow solid.

$^1$H-NMR (DMSO-d$_6$) δ: 10.60 (1H, s), 9.80 (1H, s), 9.35 (1H, d), 9.10 (1H, d), 8.55 (1H, d), 8.19 (1H, d), 8.04 (2H, d), 7.44 (1H, d), 7.11 (2H, d), 4.17-4.06 (1H, m), 3.86 (3H, s), 1.97-1.51 (8H, m).

MS m/z (M+H): 406.

Example 136

Synthesis of Compound 0136

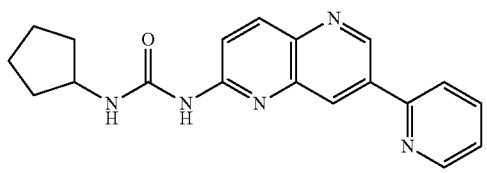

0136

A solution of the compound 0001-5 (25 mg), trimethyl (2-pyridyl)tin (36 mg), lithium chloride (9.5 mg), and tetrakis (triphenylphosphine)palladium (0) in 1,4-dioxane (1.0 mL) was stirred at 110° C. for 3 hours under a nitrogen atmosphere. The reaction solution was returned to room temperature and the solution was purified by silica gel column chromatography (chloroform-methanol, NH silica) to obtain a compound 0136 (12 mg) as a colorless solid.

$^1$H-NMR (DMSO-d$_6$) δ: 9.86 (1H, s), 9.47 (1H, d), 9.17 (1H, d), 8.79 (1H, d), 8.64 (1H, d), 8.33-8.26 (2H, m), 8.01 (1H, m), 7.62 (1H, d), 7.49 (1H, m), 4.10 (1H, m), 2.02-1.90 (2H, m), 1.84-1.52, (6H, m).

MS m/z (M+H): 334.

Example 137

Synthesis of Compound 0137

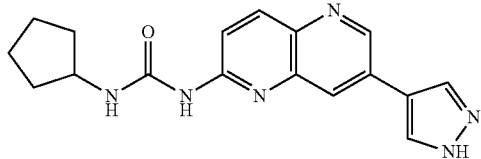

0137

The same method as in Example 1 except for using 1-tert-butoxycarbonyl-4-(4,4,5,5-tetramethyl-1,3,2-dioxaborolan-2-yl)pyrazole instead of 2-methoxy-4-(4,4,5,5-tetramethyl-1,3,2-dioxaborolan-2-yl)phenol used for the synthesis of the compound 0001 in Example 1 was used to obtain a compound 0137 (19 mg) as a white solid.

$^1$H-NMR (DMSO-d$_6$) δ: 13.20 (1H, s), 9.75 (1H, s), 9.16 (1H, d), 9.10 (1H, d), 8.54 (1H, s), 8.22 (1H, m), 8.22 (1H, s), 8.18 (1H, d), 7.49 (1H, d), 4.09 (1H, m), 2.02-1.88 (2H, m), 1.84-1.52 (6H, m).

MS m/z (M+H): 323.

Example 138

Synthesis of Compound 0138

(Synthesis of Compound 0138-1)

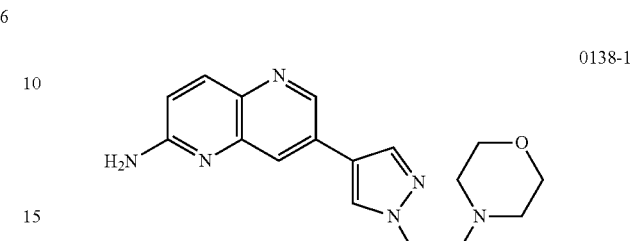

0138-1

A mixed solution of the compound 0001-4 (50 mg), sodium carbonate (47 mg), 1-(2-morpholinoethyl)-1H-pyrazole-4-boronic acid pinacol ester (137 mg), and bis(tritert-butylphosphine)palladium (0) (11 mg) in 1,4-dioxane (1 mL) and water (0.1 mL) was stirred at 140° C. for 1 hour using a microwave reaction device. The reaction solution was returned to room temperature and then the solution was purified by silica gel column chromatography (chloroform-methanol, NH silica) to obtain a compound 0138-1 (49 mg) as a colorless solid.

(Synthesis of Compound 0138)

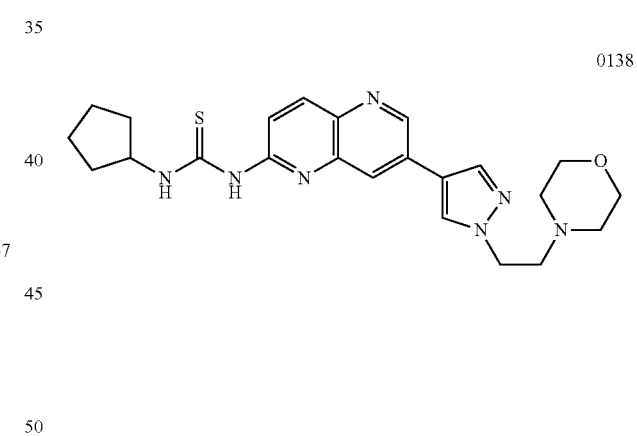

0138

A solution of the compound 0138-1 (49 mg) and cyclopentylisothiocyanate (19 mg) in N,N-dimethylformamide (1.5 ml) was cooled to 0° C., a 60% sodium hydride (7 mg) was then added thereto, and the mixture was stirred for 1 hour. Water was added to the reaction solution, and the mixture was then extracted with ethyl acetate. The organic layer was washed with brine and then dried over sodium sulfate. The solvent was evaporated under reduced pressure and the residue was then purified by silica gel column chromatography (chloroform-methanol, NH silica) to obtain a compound 0138-1 (23 mg) as a colorless solid.

$^1$H-NMR (DMSO-d$_6$) δ: 12.26 (1H, d), 10.97 (1H, s), 9.12 (1H, d), 8.52 (1H, s), 8.30 (1H, d), 8.20 (1H, s), 8.11 (1H, d), 7.48 (1H, d), 4.60 (1H, m), 4.31 (2H, m), 3.56 (4H, m), 2.77 (2H, m), 2.44 (4H, m), 2.18-2.00 (2H, m), 1.83-1.62 (6H, m).

MS m/z (M+H): 452.

Example 139

Synthesis of Compound 0139

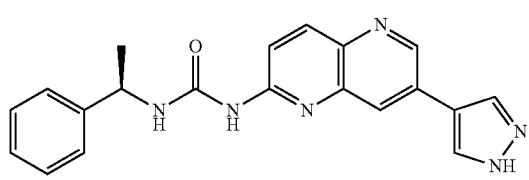

0139

The same method as in Example 53 except for using (R)-(+)-α-methylbenzyl isocyanate instead of isopropyl isocyanate used for the synthesis of the compound 0053 in Example 53 was used to obtain a compound 0139 (9 mg) as a white solid.

$^1$H-NMR (DMSO-d$_6$) δ: 13.22 (1H, s), 9.87 (1H, s), 9.76 (1H, d), 9.12 (1H, d), 8.55 (1H, s), 8.30-8.15 (4H, m), 7.52-7.23 (5H, m), 4.99 (1H, m), 1.58 (3H, d).

MS m/z (M+H): 359.

Example 140

Synthesis of Compound 0140

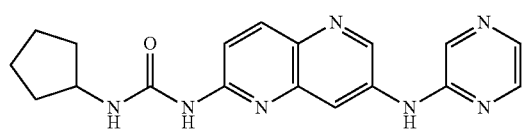

0140

The same method as in Example 8 except for using 2-aminopyrazine instead of morpholine used for the synthesis of the compound 0008 in Example 8, using (2-biphenyl)dicyclohexylphosphine instead of 2-dicyclohexylphosphino-2',4',6'-triisopropylbiphenyl used for the synthesis of the compound 0008 in Example 8, and using toluene instead of 1,4-dioxane used for the synthesis of the compound 0008 in Example 8 was used to obtain a compound 0140 (5 mg) as a white solid.

$^1$H-NMR (DMSO-d$_6$) δ: 10.17 (1H, s), 9.73 (1H, s), 9.54 (1H, d), 8.87 (1H, d), 8.70 (1H, d), 8.37 (1H, m), 8.24 (1H, m), 8.13 (1H, d), 8.08 (1H, d), 7.33 (1H, d), 4.14 (1H, m), 2.02-1.50 (8H, m).

MS m/z (M+H): 350.

Example 141

Synthesis of Compound 0141

(Synthesis of Compound 0141-1)

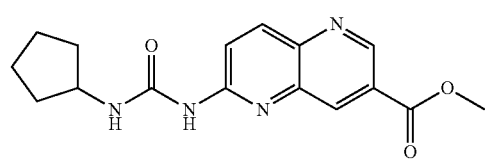

0141-1

The compound 0129 (54 mg) was dissolved in a hydrogen chloride-methanol solution (5-10%), water was added thereto in several droplets, and the mixture was stirred at 80° C. overnight. The solvent was evaporated under reduced pressure, water was added to the residue, and the resulting mixture was extracted with ethyl acetate twice. The extract was washed with water and brine, and then dried over anhydrous sodium sulfate, and the solvent was evaporated under reduced pressure. The obtained residue was purified by silica gel column chromatography (chloroform-methanol) to obtain a compound 0141-1 as a mixture (25 mg) of the compound 0141-1 and the compound 0129.

MS m/z (M+H): 315.

(Synthesis of Compound 0141-2)

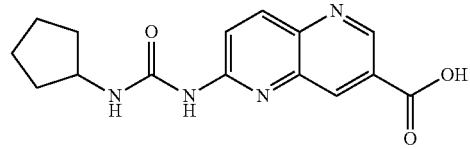

0141-2

Methanol (2 mL) was added to a mixture (25 mg) of the compounds 0141-1 and 0129, and tetrahydrofuran was added thereto until the raw materials were dissolved. To the obtained solution, a 1 M aqueous sodium hydroxide solution (240 μL) was added, and the mixture was stirred at room temperature overnight. To the reaction solution, a 1 M hydrochloric acid (240 μL) was added, and the solvent was evaporated under reduced pressure to obtain a compound 0141-2 as a crude product. The obtained compound 0141-2 was used for the next reaction without further purification.

MS m/z (M+H): 301.

(Synthesis of Compound 0141)

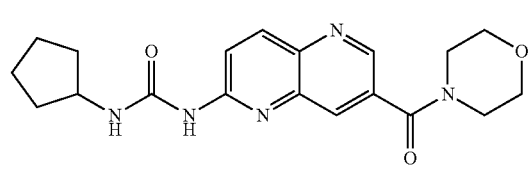

0141

The compound 0141-2 was dissolved in N,N-dimethylformamide (2 mL), and triethylamine (22 μL), morpholine (1 μL), 1-hydroxybenzotriazole (18 mg), and 1-ethyl-3-(3-dimethylaminopropyl)carbodiimide hydrochloride (23 mg) were added thereto. The mixture was stirred at room temperature overnight. To the reaction solution, water was added, and the mixture was extracted with ethyl acetate twice. The obtained organic layer was washed with water and brine, and dried over anhydrous sodium sulfate. The solvent was evaporated under reduced pressure and the residue was purified by preparative thin layer silica gel chromatography (chloroform-methanol) to obtain a compound 0141 (5 mg) as a pale yellow solid.

MS m/z (M+H): 370.

Example 142

Synthesis of Compound 0142

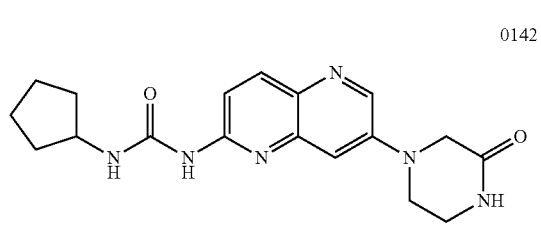 [SMILES: O=C1CN(c2cnc3ccc(NC(=O)NC4CCCC4)nc3c2)CCN1]

To the compound 0001-5 (17 mg) were added 2-piperazinone (7.5 mg), 2-dicyclohexylphosphino-2',4',6'-triisopropylbiphenyl (5.7 mg), tris(dibenzylideneacetone)dipalladium (0) (4.5 mg), sodium tert-butoxide (14 mg), and dioxane (2 mL) under a nitrogen air flow, and the mixture was stirred at 150° C. for 0.5 hours using a microwave reaction device. After air-cooling, water was added to the reaction solution, and the mixture was extracted with ethyl acetate. The obtained organic layer was washed with brine and then dried over anhydrous sodium sulfate. The solvent was evaporated under reduced pressure and the obtained residue was purified by preparative thin layer silica gel chromatography (chloroform-methanol) to obtain a compound 0142 (0.9 mg) as a white solid.

MS m/z (M+H): 355.

Example 143

Synthesis of Compound 0143

(Synthesis of Compound 0143-1)

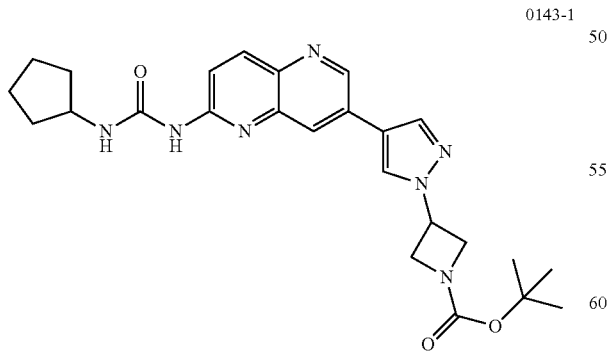

1,4-dioxane (2 mL) and a 2 M aqueous sodium carbonate solution (94 µL) were added to the compound 0001-5 (21 mg), tert-butyl 3-(4-(4,4,5,5-tetramethyl-1,3,2-dioxaborolan-2-yl)-1H-pyrazol-1-yl)azetidine-1-carboxylate (44 mg, which was synthesized according to Journal of Medicinal Chemistry, 2011, 54, 6342), and bis(di-tert-butyl(4-dimethylaminophenyl)phosphine)dichloropalladium (II) (4.4 mg) under a nitrogen air flow, and the mixture was stirred at 100° C. overnight. The reaction solution was cooled, water was then added thereto, and the mixture was extracted with ethyl acetate. The organic layer was washed with brine and then dried over anhydrous sodium sulfate, and the solvent was evaporated under reduced pressure. The obtained residue was purified by silica gel chromatography (chloroform-methanol) to obtain a compound 0143-1 (13 mg) as a white solid.

MS m/z (M+H): 478.

(Synthesis of Compound 0143)

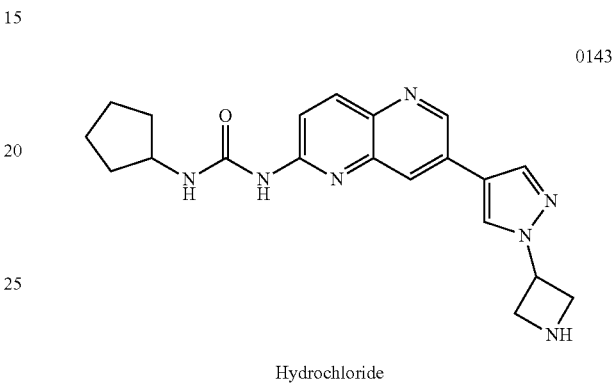

Hydrochloride

Methanol (2 mL) and a 4 M hydrogen chloride/1,4-dioxane solution (2 mL) were added to the compound 0143-1 (13 mg), and the mixture was stirred at room temperature. After completion of the reaction, the solvent was evaporated under reduced pressure. The obtained residue was dissolved in a small amount of methanol, and ethyl acetate was added thereto. The resulting solid was filtered and dried under reduced pressure to obtain a compound 0143 hydrochloride (9 mg) as a pale yellow solid.

MS m/z (M+H): 378.

Example 144

Synthesis of Compound 0144

(Synthesis of Compound 0144-1)

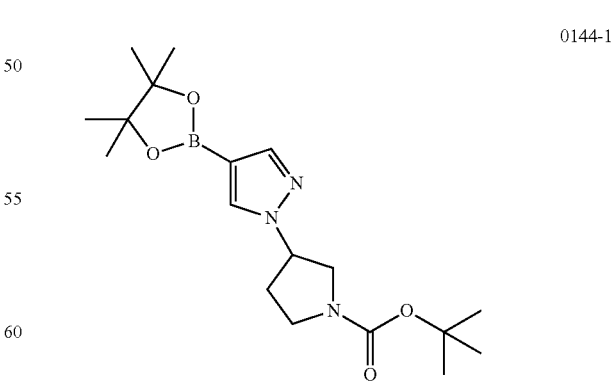

Dimethyl sulfoxide (2 mL) was added to tert-butyl-3-(4-bromo-1H-pyrazol-1-yl)pyrrolidine-1-carboxylate (100 mg, synthesized according to WO2009/150240A1), pinacol diborane (96 mg), 1,1'-bis(diphenylphosphino)ferrocene palladium (II) chloride dichloromethane complex (1:1) (13 mg), and potassium acetate (106 mg) under a nitrogen air flow, and the mixture was stirred at 80° C. for 7 hours. The reaction solution was cooled to room temperature, water was added thereto, and the obtained aqueous solution was filtered over celite. The filtrate was extracted with ethyl acetate and the organic layer was washed with water and brine, and then dried over anhydrous sodium sulfate. The solvent was evaporated under reduced pressure and the obtained residue was purified by silica gel chromatography (hexane-ethyl acetate) to obtain a compound 0144-1 (83 mg) as a colorless oily substance.

$^1$H-NMR (CDCl$_3$) δ: 7.80 (1H, s), 7.73 (1H, s), 4.92-4.87 (1H, m), 3.90-3.49 (4H, m), 2.41-2.33 (2H, m), 1.32 (9H, s), 1.24 (12H, s).

(Synthesis of Compound 0144-2)

0144-2

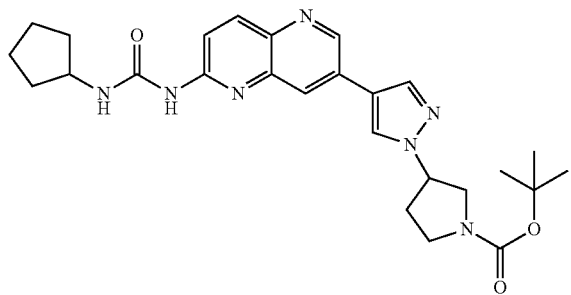

The compound 0001-5 (21 mg), the compound 0144-1 (45 mg), and bis(di-tert-butyl(4-dimethylaminophenyl)phosphine) dichloropalladium (II) (4.4 mg) were dissolved in 1,4-dioxane (2 mL) under a nitrogen air flow, and a 2 M aqueous sodium carbonate solution (93 μL) was added thereto. The reaction vessel was closed and the mixture was stirred at 100° C. for 5 hours. The reaction solution was cooled to room temperature and poured into water, and the resulting solid was separated by filtration. The solid was washed with a mixed solvent of water and hexane-ethyl acetate (1:1) to obtain a compound 0144-2 (27 mg) as a pale yellow solid.

MS m/z (M+H): 492.

(Synthesis of Compound 0144)

0144

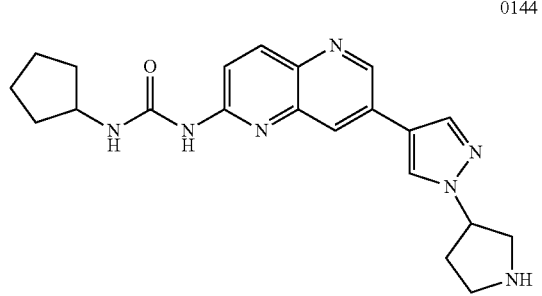

Hydrochloride

To the compound 0144-2 (25 mg), methanol (2 mL) and a 4 M hydrogen chloride/1,4-dioxane solution (2 mL) were added, and the mixture was stirred at room temperature. After completion of the reaction, the solvent was evaporated under reduced pressure. The obtained residue was dissolved in a small amount of methanol, and ethyl acetate was added thereto. The resulting solid was filtered, washed with ethyl acetate, and dried under reduced pressure to obtain a compound 0144 hydrochloride (17 mg) as a yellow solid.

MS m/z (M+H): 392.

Example 145

Synthesis of Compound 0145

0145

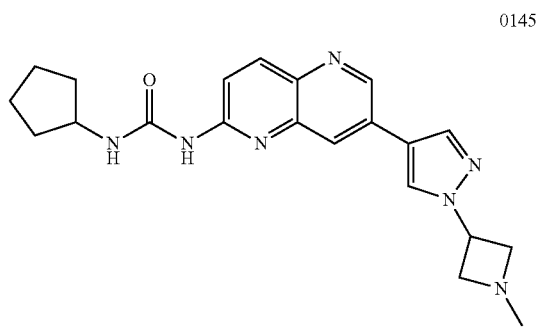 [SMILES: CN1CC(n2cc(-c3cnc4ccc(NC(=O)NC5CCCC5)nc4c3)cn2)C1]

The compound 0143 (18 mg) was dissolved in methanol (2 mL), formalin (44 μL) and sodium cyanoborohydride (11 mg) were added thereto, and the mixture was stirred at room temperature. After completion of the reaction, the reaction solution was poured into a saturated aqueous sodium hydrogen carbonate solution, and the mixture was extracted with chloroform. The organic layer was dried over anhydrous sodium sulfate. The solvent was evaporated under reduced pressure and the obtained residue was purified by preparative thin layer silica gel chromatography (chloroform-methanol) to obtain a compound 0145 (5 mg).

$^1$H-NMR (DMSO-d$_6$) δ: 9.95 (1H, bs), 8.94 (1H, d), 8.74-8.56 (1H, m), 8.20 (1H, d), 8.03 (1H, s), 7.99 (1H, s), 7.97 (1H, d), 7.08 (1H, d), 5.02 (1H, m), 4.34-4.33 (1H, m), 3.88-3.83 (2H, m), 3.64-3.60 (2H, m), 2.49 (3H, s), 2.19-2.06 (2H, m), 1.93-1.66 (6H, m).

MS m/z (M+H): 392.

Example 146

Synthesis of Compound 0146-1

0146-1

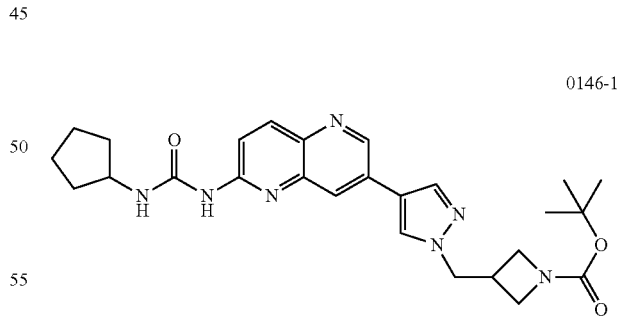

Under a nitrogen air flow, to the compound 0001-5 (33 mg), bis(pinacolato)diboron (38 mg), 1,1'-bis(diphenylphosphino)ferrocene palladium (II) chloride dichloromethane complex (1:1) (8 mg), and potassium acetate (20 mg) was added 1,4-dioxane (2 mL). The reaction vessel was closed and the mixture was stirred at 80° C. for 2 hours. The reaction solution was returned to room temperature, and tert-butyl3-((4-bromo-1H-pyrazol-1-yl)methyl)azetidine-1-carboxylate (38 mg, which was synthesized according to Journal of Medicinal Chemistry, 2011, 54, 6342), bis(di-tert-butyl(4- dimethylaminophenyl)phosphine)dichloropalladium (II) (7 mg) and a 2 M aqueous sodium carbonate solution (200 μL) were added thereto. The reaction vessel was closed and the mixture was stirred at 100° C. for 1.5 hours. The reaction solution was returned to room temperature, water was added thereto, and the mixture was filtered over celite. The filtrate was extracted with chloroform and dried over anhydrous sodium sulfate, and the solvent was evaporated under reduced pressure. The obtained residue was purified by silica gel chromatography (chloroform-methanol) to obtain a 0146-1 (14 mg) as a pale yellow solid.

MS m/z (M+H): 492.

(Synthesis of Compound 0146)

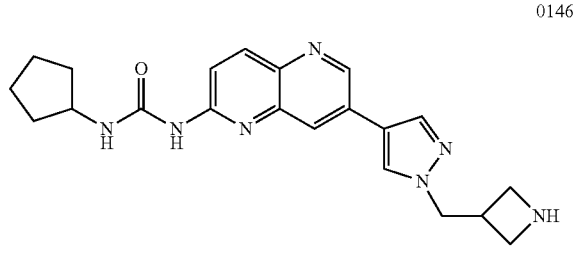 [SMILES: O=C(Nc1ccc2ncc(-c3cnn(CC4CNC4)c3)cc2n1)NC1CCCC1]

0146

The compound 0146-1 (14 mg) was dissolved in methanol (1 mL), a 4 M hydrogen chloride/1,4-dioxane solution (1 mL) was added thereto, and the mixture was stirred at room temperature. After completion of the reaction, the solvent was evaporated under reduced pressure and the obtained residue was dissolved in a small amount of methanol. Ethyl acetate was added thereto and the resulting solid was filtered. The solid was dissolved in a saturated aqueous sodium hydrogen carbonate solution, and the solution was extracted with chloroform and dried over anhydrous sodium sulfate. The solvent was evaporated under reduced pressure and the obtained residue was purified by preparative thin layer silica gel chromatography (chloroform-methanol, NH silica) to obtain a compound 0146 (2 mg) as a white solid.

$^1$H-NMR (DMSO-d$_6$) δ: 9.76 (1H, s), 9.14 (1H, bd), 9.06 (1H, d), 8.52 (1H, s), 8.22-8.19 (3H, m), 8.13 (1H, d), 7.50 (1H, d), 4.37 (2H, d), 4.18-4.03 (1H, m), 3.55-3.49 (2H, m), 3.40-3.29 (2H, m), 3.13-3.05 (1H, m), 1.98-1.91 (2H, m), 1.86-1.50 (6H, m).

MS m/z (M+H): 392.

Example 147

Synthesis of Compound 0147

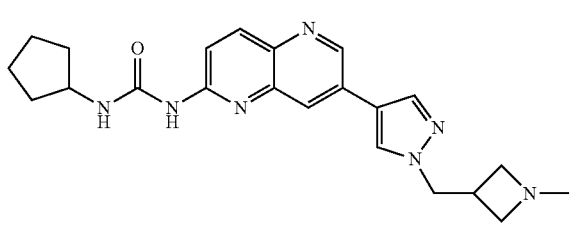

0147

The compound 0146 (22 mg) was dissolved in methanol (1 mL), formalin (22 μL) and sodium cyanoborohydride (14 mg) were added thereto, and the mixture was stirred at room temperature. After completion of the reaction, the reaction solution was poured into a saturated aqueous sodium hydrogen carbonate solution, the mixture was extracted with chloroform, and the organic layer was dried over anhydrous sodium sulfate. The solvent was evaporated under reduced pressure and the obtained residue was purified by preparative thin layer silica gel chromatography (chloroform-methanol, NH silica) to obtain a compound 0147 (5 mg) as a pale yellow solid.

$^1$H-NMR (CDCl$_3$) δ: 10.00 (1H, bd), 9.03 (1H, s), 8.92 (1H, d), 8.19 (1H, d), 7.94 (2H, s), 7.84 (1H, s), 7.12 (1H, d), 4.43 (2H, d), 4.40-4.30 (1H, m), 3.36 (2H, t), 3.11-2.97 (3H, m), 2.33 (3H, s), 2.22-2.11 (2H, m), 1.96-1.65 (6H, m).

MS m/z (M+H): 406.

Example 148

Synthesis of Compound 0148

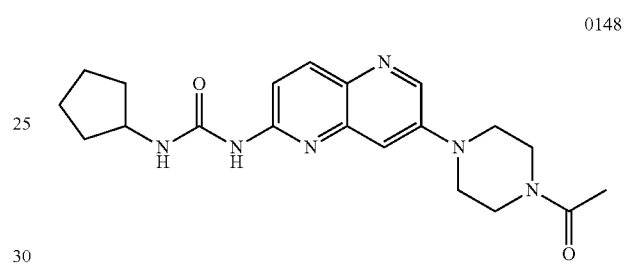

0148

The same method as in Example 142 except for using N-acetylpiperazine instead of 2-piperazinone used for the synthesis of the compound 0142 in Example 142, and using 1,4-dioxane-tert-butanol (1:1) instead of dioxane used for or the synthesis of the compound 0142 in Example 142 was used to obtain a compound 0148 (9 mg) as a pale yellow solid.

$^1$H-NMR (CDCl$_3$) δ: 9.92 (1H, bd), 8.63 (1H, d), 8.10 (1H, d), 8.04 (1H, bs), 7.17 (1H, d), 6.87 (1H, d), 4.38-4.25 (1H, m), 3.89-3.86 (2H, m), 3.75-3.72 (2H, m), 3.41-3.34 (4H, m), 2.19 (3H, s), 2.2.15-2.03 (2H, m), 1.90-1.60 (6H, m).

Example 149

Synthesis of Compound 0149

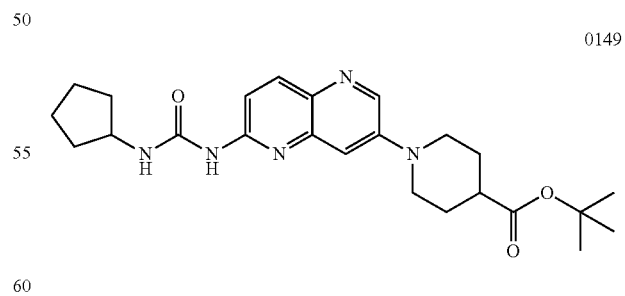

0149

The same method as in Example 148 except for using 4-tert-butoxycarbonylpiperidine instead of N-acetylpiperazine used for the synthesis of the compound 0148 in Example 148 was used to obtain a compound 0149 (10 mg) as a pale yellow solid.

MS m/z (M+H): 440.

Example 150

Synthesis of Compound 0150

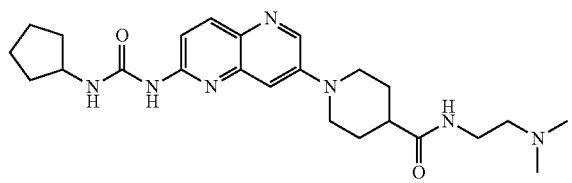

0150

The same method as in Example 148 except for using N-(2-(dimethylamino)ethyl)piperidine-4-carboxamide (which was synthesized according to Tetrahedron, 2009, 65, 8538) instead of N-acetylpiperazine used for the synthesis of the compound 0148 in Example 148 was used to obtain a compound 0150 (4 mg) as a white solid.

MS m/z (M+H): 454.

Example 151

Synthesis of Compound 0151

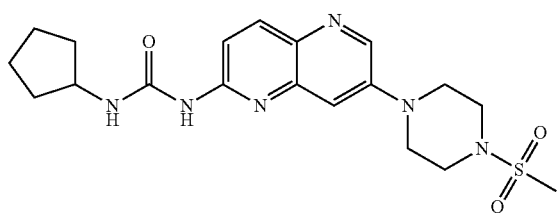

0151

The same method as in Example 148 except for using N-mesylpiperazine instead of N-acetylpiperazine used for the synthesis of the compound 0148 in Example 148 was used to obtain a compound 0151 (10 mg) as a white solid.

MS m/z (M+H): 419.

Example 152

Synthesis of Compound 0152

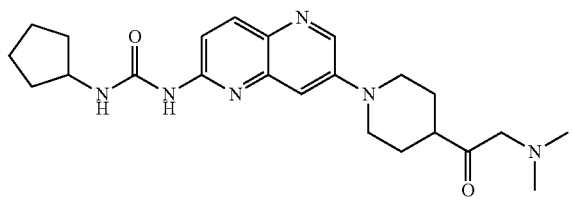

0152

The compound 0013 (30 mg) and N,N-dimethylglycine (12 mg) were dissolved in N,N-dimethylformamide (2 mL), and triethylamine (33 μL), 1-hydroxybenzotriazole (18 mg), and 1-ethyl-3-(3-dimethylaminopropyl)carbodiimide hydrochloride (23 mg) were added thereto. The mixture was stirred at room temperature overnight. The reaction solution was poured into a saturated aqueous sodium hydrogen carbonate solution, and the mixture was extracted with ethyl acetate. The obtained organic layer was washed with water and brine, and dried over anhydrous sodium sulfate. The solvent was evaporated under reduced pressure and the obtained residue was purified by silica gel chromatography (chloroform-methanol, NH silica) to obtain a compound 0152 (17 mg) as a pale yellow solid.

MS m/z (M+H): 454.

Example 153

Synthesis of Compound 0153

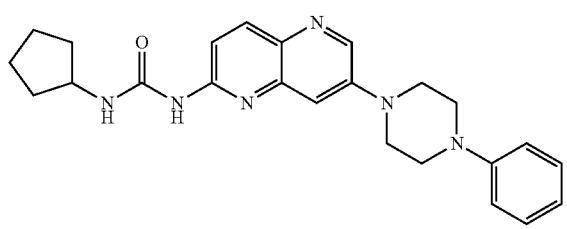

0153

The same method as in Example 148 except for using N-phenylpiperazine instead of N-acetylpiperazine used for the synthesis of the compound 0148 in Example 148 was used to obtain a compound 0153 (11 mg) as a pale yellow solid.

MS m/z (M+H): 417.

Example 154

Synthesis of Compound 0154

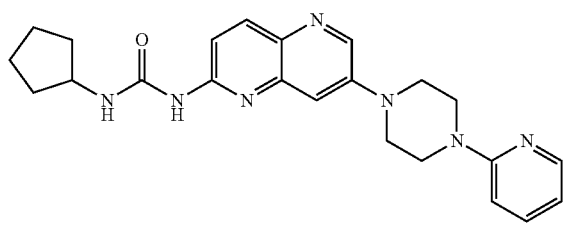

0154

The same method as in Example 148 except for using 1-(pyridine-2-yl)piperazine instead of N-acetylpiperazine used for the synthesis of the compound 0148 in Example 148 was used to obtain a compound 0154 (12 mg) as a pale yellow solid.

MS m/z (M+H): 418.

Example 155

Synthesis of Compound 0155

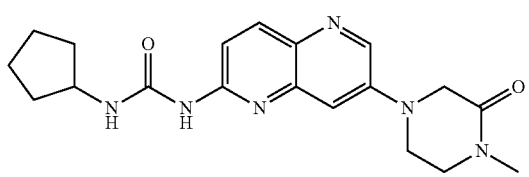

0155

The same method as in Example 148 except for using 1-methylpiperazin-2-one instead of N-acetylpiperazine used for the synthesis of the compound 0148 in Example 148 was used to obtain a compound 0155 (12 mg) as a pale yellow solid.

MS m/z (M+H): 369.

Example 156

Synthesis of Compound 0156

0156

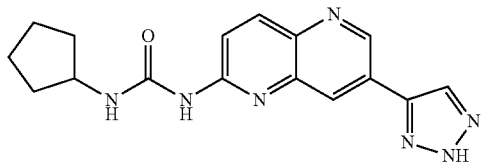

The compound 0017 (43 mg), sodium azide (29 mg), and ammonium chloride (24 mg) was dissolved in N,N-dimethylformamide (2 mL) and the solution was stirred at 100° C. for 4 hours. The reaction solution was cooled to room temperature, the insoluble materials were then filtered, and the obtained filtrate was purified by reverse phase preparative separation (0.1% $HCO_2H$ aqueous solution-0.1% $HCO_2H$ acetonitrile solution) to obtain a compound 0156 (6 mg) as a pale orange solid.

MS m/z (M+H): 324.

Example 157

Synthesis of Compound 0157

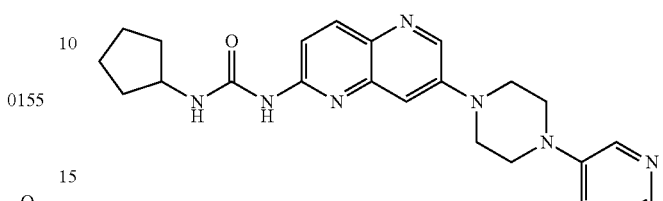

0157

The same method as in Example 148 except for using 1-(pyridin-3-yl)piperazine instead of N-acetylpiperazine used for the synthesis of the compound 0148 in Example 148 was used to obtain a compound 0157 (6 mg) as a pale yellow solid.

$^1$H-NMR ($CDCl_3$) δ: 10.00 (1H, bd), 9.03 (1H, s), 8.92 (1H, d), 8.19 (1H, d), 7.94 (2H, s), 7.84 (1H, s), 7.12 (1H, d), 4.43 (2H, d), 4.40-4.30 (1H, m), 3.36 (2H, t), 3.11-2.97 (3H, m), 2.33 (3H, s), 2.22-2.11 (2H, m), 1.96-1.65 (6H, m).

MS m/z (M+H): 418.

Example 158

Synthesis of Compound 0158

[Chem. 208]

0158

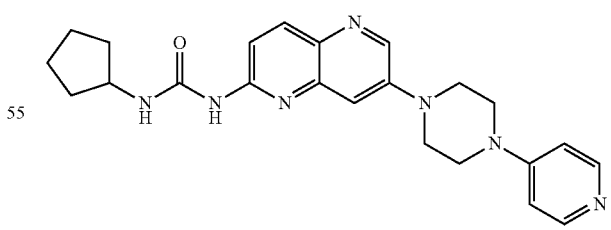

The same method as in Example 148 except for using 1-(pyridine-4-yl)piperazine instead of N-acetylpiperazine used for the synthesis of the compound 0148 in Example 148 was used to obtain a compound 0158 (6 mg) as a pale yellow solid.

MS m/z (M+H): 418.

Example 159

Synthesis of Compound 0159

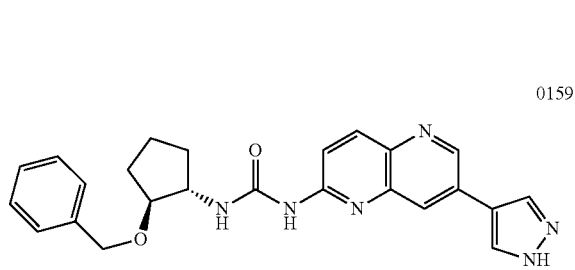 [SMILES: O=C(Nc1ccc2ncc(-c3cn[nH]c3)cc2n1)N[C@H]1CCC[C@@H]1OCc1ccccc1]

0159

The same method as in Example 64 except for using (1S, 2S)-2-(benzyloxy)cyclopentanamine instead of 4-phenylbutylamine used for the synthesis of the compound 0064 in Example 64 was used to obtain a compound 0159 (29 mg) as a pale yellow solid.

MS m/z (M+H): 429.

Example 160

Synthesis of Compound 0160

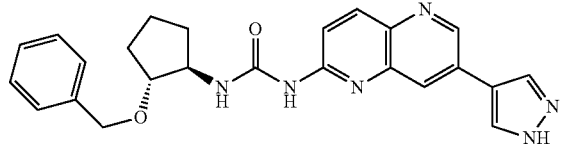

0160

The same method as in Example 64 except for using (1R, 2R)-2-(benzyloxy)cyclopentanamine instead of 4-phenylbutylamine used for the synthesis of the compound 0064 in Example 64 was used to obtain a compound 0160 (36 mg) as a pale yellow solid.

MS m/z (M+H): 429.

Example 161

Synthesis of Compound 0161-1

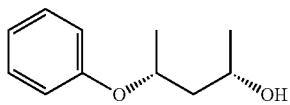

0161-1

The same method as in Example 91 except for using (2S, 4S)-(+)-2,4-pentanediol instead of trans-3-(tert-butyldimethylsilyloxy)cyclopentanol used for the synthesis of the compound 0091-1 in Example 91, and using phenol instead of phthalimido for the synthesis of the compound 0091-1 in Example 91 was used to obtain a compound 0161-1 (1.74 g) as a white solid.

(Synthesis of Compound 0161-2)

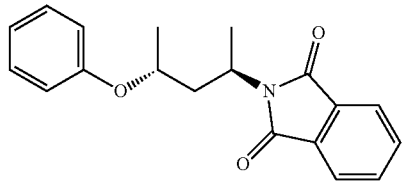

0161-2

The same method as in Example 91 except for using the compound 0161-1 instead of trans-3-(tert-butyldimethylsilyloxy)cyclopentanol used for the synthesis of the compound 0091-1 in Example 91 was used to obtain a compound 0161-2 (536 mg) as a white solid.

$^1$H-NMR (CDCl$_3$) δ: 7.79-7.76 (2H, m), 7.72-7.66 (2H, m), 7.18-7.12 (2H, m), 6.86-6.84 (1H, m), 6.72-6.71 (2H, m), 4.77-4.65 (1H, m), 4.33-4.23 (1H, m), 2.64-2.55 (1H, m), 2.05-2.02 (1H, m), 1.51 (3H, d), 1.27 (3H, t).

(Synthesis of Compound 0161-3)

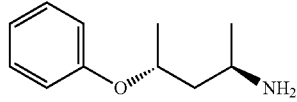

0161-3

To a solution of the compound 0161-2 (382 mg) in isopropanol (7 mL), hydrazine monohydrate (0.24 mL) was added, the mixture was warmed to 80° C., and the mixture was stirred for 17 hours. The reaction solution was cooled to room temperature, and isopropanol (15 mL) was added thereto. The mixture filtered over celite and the residue was washed with isopropanol (5 mL). The collected filtrate was concentrated, and the mixture was subjected to liquid separation by the addition of toluene (5 mL), tetrahydrofuran (1 mL), and brine (2 mL). The organic layer was dried over sodium sulfate. The solvent was evaporated under reduced pressure to obtain a compound 0161-3 (227 mg) as a pale yellow oily substance.

MS m/z (M+H): 180.

(Synthesis of Compound 0161)

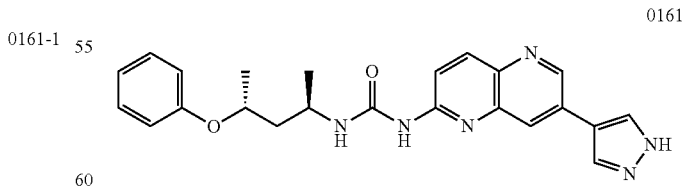

0161

The same method as in Example 64 except for using the compound 0161-3 instead of 4-phenylbutylamine in Example 64 was used to obtain a compound 0161 (30 mg) as a pale yellow solid.

MS m/z (M+H): 417.

Example 162

Synthesis of Compound 0162-1

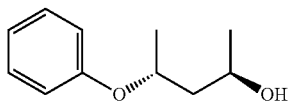
0162-1

To a solution of ((2R,4R)-4-phenoxypentane-2-yl) 4-methylbenzoate synthesized by the same method as in Example 91 except for using p-toluoyl acid instead of phthalimide used for the synthesis of the compound 0091-1 in ethanol (5 mL), water (3 mL) and a 6 M aqueous sodium hydroxide solution (1.95 mL) were added, and the mixture was warmed to 80° C. and then stirred for 5 hours. The reaction solution was cooled to room temperature and then concentrated. The mixture was subjected to liquid separation by the addition of toluene (40 mL), acetic acid (10 mL), and water (5 mL). The organic layer was washed with brine and dried over sodium sulfate, and the solvent was then evaporated under reduced pressure. The obtained residue was purified by silica gel chromatography (hexane-ethyl acetate) to obtain a compound 0162-1 (833 mg) as a white solid.

MS m/z (M+H): 181.

Synthesis of Compound 0162-2

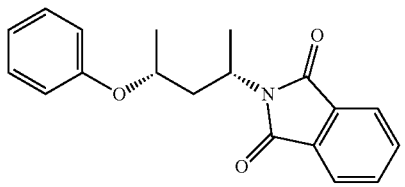
0162-2

The same method as in Example 91 except for using the compound 0161-1 instead of trans-3-(tert-butyldimethylsilyloxy)cyclopentanol used for the synthesis of the compound 0091-1 in Example 91, and using a 40% isopropyl azodicarboxylic acid solution in toluene instead of diethyl azodicarboxylic acid used for the synthesis of the compound 0091-1 in Example 91 was used to obtain a compound 0162-2 (920 mg) as a white solid.

$^1$H-NMR (CDCl$_3$) δ: 7.77-7.73 (2H, m), 7.69-7.65 (2H, m), 7.15-7.09 (2H, m), 6.83-6.81 (1H, m), 6.66-6.65 (2H, m), 4.65-4.59 (1H, m), 4.45-4.42 (1H, m), 2.54 (1H, ddd), 2.03 (1H, ddd), 1.50 (3H, d), 1.30 (3H, d).

(Synthesis of Compound 0162-3)

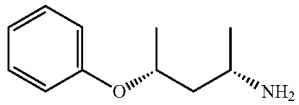
0162-3

To a solution of the compound 162-2 (920 mg) in ethanol (20 mL) was added hydrazine monohydrate (0.29 mL), and the mixture was warmed to 80° C. and stirred for 7 hours. The reaction solution was cooled to room temperature and then filtered over celite, and the residue was washed with isopropanol (5 mL). The solvent was evaporated under reduced pressure, and the mixture was then subjected to liquid separation by the addition of ethyl acetate (20 mL), brine (3 mL), water (3 mL), and a 6 M aqueous sodium hydroxide solution (0.3 mL). The aqueous layer was washed with ethyl acetate (20 mL). The organic layer was dried over sodium sulfate and the solvent was then evaporated under reduced pressure to obtain a compound 0162-3 (273 mg) as a pale yellow oily substance.

MS m/z (M+H): 180.

(Synthesis of Compound 0162)

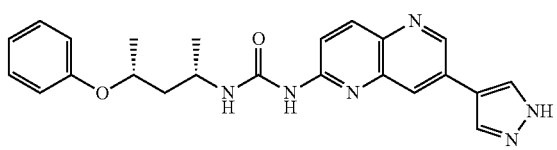
0162

The same method as in Example 64 except for using the compound 0162-3 instead of 4-phenylbutylamine used in Example 64 was used to obtain a compound 0162 (30 mg) as a pale yellow solid.

MS m/z (M+H): 417.

Example 163

Synthesis of Compound 0163

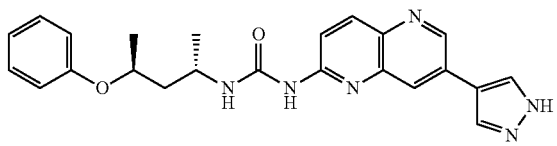
0163

The same method as in Example 161 except for using (2R,4R)-pentane-2,4-diol instead of (2S,4S)-(−)-2,4-pentanediol used in Example 161 was used to obtain a compound 0163 (26 mg) as a pale yellow solid.

MS m/z (M+H): 417.

Example 164

Synthesis of Compound 0164

(Synthesis of Compound 0164-1)

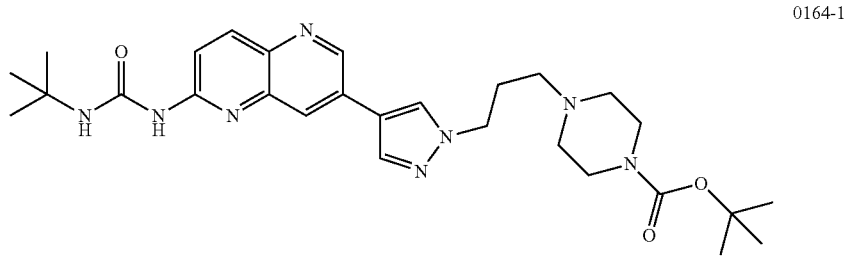 [SMILES: CC(C)(C)NC(=O)Nc1ccc2ncc(-c3cnn(CCCN4CCN(C(=O)OC(C)(C)C)CC4)c3)cc2n1]

0164-1

The same method as in Example 53 except for using tert-butyl isocyanate instead of isopropyl isocyanate and using the compound 0211-1 instead of 1-tert-butoxycarbonyl-1H-pyrazole-4-boronic acid pinacol ester in Example 53 was used to obtain a compound 0164-1 (60 mg) as a pale yellow solid.

MS m/z (M+H): 537.

(Synthesis of Compound 0164)

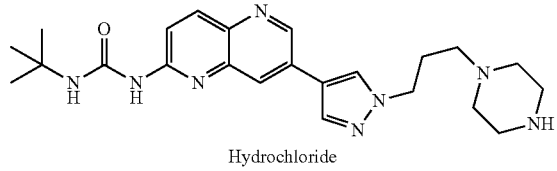

0164

Hydrochloride

The same method as in Example 73 except for using the compound 0164-1 instead of the compound 0070 in Example 73 was used to obtain a compound 0164 hydrochloride (61 mg) as a yellow solid.

MS m/z (M+H): 437.4

Example 165

Synthesis of Compound 0165

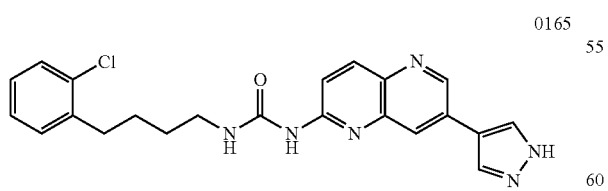

0165

The same method as in Example 64 except for using 4-(2-chlorophenyl)butan-1-amine instead of 4-phenylbutylamine used in Example 64 was used to obtain a compound 0165 (18 mg) as a pale yellow solid.

MS m/z (M+H): 421.

Example 166

Synthesis of Compound 0166

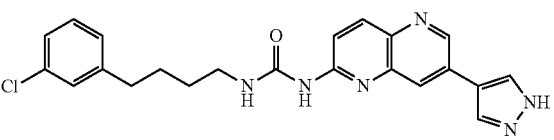

0166

The same method as in Example 64 except for using 4-(3-chlorophenyl)butan-1-amine instead of 4-phenylbutylamine used in Example 64 was used to obtain a compound 0166 (19 mg) as a pale yellow solid.

MS m/z (M+H): 421.

Example 167

Synthesis of Compound 0167

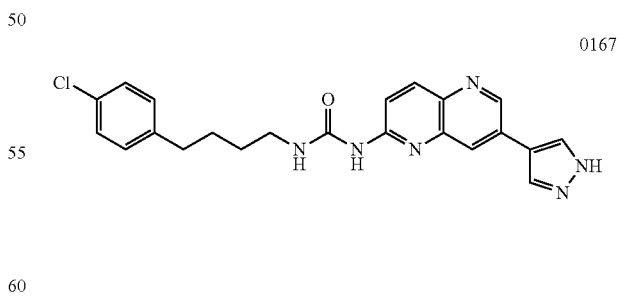

0167

The same method as in Example 64 except for using 4-(4-chlorophenyl)butan-1-amine instead of 4-phenylbutylamine used in Example 64 was used to obtain a compound 0167 (18 mg) as a pale yellow solid.

MS m/z (M+H): 421.

Example 168

Synthesis of Compound 0168

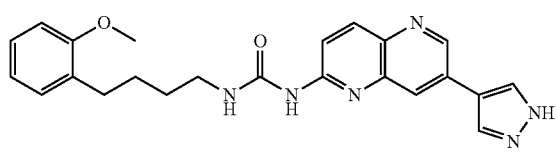
0168

The same method as in Example 64 except for using 4-(2-methoxyphenyl)butan-1-amine instead of 4-phenylbutylamine used in Example 64 was used to obtain a compound 0168 (21 mg) as a pale yellow solid.

MS m/z (M+H): 417.

Example 169

Synthesis of Compound 0169

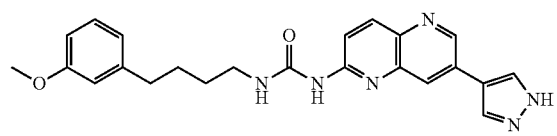
0169

The same method as in Example 64 except for using 4-(3-methoxyphenyl)butan-1-amine instead of 4-phenylbutylamine used in Example 64 was used to obtain a compound 0169 (17 mg) as a pale yellow solid.

MS m/z (M+H): 417.

Example 170

Synthesis of Compound 0170

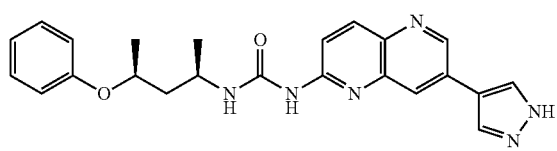
0170

The same method as in Example 161 except for using (2R,4R)-pentane-2,4-diol instead of (2S,4S)-(+)-2,4-pentane diol used for the synthesis of the compound 0161-1 in Example 161 was used to obtain a compound 0170 (11 mg) as a pale yellow solid.

MS m/z (M+H): 417.

Example 171

Synthesis of Compound 0171

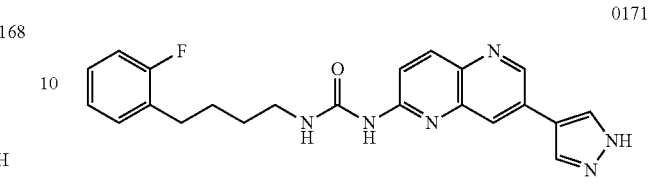
0171

The same method as in Example 64 except for using 4-(2-fluorophenyl)butan-1-amine instead of 4-phenylbutylamine used in Example 64 was used to obtain a compound 0171 (17 mg) as a pale yellow solid.

MS m/z (M+H): 405.

Example 172

Synthesis of Compound 0172

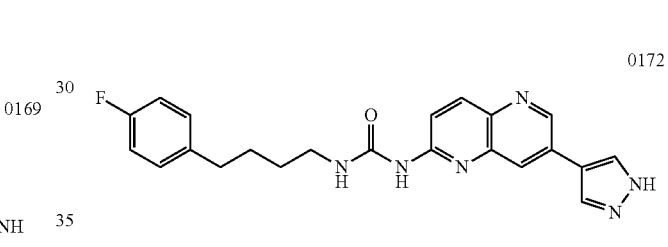
0172

The same method as in Example 64 except for using 4-(4-fluorophenyl)butan-1-amine instead of 4-phenylbutylamine used in Example 64 was used to obtain a compound 0172 (25 mg) as a pale yellow solid.

$^1$H-NMR (DMSO-$d_6$) δ: 13.21 (1H, s), 9.82 (1H, s), 9.31 (1H, t), 9.10 (1H, d), 8.48 (1H, s), 8.29 (1H, d), 8.20 (1H, d), 8.17 (1H, s), 7.44 (1H, d), 7.35-7.04 (4H, m), 2.69 (2H, t), 1.72-1.56 (4H, m).

MS m/z (M+H): 405.

Example 173

Synthesis of Compound 0173

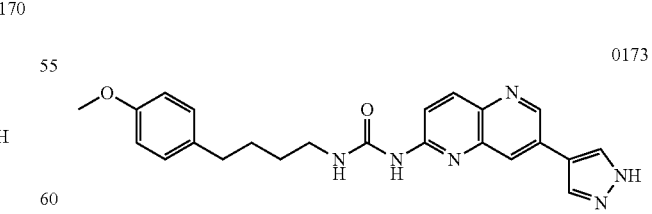
0173

The same method as in Example 64 except for using 4-(4-methoxyphenyl)butan-1-amine instead of 4-phenylbutylamine used in Example 64 was used to obtain a compound 0173 (36 mg) as a pale yellow solid.

MS m/z (M+H): 417.

Example 174

Synthesis of Compound 0174

(Synthesis of Compound 0174-1)

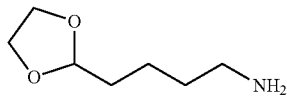
0174-1

A solution of 2-(4-bromobutyl)-1,3-dioxolane (2 mL) and potassium phthalimido (2.94 g) in N,N-dimethylformamide (15 mL) was stirred at 80° C. for 16 hours. After cooling to room temperature, the mixture was subjected to liquid separation by the addition of water (20 mL), toluene (40 mL), and ethyl acetate (10 mL), and the aqueous layer was washed with a mixed solution of toluene (40 mL) and ethyl acetate (10 mL). The organic layer was washed with brine and the solvent was then evaporated under reduced pressure, and the obtained residue was purified by silica gel column chromatography (hexane-ethyl acetate). A solution of the obtained compound and hydrazine monohydrate (1.35 mL) in isopropanol (50 mL) was stirred at 80° C. for 9 hours. After cooling to room temperature, isopropanol (20 mL) and ethanol (10 mL) were added thereto, and the mixture was subjected to sonication and filtered over celite. The solvent was evaporated under reduced pressure, and the mixture was then subjected to liquid separation by the addition of ethyl acetate (30 mL), a 6 M aqueous sodium hydroxide solution (5 mL) and brine (5 mL). The aqueous layer was washed with ethyl acetate (30 mL). The collected organic layer was dried over sodium sulfate and the solvent was then evaporated under reduced pressure to obtain a compound 0174-1 (1.87 g) as a colorless oily substance.

(Synthesis of Compound 0174)

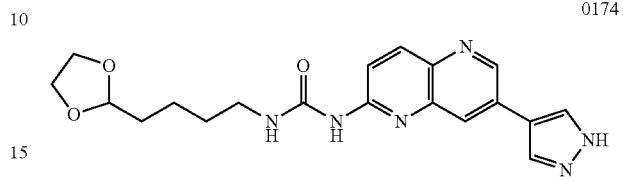
0174

The same method as in Example 64 except for using the compound 0174-1 instead of 4-phenylbutylamine used in Example 64 was used to obtain a compound 0174 (53 mg) as a pale yellow solid.

MS m/z (M+H): 383.

Example 175

Synthesis of Compound 0175

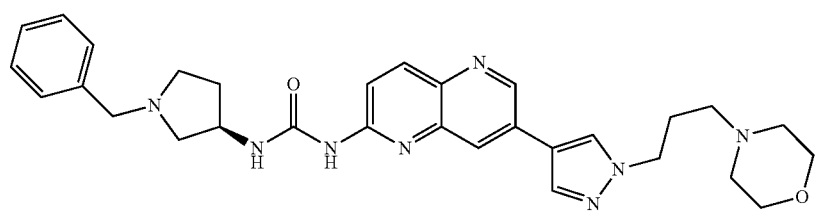
0175

The same method as in Example 64 except for using (3R)-(−)-1-benzyl-3-aminopyrrolidine instead of 4-phenylbutylamine used in Example 64, and using a 1-(3-morpholinopropyl)-1H-pyrazole-4-boronic acid pinacol ester instead of 1-tert-butoxycarbonyl-4-(4,4,5,5-tetramethyl-1,3,2-dioxaborolan-2-yl)pyrazole used in Example 64 was used to obtain a compound 0175 (34 mg) as a pale yellow solid.

$^1$H-NMR (DMSO-d$_6$) δ: 9.81 (1H, s), 9.32 (1H, d), 9.07 (1H, d), 8.45 (1H, s), 8.21 (1H, d), 8.16 (1H, d), 8.13 (1H, s), 7.51 (1H, d), 7.38-7.17 (6H, m), 4.31-4.22 (1H, m), 4.19 (2H, t), 3.67 (2H, s), 3.57 (4H, t), 2.87-2.78 (1H, m), 2.74-2.65 (1H, m), 2.62-2.53 (1H, m), 2.44-2.20 (8H, m), 2.02-1.91 (2H, m), 1.83-1.70 (1H, m).

MS m/z (M+H): 541.

Example 176

Synthesis of Compound 0176

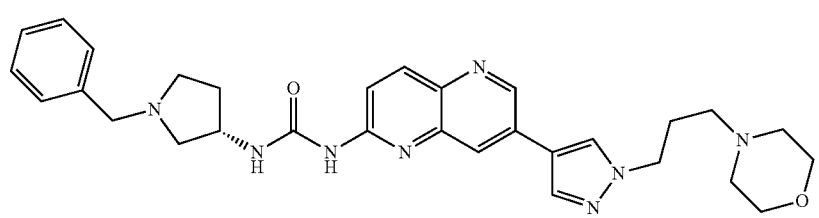
0176

The same method as in Example 0175 except for using (3S)-(+)-1-benzyl-3-aminopyrrolidine instead of (3R)-(−)-1-benzyl-3-aminopyrrolidine used in Example 0175 was used to obtain a compound 0176 (29 mg) as a pale yellow solid.
MS m/z (M+H): 541.

Example 177

Synthesis of Compound 0177

The same method as in Example 0175 except for using 3-amino-1-phenylbutane instead of (3R)-(−)-1-benzyl-3-aminopyrrolidine used in Example 0175 was used to obtain a compound 0179 (17 mg) as a pale yellow solid.
MS m/z (M+H): 514.

Example 180

Synthesis of Compound 0180

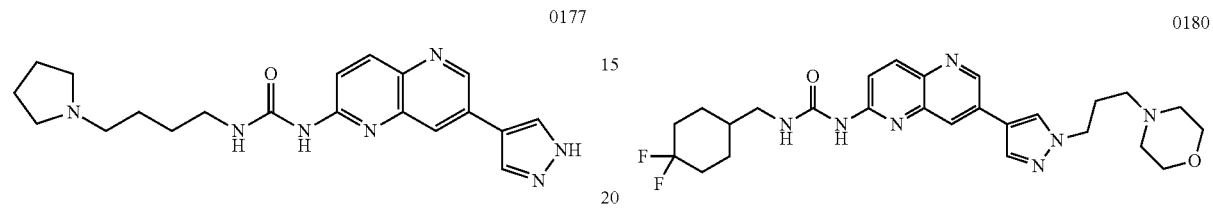

The same method as in Example 64 except for using 4-(1-pyrrolidino)butylamine instead of 4-phenylbutylamine used in Example 64 was used to obtain a compound 0177 (29 mg) as a pale yellow solid.
MS m/z (M+H): 380.

Example 178

Synthesis of Compound 0178

The same method as in Example 0175 except for using (4,4-difluorocyclohexyl)methanamine instead of (3R)-(−)-1-benzyl-3-aminopyrrolidine used in Example 0175 was used to obtain a compound 0180 (33 mg) as a pale yellow solid.
$^1$H-NMR (DMSO-$d_6$) δ: 9.88 (1H, s), 9.39 (1H, brs), 9.06 (1H, d), 8.48 (1H, s), 8.23 (1H, d), 8.21 (1H, d), 8.15 (1H, s), 7.45 (1H, d), 4.21 (2H, t), 3.57 (4H, t), 3.23 (2H t), 2.36-2.25 (6H, m), 2.12-1.68 (9H, m), 1.33 (2H, t).
MS m/z (M+H): 514.

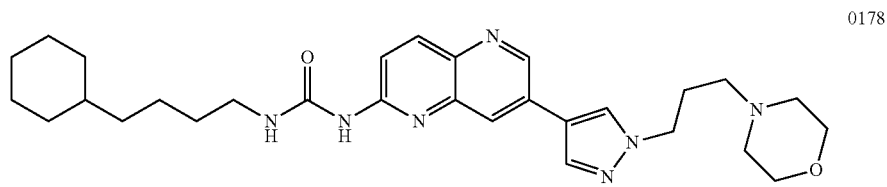 [SMILES: O=C(NCCCCC1CCCCC1)Nc1ccc2ncc(-c3cnn(CCCN4CCOCC4)c3)cc2n1]

The same method as in Example 0175 except for using 4-cyclohexyl-butylamine instead of (3R)-(−)-1-benzyl-3-aminopyrrolidine used in Example 0175 was used to obtain a compound 0178 (29 mg) as a pale yellow solid.
MS m/z (M+H): 520.

Example 179

Synthesis of Compound 0179

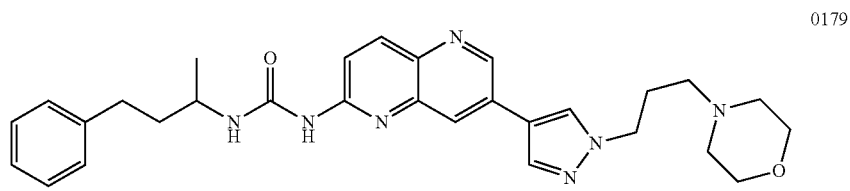 [SMILES: CC(CCc1ccccc1)NC(=O)Nc1ccc2ncc(-c3cnn(CCCN4CCOCC4)c3)cc2n1]

Example 181

Synthesis of Compound 0181

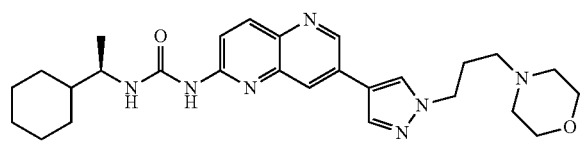

0181

The same method as in Example 0175 except for using (R)-(−)-1-cyclohexylethylamine instead of (3R)-(−)-1-benzyl-3-aminopyrrolidine used in Example 0175 was used to obtain a compound 0181 (28 mg) as a pale yellow solid.

$^1$H-NMR (DMSO-$d_6$) δ: 9.77 (1H, s), 9.24 (1H, d), 9.06 (1H, d), 8.48 (1H, s), 8.20 (1H, d), 8.14 (1H, s), 8.09 (1H, d), 7.47 (1H, d), 4.21 (2H, t), 3.78-3.65 (1H, m), 3.57 (4H, t), 2.38-2.24 (6H, m), 2.06-1.60 (6H, m), 1.54-1.42 (1H, m), 1.32-1.02 (6H, m), 1.18 (3H, d). MS m/z (M+H): 492.

Example 182

Synthesis of Compound 0182

(Synthesis of Compound 0182-1)

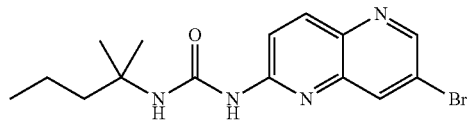

0182-1

A solution of 2,2-dimethyl valeric acid (1.90 mL), triethylamine (2.05 mL) and diphenylphosphoryl azide (3.18 mL) in toluene was heated at 80° C. for 4 hours. The reaction solution was cooled in an ice bath, saturated aqueous sodium bicarbonate (5 mL) was then added thereto, and the mixture was stirred and then subjected to liquid separation. The aqueous layer was washed with toluene (2 mL) twice. The organic layer was dried over sodium sulfate and mixed with the compound 0001-4 (1.00 g) and 1,4-dioxane (8 mL). The mixed solution was heated and stirred at 140° C. for 1 hour using a microwave reaction device. The solvent was evaporated under reduced pressure, 75 v/v % methanol in water (2 mL) was added thereto, and the mixture was subjected to sonication. Further the precipitated solid was filtered, washed with 75 v/v % methanol in water (2 mL), and methanol (1 mL), and dried to obtain a compound 0182-1 (1.38 g) as a pale orange solid.

MS m/z (M+H): 351.

(Synthesis of Compound 0182)

0182

The solution of the compound 182-1 (1.38 g), 1-(3-morpholinopropyl)-1H-pyrazole-4-boronic acid pinacol ester (5.14 g), sodium carbonate (420 mg), and bis(di-tert-butyl (4-dimethylaminophenyl)phosphine)dichloropalladium (II) (140 mg) in water (3 mL) and 1,4-dioxane (39 mL) was stirred at 100° C. for 4 hours under a nitrogen atmosphere. The solvent was evaporated from the reaction solution which had been cooled to room temperature, and purified by silica gel column chromatography (chloroform-methanol, NH silica). The solvent was evaporated under reduced pressure, and the residue was suspended with ethyl acetate (2 mL). The suspension was refluxed, and cooled under stirring at room temperature. The precipitated solid was subjected to sonication, then filtered, and washed with ethyl acetate (2 mL) twice to obtain a compound 0182 (1.31 g) as a pale yellow solid.

$^1$H-NMR (DMSO-$d_6$) δ: 9.64 (1H, s), 9.33 (1H, s), 9.05 (1H, d), 8.48 (1H, s), 8.19 (1H, d), 8.13 (1H, s), 8.02 (1H, d), 7.43 (1H, d), 4.21 (2H, t), 3.57 (4H, t), 2.38-2.24 (6H, m), 2.05-1.94 (2H, m), 1.75-1.67 (2H, m), 1.48-1.34 (8H, m), 0.97 (3H, t).

MS m/z (M+H): 466.

Example 183

Synthesis of Compound 0183

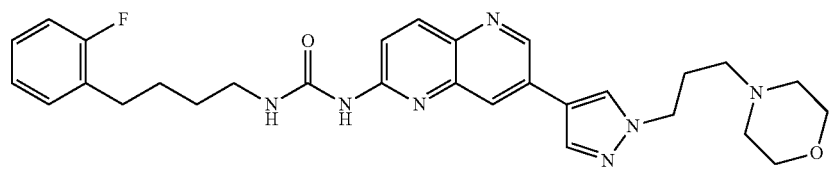

0183

The same method as in Example 0175 except for using 4-(2-fluorophenyl)butylamine instead of (3R)-(+1-benzyl-3-aminopyrrolidine used in Example 0175 was used to obtain a compound 0183 (19 mg) as a pale yellow solid.

$^1$H-NMR (DMSO-$d_6$) δ: 9.82 (1H, s), 9.32-9.27 (1H, m), 9.06 (1H, d), 8.47 (1H, s), 8.25 (1H, d), 8.20 (1H, d), 8.13 (1H, s), 7.44 (1H, d), 7.35-7.28 (1H, m), 7.25-7.03 (3H, m), 4.20 (2H, t), 3.57 (4H, t), 2.69 (2H, t), 2.31-2.28 (6H, m), 2.04-1.94 (2H, m), 1.71-1.55 (4H, m).

MS m/z (M+H): 532.

Example 184

Synthesis of Compound 0184

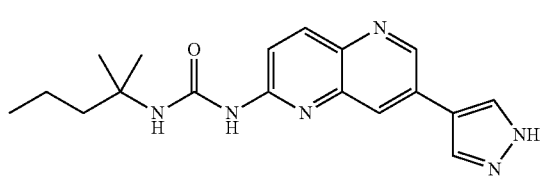

184

The same method as in Example 0182 except for using 1-tert-butoxycarbonyl-4-(4,4,5,5-tetramethyl-1,3,2-dioxaborolan-2-yl)pyrazole instead of 1-(3-morpholinopropyl)-1H-pyrazole-4-boronic acid pinacol ester used in Example 0182 was used to obtain a compound 0184 (9.9 mg) as a pale yellow solid.

MS m/z (M+H): 339.

Example 185

Synthesis of Compound 0185

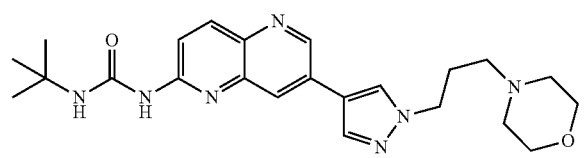

0185

The same method as in Example 53 except for using tert-butyl isocyanate instead of isopropyl isocyanate and 1-(3-morpholinopropyl)-1H-pyrazole-4-boronic acid pinacol ester instead of 1-tert-butoxycarbonyl-4-(4,4,5,5-tetramethyl-1,3,2-dioxaborolan-2-yl)pyrazole in Example 53 was used to obtain a compound 0185 (34 mg) as a pale yellow solid.

MS m/z (M+H): 438.

Example 186

Synthesis of Compound 0186

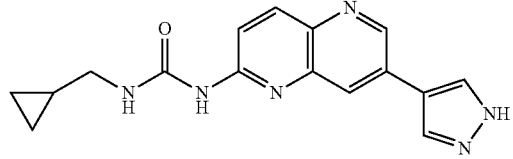

0186

The same method as in Example 64 except for using cyclopropylmethanamine instead of 4-phenylbutylamine used in Example 64 was used to obtain a compound 0186 (23 mg) as a pale yellow solid.

MS m/z (M+H): 309

Example 187

Synthesis of Compound 0187

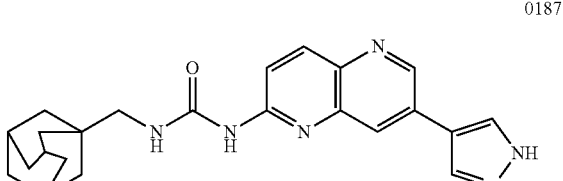

0187

The same method as in Example 64 except for using 1-adamantane methanamine instead of 4-phenylbutylamine used in Example 64 was used to obtain a compound 0187 (6.7 mg) as a pale yellow solid.

MS m/z (M+H): 403.

Example 188

Synthesis of Compound 0188

[Chem. 247]

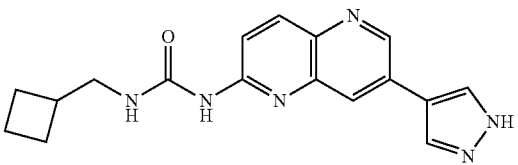

0188

The same method as in Example 64 except for using cyclobutyl methylamine instead of 4-phenylbutylamine used in Example 64 was used to obtain a compound 0188 (14 mg) as a pale yellow solid.

MS m/z (M+H): 323.

Example 189

Synthesis of Compound 0189

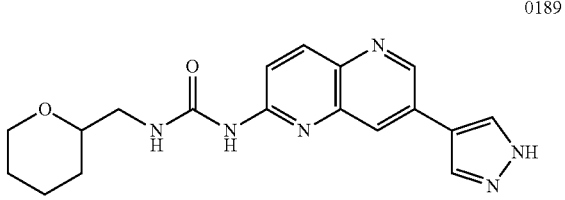 [SMILES: O=C(NCC1CCCCO1)Nc1ccc2ncc(-c3cn[nH]c3)cc2n1]

0189

The same method as in Example 64 except for using (tetrahydro-2H-pyran-2-yl)methanamine instead of 4-phenylbutylamine used in Example 64 was used to obtain a compound 0189 (24 mg) as a pale yellow solid.

MS m/z (M+H): 353.

Example 190

Synthesis of Compound 0190

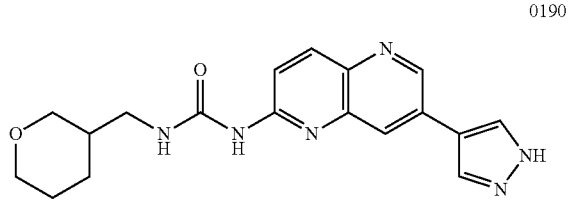 [SMILES: O=C(NCC1CCCOC1)Nc1ccc2ncc(-c3cn[nH]c3)cc2n1]
0190

The same method as in Example 64 except for using (tetrahydro-2H-pyran-3-yl)methanamine instead of 4-phenylbutylamine used in Example 64 was used to obtain a compound 0190 (15 mg) as a pale yellow solid.

MS m/z (M+H): 353.

Example 191

Synthesis of Compound 0191

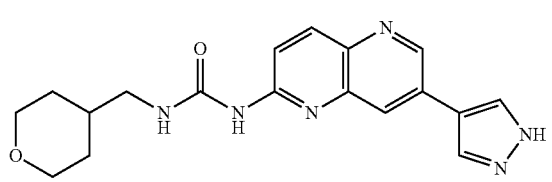
0191

The same method as in Example 64 except for using (tetrahydro-2H-pyran-4-yl)methanamine instead of 4-phenylbutylamine used in Example 64 was used to obtain a compound 0191 (15 mg) as a pale yellow solid.

MS m/z (M+H): 353.

Example 192

Synthesis of Compound 0192

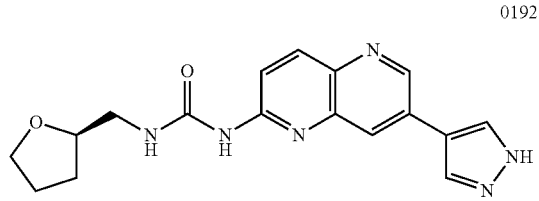 [SMILES: O=C(NC[C@H]1CCCO1)Nc1ccc2ncc(-c3cn[nH]c3)cc2n1]
0192

The same method as in Example 64 except for using (R)-(−)-tetrahydrofurfurylamine instead of 4-phenylbutylamine used in Example 64 was used to obtain a compound 0192 (14 mg) as a pale yellow solid.

MS m/z (M+H): 339.

Example 193

Synthesis of Compound 0193

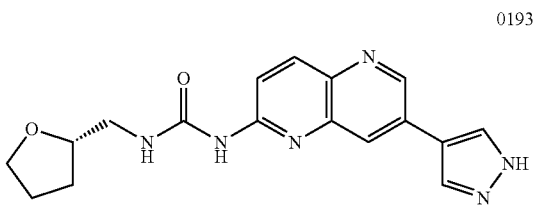 [SMILES: O=C(NC[C@@H]1CCCO1)Nc1ccc2ncc(-c3cn[nH]c3)cc2n1]
0193

The same method as in Example 64 except for using (S)-(+)-tetrahydrofurfurylamine instead of 4-phenylbutylamine used in Example 64 was used to obtain a compound 0193 (13 mg) as a pale yellow solid.

MS m/z (M+H): 339.

Example 194

Synthesis of Compound 0194

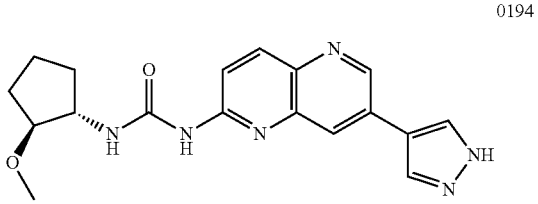 [SMILES: CO[C@H]1CCC[C@@H]1NC(=O)Nc1ccc2ncc(-c3cn[nH]c3)cc2n1]
0194

The same method as in Example 64 except for using (1S, 2S)-2-methoxycyclopentan-1-amine instead of 4-phenylbutylamine used in Example 64 was used to obtain a compound 0194 (6.7 mg) as a pale yellow solid.

MS m/z (M+H): 353.

Example 195

Synthesis of Compound 0195

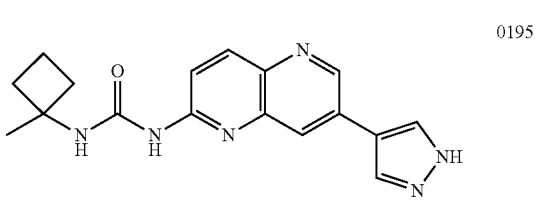 [SMILES: CC1(NC(=O)Nc2ccc3ncc(-c4cn[nH]c4)cc3n2)CCC1]
0195

The same method as in Example 64 except for using 1-methylcyclobutylamine instead of 4-phenylbutylamine used in Example 64 was used to obtain a compound 0195 (14 mg) as a pale yellow solid.

MS m/z (M+H): 323.

Example 196

Synthesis of Compound 0196

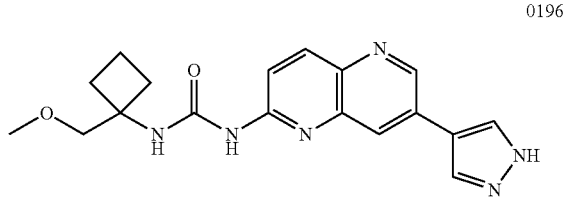 [SMILES: COCC1(NC(=O)Nc2ccc3ncc(-c4cn[nH]c4)cc3n2)CCC1]

The same method as in Example 64 except for using 1-(methoxymethyl)cyclobutanamine instead of 4-phenylbutylamine used in Example 64 was used to obtain a compound 0196 (5.9 mg) as a pale yellow solid.

MS m/z (M+H): 353.

Example 197

Synthesis of Compound 0197

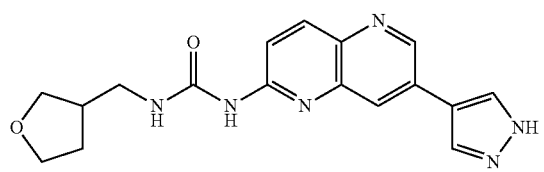

The same method as in Example 64 except for using (tetrahydrofuran-3-yl)methanamine instead of 4-phenylbutylamine used in Example 64 was used to obtain a compound 0197 (9.4 mg) as a pale yellow solid.

MS m/z (M+H): 339.

Example 198

Synthesis of Compound 0198

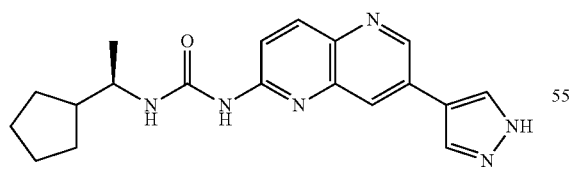

A solution of cyclopentanecarbaldehyde (0.45 mL), (S)-(−)-tert-butylsulfinamide (556 mg), and copper sulfate (1.34 g) in dichloromethane (10 mL) was stirred at room temperature for 24 hours. The reaction solution was filtered over celite, the solvent was then evaporated under reduced pressure, and the obtained residue was purified by silica gel column chromatography (hexane-ethyl acetate) to obtain a colorless oily substance. A solution of the obtained oily substance in dichloromethane (18 mL) was cooled to −45° C. and then a 35% methylmagnesium bromide solution in diethylether (2.2 mL) was added dropwise thereto. The reaction solution was stirred at −45° C. for 3 hours and then stirred at room temperature for 12 hours. The reaction solution was cooled in an ice bath, a saturated aqueous ammonium chloride solution (5 mL) and water (5 mL) were added thereto, and the mixture was stirred for 20 minutes. The reaction solution was subjected to liquid separation and further, the aqueous layer was washed with ethyl acetate (20 mL) twice. The collected organic layer was dried over sodium sulfate, the solvent was evaporated under reduced pressure, and the residue was then purified by silica gel column chromatography (hexane-ethyl acetate) to obtain (S)—N—((R)-1-cyclopentylethyl)-2-methylpropane-2-sulfinamide (723 mg) as a colorless oily substance. A methanol (1.7 mL) solution and a 4 M hydrogen chloride/1,4-dioxane solution (1.7 mL) were added thereto, and the mixture was stirred at room temperature for 2 hours. The solvent was removed under reduced pressure, diisopropylether (10 mL) was added thereto, and the mixture was subjected to sonication. The precipitated solid was filtered to obtain (R)-1-cyclopentaneethanamine hydrochloride (60 mg) as a colorless solid. A solution of the compound 0001-4 (30 mg) and phenyl chlorocarbonate (0.025 mL) in pyridine (0.9 mL) was heated and stirred at 50° C. for 4 hours. Further, (R)-1-cyclopentaneethanamine hydrochloride (60 mg) and sodium hydrogen carbonate (50 mg) were added thereto, and the mixture was then stirred at 50° C. for 3 hours. The reaction solution which had been cooled to room temperature was concentrated, water (1 mL) and a 6 M aqueous sodium hydroxide solution (0.04 mL) were added thereto, and the mixture was subjected to sonication. The precipitated solid was filtered, and the residue was washed with water (1 mL) and a methanol aqueous solution. A solution of the obtained solid, 1-tert-butoxycarbonyl-4-(4,4,5,5-tetramethyl-1,3,2-dioxaborolan-2-yl)pyrazole (59 mg), sodium carbonate (14 mg), and bis(di-tert-butyl (4-dimethylaminophenyl)phosphine)dichloropalladium (II) (7 mg) in water (0.1 mL) and 1,4-dioxane (1.9 mL) was stirred at 100° C. for 12 hours using a sealed tube. The reaction solution was cooled to room temperature, the solvent was then evaporated under reduced pressure, and the residue was purified by silica gel column chromatography (chloroform-methanol). The solvent was evaporated under reduced pressure, acetonitrile (1 mL) was added thereto, and the mixture was then subjected to sonication. The precipitated solid was filtered and the residue was washed with acetonitrile (1 mL) to obtain a compound 0198 (9.4 mg) as a pale yellow solid.

MS m/z (M+H): 351.

Example 199

Synthesis of Compound 0199

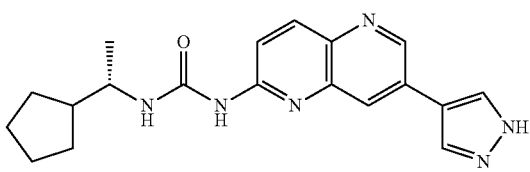

The same method as in Example 198 except for using (R)-(+)-tert-butylsulfinamide instead of (S)-(−)-tert-butylsulfinamide used in Example 198 was used to obtain a compound 0199 (4.1 mg) as a pale yellow solid.

MS m/z (M+H): 351.

Example 200

Synthesis of Compound 0200

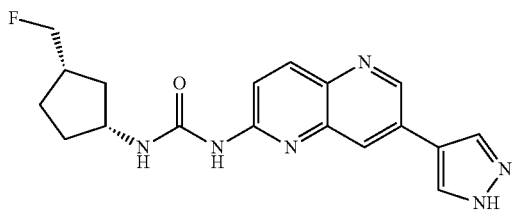

0200

A solution of (1S,4R)-2-azabicyclo[2.2.1]hept-5-en-3-one (1.0 g) in methanol (200 mL) was reacted using a hydrogenation reaction device (H-Cube, manufactured by ThalesNao) (10 bar, 1 mL/min, 40° C., 10% Pd/C). After completion of the reaction, the solvent was evaporated under reduced pressure, and a solution of the obtained residue, 4-dimethylaminopyridine (600 mg), and di-tert-butyl dicarbonate (3.3 g) in acetonitrile (30 mL) was stirred at room temperature for 2 hours. The solvent was evaporated under reduced pressure and the residue was then purified by silica gel column chromatography (hexane-ethyl acetate) to obtain (1R,4S)-tert-butyl 3-oxo-2-azabicyclo[2.2.1]heptane-2-carboxylate (1.94 g). Methanol (40 mL) was added thereto, and the mixture was cooled in an ice bath. Then, sodium borohydride (697 mg) was added thereto and the mixture was stirred for 2 hours. Then, acetic acid (1 mL) was added thereto, the solvent was evaporated under reduced pressure, and the residue was then purified by silica gel column chromatography (hexane-ethyl acetate) to obtain tert-butyl ((1S,3R)-3-(hydroxymethyl)cyclopentyl)carbamate (1.47 g). A solution of the obtained tert-butyl ((1S,3R)-3-(hydroxymethyl)cyclopentyl)carbamate and triethylamine (1.7 mL) in tetrahydrofuran (28 mL) was cooled in an ice bath, and then methanesulfonyl chloride (0.63 mL) was added dropwise thereto. The mixture was stirred at room temperature for 6 hours. Next, methanol (1 mL) was added thereto and the solvent was then evaporated under reduced pressure. The residue was subjected to liquid separation by the addition of ethyl acetate (30 mL) and water (10 mL), and the aqueous layer was washed with ethyl acetate (20 mL) twice. The organic layer was washed with brine and then dried over sodium sulfate, and the solvent was then evaporated under reduced pressure. The obtained residue was purified by silica gel column chromatography (hexane-ethyl acetate) to obtain (1S,3R)-3-((tert-butoxycarbonyl)amino) cyclopentyl)methylmethanesulfonate (532 mg). A solution of the obtained (1S,3R)-3-((tert-butoxycarbonyl)amino)cyclopentyl)methylmethanesulfonate and tetrabutylammonium bifluoride (1.0 mL) in acetonitrile (20 mL) was stirred at 85° C. for 6 hours. Further, tetrabutylammonium bifluoride (0.5 mL) was added thereto and the mixture was heated and stirred at 85° C. for 16 hours. The reaction solution was cooled to room temperature and the solvent was then evaporated under reduced pressure. Ethyl acetate (20 mL) and water (5 mL) were added thereto to perform liquid separation. The aqueous layer was washed with ethyl acetate (10 mL) twice, and the organic layer was washed with brine, and then dried over sodium sulfate. The solvent was then evaporated under reduced pressure. The residue was purified by silica gel column chromatography (hexane-ethyl acetate) to obtain tert-butyl ((1S,3R)-3-(fluoromethyl)cyclopentyl)carbamate (353 mg). Ethanol (1.5 mL) and a 4 M hydrogen chloride/1,4-dioxane solution (1.7 mL) were added thereto, and the mixture was stirred at room temperature for 6 hours and at 40° C. for 3 hours. After completion of the reaction, the solvent was evaporated under reduced pressure. Diisopropyl ether (10 mL) was added thereto and the mixture was subjected to sonication. The product was decanted and dried to obtain (1S,3R)-3-(fluoromethyl)cyclopentanamine hydrochloride (157 mg). Then, the same method as in Example 122 except for using the obtained (1S,3R)-3-(fluoromethyl)cyclopentanamine hydrochloride instead of (R)-1-cyclopentaneethanamine hydrochloride used in Example 122 was used to obtain a compound 0200 (1.4 mg) as a pale yellow solid.

MS m/z (M+H): 355.

Example 201

Synthesis of Compound 0201

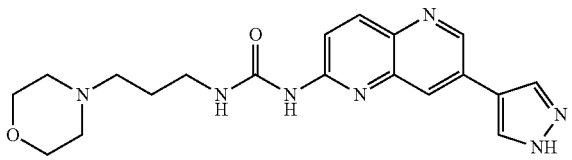

0201

The same method as in Example 95 except for using N-(3-aminopropyl)morpholine instead of 3-phenylpropylamine used for the synthesis of the compound 0095 in Example 95 was used to obtain a compound 0201 (12 mg) as a white solid.

MS m/z (M+H): 382.

Example 202

Synthesis of Compound 0202

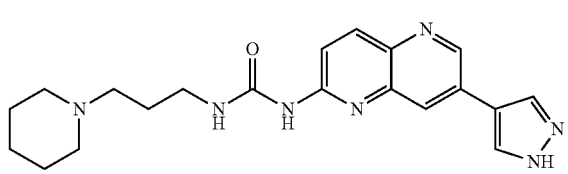

0202

The same method as in Example 95 except for using 1-piperidine-1-propanamine instead of 3-phenylpropylamine used for the synthesis of the compound 0095 in Example 95 was used to obtain a compound 0202 (14 mg) as a pale yellow solid.

MS m/z (M+H): 380.

Example 203

Synthesis of Compound 0203

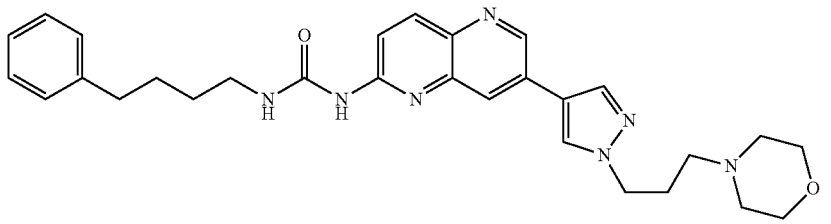

0203

The same method as in Example 95 except for using 4-phenylbutylamine instead of 3-phenylpropylamine used for the synthesis of the compound 0095 in Example 95, and using 1-(3-morpholinopropyl)-1H-pyrazole-4-boronic acid pinacol ester instead of 1-tert-butoxycarbonyl-1H-pyrazole-4-boronic acid pinacol ester used for the synthesis of the compound 0095 in Example 95 was used to obtain a compound 0203 (5 mg) as a white solid.

MS m/z (M+H): 514.

Example 204

Synthesis of Compound 0204

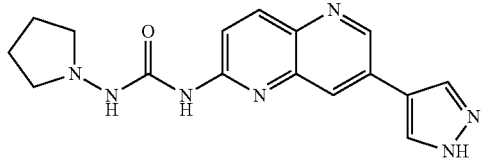

0204

The same method as in Example 95 except for using 1-pyrrolidine amine hydrochloride instead of 3-phenylpropylamine used for the synthesis of the compound 0095 in Example 95 was used to obtain a compound 0204 (6 mg) as a white solid.

MS m/z (M+H): 324.

Example 205

Synthesis of Compound 0205

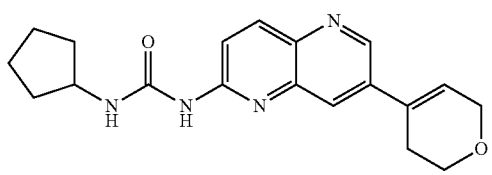

0205

The same method as in Example 1 except for using 3,6-dihydro-2H-pyran-4-boronic acid pinacol ester instead of 2-methoxy-4-(4,4,5,5-tetramethyl-1,3,2-dioxaborolan-2-yl) phenol used for the synthesis of the compound 0001 in Example 1 was used to obtain a compound 0205 (8.4 mg) as a white solid.

MS m/z (M+H): 339.

Example 206

Synthesis of Compound 0206

(Synthesis of Compound 0206-1)

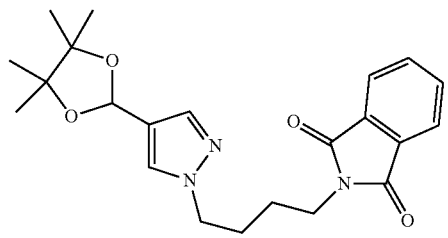

0206-1

A solution of 4-pyrazole boronic acid pinacol ester (0.22 g), N-(4-bromobutyl)phthalimide (0.35 g) and potassium carbonate (0.31 g) in N,N-dimethylformamide (2 mL) was stirred at 80° C. for 16 hours under a nitrogen atmosphere. The reaction solution was returned to room temperature and purified by silica gel column chromatography (chloroform-methanol) to obtain a compound 0206-1 (0.23 g).

MS m/z (M+H): 396.

(Synthesis of Compound 0206)

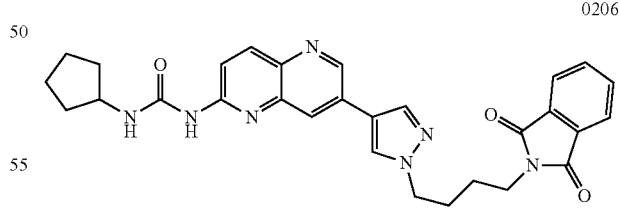

0206

The same method as in Example 1 except for using the compound 0206-1 instead of 2-methoxy-4-(4,4,5,5-tetramethyl-1,3,2-dioxaborolan-2-yl)phenol used for the synthesis of the compound 0001 in Example 1 was used to obtain a compound 0206 (59 mg) as a white solid.

MS m/z (M+H): 524.

Example 207

Synthesis of Compound 0207

(Synthesis of Compound 0207-1)

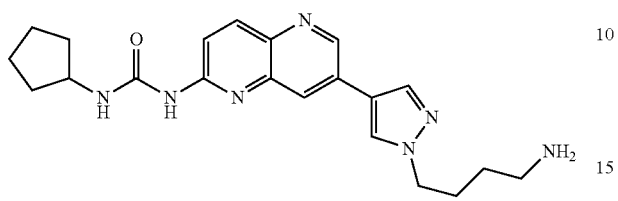

0207-1

To a solution of the compound 0206 (20 mg) in ethanol (0.20 mL) was added hydrazine monohydrate (one droplet), and the mixture was stirred at 70° C. for 0.5 hours. The reaction solution was returned to room temperature, water was added thereto, and the solvent was removed under reduced pressure. The obtained solid was filtered and washed with water and ethyl acetate to obtain a compound 0207-1 (10.9 mg) as a yellow solid.

MS m/z (M+H): 394.

(Synthesis of Compound 0207)

0207

Potassium carbonate (14 mg) and bis(2-bromoethyl)ether (3.8 μL) were added to a solution of the compound 0207-1 (10 mg) in 1,4-dioxane (0.50 mL), and the mixture was stirred at 70° C. for 15 hours. The reaction solution was returned to room temperature and purified by silica gel column chromatography (chloroform-methanol). After concentration, the obtained residue was further purified by preparative thin film chromatography (chloroform-methanol, NH silica) to obtain a compound 0207 (1.3 mg) as a white solid.

MS m/z (M+H): 464.

Example 208

Synthesis of Compound 0208

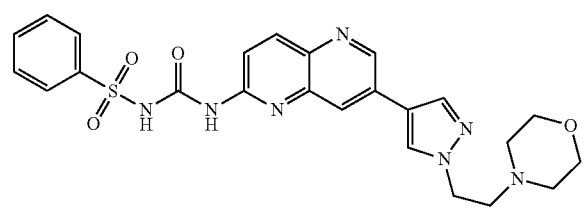

0208

To a solution of the compound 0138-1 (30 mg) in 1,4-dioxane (1.0 mL) was added benzenesulfonyl isocyanate (34 μL), and the mixture was stirred at room temperature for 0.5 hours. The precipitated solid was filtered and washed with 1,4-dioxane to obtain a compound 0208 (20 mg) as a white solid.

MS m/z (M+H): 508.

Example 209

Synthesis of Compound 0209

(Synthesis of Compound 0209-1)

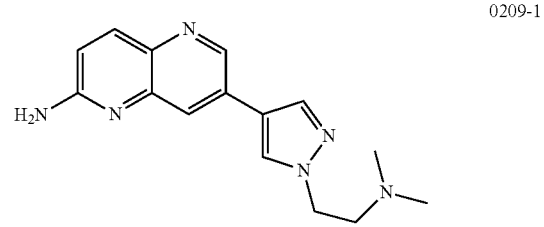 [SMILES: CN(C)CCn1cc(-c2cnc3ccc(N)nc3c2)cn1]

0209-1

The same method as in Example 138 except for using 1-(2-dimethylaminoethyl)-1H-pyrazole-4-boronic acid pinacol ester instead of 1-(2-morpholinoethyl)-1H-pyrazole-4-boronic acid pinacol ester used for the synthesis of the compound 0138-1 in Example 138 was used to obtain a compound 0209-1 (0.23 g) as a pale yellow oily substance.

MS m/z (M+H): 283.

(Synthesis of Compound 0209)

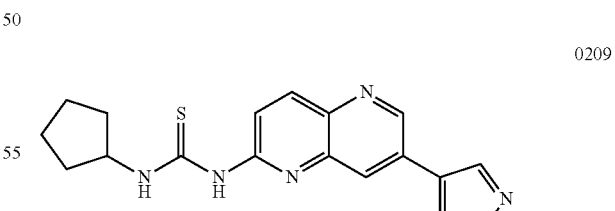

0209

The same method as in Example 138 except for using the compound 0209-1 instead of the compound 0138-1 used for the synthesis of the compound 0138 in Example 138 was used to obtain a compound 0209 (24 mg) as a white solid.

MS m/z (M+H): 410.

Example 210

Synthesis of Compound 0210

[Chem. 272]

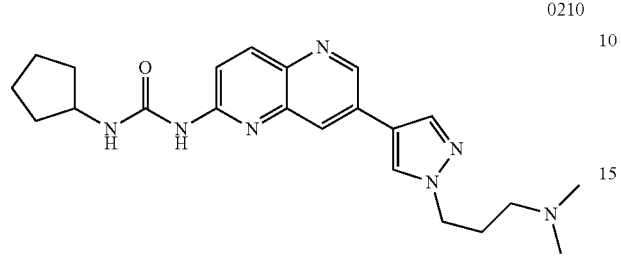

0210

The same method as in Example 1 except for using N,N-dimethyl-3-(4-(4,4,5,5-tetramethyl-1,3,2-dioxaborolan-2-yl)-1H-pyrazol-1-yl)propan-1-a mine (which was synthesized according to Journal of Heterocyclic chemistry, 2004, 41,931) instead of 2-methoxy-4-(4,4,5,5-tetramethyl-1,3,2-dioxaborolan-2-yl)phenol used for the synthesis of the compound 0001 in Example 1 was used to obtain a compound 0210 (8.1 mg) as a white solid.

$^1$H-NMR (DMSO-d$_6$) δ: 9.76 (1H, s), 9.16 (1H, bd), 9.06 (1H, d), 8.50 (1H, s), 8.25-8.16 (2H, m), 8.14 (1H, d), 7.49 (1H, d), 4.19 (2H, t), 4.15-4.02 (1H, m), 2.21 (2H, t), 2.13 (6H, s), 2.05-1.87, (4H, m), 1.84-1.44, (6H, m).

MS m/z (M+H): 408.

Example 211

Synthesis of Compound 0211

(Synthesis of Compound 0211-1)

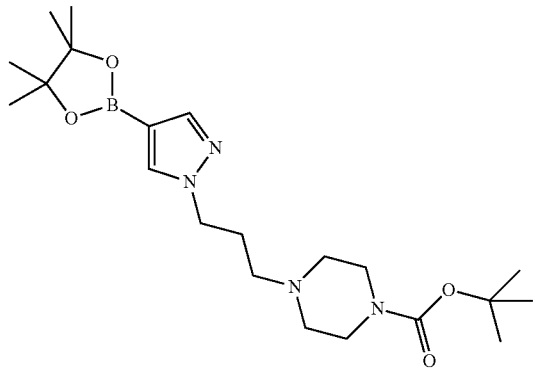

0211-1

The same method as in Example 206 except for using tert-butyl 4-(3-bromopropyl)-1-piperazinecarboxylate ester (which was synthesized according to WO2009/10491A1) instead of N-(4-bromobutyl)phthalimide used for the synthesis of the compound 0206-1 in Example 206 was used to obtain a compound 0211-1 (0.78 g) as a pale yellow oily substance.

MS m/z (M+H): 421.

(Synthesis of Compound 0211)

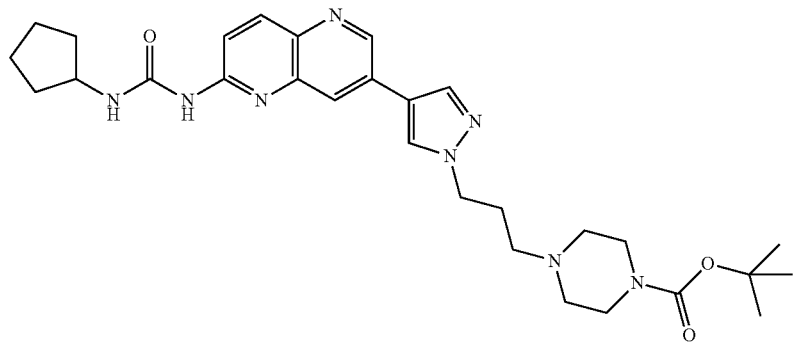

0211

The same method as in Example 1 except for using the compound 211-1 instead of 2-methoxy-4-(4,4,5,5-tetramethyl-1,3,2-dioxaborolan-2-yl)phenol used for the synthesis of the compound 0001 in Example 1 was used to obtain a compound 0211 (44 mg) as a white solid.

MS m/z (M+H): 549.

Example 212

Synthesis of Compound 0212

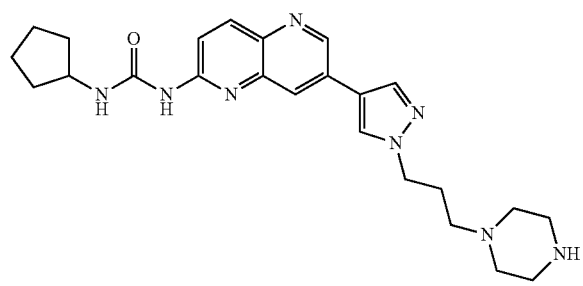

Trifluoroacetic acid (0.50 mL) was added to the compound 0211 (40 mg), and the mixture was stirred at room temperature for 0.5 hours. Methanol was added thereto and the solvent was removed under reduced pressure. Then, saturated aqueous sodium bicarbonate was added thereto, the mixture was stirred, and further, methanol was added thereto, and the solvent was removed under reduced pressure. The obtained residue was purified by silica gel column chromatography (chloroform-methanol, NH silica) to obtain a compound 0212 (27 mg) as a white solid.

MS m/z (M+H): 449.

Example 213

Synthesis of Compound 0213

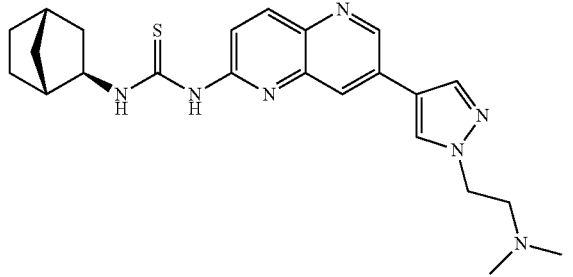

Phenyl chlorothionoformate (74 μL) was added to a solution of the compound 0209-1 (30 mg) in pyridine (1.0 mL), and the mixture was stirred at room temperature for 16 hours. phenyl chlorothionoformate (74 μL) was added to the reaction solution, and the mixture was stirred at 60° C. for 1 hour. Then, further, phenyl chlorothionoformate (74 μL) was added thereto, and the mixture was stirred for 0.5 hours. The reaction solution was returned to room temperature, (1R,2R,4S)-bicyclo[2.2.1]heptan-2-amine (0.18 mL) was added thereto, and the mixture was stirred at 60° C. for 0.5 hours. The reaction solution was returned to room temperature, the solvent was removed under reduced pressure, and then the obtained residue was purified by silica gel column chromatography (chloroform-methanol, NH silica) to obtain a compound 0213 (4.2 mg) as a white solid.

MS m/z (M+H): 436.

Example 214

Synthesis of Compound 0214

(Synthesis of Compound 0214-1)

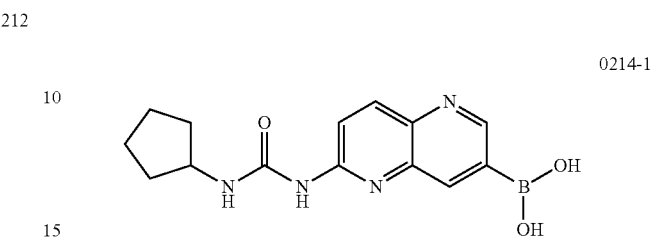

A solution of the compound 0001-5 (0.20 g), bis(pinacolato)diboron (0.23 g), [1,1-bis(diphenylphosphino)ferrocene]palladium (II) dichloride (49 mg) and potassium acetate (0.12 g) in 1,4-dioxane (2.0 mL) was stirred under a nitrogen atmosphere, and the mixture was stirred at 80° C. for 2 hours. The reaction solution was returned to room temperature, ethyl acetate and 2 M hydrochloric acid were added thereto, and the precipitated solid was filtered. The precipitated solid was washed with ethyl acetate and acetone to obtain a compound 0214-1 (0.16 g) as a grey solid.

MS m/z (M+H): 301.

(Synthesis of Compound 0214-2)

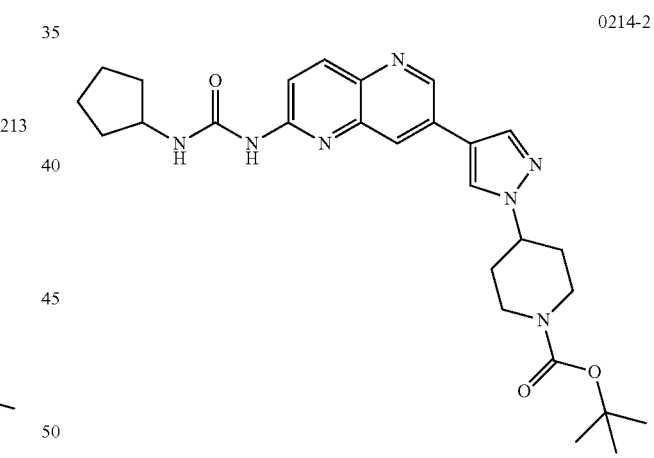

A mixed solution of the compound 0214-1 (15 mg), tert-butyl 4-(4-iodo-1H-pyrazol-1-yl)piperidine-1-carboxylate ester (19 mg), bis(di-tert-butyl (4-dimethylaminophenyl)phosphine)dichloropalladium (II) (3.6 mg), sodium carbonate (11 mg), 1,4-dioxane (1.0 mL), and water (0.1 mL) was stirred at 100° C. for 16 hours under a nitrogen atmosphere. The reaction solution was returned to room temperature and purified by silica gel column chromatography (chloroform-methanol, NH silica). After concentration, the obtained solid was washed with ethyl acetate to obtain a compound 0214-2 (4.3 mg) as a white solid.

MS m/z (M+H): 506.

147

(Synthesis of Compound 0214)

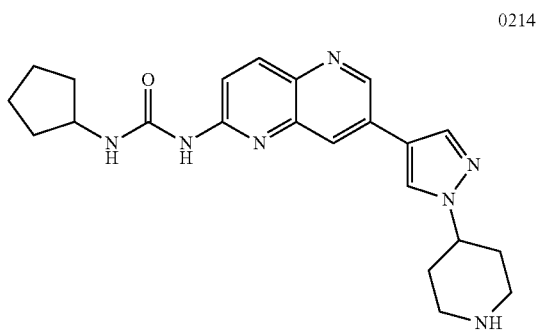 [SMILES: O=C(Nc1ccc2ncc(-c3cnn(C4CCNCC4)c3)cc2n1)NC1CCCC1]

To a solution of the compound 0214-2 (4.0 mg) in methanol (0.10 mL) was added a 4 M hydrogen chloride/1,4-dioxane solution (0.10 mL), and the mixture was stirred at room temperature for 0.5 hours. The reaction solution was neutralized by the addition of saturated aqueous sodium bicarbonate, and the solvent was removed under reduced pressure. The obtained residue was purified by silica gel column chromatography (chloroform-methanol, NH silica) to obtain a compound 0214 (2.6 mg) as a white solid. MS m/z (M+H): 406.

Example 215

Synthesis of Compound 0215

(Synthesis of Compound 0215-1)

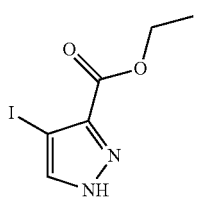

To a solution of ethyl 3-pyrazolecarboxylate (1.0 g) in N,N-dimethylformamide (7.0 mL) was added N-iodosuccinimide (1.6 g), and the mixture was stirred at room temperature for 1 hour, warmed to 60° C., and then stirred for 0.5 hours. The reaction solution was returned to room temperature, saturated aqueous sodium bicarbonate and sodium sulfite were added thereto, and the mixture was extracted with ethyl acetate. The organic layer was washed with brine and then dried over sodium sulfate. The solvent was removed under reduced pressure and the obtained residue was purified by silica gel column chromatography (hexane-ethyl acetate) to obtain a compound 0215-1 (1.0 g) as a pale yellow solid.

148

(Synthesis of Compound 0215-2)

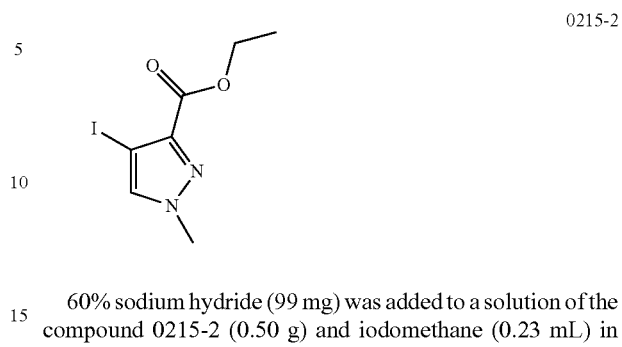

60% sodium hydride (99 mg) was added to a solution of the compound 0215-2 (0.50 g) and iodomethane (0.23 mL) in tetrahydrofuran (2.0 mL) at 0° C., and the mixture was stirred at room temperature for 0.5 hours. To the reaction solution, a saturated aqueous ammonium chloride solution was added, and the mixture was extracted with ethyl acetate. The organic layer was washed with brine and then dried over sodium sulfate. The solvent was removed under reduced pressure and the obtained residue was purified by silica gel column chromatography (hexane-ethyl acetate) to obtain a compound 0215-2 (0.37 g) as a colorless oily substance.

(Synthesis of Compound 0215)

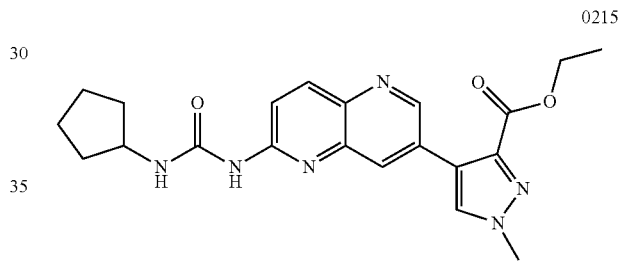

The same method as in Example 214 except for using the compound 0215-2 instead of tert-butyl 4-(4-iodo-1H-pyrazol-1-yl)piperidine-1-carboxylate used for the synthesis of the compound 0214-2 in Example 214 was used to obtain a compound 0215 (8.6 mg) as a white solid.

MS m/z (M+H): 409.

Example 216

Synthesis of Compound 0216

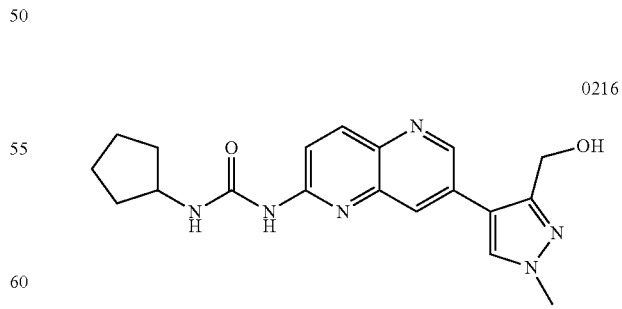

A 1 M aluminum lithium hydride solution in diethylether (24 μL) was added to a solution of the compound 0215 (5.0 mg) in tetrahydrofuran (1.0 mL) at room temperature, and the mixture was stirred for 0.5 hours. To the reaction solution, a saturated aqueous ammonium chloride solution and methanol were added, and the solvent was removed under reduced pressure. The obtained residue was purified by silica gel column chromatography (chloroform-methanol) to obtain a compound 0216 (4.5 mg).

$^1$H-NMR (DMSO-$d_6$) δ: 9.80 (1H, s), 9.38-9.25 (1H, m), 9.01 (1H, d), 8.36 (1H, d), 8.33 (1H, s), 8.22 (1H, d), 7.49 (1H, d), 5.33 (1H, t), 4.55 (2H, d), 4.16-4.03 (1H, m), 3.89 (3H, s), 2.01-1.84 (2H, m), 1.83-1.47 (6H, m).

MS m/z (M+H): 367.

Example 217

Synthesis of Compound 0217

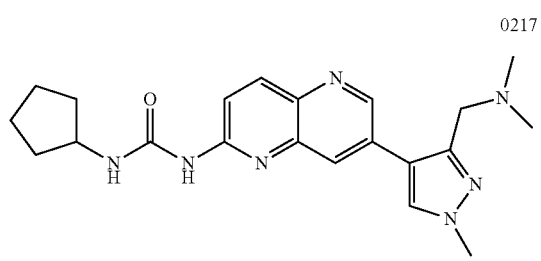 [SMILES: CN(C)Cc1nn(C)cc1-c1cnc2ccc(NC(=O)NC3CCCC3)nc2c1]

Triethylamine (20 μL) and methanesulfonyl chloride (2 μL) were added to a solution of the compound 0216 (2.0 mg) in tetrahydrofuran (0.50 mL) at 0° C., and the mixture was stirred at room temperature for 0.5 hours. Further, methanesulfonyl chloride (4 μL) was added thereto, and the mixture was stirred for 0.5 hours. Then, chloroform (0.5 mL) was added thereto, and the mixture was stirred for 10 minutes. To the reaction solution, a 2 M dimethylamine solution in tetrahydrofuran (27 μL) was added, and the mixture was stirred for 10 minutes. Then, a 2 M dimethylamine solution in tetrahydrofuran (55 μL) was further added thereto, and the mixture was stirred at 80° C. for 0.5 hours. The reaction solution was returned to room temperature, the solvent was removed under reduced pressure, and the obtained residue was purified by silica gel column chromatography (chloroform-methanol, NH silica). After concentration, the obtained solid was washed with ethyl acetate to obtain a compound 0217 (1.6 mg) as a white solid.

MS m/z (M+H): 394.

Example 218

Synthesis of Compound 0218

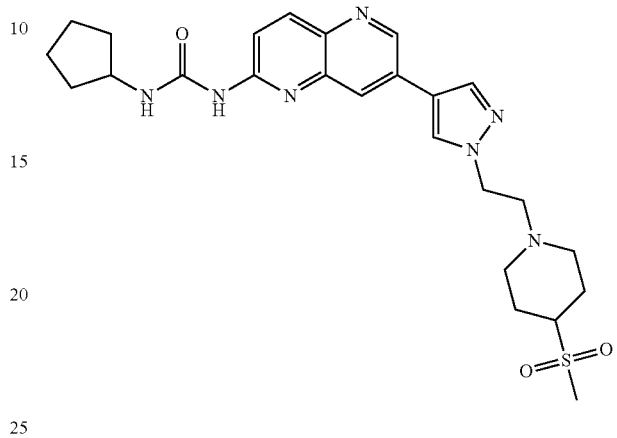

A mixed solution of the compound 0001-5 (30 mg), 1-(2-bromoethyl)-1H-pyrazole-4-boronic acid pinacol ester (30 mg), bis(di-tert-butyl (4-dimethylaminophenyl)phosphine) dichloropalladium (II) (6.3 mg), sodium carbonate (19 mg), 1,4-dioxane (1.0 mL) and water (0.10 mL) was stirred at 100° C. for 2 hours under a nitrogen atmosphere. The reaction solution was returned to room temperature, 4-(methylsulfonyl)piperidine hydrochloride (36 mg) was added thereto, and the mixture was stirred at 80° C. for 2 hours and at 100° C. for 2 hours. The reaction solution was returned to room temperature, purified by silica gel column chromatography (chloroform-methanol, NH silica), and then purified by preparative thin film chromatography (chloroform-methanol) to obtain a compound 0218 (8.5 mg) as a white solid.

MS m/z (M+H): 512.

Example 219

Synthesis of Compound 0219

(Synthesis of Compound 0219-1)

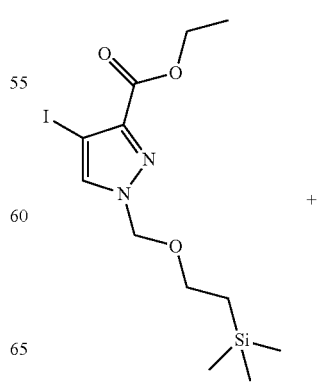

+

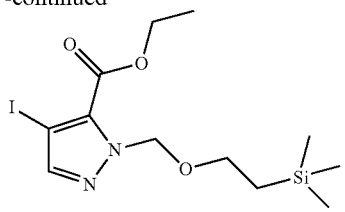

The same method as in Example 215 except for using (2-(trimethylsilyl)ethoxy)methyl chloride instead of iodomethane used for the synthesis of the compound 0215-2 in Example 215 was used to obtain a compound 0219-1 (0.273 g) as a position isomer mixture (colorless oily substance).

(Synthesis of Compound 0219-2)

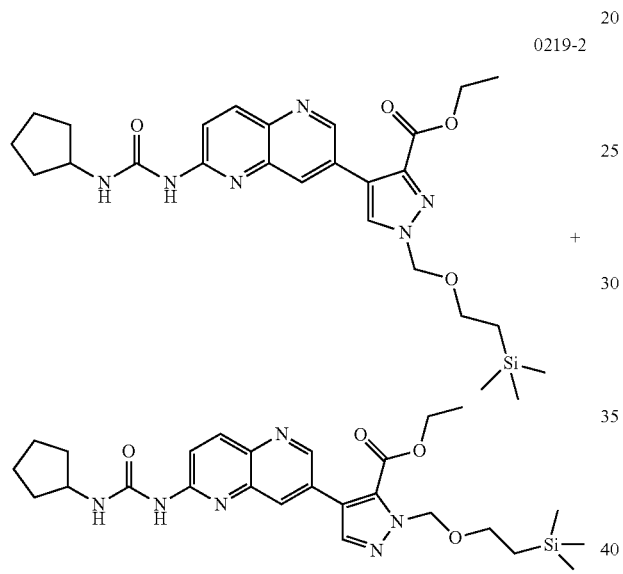

The same method as in Example 214 except for using the compound 0219-1 instead of tert-butyl 4-(4-iodo-1H-pyrazol-1-yl)piperidine-1-carboxylate used for the synthesis of the compound 0214-2 in Example 214 was used to obtain a compound 0219-2 (0.22 g) as a position isomer mixture (pale yellow solid).

MS m/z (M+H): 525.

(Synthesis of Compound 0219-3)

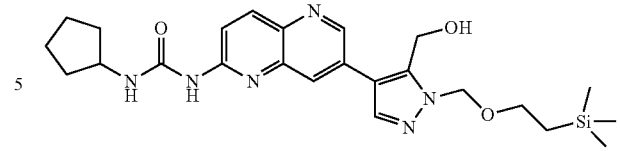

The same method as in Example 216 except for using the compound 0219-2 instead of the compound 0215 used for the synthesis of the compound 0216 in Example 216 was used to obtain a compound 0219-3 (59 mg) as a position isomer mixture (brown solid).

MS m/z (M+H): 483.

(Synthesis of Compound 0219)

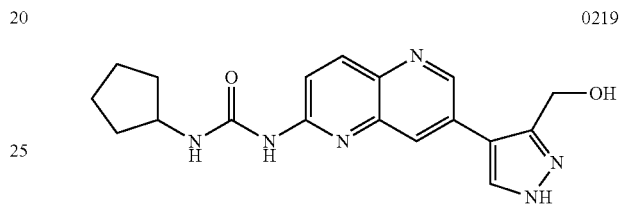

The same method as in Example 214 except for using the compound 0219-3 instead of the compound 0214-2 used for the synthesis of the compound 0214 in Example 214 was used to obtain a compound 0219 (5.3 mg) as a white solid.

MS m/z (M+H): 353.

Example 220

Synthesis of Compound 0220

(Synthesis of Compound 0220-1)

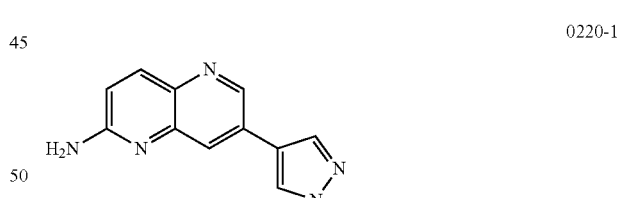

The same method as in Example 138 except for using the compound 0211-1 instead of 1-(2-morpholinoethyl)-1H-pyrazole-4-boronic acid pinacol ester in Example 138 was used to obtain a compound 0220-1 (0.17 g) as a yellow oily substance.

MS m/z (M+H): 438.

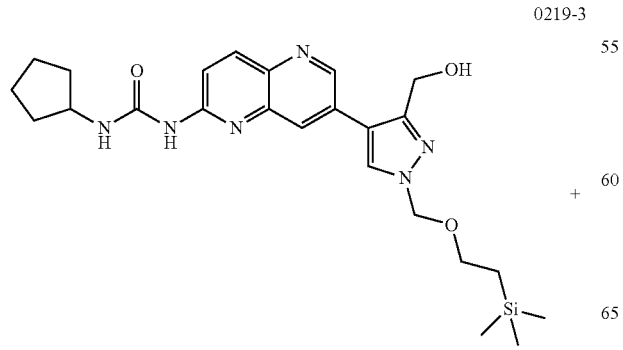

(Synthesis of Compound 0220-2)

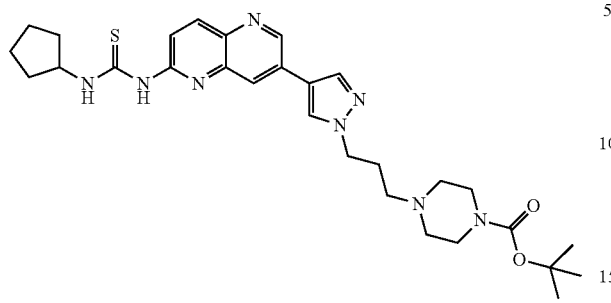

0220-2

The same method as in Example 138 except for using the compound 0220-1 instead of the compound 0138-1 in Example 138 was used to obtain a compound 0220-2 (44 mg) as a white solid.
MS m/z (M+H): 565.

(Synthesis of Compound 0220)

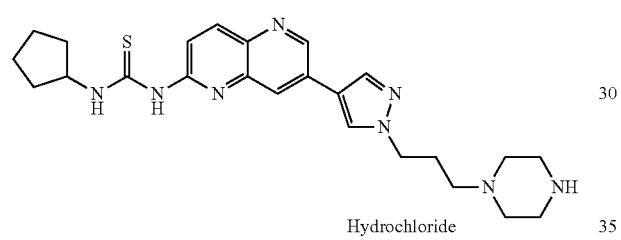

0220

Hydrochloride

To a solution of the compound 0220-2 (40 mg) in methanol (1.0 mL), a 4 M hydrogen chloride/1,4-dioxane solution (1.0 mL) was added, and the mixture was stirred at room temperature for 2 hours. The precipitated solid was separated by filtration and then washed with ethyl acetate to obtain a compound 0220 hydrochloride (25 mg) as a yellow solid.
MS m/z (M+H): 465.

Example 221

Synthesis of Compound 0221

(Synthesis of Compound 0221-1)

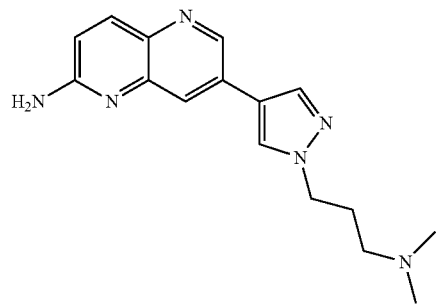

0221-1

The same method as in Example 138 except for using N,N-dimethyl-3-(4-(4,4,5,5-tetramethyl-1,3,2-dioxaborolan-2-yl)-1H-pyrazol-1-yl)propan-1-amine instead of 1-(2-morpholinoethyl)-1H-pyrazole-4-boronic acid pinacol ester used for the synthesis of the compound 0138-1 in Example 138 was used to obtain a compound 0221-1 (76 mg) as a white solid.
MS m/z (M+H): 297.

(Synthesis of Compound 0221)

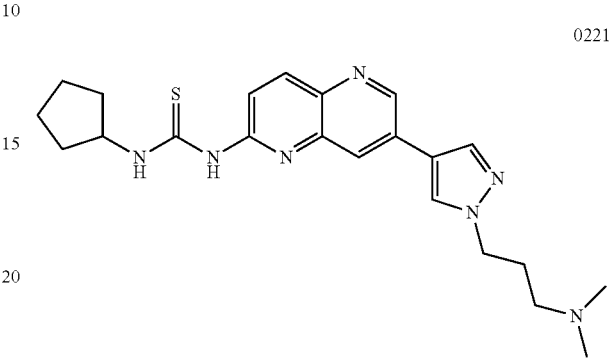

0221

The same method as in Example 138 except for using the compound 0221-1 instead of the compound 0138-1 used for the synthesis of the compound 0138 in Example 138 was used to obtain a compound 0221 (31 mg) as a pale yellow solid.
MS m/z (M+H): 424.

Example 222

Synthesis of Compound 0222

(Synthesis of Compound 0222-1)

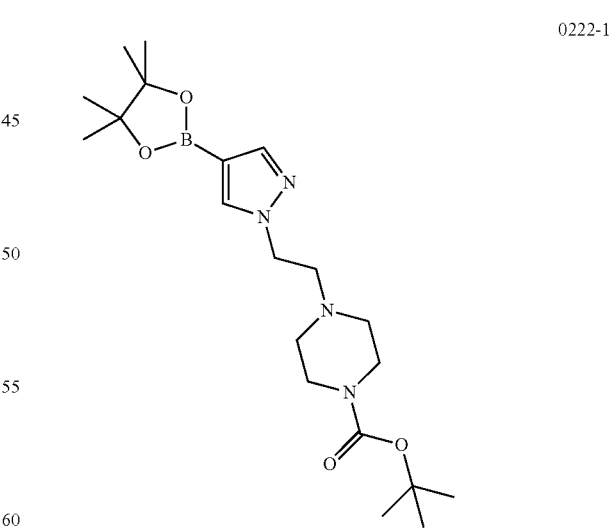

0222-1

The same method as in Example 24 except for using 1-piperazinecarboxylic acid tert-butylester instead of azetidine used for the synthesis of the compound 0024-1 in Example 24 was used to obtain a compound 0222-1 (0.43 g) as a colorless oily substance.

155
(Synthesis of Compound 0222-2)

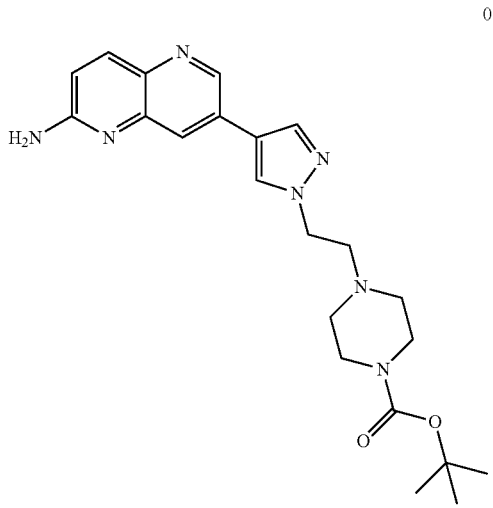
0222-2

The same method as in Example 138 except for using the compound 0222-1 instead of 1-(2-morpholinoethyl)-1H-pyrazole-4-boronic acid pinacol ester used for the synthesis of the compound 0138-1 in Example 138 was used to obtain a compound 0222-2 (0.21 g) as a white solid.

MS m/z (M+H): 424.

(Synthesis of Compound 0222-3)

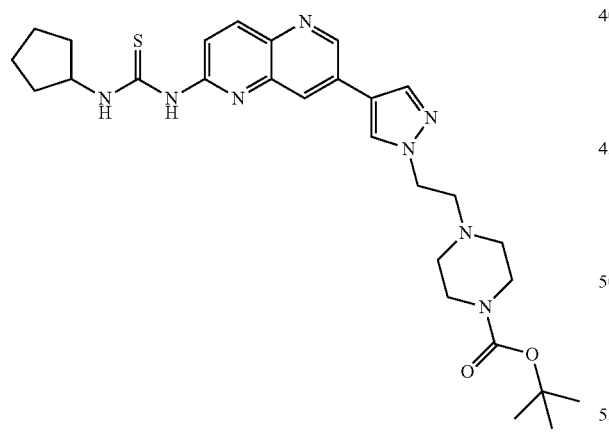
0222-3

The same method as in Example 138 except for using the compound 0222-2 instead of the compound 0138-1 used for the synthesis of the compound 0138 in Example 138 was used to obtain a compound 0222-3 (44 mg) as a white solid.

MS m/z (M+H): 551.

156
(Synthesis of Compound 0222)

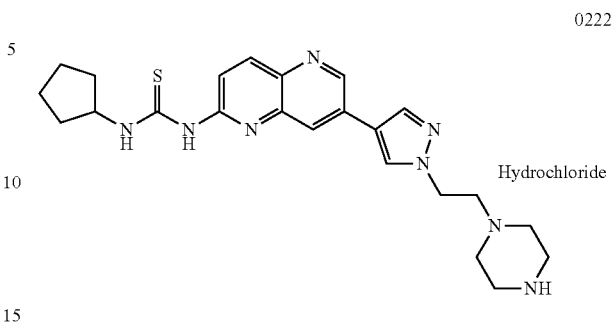
0222

The same method as in Example 220 except for using the compound 0222-3 instead of the compound 0220-2 used for the synthesis of the compound 0220 in Example 220 was used to obtain a compound 0222 hydrochloride (39 mg) as a yellow solid.

MS m/z (M+H): 451.

Example 223

Synthesis of Compound 0223

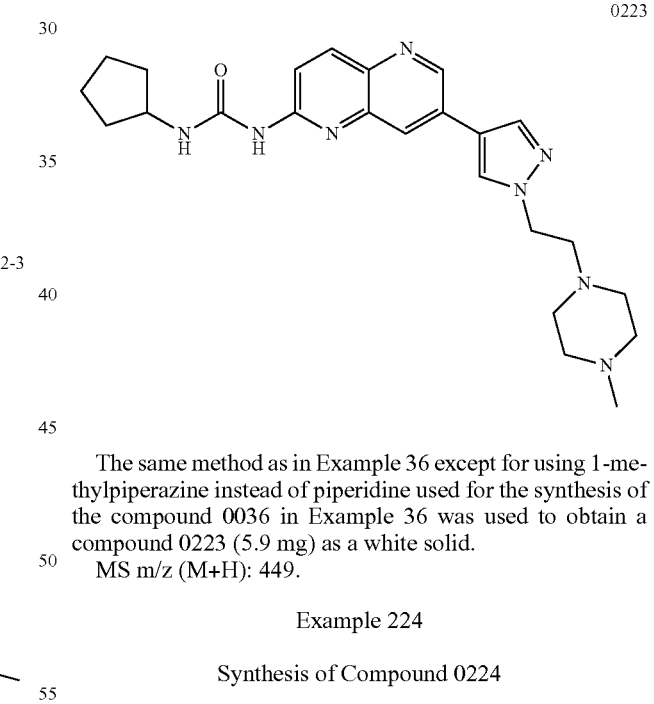
0223

The same method as in Example 36 except for using 1-methylpiperazine instead of piperidine used for the synthesis of the compound 0036 in Example 36 was used to obtain a compound 0223 (5.9 mg) as a white solid.

MS m/z (M+H): 449.

Example 224

Synthesis of Compound 0224

(Synthesis of Compound 0222-1)

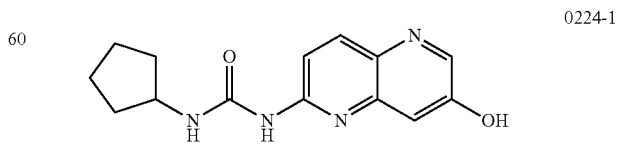
0224-1

A solution of the compound 0001-5 (0.10 g), bis(pinacolato)diboron (0.11 g), [1,1-bis(diphenylphosphino)ferrocene]palladium (II) dichloride (24 mg), and potassium acetate (59 mg) in 1,4-dioxane (1.0 mL) was stirred at 100° C. for 1 hour under a nitrogen atmosphere. The reaction solution was returned to room temperature, a 30% aqueous hydrogen peroxide solution (68 μL) and saturated aqueous sodium bicarbonate (1.0 mL) were added thereto, and the mixture was stirred at room temperature for 0.5 hours. To the reaction solution, methanol was added, the solvent was removed under reduced pressure, and the obtained residue was purified by silica gel column chromatography (ethyl acetate-methanol, NH silica) to obtain a compound 0224-1 (70 mg) as a white solid.

MS m/z (M+H): 273.

(Synthesis of Compound 0224)

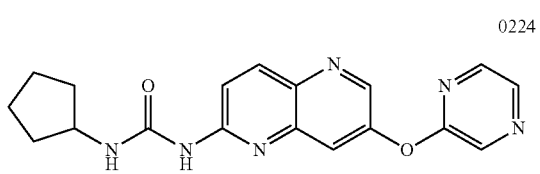 [SMILES: O=C(Nc1ccc2ncc(Oc3cnccn3)cc2n1)NC1CCCC1]

0224

To a solution of the compound 0224-1 (20 mg) in N,N-dimethylformamide (1.0 mL), 60% sodium hydride (13 mg) was added under a nitrogen atmosphere, and the mixture was stirred at room temperature for 10 minutes. Then, chloropyrazine (13 μL) was added thereto and the mixture was stirred at 80° C. for 1 hour. The reaction solution was returned to room temperature, methanol was added thereto, and the solvent was removed under reduced pressure. The obtained residue was purified by silica gel column chromatography (ethyl acetate-methanol, NH silica) to obtain a compound 0224 (6.6 mg) as a white solid.

MS m/z (M+H): 351.

Examples 225 and 226

Synthesis of Compounds 0225 and 0226

(Synthesis of Compound 0225-1)

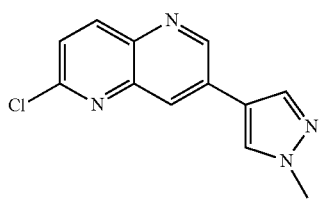

0225-1

The same method as in Example 1 except for using the compound 0001-3 instead of the compound 0001-5 and using 1-methylpyrazole-4-boronic acid pinacol ester instead of 2-methoxy-4-(4,4,5,5-tetramethyl-1,3,2-dioxaborolan-2-yl)phenol in Example 1 was used to obtain a compound 0225-1 (0.35 g) as a white solid.

MS m/z (M+H): 245.

(Synthesis of Compound 0225-2)

[Chem. 303]

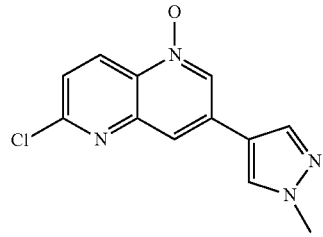

0225-2

To a solution of the compound 0225-1 (0.20 g) in dichloromethane (4.0 mL), 70% methachlorobenzoic acid (1.2 g) was added, and the mixture was stirred at room temperature for 2.5 hours. To the reaction solution, saturated aqueous sodium bicarbonate and sodium sulfite were added, and the mixture was extracted with ethyl acetate. The organic layer was washed with brine, and then dried over sodium sulfate. The solvent was removed under reduced pressure to obtain a compound 0225-2 (0.24 g) as a yellow solid.

MS m/z (M+H): 261.

(Synthesis of Compound 0225-3)

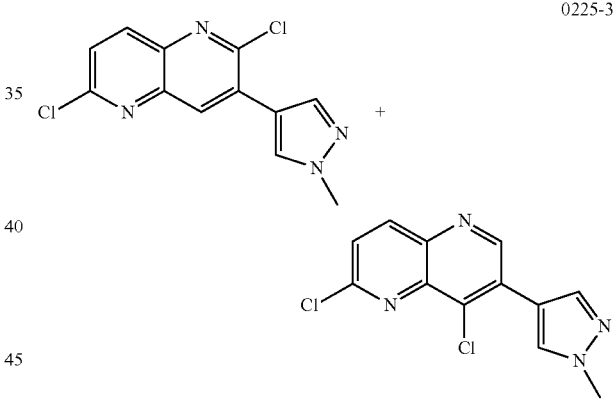

0225-3

The same method as in Example 1 except for using the compound 0225-2 instead of the compound 0001-1 used for the synthesis of the compound 0001-2 in Example 1 was used to obtain a compound 0225-3 (0.20 g) as a mixture of regioisomers (yellow solid).

MS m/z (M+H): 279.

(Synthesis of Compound 0225-4)

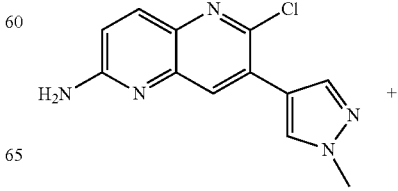

0225-4

159
-continued

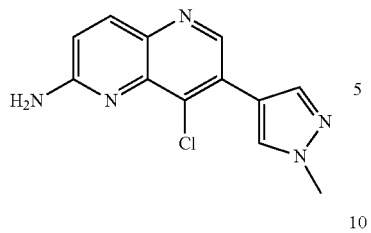

A mixed solution of the compound 0225-3 (0.2 g), 1,4-dioxane (5.0 mL) and a 25% aqueous ammonia solution (5.0 mL) was stirred at 120° C. for 2 hours and at 140° C. for 2 hours using a microwave reaction device. The reaction solution was returned to room temperature and the solvent was removed under reduced pressure. Then, the obtained residue was purified by silica gel column chromatography (chloroform-methanol, NH silica) to obtain a compound 0225-4 (55 mg) as a mixture of regioisomers (white solid).

MS m/z (M+H): 260.

(Synthesis of Compounds 0225 and 0226)

0225

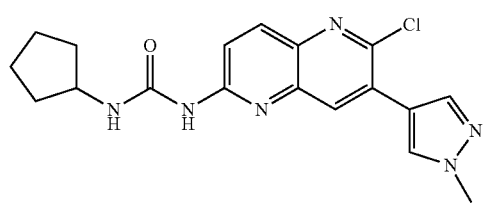

0226

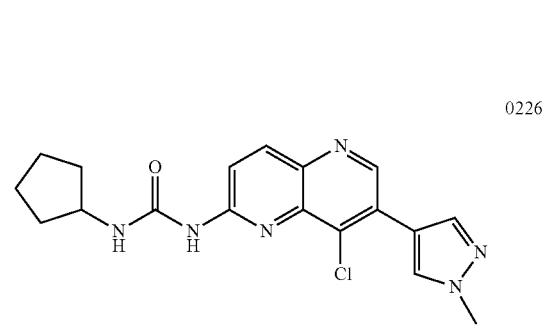 [SMILES: Cn1cc(-c2cc3nc(NC(=O)NC4CCCC4)ccc3nc2N)cn1]

The same method as in Example 1 except for using the compound 0225-4 instead of the compound 0001-4 used for the synthesis of the compound 0001 in Example 1 was used to obtain a compound 0225 (6.9 mg) and a compound 0226 (2.5 mg), respectively, as a white solid.

Compound 0225

MS m/z (M+H): 371.

Compound 0226

MS m/z (M+H): 371.

160

Example 227

Synthesis of Compound 0227

0227

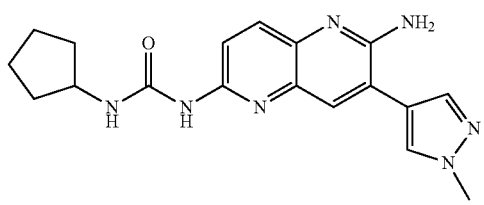

A mixed solution of a mixture of the compound 0225 and the compound 0226 obtained in accordance with Examples 225 and 226 (compound 0225:compound 0226=6.6:1, mg), benzophenonimine (27 µL), tris(dibenzylideneacetone)dipalladium (0) (7.4 mg), 4,5-bis(diphenylphosphino)-9,9-dimethylxanthene (9.4 mg), cesium carbonate (53 mg), and 1,4-dioxane (1.0 mL) was stirred at 120° C. for 0.5 hours and at 150° C. for 0.5 hours using a microwave reaction device. The reaction solution was returned to room temperature, tris(dibenzylideneacetone) dipalladium (0) (7.4 mg), 4,5-bis(diphenylphosphino)-9,9-dimethylxanthene (9.4 mg), and cesium carbonate (53 mg) were added thereto, and the mixture was stirred at 150° C. for 1 hour. The reaction solution was returned to room temperature, 2 M hydrochloric acid (1.0 mL) was added thereto, and then the solvent was removed under reduced pressure. The obtained residue was neutralized by the addition of methanol and saturated aqueous sodium bicarbonate, and then the solvent was removed under reduced pressure. The obtained residue was purified by silica gel column chromatography (chloroform-methanol, NH silica) to obtain a compound 0227 (3.8 mg) as a yellow solid.

MS m/z (M+H): 352.

Example 228

Synthesis of Compound 0228

0228

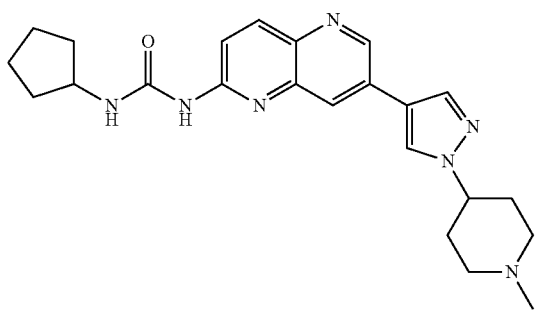

Sodium triacetoxyborohydride (42 mg) was added to a solution of the compound 0214 (16 mg) and a 36% aqueous formaldehyde solution (17 µL) in methanol (0.4 mL) and dichloromethane (0.40 mL) at room temperature, and the mixture was stirred at room temperature for 19 hours. The solvent was removed under reduced pressure and the obtained residue was purified by silica gel column chromatography (ethyl acetate-methanol, NH silica) to obtain a compound 0228 (11 mg) as a white solid.

$^1$H-NMR (DMSO-$d_6$) δ: 9.75 (1H, s), 9.14 (1H, bd), 9.08 (1H, d), 8.58 (1H, s), 8.23-8.17 (2H, m), 8.15 (1H, d), 7.50 (1H, d), 4.26-3.99 (2H, m), 2.93-2.82 (2H, m), 2.22 (3H, s), 2.15-1.87 (8H, m), 1.83-1.47 (6H, m).

MS m/z (M+H): 420.

Example 229

Synthesis of Compound 0229

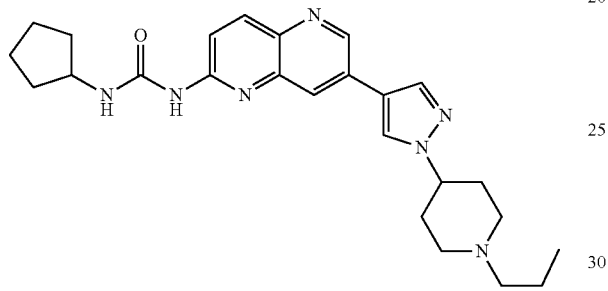

0229

The same method as in Example 228 except for using propionaldehyde instead of the 36% aqueous formaldehyde solution used for the synthesis of the compound 0228 in Example 228 was used to obtain a compound 0229 (3.7 mg) as a white solid.

MS m/z (M+H): 448.

Example 230

Synthesis of Compound 0230

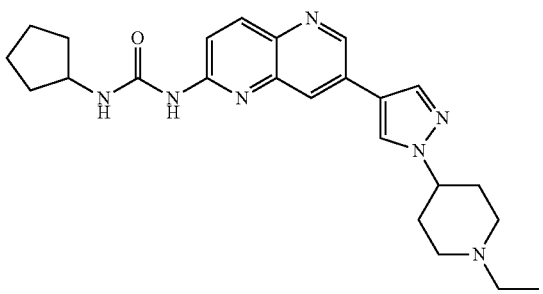

0230

The same method as in Example 228 except for using acetaldehyde instead of the 36% aqueous formaldehyde solution used for the synthesis of the compound 0228 in Example 228 was used to obtain a compound 0230 (4.1 mg) as a white solid.

MS m/z (M+H): 434.

Example 231

Synthesis of Compound 0231

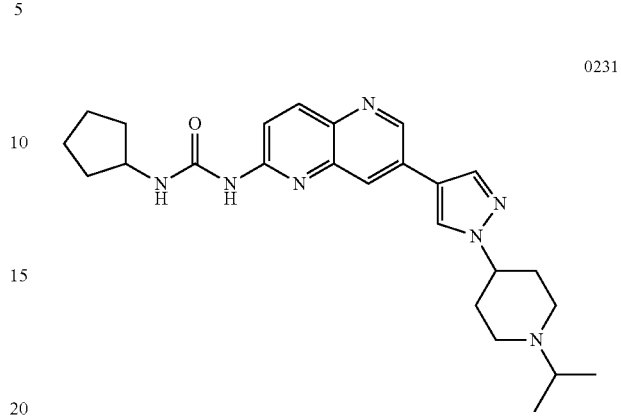

0231

The same method as in Example 228 except for using acetone instead of the 36% aqueous formaldehyde solution used for the synthesis of the compound 0228 in Example 228 was used to obtain a compound 0231 (4.9 mg) as a white solid.

MS m/z (M+H): 448.

Example 232

Synthesis of Compound 0232

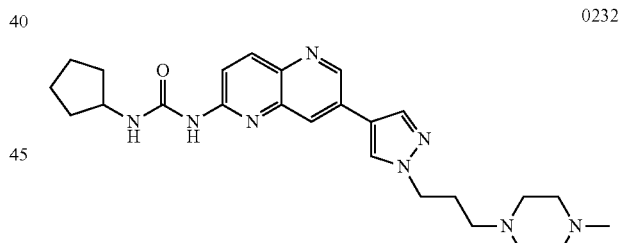

0232

Sodium triacetoxyborohydride (17 mg) was added to a solution of the compound 0212 (7.0 mg) and a 36% aqueous formaldehyde solution (10 μL) in methanol (0.20 mL) and dichloromethane (0.20 mL) at room temperature, and the mixture was stirred at room temperature for 2 hours. The solvent was removed under reduced pressure and the obtained residue was purified by silica gel column chromatography (chloroform-methanol, NH silica) to obtain a compound 0232 (3.4 mg) as a white solid.

$^1$H-NMR (DMSO-$d_6$) δ: 9.76 (1H, s), 9.17 (1H, bd), 9.0 (1H, d), 8.49 (1H, s), 8.24-8.15 (2H, m), 8.13 (1H, d), 7.49 (1H, d), 4.19 (2H, t), 4.15-4.01 (1H, m), 2.45-2.20 (6H, m), 2.14 (3H, s), 2.04-1.88 (4H, m), 1.84-1.48 (6H, m).

MS m/z (M+H): 463.

Example 233

Synthesis of Compound 0233

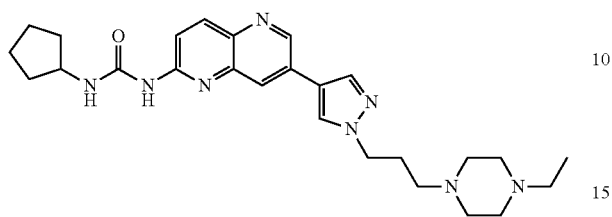

The same method as in Example 232 except for using acetaldehyde instead of the 36% aqueous formaldehyde solution used for the synthesis of the compound 0232 in Example 232 was used to obtain a compound 0233 (1.6 mg) as a white solid.

MS m/z (M+H): 477.

Examples 234 and 235

Synthesis of Compounds 0234 and 0235

(Synthesis of Compounds 0234 and 0235)

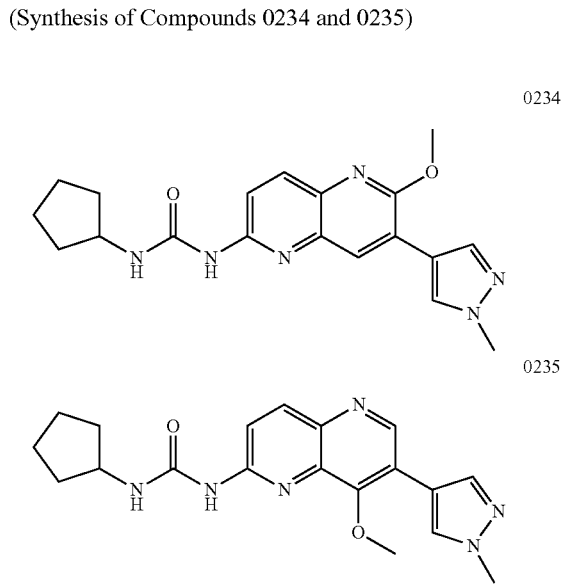

A 5 M sodiummethoxide solution in methanol was added to a solution of a mixture of the compound 0225 and the compound 0226 obtained in accordance with Examples 225 and 226 (compound 0225:compound 0226=6.6:1, 18 mg) in methanol (0.50 mL) at room temperature, and the mixture was stirred at 120° C. for 1 hour and at 150° C. for 0.5 hours, using a microwave reaction device. The reaction solution was returned to room temperature, a saturated aqueous ammonium chloride solution was added thereto, and the mixture was then extracted with ethyl acetate. The organic layer was washed with brine and then dried over sodium sulfate. The solvent was removed under reduced pressure and the obtained residue was purified by silica gel column chromatography (chloroform-methanol) to obtain a compound 0234 (7.2 mg) and a compound 0235 (2.1 mg), respectively, as a white solid.

Compound 0234
MS m/z (M+H): 367.
Compound 0235
MS m/z (M+H): 367.

Example 236, 237

Synthesis of Compounds 0236 and 0237

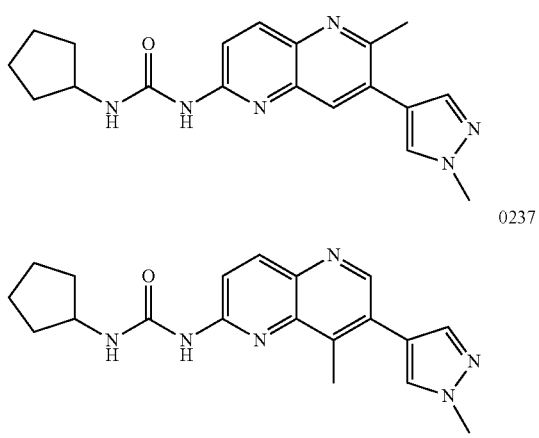

A mixed solution of a mixture of the compound 0225 and the compound 0226 obtained in accordance with Examples 225 and 226 (compound 0225:compound 0226=6.6:1, 50 mg), methylboric acid (24 mg), bis(di-tert-butyl (4-dimethylaminophenyl)phosphine)dichloropalladium (II) (9.6 mg), sodium carbonate (29 mg), 1,4-dioxane (1.0 mL), and water (0.10 mL) was stirred at 100° C. for 28 hours under a nitrogen atmosphere. The reaction solution was returned to room temperature and purified by silica gel column chromatography (chloroform-methanol, NH silica), and after concentration, the obtained solid was further purified by preparative thin layer silica gel chromatography (ethyl acetate-methanol) to obtain a compound 0236 (10 mg) and a compound 0237 (1.3 mg), respectively, as a white solid.

Compound 0236
MS m/z (M+H): 351.
Compound 0237
MS m/z (M+H): 351.

Example 238

Synthesis of Compound 0238

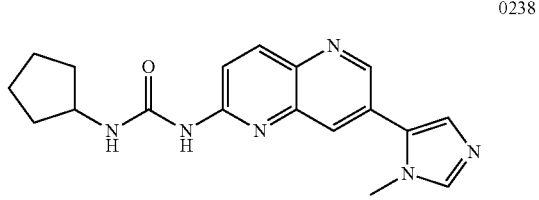 [SMILES: Cn1cncc1-c1cnc2ccc(NC(=O)NC3CCCC3)nc2c1]

The same method as in Example 214 except for using 5-bromo-1-methyl-1H-imidazole instead of a tert-butyl 4-(4-iodo-1H-pyrazol-1-yl)piperidine-1-carboxylate used for the synthesis of the compound 0214-2 in Example 214 was used to obtain a compound 0238 (7.7 mg) as a white solid.

MS m/z (M+H): 337.

Example 239

Synthesis of Compound 0239

(Synthesis of Compound 0239-1)

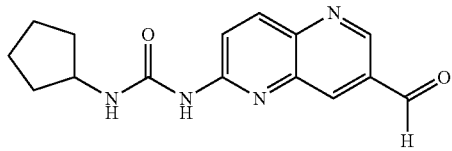

0239-1

To a solution of the compound 0001-5 (50 mg) in tetrahydrofuran (1.5 mL), a 1.64 M butyllithium solution in hexane (0.23 mL) was added at −78° C. under a nitrogen atmosphere, and the mixture was stirred for 1.5 hours. To the reaction solution was added N,N-dimethylformamide (56 μL), and the mixture was stirred at −78° C. for 1.5 hours, warmed to room temperature, and then stirred for 1 hour. A saturated aqueous ammonium chloride solution and ethyl acetate were added to the reaction solution, and the precipitated solid was filtered, and washed with ethyl acetate and water to obtain a compound 0239-1 (21 mg) as a white solid.

MS m/z (M+H): 285.

(Synthesis of Compound 0239)

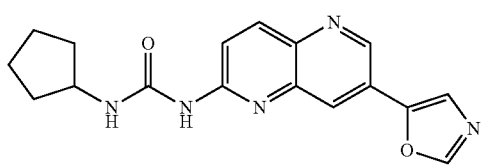

0239

To a solution of the compound 0239-1 (21 mg) and potassium carbonate (30 mg) in methanol (1.0 mL), p-toluenesulfonylmethyl isocyanide (28 mg) was added, and the mixture was stirred at 80° C. for 2 hours. The reaction solution was returned to room temperature and the solvent was removed under reduced pressure. The obtained residue was purified by silica gel column chromatography (chloroform-methanol, NH silica) to obtain a compound 0239 (3.3 mg) as a white solid.

MS m/z (M+H): 324.

Example 240

Synthesis of Compound 0240

(Synthesis of Compound 0240-1)

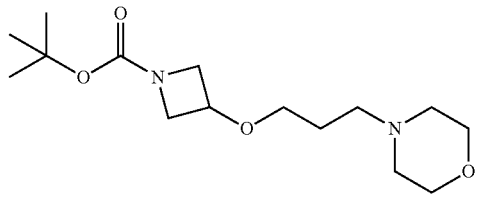

0240-1

To a solution of tert-butyl 3-(3-morpholinopropoxy)azetidine 1-carboxylate (0.20 g) in N,N-dimethylformamide (2.0 mL), 60% sodium hydride (69 mg) was added at 0° C., and the mixture was stirred at 0° C. for 10 minutes and at room temperature for 0.5 hours. To the reaction solution, 4-(3-bromopropyl)morpholine (0.26 g) was added, and the mixture was stirred at 0° C. for 0.5 hours and at room temperature for 1 hour. Then, a saturated aqueous ammonium chloride solution was added thereto, and the mixture was extracted with ethyl acetate. The organic layer was washed with water and brine, and then dried over sodium sulfate. The solvent was removed under reduced pressure to obtain a compound 0240-1 (0.33 g) as a yellow oily substance.

(Synthesis of Compound 0240-2)

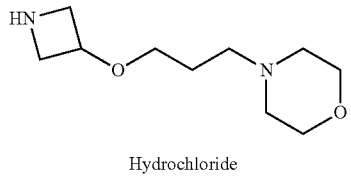

0240-2

Hydrochloride

To a solution of the compound 0240-1 (0.33 g) in methanol (2.0 mL) was added a 4 M hydrogen chloride/1,4-dioxane solution (2.0 mL), and the mixture was stirred at room temperature for 1.5 hours. The solvent was removed under reduced pressure to obtain a compound 0240-2 hydrochloride (0.23 g) as a yellow solid.

(Synthesis of Compound 0240)

0240

The same method as in Example 8 except for using the compound 0240-2 instead of morpholine used for the synthesis of the compound 0008 in Example 8 was used to obtain a compound 0240 (18 mg) as a pale yellow solid.

MS m/z (M+H): 455.

Example 241

Synthesis of Compound 0241

(Synthesis of Compound 0241-1)

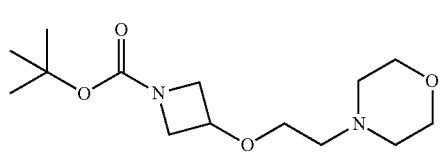

0241-1

The same method as in Example 240 except for using 4-(2-bromoethyl)morpholine instead of 4-(3-bromopropyl)-morpholine used for the synthesis of the compound 0240-1 in Example 240 was used to obtain a compound 0241-1 (0.17 g) as a colorless oily substance.

(Synthesis of Compound 0241-2)

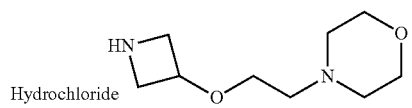

0241-2

The same method as in Example 240 except for using the compound 0241-1 instead of the compound 0240-1 used for the synthesis of the compound 0240-2 in Example 240 was used to obtain a compound 0241-2 (0.14 g) as a colorless oily substance.

(Synthesis of Compound 0241)

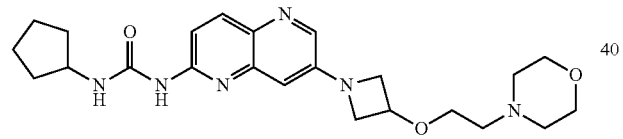

0241

The same method as in Example 8 except for using the compound 0241-2 instead of morpholine used for the synthesis of the compound 0008 in Example 8 was used to obtain a compound 0241 (16 mg) as a white solid.
MS m/z (M+H): 441.

Example 242

Synthesis of Compound 0242

[Chem. 325]

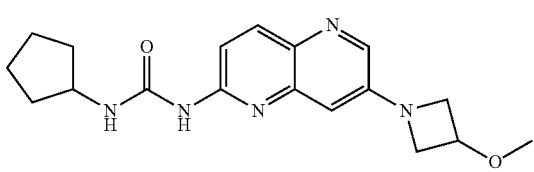

0242

The same method as in Example 8 except for using 3-methoxyazetidine hydrochloride instead of morpholine used for the synthesis of the compound 0008 in Example 8 was used to obtain a compound 0242 (17 mg) as a white solid.
MS m/z (M+H): 342.

Example 243

Synthesis of Compound 0243

(Synthesis of Compound 0243-1)

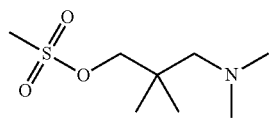

0243-1

To a solution of 3-dimethylamino-2,2-dimethyl-1-propanol (0.50 g) in pyridine (3.8 mL), methanesulfonylchloride (0.33 mL) was added at 0° C., and the mixture was stirred at room temperature for 30 minutes. To the reaction solution, saturated aqueous sodium bicarbonate was added, the mixture was extracted with ethyl acetate, and the organic layer was washed with brine, and then dried over sodium sulfate. The solvent was removed under reduced pressure and the obtained solid was washed with ethyl acetate to obtain a compound 0243-1 (0.33 g) as a white solid.

(Synthesis of Compound 0243-2)

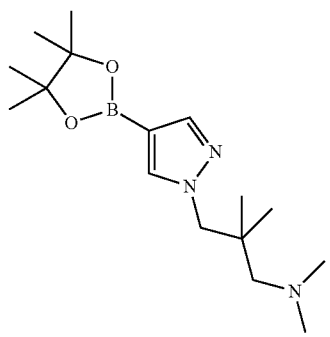

0243-2

The same method as in Example 206 except for using the compound 0243-1 instead of N-(4-bromobutyl)phthalimide used for the synthesis of the compound 0206-1 in Example 206 was used to obtain a compound 0243-2 (0.30 g) as a colorless oily substance.

(Synthesis of Compound 0243)

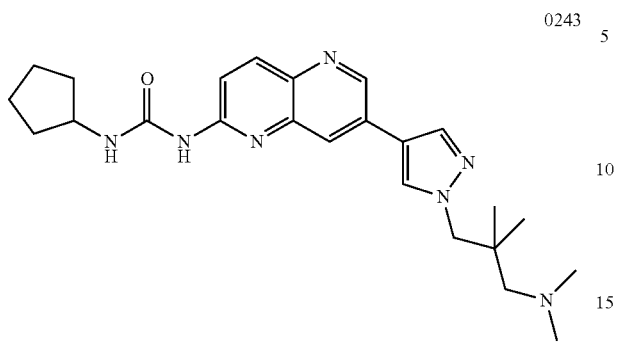

The same method as in Example 1 except for using the compound 0243-2 instead of 2-methoxy-4-(4,4,5,5-tetramethyl-1,3,2-dioxaborolan-2-yl)phenol used for the synthesis of the compound 0001 in Example 1 was used to obtain a compound 0243 (26 mg) as a white solid.

$^1$H-NMR (DMSO-d$_6$) δ: 9.76 (1H, s), 9.16 (1H, bd), 9.07 (1H, d), 8.46 (1H, s), 8.26-8.08 (3H, m), 7.50 (1H, d), 4.15-3.97 (3H, m), 2.30 (6H, s), 2.19 (2H, s), 2.03-1.86 (2H, m), 1.84-1.47 (6H, m), 0.88 (6H, s).

MS m/z (M+H): 436.

Example 244

Synthesis of Compound 0244

(Synthesis of Compound 0244-1)

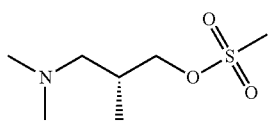

A mixed solution of (S)-(+)-3-bromo-2-methyl-1-propanol (0.30 g), potassium carbonate (0.54 g), and 2 M dimethylamine in tetrahydrofuran (4.9 mL) was heated and refluxed for 9 hours. The reaction solution was returned to room temperature, the solid was filtered, and the filtrate was then concentrated under reduced pressure to obtain a compound 0244-1 (0.19 g) as a yellow oily substance.

(Synthesis of Compound 0244-2)

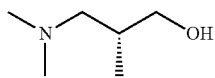

The same method as in Example 243 except for using the compound 0244-1 instead of 3-dimethylamino-2,2-dimethyl-1-propanol used for the synthesis of the compound 0243-1 in Example 243 was used to obtain a compound 0244-2 (0.17 g) as a colorless oily substance.

(Synthesis of Compound 0244-3)

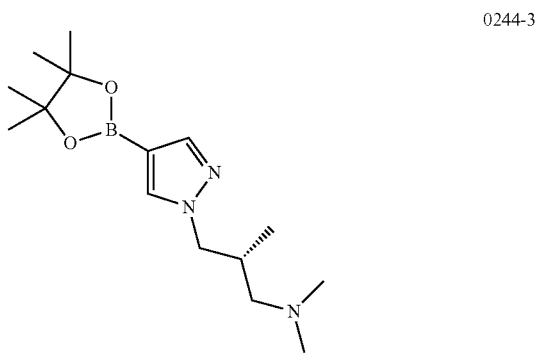

The same method as in Example 206 except for using the compound 0244-2 instead of N-(4-bromobutyl)phthalimide used for the synthesis of the compound 0206-1 in Example 206 was used to obtain a compound 0244-3 (29 mg) as a colorless oily substance.

(Synthesis of Compound 0244)

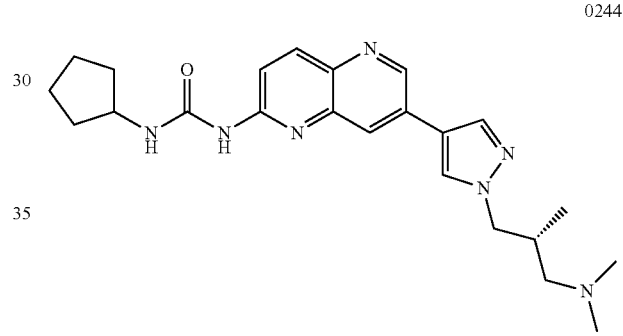

The same method as in Example 1 except for using the compound 0244-3 instead of 2-methoxy-4-(4,4,5,5-tetramethyl-1,3,2-dioxaborolan-2-yl)phenol used for the synthesis of the compound 0001 in Example 1 was used to obtain a compound 0244 (13 mg) as a white solid.

MS m/z (M+H): 422.

Example 245

Synthesis of Compound 0245

(Synthesis of Compound 0245-1)

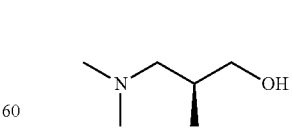

The same method as in Example 244 except for using (R)-(−)-3-bromo-2-methyl-1-propanol instead of (S)-(+)-3-bromo-2-methyl-1-propanol used for the synthesis of the compound 0244-1 in Example 244 was used to obtain a compound 0245-1 (0.20 g) as a colorless oily substance.

171

(Synthesis of Compound 0245-2)

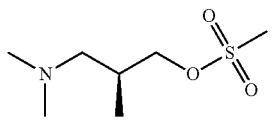

0245-2

The same method as in Example 243 except for using the compound 0245-1 instead of 3-dimethylamino-2,2-dimethyl-1-propanol used for the synthesis of the compound 0243-1 in Example 243 was used to obtain a compound 0245-2 (0.21 g) as a colorless oily substance.

(Synthesis of Compound 0245-3)

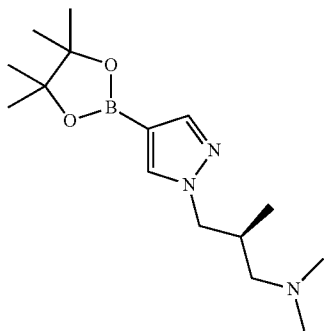

0245-3

The same method as in Example 206 except for using the compound 0245-2 instead of N-(4-bromobutyl)phthalimide used for the synthesis of the compound 0206-1 in Example 206 was used to obtain a compound 0245-3 (26 mg) as a colorless oily substance.

(Synthesis of Compound 0245)

Example 246

Synthesis of Compound 0246

(Synthesis of Compound 0246-1)

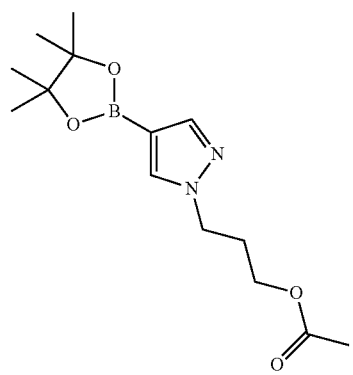

0246-1

The same method as in Example 206 except for using 3-bromopropyl acetate instead of N-(4-bromobutyl)phthalimide used for the synthesis of the compound 0206-1 in Example 206 was used to obtain a compound 0246-1 (1.2 g) as a yellow oily substance.

MS m/z (M+H): 295.

(Synthesis of Compound 0246-2)

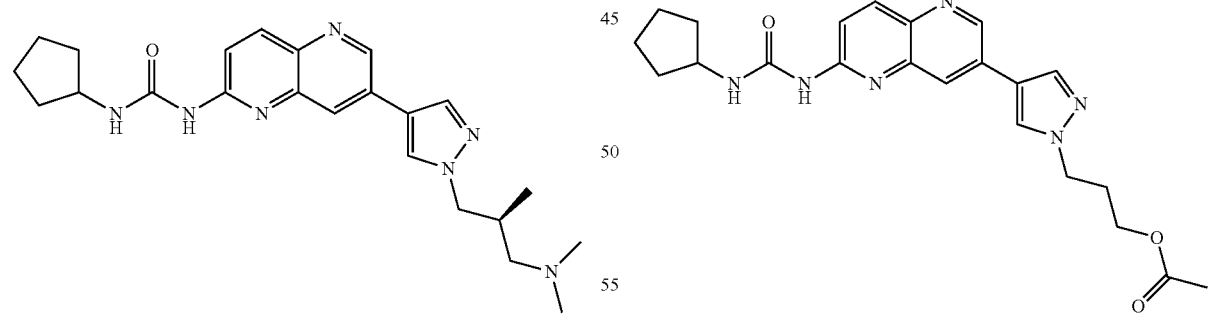

0245

0246-2

The same method as in Example 1 except for using the compound 0245-3 instead of 2-methoxy-4-(4,4,5,5-tetramethyl-1,3,2-dioxaborolan-2-yl)phenol used for the synthesis of the compound 0001 in Example 1 was used to obtain a compound 0245 (17 mg) as a white solid.

MS m/z (M+H): 422.

The same method as in Example 1 except for using the compound 0246-1 instead of 2-methoxy-4-(4,4,5,5-tetramethyl-1,3,2-dioxaborolan-2-yl)phenol used for the synthesis of the compound 0001 in Example 1 was used to obtain a compound 0246-2 (0.18 g) as a white solid.

MS m/z (M+H): 423.

(Synthesis of Compound 0246-3)

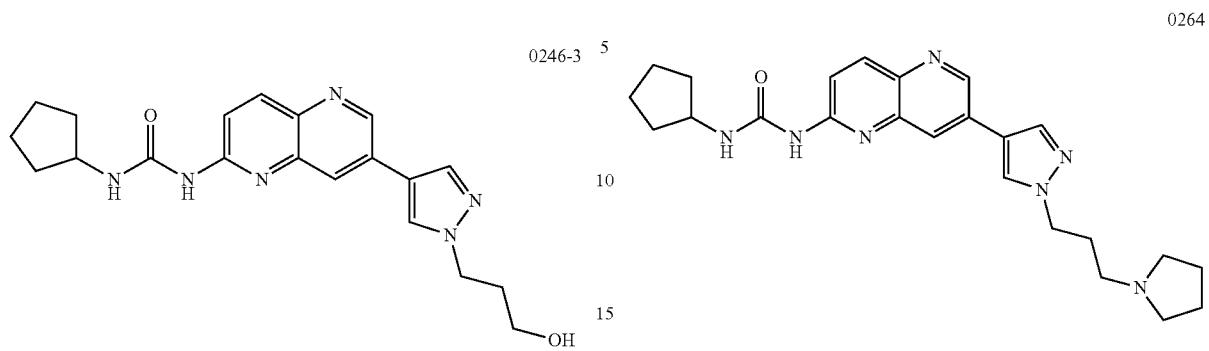

0246-3

To a solution of the compound 0264-2 (0.18 g) in ethanol (2.0 mL) was added a 5 M aqueous sodium hydroxide solution (0.26 mL), and the mixture was stirred at room temperature for 1 hour. The reaction solution was neutralized by the addition of 3 M hydrochloric acid and the solvent was removed under reduced pressure. The obtained residue was purified by silica gel column chromatography (chloroform-methanol, NH silica) to obtain a compound 0246-3 (96 mg) as a white solid.

MS m/z (M+H): 381.

(Synthesis of Compound 0246-4)

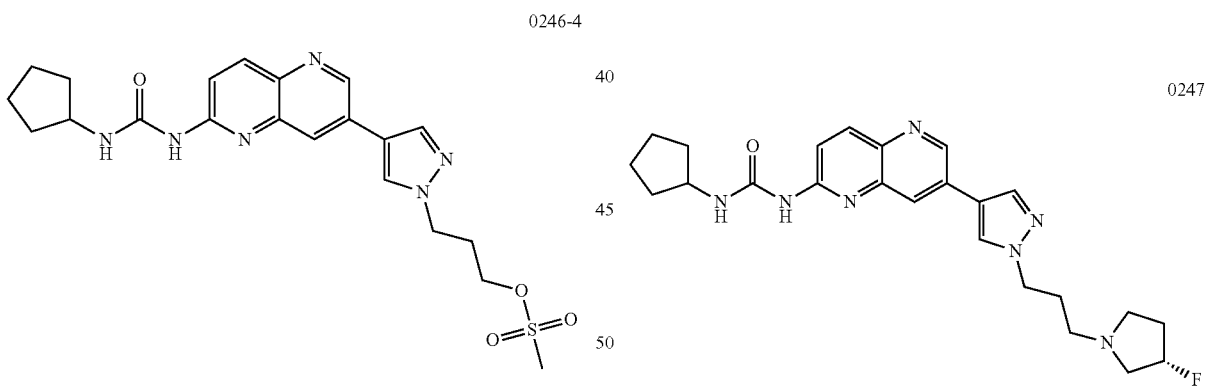

0246-4

To a solution of the compound 0246-3 (96 mg) in pyridine (2.5 mL), methanesulfonyl chloride (39 μL) was added at 0° C., and the mixture was stirred at room temperature for 1.5 hours. To the reaction solution, saturated aqueous sodium bicarbonate was added, and the solvent was removed under reduced pressure. The obtained residue was purified by silica gel column chromatography (chloroform-methanol, NH silica) to obtain a compound 0246-4 (98 mg) as a white solid.

MS m/z (M+H): 459.

(Synthesis of Compound 0246)

0264

The same method as in Example 36 except for using the compound 0246-4 instead of the compound 0036-1 used for the synthesis of the compound 0036 in Example 36 and using pyrrolidine instead of piperidine used for the synthesis of the compound 0036 in Example 36 was used to obtain a compound 0246 (12 mg) as a white solid.

$^1$H-NMR (DMSO-d$_6$) δ: 9.76 (1H, s), 9.17 (1H, bd), 9.06 (1H, d), 8.51 (1H, s), 8.25-8.06 (3H, m), 7.49 (1H, d), 4.21 (2H, t), 4.16-3.99 (1H, m), 2.46-2.32 (6H, m), 2.09-1.88 (4H, m), 1.85-1.46 (10H, m).

MS m/z (M+H): 434.

Example 247

Synthesis of Compound 0247

0247

The same method as in Example 36 except for using the compound 0246-4 instead of the compound 0036-1 used for the synthesis of the compound 0036 in Example 36 and using (S)-(+)-fluoropyrrolidin hydrochloride instead of piperidine used for the synthesis of the compound 0036 in Example 36 was used to obtain a compound 0247 (3.3 mg) as a white solid.

$^1$H-NMR (DMSO-d$_6$) δ: 9.76 (1H, s), 9.16 (1H, bd), 9.06 (1H, d), 8.51 (1H, s), 8.24-8.10 (3H, m), 7.49 (1H, d), 5.35-5.02 (1H, m), 4.22 (2H, t), 4.16-3.99 (1H, m), 2.89-2.69 (2H, m), 2.42 (2H, t), 2.34-1.49 (12H, m).

MS m/z (M+H): 452.

Example 248

Synthesis of Compound 0248

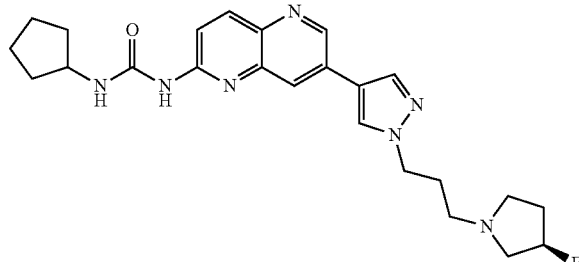

0248

The same method as in Example 36 except for using compound 0246-4 instead of the compound 0036-1 used for the synthesis of the compound 0036 in Example 36 and using (R)-(−)-fluoropyrrolidin hydrochloride instead of piperidine used for the synthesis of the compound 0036 in Example 36 was used to obtain a compound 0248 (2.6 mg) as a white solid.

$^1$H-NMR (DMSO-d$_6$) δ: 9.76 (1H, s), 9.16 (1H, bd), 9.06 (1H, d), 8.51 (1H, s), 8.24-8.10 (3H, m), 7.49 (1H, d), 5.35-5.02 (1H, m), 4.22 (2H, t), 4.16-3.99 (1H, m), 2.89-2.69 (2H, m), 2.42 (2H, t), 2.34-1.49 (12H, m).

MS m/z (M+H): 452.

Example 249

Synthesis of Compound 0249

(Synthesis of Compound 0249-1)

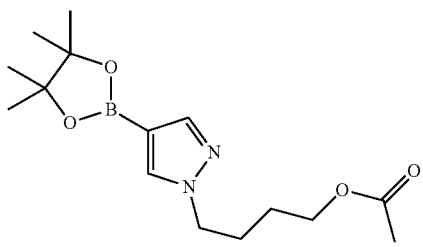

0249-1

The same method as in Example 206 except for using 4-bromobutyl acetate instead of N-(4-bromobutyl)phthalimide used for the synthesis of the compound 0206-1 in Example 206 was used to obtain a compound 0249-1 (0.17 g) as a colorless liquid.

MS m/z (M+H): 309.

(Synthesis of Compound 0249)

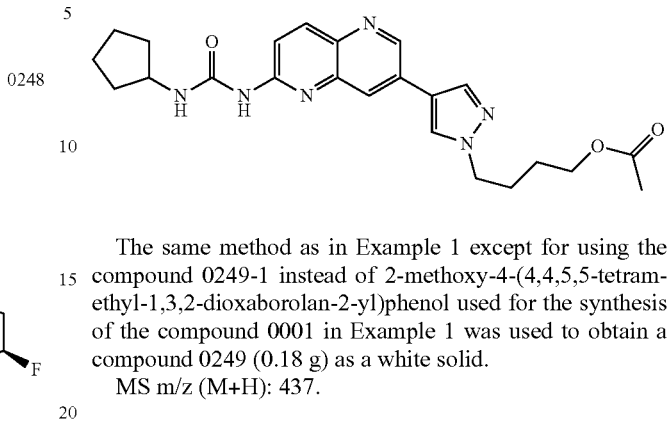

0249

The same method as in Example 1 except for using the compound 0249-1 instead of 2-methoxy-4-(4,4,5,5-tetramethyl-1,3,2-dioxaborolan-2-yl)phenol used for the synthesis of the compound 0001 in Example 1 was used to obtain a compound 0249 (0.18 g) as a white solid.

MS m/z (M+H): 437.

Example 250

Synthesis of Compound 0250

(Synthesis of Compound 0250-1)

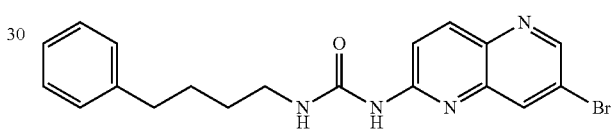

0250-1

Pyridine (3 mL) was added to the compound 0095-1 (100 mg) and phenyl chloroformate (88 μL), and the mixture was stirred at 40° C. for 6 hours. Further, 4-phenylbutylamine was added thereto and the mixture was stirred at 50° C. for 2 hours. The solvent of the reaction solution was evaporated under reduced pressure. The residue was purified by silica gel column chromatography (chloroform-methanol) to obtain a compound 0250-1 (65 mg) as a white solid.

MS m/z (M+H): 399.

(Synthesis of Compound 0250)

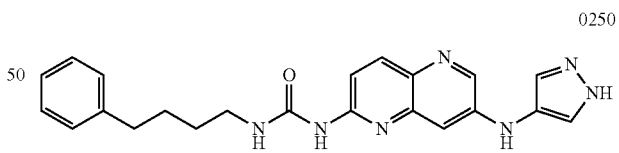

0250

Tert-butyl 4-amino-1H-pyrazole-1-carboxylate (20 mg, which was synthesized according to WO2008/139161), cesium carbonate (82 mg), 4,5-bis(diphenylphosphino)-9,9-dimethylxanthene (14 mg), and tris(dibenzylideneacetone)dipalladium (0) (14 mg) were added to a solution of the compound 0250-1 (40 mg) in 1,4-dioxane (1 mL), and the mixture was stirred for 4.75 hours while heating and refluxing under a nitrogen atmosphere. The reaction solution was returned to room temperature, a saturated aqueous ammonium chloride solution was added thereto, and the mixture was extracted with a chloroform-methanol mixed solvent. The organic layer was dried over sodium sulfate and the solvent was then evaporated under reduced pressure. To the obtained residue, dichloromethane (1 mL) and trifluoroacetic acid (0.6 mL) were added, and the mixture was stirred at room temperature for 8 hours. To the reaction solution, a saturated aqueous sodium hydrogen carbonate solution was added, and the mixture was extracted with a chloroform-methanol mixed solvent. The organic layer was dried over sodium sulfate and the solvent was evaporated under reduced pressure. The residue was purified by silica gel column chromatography (chloroform-methanol) to obtain a compound 0250 (10 mg) as a yellow solid.

MS m/z (M+H): 402.

Example 251

Synthesis of Compound 0251

(Synthesis of Compound 0251-1)

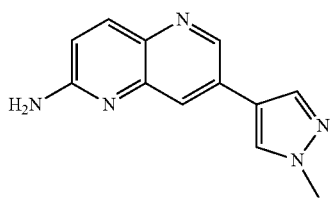

0251-1

The same method as in Example 138 except for using 1-methylpyrazole-4-boronic acid pinacol ester instead of 1-(2-morpholinoethyl)-1H-pyrazole-4-boronic acid pinacol ester used for the synthesis of the compound 138-1 in Example 138 was used to obtain a compound 0251-1 (300 mg) as a white solid.

MS m/z (M+H): 226.

(Synthesis of Compound 0251)

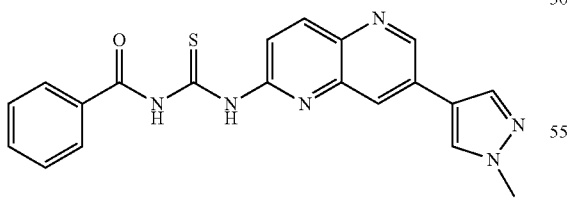

0251

To the compound 0251-1 (201 mg) were added 1,4-dioxane (8.9 mL) and benzoyl isothiocynate (0.24 mL) under ice-cooling, and the mixture was returned to room temperature and stirred for 1 hour and then at 55° C. for 2 hours. The reaction solution was evaporated under reduced pressure and the obtained residue was washed with ethyl acetate to obtain a compound 0251 (232 mg) as a yellow solid.

MS m/z (M+H): 389.

Example 252

Synthesis of Compound 0252

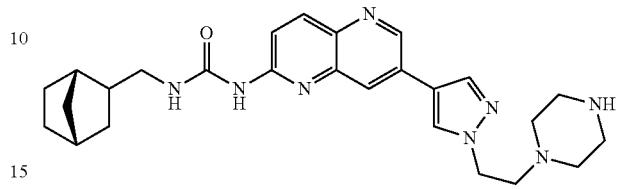

0252

1,4-dioxane (1.5 mL) was added to the compound 0095-1 (30 mg) and bicyclo[2.2.1]hept-2-ylmethylamine (18 mg), and the mixture was stirred at 100° C. for 0.5 hours using a microwave reaction device. To this reaction, 1,4-dioxane (1.5 mL), water (50 uL), bicyclo[2.2.1]hept-2-ylmethylamine (53 mg), sodium carbonate (18.5 mg), and bis(di-tert-butyl (4-dimethylaminophenyl)phosphine)dichloropalladium (II) (6.2 mg) were added, and the mixture was stirred at 100° C. for 2 hours using a microwave reaction device. The reaction solution was purified by silica gel column chromatography (chloroform-methanol, NH silica) to obtain a yellow solid. The obtained solid was dissolved in a 4 M hydrogen chloride/1,4-dioxane solution (1.5 mL) and the mixture was stirred for 2 hours. The solvent was evaporated under reduced pressure and purified by silica gel column chromatography (chloroform-methanol, NH silica) to obtain a compound 0252 (12.5 mg) as a white solid.

MS m/z (M+H): 475.

Example 253

Synthesis of Compound 0253

(Synthesis of Compound 0253-1)

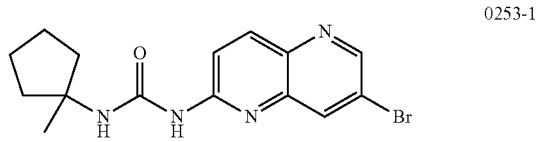 [SMILES: CC1(NC(=O)Nc2ccc3ncc(Br)cc3n2)CCCC1]

0253-1

Pyridine (1.5 mL) was added to the compound 0095-1 (50 mg) and phenyl chloroformate (44 µL), and the mixture was stirred at 40° C. for 6 hours. Further, 1-amino-1-methylcyclopentane hydrochloride and triethylamine (124 µL) were added thereto, and the mixture was stirred at 50° C. for 2 hours. The solvent of the reaction solution was evaporated under reduced pressure and the residue was purified by silica gel column chromatography (chloroform-methanol) to obtain a compound 0253-1 (31.5 mg) as a white solid.

MS m/z (M+H): 349.

(Synthesis of Compound 0253)

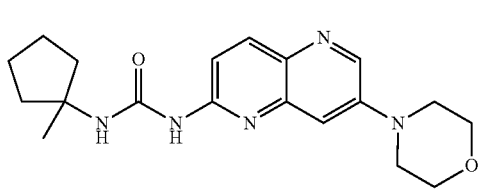

1,4-dioxane (1.7 mL) was added to the compound 0253-1 (30 mg), morpholine (29.9 uL), tris(dibenzylideneacetone)dipalladium (0) (4.9 mg), 2-dicyclohexylphosphino-2',4',6'-triisopropylbiphenyl (8.1 mg) and sodium tert-butoxide (16.5 mg) under a nitrogen atmosphere, and the mixture was stirred at 100° C. for 1 hour. The reaction solution was returned to room temperature, the solvent was evaporated under reduced pressure, and the obtained residue was purified by silica gel column chromatography (chloroform-methanol, NH silica). After concentration, the obtained solid was washed with ethyl acetate to obtain a compound 0253 (13.6 mg) as a white solid.

$^1$H-NMR (DMSO-$d_6$) δ: 9.53 (1H, s), 9.40 (1H, bs), 8.64 (1H, d), 8.08 (1H, d), 7.24 (1H, d), 7.14 (1H, d), 3.80 (4H, t), 2.03-2.13 (2H, m), 1.56-1.76 (6H, m), 1.46 (3H, s).

MS m/z (M+H): 356.

Example 254

Synthesis of Compound 0254

(Synthesis of Compound 0254-1)

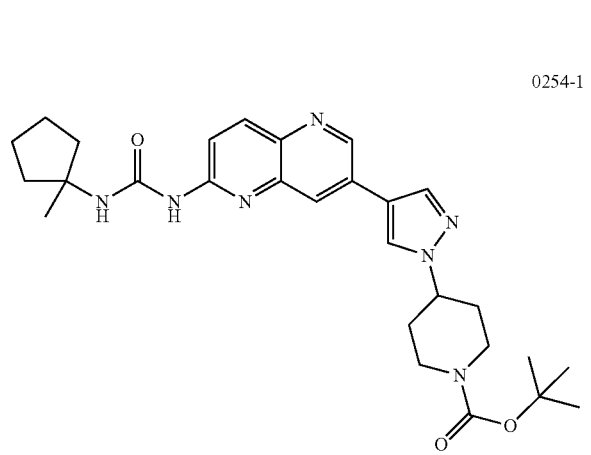 [SMILES: CC1(NC(=O)Nc2ccc3ncc(-c4cnn(C5CCN(C(=O)OC(C)(C)C)CC5)c4)cc3n2)CCCC1]

The same method as in Example 146 except for using tert-butyl 4-(4-iodo-1H-pyrazol-1-yl)piperidine-1-carboxylate instead of tert-butyl 3-((4-bromo-1H-pyrazol-1-yl)methyl)azetidine-1-carboxylate used for the synthesis of the compound 146-1 in Example 0146 was used to obtain a compound 0254-1 (35.5 mg) as a white solid.

(Synthesis of Compound 0254)

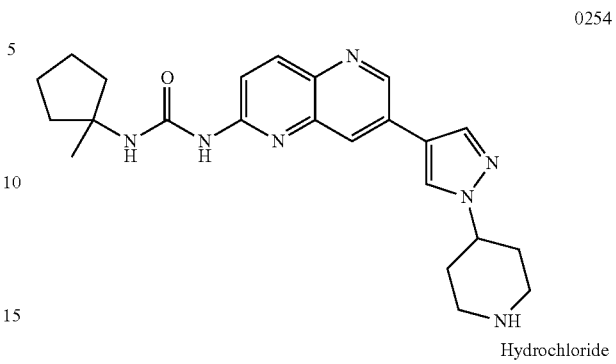

The same method as in Example 220 except for using the compound 0254-1 instead of the compound 0220-2 used for the synthesis of the compound 0220 in Example 0220 was used to obtain a compound 0254 hydrochloride (28.4 mg) as a white solid.

$^1$H-NMR (DMSO-$d_6$) δ: 9.72 (1H, bs), 9.23 (1H, bs), 9.11 (1H, d), 8.90-8.79 (2H, m), 8.58 (1H, s), 8.58 (1H, s), 8.27 (1H, s), 8.21 (1H, d), 8.15 (1H, d), 4.57 (1H, m), 3.20-3.02 (2H, m), 2.73 (1H, m), 2.27 (1H, m), 2.32-2.08 (8H, m), 1.80-1.58 (6H, m), 1.47 (3H, s).

MS m/z (M+H): 420.

Example 255

Synthesis of Compound 0255

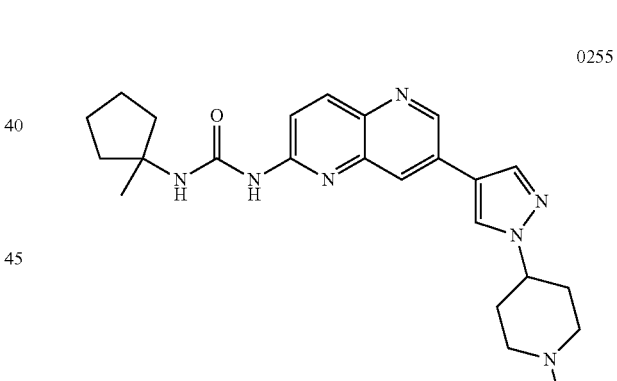

20% formalin (660 uL) was added to the compound 0254 hydrochloride (14.3 mg), methanol (1.1 mL), and dichloromethane (1.1 mL), and the mixture was stirred for 30 minutes. To this reaction solution, sodium triacetoxyborohydride (34.1 mg) was added, and the mixture was stirred at room temperature for 2 hours. The solvent of the reaction solution was evaporated under reduced pressure. The residue was purified by silica gel column chromatography (chloroform-methanol, NH silica) to obtain a yellow solid. The obtained solid was dissolved in a 4 M hydrogen chloride/1,4-dioxane solution (1.5 mL) and the mixture was stirred for 2 hours. The solvent was evaporated under reduced pressure, and the reside was purified by silica gel column chromatography (chloroform-methanol, NH silica) to obtain a compound 0255 (12.5 mg) as a white solid.

¹H-NMR (DMSO-d₆) δ: 9.65 (1H, s), 9.25 (1H, bs), 9.07 (1H, d), 8.58 (1H, s), 8.21-8.16 (2H, m), 8.08 (1H, d), 7.47 (1H, d), 4.18 (1H, m), 2.92-2.84 (2H, m), 2.73 (1H, m), 2.27 (1H, m), 2.22 (3H, s), 2.16-1.96 (8H, m), 1.80-1.58 (6H, m), 1.47 (3H, s).

MS m/z (M+H): 434.

Example 256

Synthesis of Compound 0256

(Synthesis of Compound 0256-1)

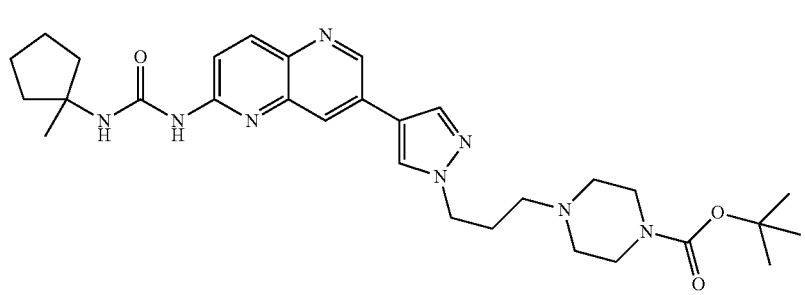

0256-1

The same method as in Example 0211 except for using the compound 0253-1 instead of the compound 0001-5 used for the synthesis of the compound 0211 in Example 0211 was used to obtain a compound 0256-1 (42 mg) as a white solid.

(Synthesis of Compound 0256)

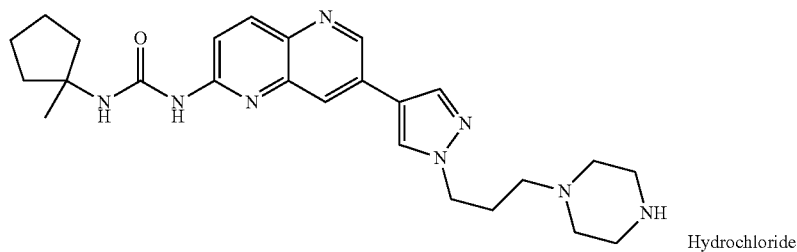

0256

Hydrochloride

The same method as in Example 212 except for using the compound 0256-1 instead of the compound 0211 used for the synthesis of the compound 0212 in Example 212 was used to obtain a compound 0256 hydrochloride (29.8 mg) as a white solid.

¹H-NMR (DMSO-d₆) δ: 10.80-9.92 (1H, m), 9.74-9.53 (2H, m), 9.16-9.13 (2H, d), 9.07-8.99 (1H, m), 8.60 (1H, s), 8.33-8.24 (2H, m), 7.57 (1H, d), 4.36-4.28 (2H, m), 3.25-3.16 (2H, m), 2.40-2.24 (2H, m), 2.16-2.05 (2H, m), 1.80-1.60 (6H, m), 1.47 (3H, s).

MS m/z (M+H): 477.

Example 257

Synthesis of Compound 0257

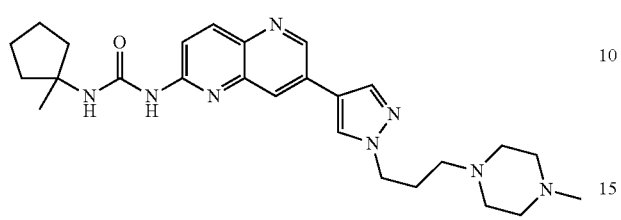

The same method as in Example 255 except for using the compound 0256-1 instead of the compound 0254 used for the synthesis of the compound 0255 in Example 255 was used to obtain a compound 0257 hydrochloride (9.9 mg) as a white solid.

$^1$H-NMR (DMSO-d$_6$) δ: 9.66 (1H, s), 9.28 (1H, bs), 9.06 (1H, d), 8.49 (1H, s), 8.20-8.18 (2H, m), 8.06 (1H, d), 7.46 (1H, d), 4.19 (2H, t), 2.40-2.23 (6H, m), 2.14 (3H, s), 2.04-1.88 (4H, m), 1.80-1.58 (6H, m), 1.47 (3H, s).

MS m/z (M+H): 477.

Example 258

Synthesis of Compound 0258

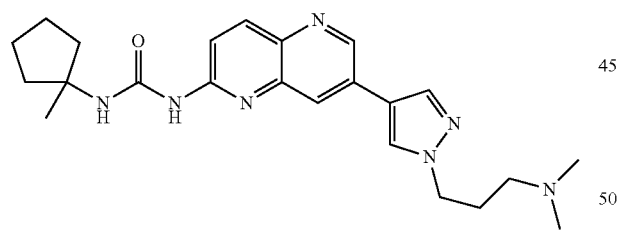

The same method as in Example 210 except for using the compound 0253-1 instead of the compound 0001-5 used for the synthesis of the compound 0210 in Example 210 was used to obtain a compound 0258 (17.9 mg) as a white solid.

$^1$H-NMR (DMSO-d$_6$) δ: 9.66 (1H, s), 9.28 (1H, bs), 9.06 (1H, d), 8.50 (1H, s), 8.20-8.18 (2H, m), 8.07 (1H, d), 7.47 (1H, d), 4.19 (2H, t), 2.21 (2H, t), 2.14 (6H, s), 2.01-1.90 (4H, m), 1.80-1.60 (6H, m), 1.47 (3H, s).

MS m/z (M+H): 422.

Example 259

Synthesis of Compound 0259

(Synthesis of Compound 0259-1)

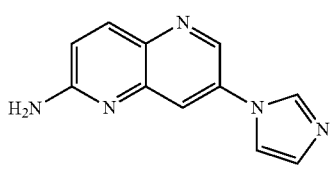

Dimethylsulfoxide (1.7 mL) was added to the compound 0001-4 (50 mg), imidazole (23.8 mg), copper iodide (17 mg), N,N-dimethyl glycine (18.4 mg), and cesium carbonate (94.5 mg), and the mixture was stirred at 150° C. for 2 hours. The reaction solution was returned to room temperature, the solvent was evaporated under reduced pressure, and the obtained residue was purified by silica gel column chromatography (chloroform-methanol, NH silica). After concentration, the obtained solid was washed with ethyl acetate to obtain a compound 0259-1 (12 mg) as a white solid.

(Synthesis of Compound 0256)

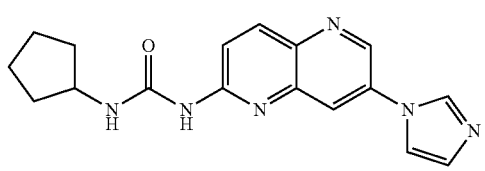

The same method as in Example 1 except for using the compound 0259-1 instead of the compound 0001-4 used for the synthesis of the compound 0001-5 in Example 1 was used to obtain a compound 0259 (10.4 mg) as a white solid.

MS m/z (M+H): 323.

Next, the usability of the representative compounds of the present invention is described with reference to Test Examples below.

Test Example 1

PI3Kα Enzyme Assay

Evaluation of the PI3Kα inhibitory activity of the compound of the present invention was carried out according to the method as described below.

For the PI3Kα enzyme assay, biotinylated product of a human PI3Kα protein produced using a Baculovirus expression system (Carna Biosciences, Inc.) was used. Further, for the detection of the enzyme activity, an ADP-Glo kinase assay (PROMEGA Corporation) was used.

10 μL of a reaction solution (3 nM PI3Kα, 40 mM Tris-HCl, 20 mM MgCl$_2$, 0.1% BSA, pH 7.5) including the human PI3Kα protein and a test compound at a predetermined concentration was incubated at room temperature for 15 minutes. Thereafter, 5 μL of a mixed solution of L-α-Phosphatidylinositol 4,5-diphosphate (PIP2) (SIGMA-ALDLICH) which was a substrate and ATP(SIGMA-ALDLICH) was added thereto to a final concentration of 50 μM and 100 μM, respectively, and the reaction solution was further incubated at 25° C. for 60 minutes to carry out an enzyme reaction.

After the reaction, 15 μL of an ADP-Glo reagent (PROMEGA Corporation) was added and the resulting liquid was incubated at room temperature for 60 minutes, whereby the enzyme reaction was stopped. Thereafter, after further adding 30 μL of a Kinase Detection Reagent (PROMEGA Corporation) and standing the resulting solution at room temperature for 40 minutes, ADP produced by the enzyme reaction was quantified by luminescence intensity.

For the measurement of luminescence intensity, EnVision (PerkinElmer, Inc.) was used.

Test Example 2

ERK2 Enzyme Assay

Evaluation of the ERK2 inhibitory activity of the compound of the present invention was carried out according to the method as described below.

For the ERK2 enzyme assay, a glutathione S-transferase (GST)-fusion human ERK2 protein (Carna Biosciences, Inc.) produced using an *E. coli* expression system was used.

12 μL of the reaction solution (2 nM ERK2, 100 mM Hepes, 10 mM $MgCl_2$, 1.5 mM DTT, 0.003% Brij35, pH 7.5) including the ERK2 protein and a test compound at a predetermined concentration was incubated at room temperature for 15 minutes. Thereafter, 3 μL of a mixed solution of FL-Peptide 8 (5-FAM-IPTSPITTTYFFFKKK-COOH) (Caliper Lifescience) which was a substrate and ATP(SIGMA-ALDLICH) were added thereto to a final concentration of 4.25 μM and 43 μM, respectively. The reaction solution was further incubated at 25° C. for 120 minutes to carry out an enzyme reaction.

The enzyme reaction was stopped by adding 27 μL of a reaction-stopping solution (100 mM HEPES, 11.2 mM EDTA, 5.6% Brij35, pH 7.5) including a 0.5% Coating reagent 8 (PerkinElmer, Inc.) after the reaction. Thereafter, non-phosphorylated peptides and phosphorylated peptides were separated using LabChip Ez Reader (Caliper LifeScience, Inc.) to quantify the proportion of phosphorylated peptides.

The inhibitory activity of the compounds was evaluated using an $IC_{50}$ (50% inhibitory concentration). The $IC_{50}$ was calculated using XLfit (IDBS).

The results of $IC_{50}$ were evaluated according to the following evaluation criteria. The evaluation results are shown in Tables 1 to 14 below. Further, the $IC_{50}$s of the representative compounds are shown in Table 15.

—Evaluation Criteria—
+++ 0.1 μM>$IC_{50}$
++ 0.1 μM<$IC_{50}$<1 μM
+ 1 μM<$IC_{50}$<10 μM
− 10 μM<$IC_{50}$

TABLE 1

| Compound No. | PI3Kα Inhibitory Activity | ERK2 Inhibitory Activity |
|---|---|---|
| 0001 | +++ | +++ |
| 0002 | +++ | +++ |
| 0003 | +++ | +++ |
| 0004 | +++ | +++ |
| 0005 | ++ | ++ |
| 0006 | ++ | ++ |
| 0007 | +++ | +++ |
| 0008 | +++ | +++ |
| 0009 | +++ | ++ |
| 0010 | +++ | + |
| 0011 | ++ | + |
| 0012 | ++ | + |
| 0013 | ++ | ++ |
| 0014 | ++ | ++ |
| 0015 | +++ | +++ |
| 0016 | +++ | +++ |
| 0017 | ++ | + |
| 0018 | +++ | ++ |
| 0019 | +++ | +++ |
| 0020 | ++ | +++ |

TABLE 2

| Compound No. | PI3Kα Inhibitory Activity | ERK2 Inhibitory Activity |
|---|---|---|
| 0021 | ++ | +++ |
| 0022 | +++ | +++ |
| 0023 | +++ | ++ |
| 0024 | +++ | ++ |
| 0025 | +++ | ++ |
| 0026 | +++ | ++ |
| 0027 | ++ | ++ |
| 0028 | +++ | − |
| 0029 | +++ | − |
| 0030 | +++ | − |
| 0031 | +++ | + |
| 0032 | +++ | +++ |
| 0033 | ++ | +++ |
| 0034 | +++ | +++ |
| 0035 | +++ | +++ |
| 0036 | +++ | +++ |
| 0037 | +++ | +++ |
| 0038 | +++ | +++ |
| 0039 | ++ | +++ |
| 0040 | + | ++ |

TABLE 3

| Compound No. | PI3Kα Inhibitory Activity | ERK2 Inhibitory Activity |
|---|---|---|
| 0041 | ++ | +++ |
| 0042 | ++ | +++ |
| 0043 | +++ | +++ |
| 0044 | +++ | +++ |
| 0045 | +++ | +++ |
| 0046 | +++ | ++ |
| 0047 | +++ | ++ |
| 0048 | +++ | +++ |
| 0049 | +++ | +++ |
| 0050 | ++ | ++ |
| 0051 | +++ | +++ |
| 0052 | +++ | +++ |
| 0053 | +++ | +++ |
| 0054 | ++ | +++ |
| 0055 | ++ | +++ |
| 0056 | ++ | +++ |
| 0057 | +++ | +++ |
| 0058 | +++ | +++ |
| 0059 | +++ | +++ |
| 0060 | ++ | +++ |

TABLE 4

| Compound No. | PI3Kα Inhibitory Activity | ERK2 Inhibitory Activity |
|---|---|---|
| 0061 | +++ | +++ |
| 0062 | + | ++ |
| 0063 | ++ | +++ |
| 0064 | +++ | +++ |
| 0065 | ++ | +++ |

TABLE 4-continued

| Compound No. | PI3Kα Inhibitory Activity | ERK2 Inhibitory Activity |
| --- | --- | --- |
| 0066 | + | +++ |
| 0067 | ++ | +++ |
| 0068 | +++ | +++ |
| 0069 | ++ | +++ |
| 0070 | ++ | +++ |
| 0071 | +++ | ++ |
| 0072 | +++ | +++ |
| 0073 | + | +++ |
| 0074 | + | +++ |
| 0075 | ++ | +++ |
| 0076 | ++ | +++ |
| 0077 | ++ | +++ |
| 0078 | + | ++ |
| 0079 | +++ | +++ |
| 0080 | +++ | +++ |

TABLE 5

| Compound No. | PI3Kα Inhibitory Activity | ERK2 Inhibitory Activity |
| --- | --- | --- |
| 0081 | +++ | +++ |
| 0082 | +++ | +++ |
| 0083 | +++ | +++ |
| 0084 | +++ | +++ |
| 0085 | +++ | ++ |
| 0086 | +++ | +++ |
| 0087 | +++ | +++ |
| 0088 | +++ | +++ |
| 0089 | ++ | +++ |
| 0090 | +++ | ++ |
| 0091 | +++ | +++ |
| 0092 | +++ | ++ |
| 0093 | +++ | +++ |
| 0094 | +++ | +++ |
| 0095 | ++ | +++ |
| 0096 | ++ | +++ |
| 0097 | + | ++ |
| 0098 | ++ | +++ |
| 0099 | ++ | +++ |
| 0100 | ++ | +++ |

TABLE 6

| Compound No. | PI3Kα Inhibitory Activity | ERK2 Inhibitory Activity |
| --- | --- | --- |
| 0101 | + | +++ |
| 0102 | + | +++ |
| 0103 | ++ | ++ |
| 0104 | ++ | +++ |
| 0105 | ++ | +++ |
| 0106 | + | ++ |
| 0107 | ++ | +++ |
| 0108 | ++ | +++ |
| 0109 | − | + |
| 0110 | +++ | +++ |
| 0111 | + | ++ |
| 0112 | ++ | +++ |
| 0113 | ++ | +++ |
| 0114 | +++ | +++ |
| 0115 | +++ | +++ |
| 0116 | ++ | + |
| 0117 | +++ | ++ |
| 0118 | ++ | +++ |
| 0119 | ++ | +++ |
| 0120 | ++ | ++ |

TABLE 7

| Compound No. | PI3Kα Inhibitory Activity | ERK2 Inhibitory Activity |
| --- | --- | --- |
| 0121 | + | + |
| 0122 | +++ | +++ |
| 0123 | ++ | + |
| 0124 | +++ | +++ |
| 0125 | +++ | ++ |
| 0126 | +++ | ++ |
| 0127 | ++ | + |
| 0128 | ++ | + |
| 0129 | + | + |
| 0130 | ++ | ++ |
| 0131 | +++ | ++ |
| 0132 | + | + |
| 0133 | +++ | +++ |
| 0134 | +++ | + |
| 0135 | +++ | − |
| 0136 | +++ | +++ |
| 0137 | +++ | +++ |
| 0138 | +++ | +++ |
| 0139 | ++ | +++ |
| 0140 | +++ | ++ |

TABLE 8

| Compound No. | PI3Kα Inhibitory Activity | ERK2 Inhibitory Activity |
| --- | --- | --- |
| 0141 | − | − |
| 0142 | +++ | ++ |
| 0143 | +++ | ++ |
| 0144 | +++ | ++ |
| 0145 | +++ | ++ |
| 0146 | +++ | +++ |
| 0147 | +++ | +++ |
| 0148 | +++ | ++ |
| 0149 | ++ | + |
| 0150 | ++ | + |
| 0151 | +++ | +++ |
| 0152 | +++ | ++ |
| 0153 | ++ | − |
| 0154 | ++ | ++ |
| 0155 | +++ | ++ |
| 0156 | +++ | +++ |
| 0157 | +++ | ++ |
| 0158 | +++ | ++ |
| 0159 | +++ | ++ |
| 0160 | + | +++ |

TABLE 9

| Compound No. | PI3Kα Inhibitory Activity | ERK2 Inhibitory Activity |
| --- | --- | --- |
| 0161 | ++ | +++ |
| 0162 | ++ | ++ |
| 0163 | ++ | ++ |
| 0164 | +++ | +++ |
| 0165 | ++ | +++ |
| 0166 | ++ | +++ |
| 0167 | ++ | +++ |
| 0168 | +++ | +++ |
| 0169 | ++ | +++ |
| 0170 | ++ | +++ |
| 0171 | +++ | +++ |
| 0172 | ++ | +++ |
| 0173 | ++ | +++ |
| 0174 | +++ | +++ |
| 0175 | ++ | +++ |
| 0176 | ++ | ++ |
| 0177 | − | ++ |
| 0178 | ++ | ++ |
| 0179 | +++ | +++ |
| 0180 | +++ | +++ |

TABLE 10

| Compound No. | PI3Kα Inhibitory Activity | ERK2 Inhibitory Activity |
|---|---|---|
| 0181 | +++ | +++ |
| 0182 | +++ | +++ |
| 0183 | +++ | +++ |
| 0184 | +++ | +++ |
| 0185 | + | ++ |
| 0186 | ++ | +++ |
| 0187 | + | +++ |
| 0188 | +++ | +++ |
| 0189 | ++ | +++ |
| 0190 | ++ | +++ |
| 0191 | ++ | +++ |
| 0192 | ++ | +++ |
| 0193 | ++ | +++ |
| 0194 | ++ | +++ |
| 0195 | +++ | ++ |
| 0196 | ++ | ++ |
| 0197 | ++ | +++ |
| 0198 | ++ | +++ |
| 0199 | ++ | +++ |
| 0200 | +++ | +++ |

TABLE 11

| Compound No. | PI3Kα Inhibitory Activity | ERK2 Inhibitory Activity |
|---|---|---|
| 0201 | + | ++ |
| 0202 | + | ++ |
| 0203 | +++ | +++ |
| 0204 | ++ | ++ |
| 0205 | +++ | +++ |
| 0206 | +++ | ++ |
| 0207 | +++ | +++ |
| 0208 | − | − |
| 0209 | +++ | +++ |
| 0210 | +++ | ++ |
| 0211 | +++ | +++ |
| 0212 | +++ | +++ |
| 0213 | ++ | +++ |
| 0214 | +++ | ++ |
| 0215 | +++ | ++ |
| 0216 | +++ | +++ |
| 0217 | +++ | ++ |
| 0218 | +++ | +++ |
| 0219 | +++ | +++ |
| 0220 | +++ | +++ |

TABLE 12

| Compound No. | PI3Kα Inhibitory Activity | ERK2 Inhibitory Activity |
|---|---|---|
| 0221 | +++ | +++ |
| 0222 | +++ | +++ |
| 0223 | +++ | +++ |
| 0224 | ++ | + |
| 0225 | − | − |
| 0226 | +++ | +++ |
| 0227 | +++ | + |
| 0228 | +++ | +++ |
| 0229 | +++ | ++ |
| 0230 | +++ | ++ |
| 0231 | +++ | ++ |
| 0232 | +++ | +++ |
| 0233 | +++ | +++ |
| 0234 | + | − |
| 0235 | +++ | +++ |
| 0236 | ++ | − |
| 0237 | +++ | +++ |
| 0238 | ++ | +++ |
| 0239 | +++ | +++ |
| 0240 | +++ | ++ |

TABLE 13

| Compound No. | PI3Kα Inhibitory Activity | ERK2 Inhibitory Activity |
|---|---|---|
| 0241 | +++ | ++ |
| 0242 | ++ | ++ |
| 0243 | +++ | ++ |
| 0244 | +++ | +++ |
| 0245 | +++ | ++ |
| 0246 | +++ | +++ |
| 0247 | +++ | +++ |
| 0248 | +++ | +++ |
| 0249 | +++ | +++ |
| 0250 | +++ | +++ |
| 0251 | ++ | ++ |
| 0252 | ++ | ++ |
| 0253 | +++ | +++ |
| 0254 | +++ | ++ |
| 0255 | +++ | ++ |
| 0256 | +++ | ++ |
| 0257 | +++ | ++ |
| 0258 | +++ | ++ |
| 0259 | ++ | +++ |

TABLE 14

| Compound No. | PI3Kα, $IC_{50}$ (μM) | ERK2, $IC_{50}$ (μM) |
|---|---|---|
| 0002 | 0.084 | 0.042 |
| 0009 | <0.003 | 1.220 |
| 0043 | 0.011 | 0.007 |
| 0044 | 0.004 | 0.049 |
| 0051 | 0.006 | 0.035 |
| 0064 | 0.050 | <0.003 |
| 0068 | 0.030 | 0.004 |
| 0069 | 0.133 | <0.003 |
| 0080 | 0.060 | <0.003 |
| 0125 | <0.003 | 0.324 |
| 0137 | 0.010 | 0.007 |

The compound of the present invention showed a strong inhibitory activity with respect to at least one of the PI3Kα pathway or the ERK2 pathway.

Test Example 3

Cell Growth Inhibition Test

Evaluation of the cell proliferation inhibitory activity of the compound of the present invention was carried out according to the method below.

For the cell growth inhibition test, the following materials was used.

[Cells]
Human colon cancer cell line (HCT116)

[Maintenance Medium]
McCoy's 5A (INVITROGEN)+Final Concentration 10% FBS+GLUTA Max (INVITROGEN)

[Detection Reagent]
Celltiter-Glo™ Luminescent Cell Viability Assay (Promega Corporation)

HCT116 was seeded on a 96-well culture microplate (Corning Inc.) at 750/well (90 uL/well), and a compound for evaluation (final concentration: 25.00 μM to 0.01 μM, 3-fold common ratio 8 points) was added thereto. After culturing in a $CO_2$ incubator (37° C.) for 72 hours, the number of viable cells were calculated by Celltiter-Glo. For the measurement of luminescence intensity, EnVision (PerkinElmer, Inc.) was used.

The inhibitory activity of the compound was calculated using $IC_{50}$ (50% inhibitory concentration). The $IC_{50}$ was calculated using XLfit (IDBS). The results of $IC_{50}$ were evaluated according to the following evaluation criteria. The evaluation results are shown in Table 15.

—Evaluation Criteria—
++ IC$_{50}$<1 µM
+ 1 µM<IC$_{50}$<10 µM

TABLE 15

| Compound No. | HCT116 IC$_{50}$ |
|---|---|
| 0041 | + |
| 0046 | + |
| 0136 | + |
| 0148 | + |
| 0154 | ++ |
| 0157 | ++ |
| 0158 | ++ |
| 0182 | ++ |
| 0243 | ++ |
| 0255 | ++ |

The compound of the invention exhibited a strong inhibitory activity with respect to HCT-116 cells.

INDUSTRIAL APPLICABILITY

The 1,5-naphthyridine derivative or a salt thereof and the PI3K inhibitor of the present invention have an excellent inhibitory activity for at least one of the PI3K-AKT pathways, and are useful for treatments such as prophylactic and therapeutic treatments of diseases such as cell proliferative diseases, allergy and autoimmune diseases, neurodegenerative diseases, cardiovascular diseases, inflammatory diseases, endocrine abnormalities, metabolic abnormalities, and infectious diseases. The preparation method of the present invention is useful as a method for preparing an intermediate for the preparation of a compound having an excellent inhibitory activity against a PI3K-AKT pathway.

The invention claimed is:
1. A 1,5-naphthyridine derivative represented by Formula [1], or a salt thereof:

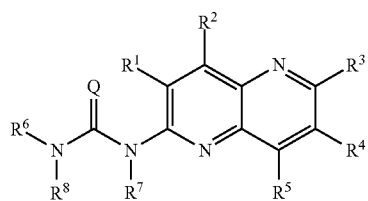

[1]

wherein:
each of $R^1$, $R^2$, $R^3$, $R^4$ and $R^5$ independently represents a hydrogen atom, a halogen atom, a cyano group, an optionally substituted $C_{1-6}$ alkyl group, an optionally substituted $C_{2-6}$ alkenyl group, an optionally substituted $C_{2-6}$ alkynyl group, or a monovalent group represented by —OR$^9$, —SR$^9$, —N(R$^9$)$_2$, —S(=O)$_n$R$^9$, —C(=O)R$^9$, —C(=NR$^9$)R$^9$, —C(=N—OR$^9$)R$^9$, —S(=O)$_n$N(R$^9$)$_2$, —C(=O)N(R$^9$)$_2$, —C(=O)OR$^9$, —S(=O)$_n$OR$^9$, —C(=NR$^9$)N(R$^9$)$_2$, —C(=NR$^9$)OR$^9$, —NR$^9$S(=O)$_n$R$^9$, —NR$^9$C(=O)R$^9$, —NR$^9$C(=NR$^9$)R$^9$, —OC(=O)R$^9$, —OC(=NR$^9$)R$^9$, —OS(=O)$_n$R$^9$, —NR$^9$C(=O)N(R$^9$)$_2$, —NR$^9$C(=S)N(R$^9$)$_2$, —NR$^9$C(=O)OR$^9$, —OC(=O)N(R$^9$)$_2$, or -L-Z, wherein each of R$^9$ independently represents a hydrogen atom, an optionally substituted $C_{1-6}$ alkyl group, an optionally substituted $C_{3-8}$ cycloalkyl group, an optionally substituted non-aromatic heterocyclic group, an optionally substituted aryl group, or an optionally substituted heteroaryl group; n represents 1 or 2; Z represents an optionally substituted $C_{3-8}$ cycloalkyl group, an optionally substituted non-aromatic heterocyclic group, an optionally substituted aryl group, or an optionally substituted heteroaryl group; L represents a single bond or a divalent linking group containing a hydrogen atom and at least one selected from the group consisting of a carbon atom, a nitrogen atom, an oxygen atom, and a sulfur atom;

$R^6$ represents a hydrogen atom, an optionally substituted $C_{1-6}$ alkyl group, an optionally substituted $C_{2-6}$ alkenyl group, an optionally substituted $C_{2-6}$ alkynyl group or a monovalent group represented by -L-Z, wherein L and Z represent the same as described above for $R^1$, $R^2$, $R^3$, $R^4$ and $R^5$;

each of $R^7$ and $R^8$ independently represents a hydrogen atom, an optionally substituted $C_{1-6}$ alkyl group, an optionally substituted $C_{3-8}$ cycloalkyl group, an optionally substituted $C_{2-6}$ alkenyl group or an optionally substituted $C_{2-6}$ alkynyl group; and Q represents an oxygen atom, a sulfur atom, or a nitrogen atom having a hydrogen atom, an optionally substituted $C_{1-6}$ alkyl group, an optionally substituted $C_{1-6}$ alkoxy group, an optionally substituted $C_{3-8}$ cycloalkyl group, an optionally substituted $C_{2-6}$ alkenyl group, or an optionally substituted $C_{2-6}$ alkynyl group, provided that the 1,5-naphthyridine derivative represented by Formula [1] is not any of the following compounds A1 to A16:

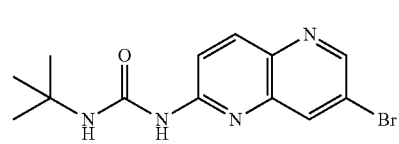

A1

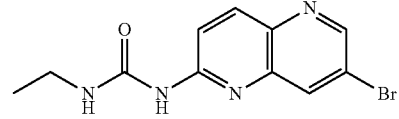

A2

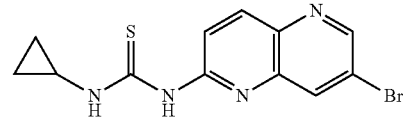

A3

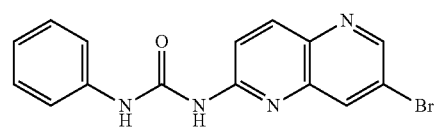

A4

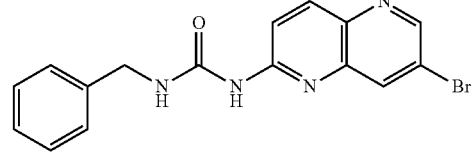

A5

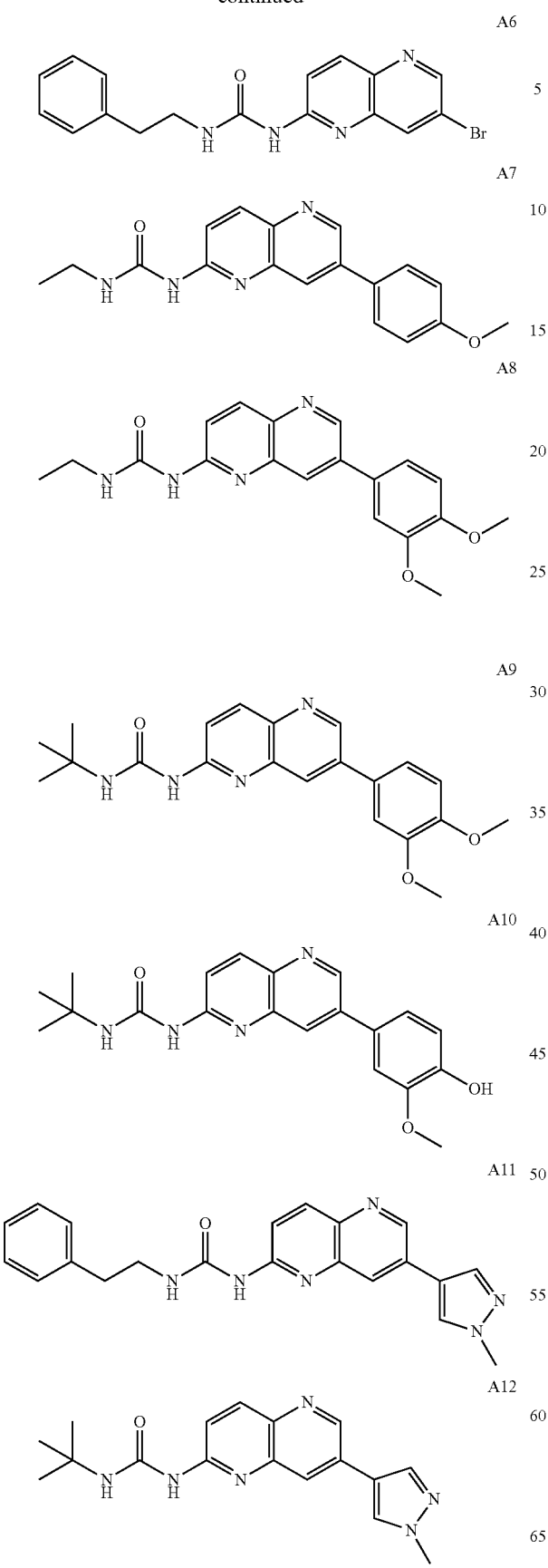
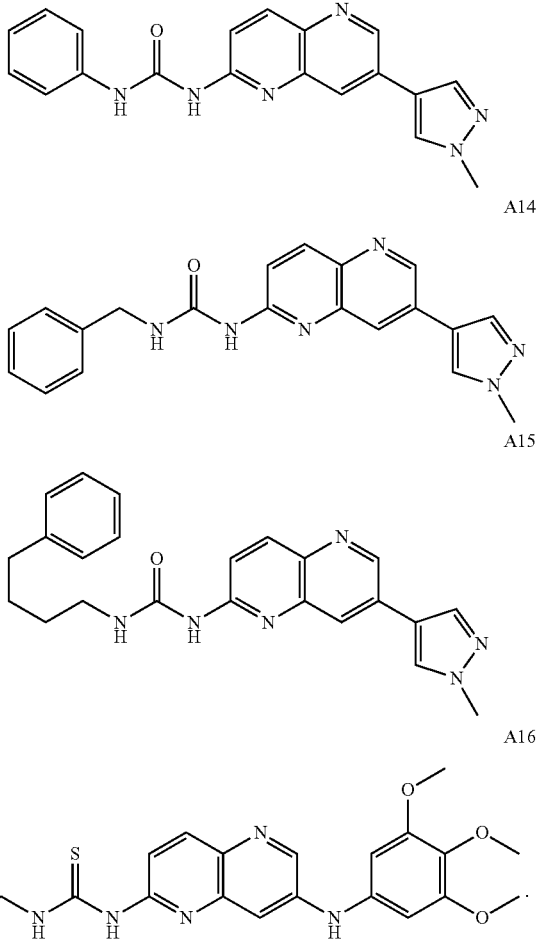

2. The 1,5-naphthyridine derivative or a salt thereof according to claim 1, wherein:

each of $R^1$, $R^2$, $R^3$ and $R^5$ independently represents a hydrogen atom, a halogen atom, a cyano group, an optionally substituted $C_{1-6}$ alkyl group, or a monovalent group represented by —$OR^9$, wherein $R^9$ represents a hydrogen atom, an optionally substituted $C_{1-6}$ alkyl group, an optionally substituted $C_{3-8}$ cycloalkyl group, an optionally substituted non-aromatic heterocyclic group, an optionally substituted aryl group, or an optionally substituted heteroaryl group;

$R^4$ represents a hydrogen atom, a halogen atom, a cyano group, an optionally substituted $C_{1-6}$ alkyl group, an optionally substituted $C_{2-6}$ alkenyl group, an optionally substituted $C_{2-6}$ alkynyl group, or a monovalent group represented by —$OR^9$, —$N(R^9)_2$, —$C(=O)R^9$, —$C(=O)N(R^9)_2$, —$NR^9C(=O)R^9$ or —Z, wherein Z represents an optionally substituted $C_{3-8}$ cycloalkyl group, an optionally substituted non-aromatic heterocyclic group, an optionally substituted aryl group, or an optionally substituted heteroaryl group; and each of $R^9$ independently represents the same as described above for $R^1$, $R^2$, $R^3$ and $R^5$;

$R^6$ represents an optionally substituted $C_{1-6}$ alkyl group, an optionally substituted $C_{2-6}$ alkenyl group, an optionally substituted $C_{2-6}$ alkynyl group, or a monovalent group represented by -$L^a$-Z, wherein $L^a$ represents a single bond or a group represented by —S(O)$_2$N(R$^9$)— or —C(=O)—, R$^9$ represents the same as described above for R$^1$, R$^2$, R$^3$ and R$^5$, and Z represents the same as described above for R$^4$;

each of R$^7$ and R$^8$ independently represents a hydrogen atom, an optionally substituted C$_{1-6}$ alkyl group, or an optionally substituted C$_{3-8}$ cycloalkyl group;

Q represents an oxygen atom or a sulfur atom; and provided that in the case where R$^6$ is an ethyl group, a cyclopropyl group, a tert-butyl group, a phenyl group, a benzyl group, a 2-phenylethyl group, or a 4-phenylbutyl group, R$^4$ represents an optionally substituted non-aromatic heterocyclic group, a heteroaryl group substituted with an optionally substituted di(C$_{1-6}$ alkyl)amino group, or a heteroaryl group substituted with an optionally substituted non-aromatic heterocyclic C$_{1-6}$ alkyl group.

3. The 1,5-naphthyridine derivative or a salt thereof according to claim 1, wherein each of R$^1$, R$^2$, R$^3$, R$^7$ and R$^8$ is a hydrogen atom; and R$^5$ is a hydrogen atom, a halogen atom, an optionally substituted C$_{1-3}$ alkyl group, or a monovalent group represented by —OR$^9$, wherein R$^9$ represents a hydrogen atom, an optionally substituted C$_{1-6}$ alkyl group, an optionally substituted C$_{3-8}$ cycloalkyl group, an optionally substituted non-aromatic heterocyclic group, an optionally substituted aryl group, or an optionally substituted heteroaryl group.

4. The 1,5-naphthyridine derivative or a salt thereof according to claim 1, wherein R$^4$ is a monovalent group represented by —NH(R$^{9a}$) or —Z$^a$, wherein R$^{9a}$ represents an optionally substituted non-aromatic heterocyclic group, an optionally substituted aryl group, or an optionally substituted heteroaryl group; and Z$^a$ represents an optionally substituted non-aromatic heterocyclic group, an optionally substituted aryl group, or an optionally substituted heteroaryl group.

5. The 1,5-naphthyridine derivative or a salt thereof according to claim 1, wherein R$^6$ is an optionally substituted C$_{1-6}$ alkyl group or a monovalent group represented by —Z, wherein Z represents an optionally substituted C$_{3-8}$ cycloalkyl group, an optionally substituted non-aromatic heterocyclic group, an optionally substituted aryl group, or an optionally substituted heteroaryl group.

6. The 1,5-naphthyridine derivative or a salt thereof according to claim 1, wherein R$^4$ is an optionally substituted pyrazolyl group, and R$^6$ is a C$_{5-8}$ cycloalkyl group.

7. The 1,5-naphthyridine derivative or a salt thereof according to claim 1, wherein Q is an oxygen atom.

8. A pharmaceutical composition comprising the 1,5-naphthyridine derivative or a salt thereof according to claim 1.

9. A treatment agent for malignant tumors, comprising the 1,5-naphthyridine derivative or a salt thereof according to claim 1.

10. A method for preparing a compound represented by Formula [6], wherein a compound represented by Formula [2] is reacted with a compound represented by Formula [3] to obtain a compound represented by Formula [4], the compound represented by Formula [4] is then reacted with a halogenating agent, sulfonic acid anhydride, or sulfonic acid halide to obtain a compound represented by Formula [5], and the compound represented by Formula [5] is then reacted with a brominating agent:

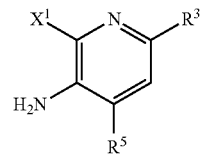

[2]

wherein in Formula [2], each of R$^3$ and R$^5$ independently represents a hydrogen atom, a halogen atom, a cyano group, an optionally substituted C$_{1-6}$ alkyl group, an optionally substituted C$_{2-6}$ alkenyl group, an optionally substituted C$_{2-6}$ alkynyl group, or a monovalent group represented by —OR$^9$, —SR$^9$, —N(R$^9$)$_2$, —S(=O)$_n$R$^9$, —C(=O)R$^9$, —C(=NR$^9$)R$^9$, —C(=N—OR$^9$)R$^9$, —S(=O)$_n$N(R$^9$)$_2$, —C(=O)N(R$^9$)$_2$, —C(=O)OR$^9$, —S(=O)$_n$R$^9$, —C(=NR$^9$)N(R$^9$)$_2$, —C(=NR$^9$)OR$^9$, —NR$^9$S(=O)$_n$R$^9$, —NR$^9$C(=O)R$^9$, —NR$^9$C(=NR$^9$)R$^9$, —OC(=O)R$^9$, —OC(=NR$^9$)R$^9$, —OS(=O)$_n$R$^9$, —NR$^9$C(=O)N(R$^9$)$_2$, —NR$^9$C(=S)N(R$^9$)$_2$, —NR$^9$C(=O)OR$^9$, —OC(=O)N(R$^9$)$_2$, or -L-Z, wherein each of R$^9$ independently represents a hydrogen atom, an optionally substituted C$_{1-6}$ alkyl group, an optionally substituted C$_{3-8}$ cycloalkyl group, an optionally substituted non-aromatic heterocyclic group, an optionally substituted aryl group, or an optionally substituted heteroaryl group; n represents 1 or 2; Z represents an optionally substituted C$_{3-8}$ cycloalkyl group, an optionally substituted non-aromatic heterocyclic group, an optionally substituted aryl group, or an optionally substituted heteroaryl group; and L represents a single bond or a divalent linking group containing a hydrogen atom and at least one selected from the group consisting of a carbon atom, a nitrogen atom, an oxygen atom, and a sulfur atom, and X$^1$ represents a halogen atom, an optionally substituted C$_{1-6}$ alkylsulfonyloxy group, or an optionally substituted arylsulfonyloxy group;

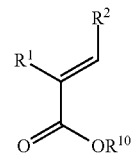

[3]

wherein in Formula [3], each of R$^1$ and R$^2$ independently represents a hydrogen atom, a halogen atom, a cyano group, an optionally substituted C$_{1-6}$ alkyl group, an optionally substituted C$_{2-6}$ alkenyl group, an optionally substituted C$_{2-6}$ alkynyl group, or a monovalent group represented by —OR$^9$, —SR$^9$, —N(R$^9$)$_2$, —S(=O)$_n$R$^9$, —C(=O)R$^9$, —C(=NR$^9$)R$^9$, —C(=N—OR$^9$)R$^9$, —S(=O)$_n$N(R$^9$)$_2$, —C(=O)N(R$^9$)$_2$, —C(=O)OR$^9$, —S(=O)$_n$R$^9$, —C(=NR$^9$)N(R$^9$)$_2$, —C(=NR$^9$)OR$^9$, —NR$^9$S(=O)$_n$R$^9$, —NR$^9$C(=O)R$^9$, —NR$^9$C(=NR$^9$)R$^9$, —OC(=O)R$^9$, —OC(=NR$^9$)R$^9$, —OS(=O)$_n$R$^9$, —NR$^9$C(=O)N(R$^9$)$_2$, —NR$^9$C(=S)N(R$^9$)$_2$, —NR$^9$C(=O)OR$^9$, —OC(=O)N(R$^9$)$_2$, or -L-Z, wherein R$^9$, L, Z and n represent the same as described above for Formula [2]; and $R^{10}$ represents a carboxyl protecting group;

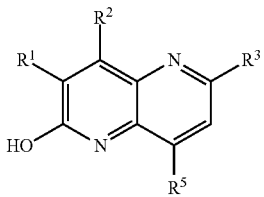
[4]

wherein in Formula [4], $R^1$, $R^2$, $R^3$ and $R^5$ represent the same as described above for Formula [2] and Formula [3];

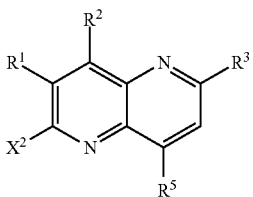
[5]

wherein in Formula [5], $X^2$ represents a halogen atom, an optionally substituted $C_{1-6}$ alkylsulfonyloxy group, or an optionally substituted arylsulfonyloxy group; and $R^1$, $R^2$, $R^3$ and $R^5$ represent the same as described above for Formula [2] and Formula [3];

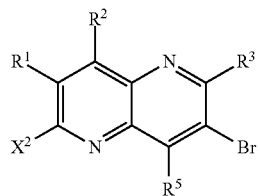
[6]

wherein in Formula [6], $R^1$, $R^2$, $R^3$, $R^5$ and $X^2$ represent the same as described above for Formula [2] and Formula [3] and Formula [5].

11. The preparation method according to claim 10, wherein:
$X^1$ is a halogen atom; and
$X^2$ is a halogen atom.

12. The preparation method according to claim 10, wherein:
each of $R^1$, $R^2$ and $R^3$ is a hydrogen atom; and
$R^5$ is a hydrogen atom, a halogen atom, an optionally substituted $C_{1-3}$ alkyl group, or a monovalent group represented by —$OR^9$, wherein $R^9$ represents a hydrogen atom, an optionally substituted $C_{1-6}$ alkyl group, an optionally substituted $C_{3-8}$ cycloalkyl group, an optionally substituted non-aromatic heterocyclic group, an optionally substituted aryl group, or an optionally substituted heteroaryl group.

* * * * *